United States Patent
Bradner et al.

(10) Patent No.: US 9,567,301 B2
(45) Date of Patent: Feb. 14, 2017

(54) PYRROL-1-YL BENZOIC ACID DERIVATIVES USEFUL AS MYC INHIBITORS

(71) Applicants: Whitehead Institute for Biomedical Research, Cambridge, MA (US); Dana-Farber Cancer Institute, Inc., Boston, MA (US)

(72) Inventors: James E. Bradner, Weston, MA (US); Michael R. McKeown, Brookline, MA (US); Peter B. Rahl, Natick, MA (US); Richard A. Young, Boston, MA (US); Jason J. Marineau, Franklin, MA (US)

(73) Assignees: Dana-Farber Cancer Institute, Inc., Boston, MA (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/440,200

(22) PCT Filed: Nov. 1, 2013

(86) PCT No.: PCT/US2013/068159
§ 371 (c)(1),
(2) Date: May 1, 2015

(87) PCT Pub. No.: WO2014/071247
PCT Pub. Date: May 8, 2014

(65) Prior Publication Data
US 2015/0291521 A1    Oct. 15, 2015

Related U.S. Application Data

(60) Provisional application No. 61/721,957, filed on Nov. 2, 2012.

(51) Int. Cl.
*C07D 207/327* (2006.01)
*C07D 401/12* (2006.01)
(Continued)

(52) U.S. Cl.
CPC ......... *C07D 207/327* (2013.01); *C07D 207/27* (2013.01); *C07D 209/04* (2013.01);
(Continued)

(58) Field of Classification Search
CPC .................................................. C07D 207/327
(Continued)

(56) References Cited

U.S. PATENT DOCUMENTS 7,473,767 B2   1/2009   Dimitrov
2010/0227864 A1   9/2010   Shimizu et al.
(Continued)

FOREIGN PATENT DOCUMENTS

DE    10 48 582 B    1/1959
EP    2 133 331 A1    12/2009
(Continued)

OTHER PUBLICATIONS

Invitation to Pay Additional Fees for PCT/US2013/068159, mailed Dec. 20, 2013.
(Continued)

*Primary Examiner* — Taofiq A Solola
(74) *Attorney, Agent, or Firm* — Wolf, Greenfield & Sacks, P.C.

(57) ABSTRACT

The present invention provides compounds of Formula (I-A), (I-B), and (I-C), pharmaceutically acceptable salts thereof, and pharmaceutical compositions thereof. Compounds of the present invention are useful for inhibiting Myc (e.g., c-Myc) activity. The present invention further provides methods of using the compounds described herein for treating Myc-mediated disorders (e.g., cancer and other proliferative diseases). The present invention also provides assays for identifying Myc inhibitors.

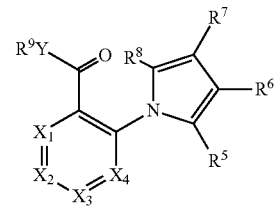

I-A

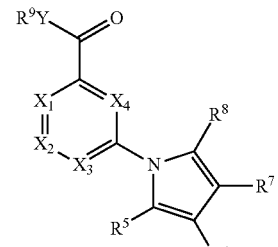

I-B

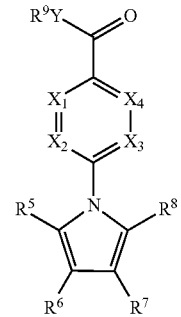

I-C

10 Claims, 15 Drawing Sheets

(51) Int. Cl.
  C07D 207/27  (2006.01)
  C07D 209/04  (2006.01)
  C07D 403/06  (2006.01)
  C07D 409/04  (2006.01)
  C07D 413/12  (2006.01)
  C07D 417/06  (2006.01)

(52) U.S. Cl.
  CPC ......... *C07D 401/12* (2013.01); *C07D 403/06* (2013.01); *C07D 409/04* (2013.01); *C07D 413/12* (2013.01); *C07D 417/06* (2013.01)

(58) Field of Classification Search
  USPC ........................................................ 435/61
  See application file for complete search history.

(56) References Cited

U.S. PATENT DOCUMENTS

2010/0256214 A1  10/2010  Pasquale et al.
2012/0289506 A1  11/2012  Shimizu et al.

FOREIGN PATENT DOCUMENTS

GB           1 263 940 A      2/1972
WO    WO 2010/114921 A1     10/2010

OTHER PUBLICATIONS

International Search Report and Written Opinion for PCT/US2013/068159, mailed Feb. 24, 2014.
International Preliminary Report on Patentability for PCT/US2013/068159, mailed May 14, 2015.
Campbell et al., A homogeneous immunoassay for cyclic nucleotides based on chemiluminescence energy transfer. Biochem J. Oct. 15, 1983;216(1):185-94.
Cree et al., Measurement of cytotoxicity by ATP-based luminescence assay in primary cell cultures and cell lines. Toxicol In Vitro. Oct. 1997;11(5):553-6.
He et al., Identification of c-MYC as a target of the APC pathway. Science. Sep. 4, 1998;281(5382):1509-12.
Koehler, A complex task? Direct modulation of transcription factors with small molecules. Curr Opin Chem Biol. Jun. 2010;14(3):331-40. doi: 10.1016/j.cbpa.2010.03.022. Epub Apr. 13, 2010.
Liu et al., Design, synthesis, and biological evaluation of N-carboxyphenylpyrrole derivatives as potent HIV fusion inhibitors targeting gp41. J Med Chem. Dec. 25, 2008;51(24):7843-54. doi: 10.1021/jm800869t.
Mathis, Probing molecular interactions with homogeneous techniques based on rare earth cryptates and fluorescence energy transfer. Clin Chem. Sep. 1995;41(9):1391-7.
Nesbit et al., MYC oncogenes and human neoplastic disease. Oncogene. May 13, 1999;18(19):3004-16.
Noberini et al., Small molecules can selectively inhibit ephrin binding to the EphA4 and EphA2 receptors. J Biol Chem. Oct. 24, 2008;283(43):29461-72. doi: 10.1074/jbc.M804103200. Epub Aug. 26, 2008.
Soucek et al., Modelling Myc inhibition as a cancer therapy. Nature. Oct. 2, 2008;455(7213):679-83. doi: 10.1038/nature07260. Epub Aug. 17, 2008.
Stryer, Fluorescence energy transfer as a spectroscopic ruler. Annu Rev Biochem. 1978;47:819-46.
Wang et al., Structure-based design, synthesis and biological evaluation of new N-carboxyphenylpyrrole derivatives as HIV fusion inhibitors targeting gp41. Bioorg Med Chem Lett. Jan. 1, 2010;20(1):189-92. doi: 10.1016/j.bmcl.2009.10.139. Epub Nov. 5, 2009.
Xu et al., A bioluminescence resonance energy transfer (BRET) system: application to interacting circadian clock proteins. Proc Natl Acad Sci U S A. Jan. 5, 1999;96(1):151-6.
Aiello et al., Efficient synthesis of 9H-pyrrolo[1,2-a]indol-9-one derivatives based on active manganese dioxide promoted intramolecular cyclization. Tetrahedron. Jan. 2010;66(1):274-77.
Balli et al., Neue Heteroarene: Synthese und spektrale Daten von Indolizino [6,5.4.3-ij] chinolin und einigen Derivaten. Helvetica Chimica Acta. Nov. 2, 1983;66(7):2135-39. German.
Bouyazza et al., Synthese de Pyrrolo[1,2-alpha] quinoleines. Jan. 1, 1991;28(1):77-80. French.
Carosati et al., Calcium channel antagonists discovered by a multidisciplinary approach. J Med Chem. Aug. 24, 2006;49(17):5206-16.
Eswaran et al., Crystal structures and inhibitor identification for PTPN5, PTPRR and PTPN7: a family of human MAPK-specific protein tyrosine phosphatases. Biochem J. May 1, 2006;395(3):483-91.
Faigl et al., Competition and co-operation between ortho directing groups and activating agents: regioselective metalation of 1-(Methoxyphenyl) pyrroles. Tetrahedron. Mar. 31, 1997;53(13):4883-88.
Fogassy et al., Solvent and ligand effects on selective mono- and dilithiation of 1-(chlorophenyppyrroles and 1-(methoxyphenyl)pyrroles. J Chem Soc. Jan. 1, 2001;1(9):1039-43.
Kobayashi et al., A facile synthesis of 9-dialkylamino-9H-pyrrolo[1,2-alpha]indoles via iminium salts generated from 2-(pyrrol-1-yl)-benzaldehydes and secondary amine hydrochlorides in the presence of NaI/TMSCl/ET3N. Tetrahedron. Mar. 27, 2006;62(13):3158-61.
Rault et al., Synthesis of preliminary study of psychotropic effect of alkylamino and imino pyrrolo[1,2-alpha]indoles, European J Med Chem. Dec. 1, 1991; 26 (9):939-46, French.
Berg et al., Small-molecule antagonists of Myc/Max dimerization inhibit Myc-induced transformation of chicken embryo fibroblasts. Proc Natl Acad Sci U S A. Mar. 19, 2002; 99(6):3830-5. Epub Mar. 12, 2002.
Prochownik eet al., Therapeutic Targeting of Myc. Genes & Cancer. Jun. 2010;1(6):650-659.
Wang et al., Improved low molecular weight Myc-Max inhibitors. Mol Cancer Ther. Sep. 2007;6(9):2399-2408.

PYRROL-1-YL BENZOIC ACID DERIVATIVES USEFUL AS MYC INHIBITORS

RELATED APPLICATIONS

The present application is a national stage filing under 35 U.S.C. §371 of international PCT application, PCT/US2013/068159, filed Nov. 1, 2013, which claims priority under 35 U.S.C. §119(e) to U.S. provisional patent application, U.S. Ser. No. 61/721,957, filed Nov. 2, 2012, each of which is incorporated herein by reference.

GOVERNMENT SUPPORT

This invention was made with U.S. Government support under grant RO1-HG002668 awarded by National Institutes of Health. The U.S. Government has certain rights in the invention.

BACKGROUND OF THE INVENTION

The transcription factor Myc plays a role in regulating cell proliferation, the cell cycle, cell growth, angiogenesis, apoptosis, and oncogenesis. Myc's activity can increase in tumors as a consequence of mutations, chromosomal rearrangements, increased expression, or gene amplification (see, e.g., Nesbit, et al. (1999) *Oncogene* 18:3004-3016; Zeller, et al. (2001) *J. Biol. Chem.* 276:48285-48291; He, et al. (1998) *Science* 281:1509-1512; McMahon, et al. (1998) *Cell* 94:363-374; Erisman, et al. (1985) *Mol. Cell Biol.* 5:1969-1976; Rochlitz, et al. (1996). *Oncology* 53:448-454). Increased Myc levels have been found, for example, in breast cancer and prostate cancer (Liao, et al. (2000) *Endocrine-Related Cancer* 7:143-164; Jenkins, et al. (1997) *Cancer Res.* 57:524-531).

When Myc acts as a cell cycle regulator, it can promote entry of a cell into the cell cycle (Trumpp, et al. (2001) *Nature* 414:768-773; Holzel, et al. (2001) *EMBO Reports* 21:1125-1132; Bouchard, et al. (2001) *Genes Devel.* 15:2042-2047). Myc has been found to act in certain phases of the cell cycle, where cell cycle genes, e.g., cyclins and protein kinases, may be directly or indirectly regulated by Myc. Myc also regulates growth, as it plays a role in regulating genes required for protein synthesis, e.g., genes encoding transcription factors and ribosomal proteins (Greasley, et al. (2000) *Nucleic Acids Res.* 28:446-453); Zeller, et al. (2001) supra; Menssen, et al. (2002) *Proc. Natl. Acad. Sci. USA* 59:6274-6279). Myc regulates apoptosis, which can be impaired in cancer cells. Myc has been shown to regulate key apoptosis pathway proteins (Nesbit, et al. (1998) *Blood* 92:1003-1010).

Many diseases are associated with abnormal cell signaling triggered by Myc-mediated events described above, including proliferative diseases (e.g., cancer) and cardiovascular diseases. Accordingly, there is a need to identify Myc inhibitors useful as therapeutic agents and research tools.

SUMMARY OF THE INVENTION

Transcription factors are key regulators of cell state as they commonly are terminal components of signaling cascades, control gene expression programs that drive cell type specification, and are often deregulated in disease states (Ptashne and Gann, (1997) *Nature* 386:569-577; Ptashne, M., and Gann, A. (2002) *Genes & signals* (Cold Spring Harbor, N.Y., Cold Spring Harbor Laboratory Press)). This makes transcription factors an ideal class of proteins for therapeutic targeting (Darnell, (2002) *Nat Rev Cancer* 2:740-749; Koehler, (2010) *Curr Opin Chem Biol* 14:331-340). However, most transcription factors lack clear pockets for small molecule binding and therefore have been largely considered beyond the scope of conventional ligand discovery. Methods are described herein for the discovery of inhibitors of transcription factor that utilizes a robust high throughput screening technology supported by a series of secondary and tertiary assays for use in screening or iterative rounds of medicinal chemistry.

The methods described herein were initially developed to focus on the identification of inhibitors of c-Myc dimerization with Max and subsequent DNA binding. However, these methods can be adapted to any transcription factors relying on dimerization and DNA binding for function, factors that interact with signaling components or factors that interact with cofactors to regulate transcriptional output. c-Myc is a basic helix-loop-helix transcription factor that is expressed in most proliferating cell types and regulates cellular proliferation through controlling the expression of a network of genes (Eilers and Eisenman, (2008) *Genes Dev* 22:2755-2766). c-Myc requires heterodimerization with Max to bind DNA to regulate transcription. MYC function is deregulated in at least 30% of human cancers, occurring in a wide range of cancers including breast, prostate, colon, and lung cancer. Studies using transgenic mouse models have found that in many MYC-dependent tumors tumors, MYC inactivation leads to tumor regression. Therefore, inhibiting c-Myc function could be a powerful anticancer therapeutic approach.

There are multiple potential modes of action of a c-Myc inhibitor, including stabilizing the unstructured monomeric c-Myc, blocking c-Myc/Max dimerization, blocking c-Myc/Max dimer binding to DNA and intercalating DNA to disrupt the DNA structure at a c-Myc/Max binding site. The methods described herein allow for identification of inhibitors functioning through any of these mechanisms. Secondary and tertiary assays have been developed to identify the mode of action, measure selectivity and optimize ligands.

In one aspect, the present invention provides a compound of Formula (I-A), (I-B), or (I-C):

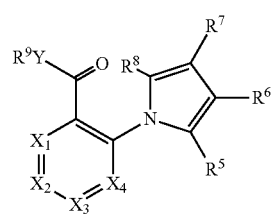

I-A

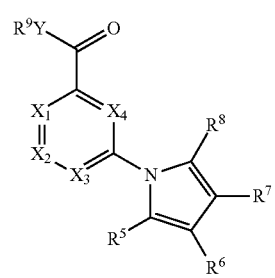

I-B

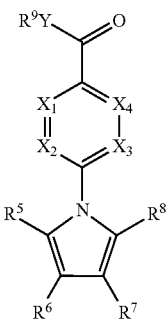

I-C or a pharmaceutically acceptable salt thereof, wherein $X_1$, $X_2$, $X_3$, $X_4$, Y, $R^5$, $R^6$, $R^7$, $R^8$, and $R^9$ are as defined herein.

In certain embodiments, a compound of the invention is a compound of Formula (I-a), (I-b), or (I-c):

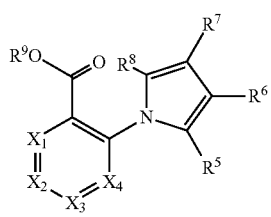

I-a

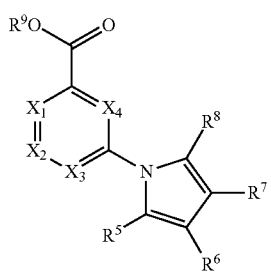

I-b

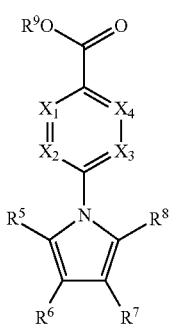

I-c or a pharmaceutically acceptable salt thereof. In certain embodiments, the present invention provides a compound of Formula (II-a), (II-b), (II-c), or (II-d):

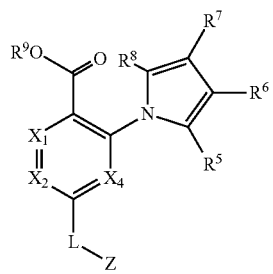

II-a

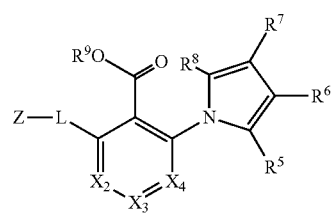

II-b

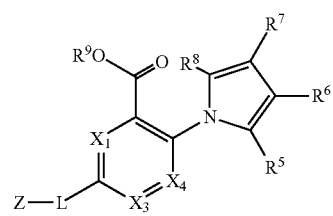

II-c

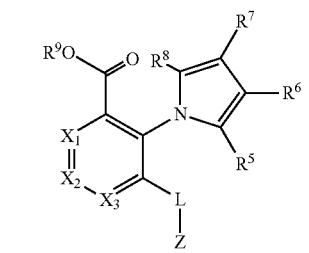

II-d or a pharmaceutically acceptable salt thereof, wherein $X_1$, $X_2$, $X_3$, $X_4$, $R^5$, $R^6$, $R^7$, $R^8$, $R^9$, L, and Z are as defined herein. In certain embodiments, the present invention provides a compound of Formula (III-a) or (III-b):

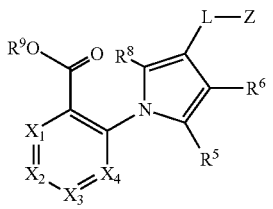

III-a

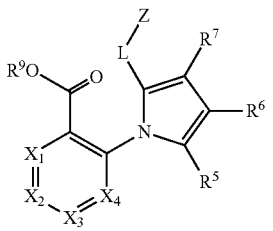

III-b or a pharmaceutically acceptable salt thereof, wherein X₁, X₂, X₃, X₄, R⁵, R⁶, R⁷, R⁸, R⁹, L, and Z are as defined herein. In certain embodiments, the present invention provides a compound of Formula (IV):

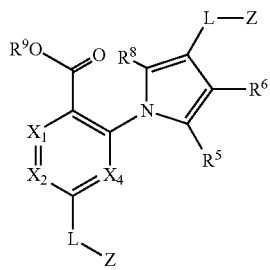

IV or a pharmaceutically acceptable salt thereof, wherein X₁, X₂, X₄, R⁵, R⁶, R⁸, R⁹, L, and Z are as defined herein.

In another aspect, pharmaceutical compositions are provided which comprise a compound described herein (e.g., a compound of Formula I-A, I-B, I-C, I-a, I-b, or I-c), or a pharmaceutically acceptable salt thereof, and optionally a pharmaceutically acceptable excipient. The pharmaceutical composition may contain a therapeutically effective amount of the compound for treating a condition associated with aberrant Myc activity (e.g., a proliferative disease such as cancer).

In certain embodiments, compounds described herein inhibit Myc (e.g., c-Myc, 1-Myc, n-Myc) activity. In certain embodiments, methods of inhibiting Myc are provided which comprise contacting Myc, or a mutant, homolog, or variant thereof, with an effective amount of a compound described herein, or a pharmaceutically acceptable salt thereof. The Myc may be purified or crude, and may be present in a cell, tissue, or a subject. Thus, such methods encompass both inhibition of Myc activity in vitro and in vivo. In certain embodiments, methods of inhibiting c-Myc are provided which comprise contacting c-Myc, or a mutant, homolog, or variant thereof, with an effective amount of a compound described herein (e.g., a compound of Formula I-A, I-B, I-C, I-a, I-b, or I-c), or a pharmaceutically acceptable salt thereof. In certain embodiments, c-Myc is wild-type c-Myc. In certain embodiments, c-Myc is in a cell. In certain embodiments, c-Myc is in a cell in a living subject (e.g., a human).

In another aspect, methods of treating a Myc-mediated disorder are provided which comprise administering to a subject suffering from a Myc-mediated disorder an effective amount of a compound described herein (e.g., a compound of Formula I-A, I-B, I-C, I-a, I-b, or I-c), or a pharmaceutically acceptable salt thereof. In certain embodiments, methods of treating a c-Myc-mediated disorder are provided which comprise administering to a subject suffering from a c-Myc-mediated disorder an effective amount of a compound described herein (e.g., a compound of formula I-A, I-B, I-C, I-a, I-b, or I-c), or a pharmaceutically acceptable salt thereof. In certain embodiments, the Myc-mediated disorder is a proliferative disorder (e.g., cancer). In certain embodiments, the Myc-mediated disorder is a cardiovascular disorder.

In another aspect, compounds described herein are useful as research tools for investigating the role of Myc, e.g., c-Myc, in the pathophysiology of various conditions and disorders.

This application refers to various issued patent, published patent applications, journal articles, and other publications, all of which are incorporated herein by reference.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., Inside Cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1 butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$), —OC(=NR$^{bb}$)N(R$^{bb}$)$_2$, —NR$^{bb}$C (=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=S)R$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$R$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl)$_2$, —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substitutents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$) N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, 0e, ft and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O) OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10, 10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N, N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3 d edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7α-octahydro-7,8,8-trimethyl-4,7-methanobenzofuran-2-yl, 1-ethoxyethyl, 1-(2-chloroethoxyl)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

These and other exemplary substituents are described in more detail in the Detailed Description, Examples, and Claims. The present disclosure is not intended to be limited in any manner by the above exemplary listing of substituents.

Other Definitions

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceu-* tical Sciences (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

The term "prodrugs" refer to compounds, including derivatives of the compounds of any one of Formulae (I-A), (I-B), and (I-C), which have cleavable groups and become by solvolysis or under physiological conditions the compounds of any one of Formulae (I-A), (I-B), and (I-C), which are pharmaceutically active in vivo. Such examples include, but are not limited to, ester derivatives and the like. Other derivatives of the compounds of the invention have activity in both their acid and acid derivative forms, but in the acid sensitive form often offers advantages of solubility, tissue compatibility, and/or delayed release in the mammalian organism (see, Bundgard, H., *Design of Prodrugs*, pp. 7-9, 21-24, Elsevier, Amsterdam 1985). Prodrugs include acid derivatives well known to those skilled in the art, such as esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of the invention are exemplary prodrugs. In certain embodiments, the prodrug is an ester type prodrug. In certain embodiments, the prodrug is an ester type prodrug including one cleavable ester group. In certain embodiments, the prodrug is an ester type prodrug including two cleavable ester groups. In certain embodiments, the prodrug is a double ester type prodrug, such as an (acyloxy)alkyl ester or ((alkoxycarbonyl)oxy)alkyl ester. In certain embodiments, the prodrug is a $C_{1-8}$ alkyl ester, $C_{2-8}$ alkenyl ester, $C_{2-8}$ alkynyl ester, aryl ester, $C_{7-12}$ substituted aryl ester, or $C_{7-12}$ arylalkyl ester of a compound of Formula (I-A), (I-B), or (I-C).

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the animal is a mammal. The animal may be a male or female at any stage of development. An animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, i.e., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of a therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

"Myc" refers to a family of genes and corresponding polypeptides. Myc is a regulator gene that encodes a transcription factor. Myc proteins are most closely homologous at the MB1 and MB2 regions in the N-terminal region and at the basic helix-loop-helix leucine zipper (bHLHLZ) motif in the C-terminal region (Osier et al. (2002) *Adv Cancer Res* 84:81-154; Grandori et al. (2000) *Annu Rev Cell Dev Biol* 16:653-699. In the human genome, Myc is located on chromosome 8 and is believed to regulate expression of 15% of all gene through binding Enhancer Box sequences (E-boxes) and recruiting histone acetyltransferases (HATs). Myc protein, through its bHLH domain binds DNA, while the leucine zipper domain allows the dimerization with its partner, myc-associated factor X (Max), another bHLH transcription factor. The transcriptionally active Max/Myc dimer promotes cell proliferation as well as apoptosis. Examples of Myc activated target genes include, but are not limited to, cyclin D2, and CDK4 which are important for cycle progression, the translation initiation factors eIF4 and eIF2, that are important for cell growth, as well as ornithine decarboxylase, and carbamyl-phosphate synthase enzymes required for polyamine and pyrimidine biosynthesis respectively.

The Myc family encompasses Myc proteins having Myc transcriptional activity, including but not limited to, c-Myc (GenBank Accession No P01106), N-Myc (GenBank Accession No P04198), L-Myc (GenBank Accession No. CAA30249), S-Myc (GenBank Accession No. BAA37155) and B-Myc (GenBank Accession No. NP_075815). The term "Myc" also refers to nucleic acid sequences encoding any Myc protein having Myc activity. The term "Myc" is also meant to include Myc homologous proteins, variants, and mutants.

A "variant" of a polypeptide or protein is any analogue, fragment, derivative or mutant which is derived from a Myc polypeptide or protein and which retains Myc activity. Different variants of the Myc protein may exist in nature. These variants may be allelic variations characterized by differences in the nucleotide sequences of the structural gene coding for the protein, or may involve differential splicing or post translational modification. The skilled artisan can produce variants having single or multiple amino acid substitutions, deletions, additions, or replacements. These variants may include, inter alia: (a) variants in which one or more amino acid residues are substituted with conservative or non-conservative amino acids; (b) variants in which one or more amino acids are added to the polypeptide or protein; (c) variants in which one or more of the amino acids includes a substituent group; and (d) variants in which the polypeptide or protein is fused with another polypeptide. The techniques for obtaining these variants, including genetic (suppressions, deletions, mutations), chemical and enzymatic techniques are known to persons having ordinary skill in the art. If such allelic variations, analogues, fragments, derivatives, mutants and modifications, including alternative mRNA splicing forms and alternative post translationally modified forms result in derivatives of the polypeptide which retain any of the biological properties of the polypeptide they are intended to be included within the scope of this invention In some embodiments, the variant has an amino acid that is at least 70%, 80%, 90%, 95%, 99% identical to known Myc protein sequences.

The term "nucleic acid" refers to a polynucleotide wherein said polynucleotide comprises a binding site for the Myc/Max heterodimer. In some embodiments, the nucleic acid comprises Enhancer box (E-box) sequences. In some embodiments, the sequence of the E-box element is CANNTG, wherein N is independently G, A, T, or C. In certain embodiments, the sequence of the E-box element is the palindromic canonical sequence CACGTG. The terms "polynucleotides" and "oligonucleotides" are used interchangeably and refer to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages). Oligonucleotides are generally single stranded nucleic acid polymers, while polynucleotides may be either double stranded DNAs, including annealed oligonucleotides wherein the second strand is an oligonucleotide with the reverse complement sequence of the first oligonucleotide, single stranded nucleic acid polymers comprising deoxythymidine, single stranded RNAs or RNA/DNA heteroduplexes.

BRIEF DESCRIPTION OF THE DRAWINGS

FIG. 2 (right) shows a Z-prime analysis for assay robustness. This assay has a 0.82 Z-prime, indicating a highly robust assay. The assay was performed in 16-plicate using a positive control compound (Positive). Leaving c-Myc out of the reaction (No Myc) also reduces signal, indicating c-Myc-dependent signal.

FIG. 7 (top panel) describes how 64 induces the expression of three differentiation markers (CD14, CD11c, and CCL4) as measured by qRT-PCR. FIG. 7 (bottom panel) describes how FACS analysis revealed that HL-60 cells express the differentiation marker CD11c following 64 treatment for 4 days.

DETAILED DESCRIPTION OF CERTAIN EMBODIMENTS

Figure 1:
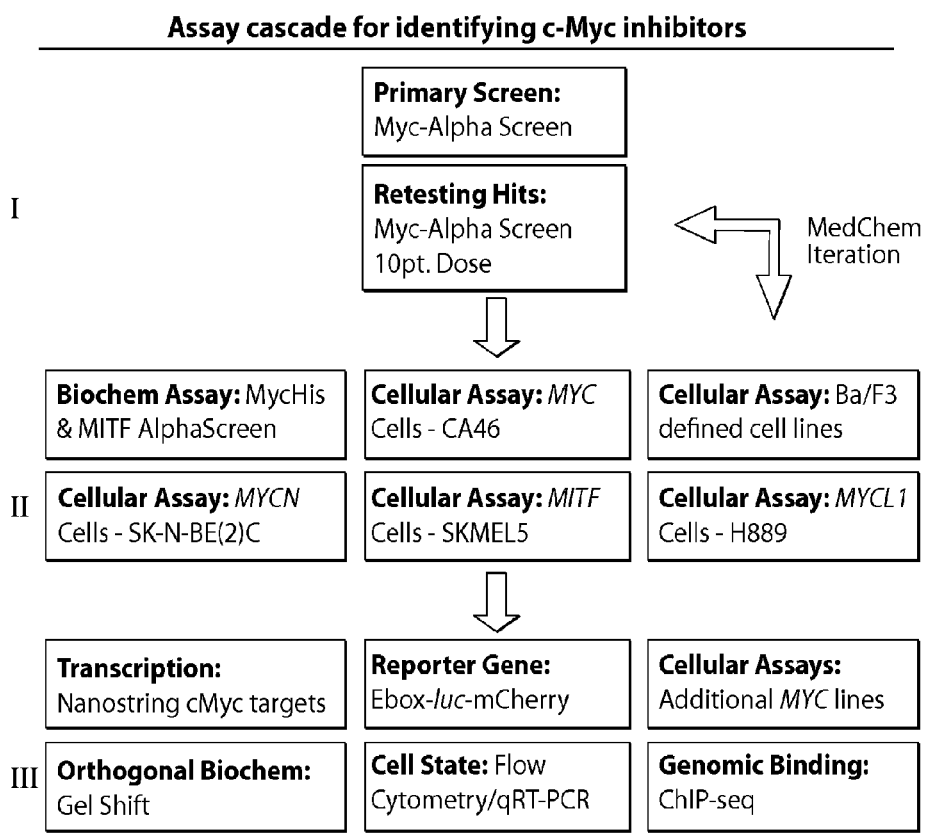
FIG. 1 depicts the an approach for the identification of inhibitors of c-Myc dimerization with Max and subsequent DNA binding. However, this approach can be adapted more broadly, for example, to any transcription factors relying on dimerization and DNA binding for function, factors that interact with signaling components, or factors that interact with cofactors to regulate transcriptional output.

The present disclosure provides systems and methods for identifying inhibitors of Myc as well as compounds which are useful for inhibiting Myc, e.g., c-Myc, 1-Myc, or n-Myc. In some embodiments, the provided compounds inhibit c-Myc. The present disclosure further provides pharmaceutical compositions of compounds described herein and methods of using compounds described herein. In certain embodiments, a provided compound is used to prevent and/or treat a Myc-mediated disorder or a condition associated with aberrant Myc activity (e.g., a proliferative disease) in a subject.

Compounds

As generally described above, provided herein are compounds useful as Myc inhibitors, e.g., c-Myc inhibitors. In one aspect, the present invention provides a compound of Formula (I-A), (I-B), or (I-C):

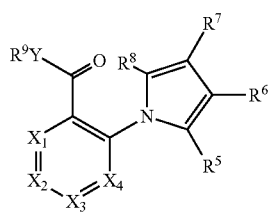

I-A

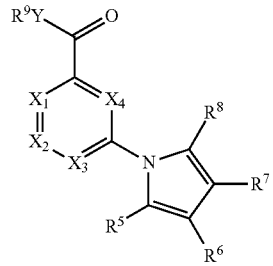

I-B

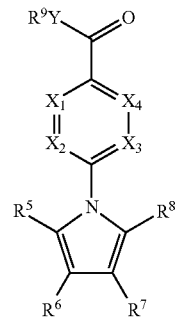

I-C or a pharmaceutically acceptable salt thereof, wherein:

$X_1$ is $CR^1$ or N;
$X_2$ is $CR^2$ or N;
$X_3$ is $CR^3$ or N;
$X_4$ is $CR^4$ or N;
wherein no more than three of $X_1$, $X_2$, $X_3$, and $X_4$ are N;
Y is —O— or —S(=O)$_2$—N($R^N$)—;
$R^1$, $R^2$, $R^3$, and $R^4$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^B$ groups are taken together with their intervening atoms to form an optionally substituted heterocyclic ring;

$R^5$, $R^6$, $R^7$, and $R^8$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or R$^5$ and R$^6$ are taken together with their intervening atoms to form an optionally substituted, fused, partially unsaturated or aromatic ring having 0-3 heteroatoms independently selected from nitrogen, oxygen, and sulfur; or R$^6$ and R$^7$ are taken together with their intervening atoms to form an optionally substituted, fused, partially unsaturated or aromatic ring having 0-3 heteroatoms independently selected from nitrogen, oxygen, and sulfur; or R$^7$ and R$^8$ are taken together with their intervening atoms to form an optionally substituted, fused, partially unsaturated or aromatic ring having 0-3 heteroatoms independently selected from nitrogen, oxygen, and sulfur;

R$^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;

R$^N$ is hydrogen, optionally substituted alkyl, or a nitrogen protecting group;

each L is independently a bond, —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, an optionally substituted phenylene, or an optionally substituted, straight or branched, C$_{1-6}$ alkylene, C$_{2-6}$ alkenylene, or C$_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, or an optionally substituted phenylene;

each R is independently hydrogen, optionally substituted C$_{1-6}$ alkyl, optionally substituted C$_{2-6}$ alkenyl, or optionally substituted C$_{2-6}$ alkynyl, or R and an optional substituent on Cy are taken together with their intervening atoms to form a 5-6 membered heterocyclic fused ring;

each R' is independently hydrogen, optionally substituted alkyl, optionally substituted alkenyl, optionally substituted alkynyl, or an optionally substituted, monocyclic or bicyclic, saturated, partially unsaturated, or aromatic ring having 0-4 heteroatoms independently selected from nitrogen, oxygen, and sulfur, or R' and an optional substituent on Cy are taken together with their intervening atoms to form a 5-6 membered carbocyclic or heterocyclic fused ring;

each Z is independently optionally substituted alkyl, optionally substituted alkenyl, optionally substituted alkynyl, or Cy; and each Cy is independently an optionally substituted, monocyclic or bicyclic, saturated, partially unsaturated, or aromatic ring having 0-4 heteroatoms independently selected from nitrogen, oxygen, and sulfur;

wherein at least one of R$^1$, R$^2$, R$^3$, R$^4$, R$^5$, R$^6$, R$^7$, and R$^8$ is -L-Z.

In certain embodiments, a provided compound is of Formula (I-a), (I-b), or (I-c):

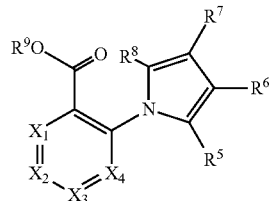

I-a

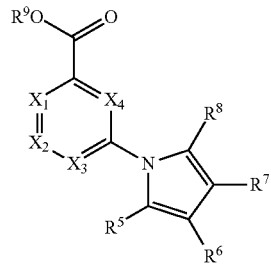

I-b

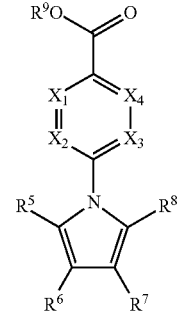

I-c or a pharmaceutically acceptable salt thereof, wherein:
X$_1$ is CR$^1$ or N;
X$_2$ is CR$^2$ or N;
X$_3$ is CR$^3$ or N;
X$_4$ is CR$^4$ or N;
wherein no more than three of X$_1$, X$_2$, X$_3$, and X$_4$ are N;
R$^1$, R$^2$, R$^3$, and R$^4$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^B$ groups are taken together with their intervening atoms to form an optionally substituted heterocyclic ring;

R$^5$, R$^6$, R$^7$, and R$^8$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O) SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or R$^5$ and R$^6$ are taken together with their intervening atoms to form an optionally substituted, fused, partially unsaturated or aromatic ring having 0-3 heteroatoms independently selected from nitrogen, oxygen, and sulfur; or R$^6$ and R$^7$ are taken together with their intervening atoms to form an optionally substituted, fused, partially unsaturated or aromatic ring having 0-3 heteroatoms independently selected from nitrogen, oxygen, and sulfur; or R$^7$ and R$^8$ are taken together with their intervening atoms to form an optionally substituted, fused, partially unsaturated or aromatic ring having 0-3 heteroatoms independently selected from nitrogen, oxygen, and sulfur;

R$^9$ is hydrogen, optionally substituted alkyl, optionally substituted alkenyl, optionally substituted alkynyl, or an oxygen protecting group;

each L is independently a bond, —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, an optionally substituted phenylene, or an optionally substituted, straight or branched, C$_{1-6}$ alkylene, C$_{2-6}$ alkenylene, or C$_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, or an optionally substituted phenylene;

each R is independently hydrogen, optionally substituted C$_{1-6}$ alkyl, optionally substituted C$_{2-6}$ alkenyl, or optionally substituted C$_{2-6}$ alkynyl, or R and an optional substituent on Cy are taken together with their intervening atoms to form a 5-6 membered heterocyclic fused ring;

each R' is independently hydrogen, optionally substituted alkyl, optionally substituted alkenyl, optionally substituted alkynyl, or an optionally substituted, monocyclic or bicyclic, saturated, partially unsaturated, or aromatic ring having 0-4 heteroatoms independently selected from nitrogen, oxygen, and sulfur, or R' and an optional substituent on Cy are taken together with their intervening atoms to form a 5-6 membered carbocyclic or heterocyclic fused ring;

each Z is independently optionally substituted alkyl, optionally substituted alkenyl, optionally substituted alkynyl, or Cy; and each Cy is independently an optionally substituted, monocyclic or bicyclic, saturated, partially unsaturated, or aromatic ring having 0-4 heteroatoms independently selected from nitrogen, oxygen, and sulfur;

wherein at least one of R$^1$, R$^2$, R$^3$, R$^4$, R$^5$, R$^6$, R$^7$, and R$^8$ is -L-Z.

In certain embodiments, a provided compound is of Formula (I-a):

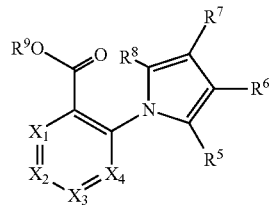

I-a or a pharmaceutically acceptable salt thereof, wherein X$_1$, X$_2$, X$_3$, X$_4$, R$^5$, R$^6$, R$^7$, R$^8$, and R$^9$ are as described herein.

In certain embodiments, a provided compound is of the formula:

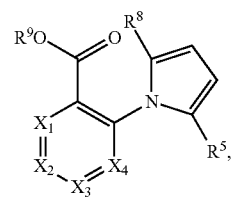

or a pharmaceutically acceptable salt thereof, wherein R$^9$ is hydrogen or optionally substituted alkyl.

In certain embodiments, a provided compound is of the formula:

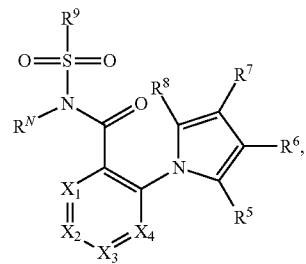

or a pharmaceutically acceptable salt thereof.

In certain embodiments, a provided compound is of the formula:

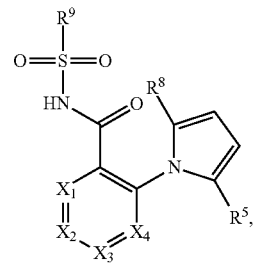

or a pharmaceutically acceptable salt thereof.

In some embodiments, Z is Cy. In some embodiments, Cy is an optionally substituted, monocyclic or bicyclic, or aromatic ring having 0-4 heteroatoms independently selected from nitrogen, oxygen, and sulfur. In certain embodiments, Cy is an optionally substituted, monocyclic or bicyclic heterocyclic ring, wherein 1, 2, 3, or 4 atoms in the heterocyclic ring system are independently selected from the group consisting of nitrogen, oxygen, and sulfur. In certain embodiments, Cy is an optionally substituted, 3- to 7-membered, monocyclic heterocyclic ring, wherein 1, 2, or 3 atoms in the heterocyclic ring system are independently selected from the group consisting of nitrogen, oxygen, and sulfur.

In certain embodiments, a provided compound is of Formula (II-A):

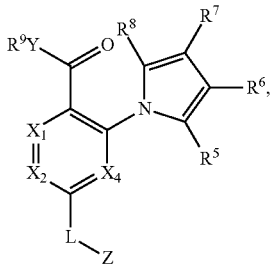

II-A or a pharmaceutically acceptable salt thereof. In some embodiments, for a compound of Formula (II-A), $R^1$, $R^2$, $R^4$, $R^5$, $R^6$, $R^7$, and $R^8$ are not -L-Z.

In certain embodiments, a provided compound is of Formula (II-a):

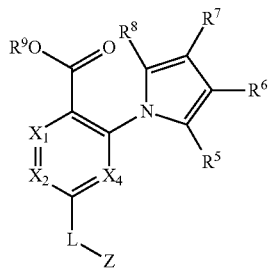

II-a or a pharmaceutically acceptable salt thereof, wherein $X_1$, $X_2$, $X_4$, $R^5$, $R^6$, $R^7$, $R^8$, and $R^9$ are as described herein. In some embodiments, for a compound of Formula (II-a), $R^1$, $R^2$, $R^4$, $R^5$, $R^6$, $R^7$, and $R^8$ are not -L-Z.

In certain embodiments, for a compound of Formula (II-A), Z is Cy to give a compound of Formula (II-A-i):

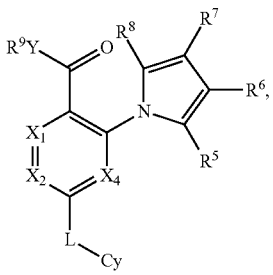

II-A-i or a pharmaceutically acceptable salt thereof. In some embodiments, for a compound of Formula (II-A-i), $R^1$, $R^2$, $R^4$, $R^5$, $R^6$, $R^7$, and $R^8$ are not -L-Cy.

In certain embodiments, for a compound of Formula (II-a), Z is Cy to give a compound of Formula (II-a-i):

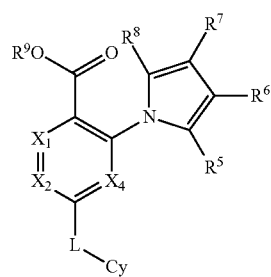

II-a-i or a pharmaceutically acceptable salt thereof. In some embodiments, for a compound of Formula (II-a-i), $R^1$, $R^2$, $R^4$, $R^5$, $R^6$, $R^7$, and $R^8$ are not -L-Cy.

In certain embodiments, a provided compound is of Formula (II-B):

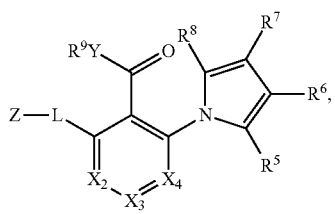

II-B or a pharmaceutically acceptable salt thereof. In some embodiments, for a compound of Formula (II-B), $R^2$, $R^3$, $R^4$, $R^5$, $R^6$, $R^7$, and $R^8$ are not -L-Z.

In certain embodiments, a provided compound is of Formula (II-b):

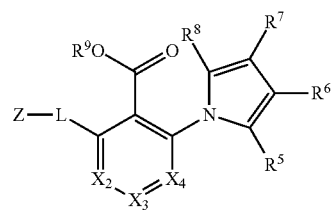

II-b or a pharmaceutically acceptable salt thereof, wherein $X_2$, $X_3$, $X_4$, $R^5$, $R^6$, $R^7$, $R^8$, and $R^9$ are as described herein. In some embodiments, for a compound of Formula (II-b), $R^2$, $R^3$, $R^4$, $R^5$, $R^6$, $R^7$, and $R^8$ are not -L-Z.

In certain embodiments, for a compound of Formula (II-B), Z is Cy to give a compound of Formula (II-B-i):

II-B-i

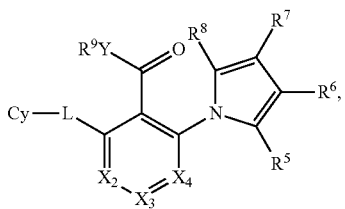

or a pharmaceutically acceptable salt thereof. In some embodiments, for a compound of Formula (II-B-i), $R^2$, $R^3$, $R^4$, $R^5$, $R^6$, $R^7$, and $R^8$ are not -L-Cy.

In certain embodiments, for a compound of Formula (II-b), Z is Cy to give a compound of Formula (II-b-i):

II-b-i

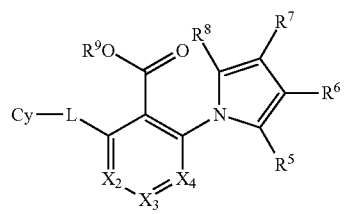

or a pharmaceutically acceptable salt thereof. In some embodiments, for a compound of Formula (II-b-i), $R^2$, $R^3$, $R^4$, $R^5$, $R^6$, $R^7$, and $R^8$ are not -L-Cy.

In certain embodiments, a provided compound is of Formula (II-C):

II-C

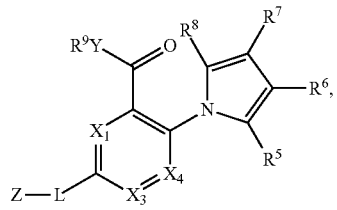

or a pharmaceutically acceptable salt thereof. In some embodiments, for a compound of Formula (II-C), $R^1$, $R^3$, $R^4$, $R^5$, $R^6$, $R^7$, and $R^8$ are not -L-Z.

In certain embodiments, a provided compound is of Formula (II-c):

II-c

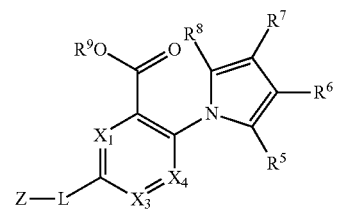

or a pharmaceutically acceptable salt thereof, wherein $X_1$, $X_3$, $X_4$, $R^5$, $R^6$, $R^7$, $R^8$, and $R^9$ are as described herein. In some embodiments, for a compound of Formula (II-c), $R^1$, $R^3$, $R^4$, $R^5$, $R^6$, $R^7$, and $R^8$ are not -L-Z.

In certain embodiments, for a compound of Formula (II-C), Z is Cy to give a compound of Formula (II-C-i):

II-C-i

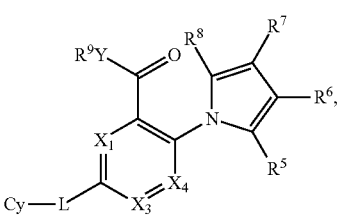

or a pharmaceutically acceptable salt thereof. In some embodiments, for a compound of Formula (II-C-i), $R^1$, $R^3$, $R^4$, $R^5$, $R^6$, $R^7$, and $R^8$ are not -L-Cy.

In certain embodiments, for a compound of Formula (II-c), Z is Cy to give a compound of Formula (II-c-i):

II-c-i

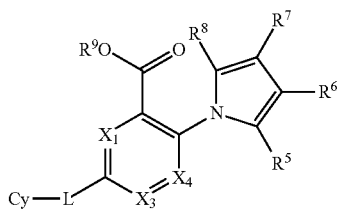

or a pharmaceutically acceptable salt thereof. In some embodiments, for a compound of Formula (II-c-i), $R^1$, $R^3$, $R^4$, $R^5$, $R^6$, $R^7$, and $R^8$ are not -L-Cy.

In certain embodiments, a provided compound is of Formula (II-D):

II-D

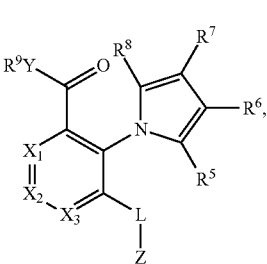

or a pharmaceutically acceptable salt thereof. In some embodiments, for a compound of Formula (II-D), $R^1$, $R^2$, $R^3$, $R^5$, $R^6$, $R^7$, and $R^8$ are not -L-Z.

In certain embodiments, a provided compound is of Formula (II-d):

II-d

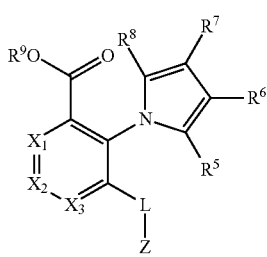

or a pharmaceutically acceptable salt thereof, wherein $X_1$, $X_2$, $X_3$, $R^5$, $R^6$, $R^7$, $R^8$, and $R^9$ are as described herein. In some embodiments, for a compound of Formula (II-d), $R^1$, $R^2$, $R^3$, $R^5$, $R^6$, $R^7$, and $R^8$ are not -L-Z.

In certain embodiments, for a compound of Formula (II-D), Z is Cy to give a compound of Formula (II-D-i):

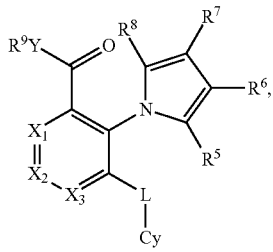

II-D-i or a pharmaceutically acceptable salt thereof. In some embodiments, for a compound of Formula (II-D-i), $R^1$, $R^2$, $R^3$, $R^5$, $R^6$, $R^7$, and $R^8$ are not -L-Cy.

In certain embodiments, for a compound of Formula (II-d), Z is Cy to give a compound of Formula (II-d-i):

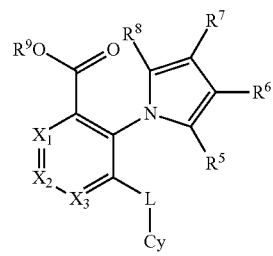

II-d-i or a pharmaceutically acceptable salt thereof. In some embodiments, for a compound of Formula (II-d-i), $R^1$, $R^2$, $R^3$, $R^5$, $R^6$, $R^7$, and $R^8$ are not -L-Cy.

In certain embodiments, a provided compound is of Formula (III-A):

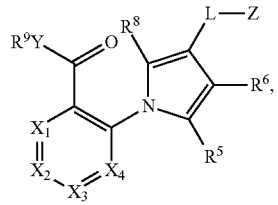

III-A or a pharmaceutically acceptable salt thereof. In some embodiments, for a compound of Formula (III-A), $R^1$, $R^2$, $R^3$, $R^4$, $R^5$, $R^6$, and $R^8$ are not -L-Z.

In certain embodiments, a provided compound is of Formula (III-a):

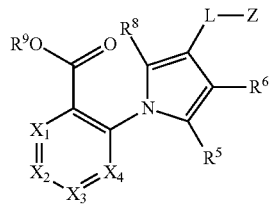

III-a or a pharmaceutically acceptable salt thereof, wherein $X_1$, $X_2$, $X_3$, $X_4$, $R^5$, $R^6$, $R^8$, and $R^9$ are as described herein. In some embodiments, for a compound of Formula (III-a), $R^1$, $R^2$, $R^3$, $R^4$, $R^5$, $R^6$, and $R^8$ are not -L-Z.

In certain embodiments, for a compound of Formula (III-A), Z is Cy to give a compound of Formula (III-A-i):

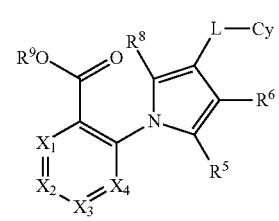

III-A-i or a pharmaceutically acceptable salt thereof. In some embodiments, for a compound of Formula (III-A-i), $R^1$, $R^2$, $R^3$, $R^4$, $R^5$, $R^6$, and $R^8$ are not -L-Cy.

In certain embodiments, for a compound of Formula (III-a), Z is Cy to give a compound of Formula (III-a-i):

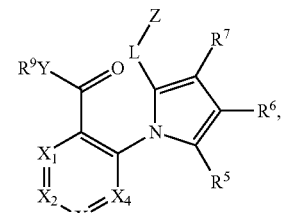

III-a-i or a pharmaceutically acceptable salt thereof. In some embodiments, for a compound of Formula (III-a-i), $R^1$, $R^2$, $R^3$, $R^4$, $R^5$, $R^6$, and $R^8$ are not -L-Cy.

In certain embodiments, a provided compound is of Formula (III-B):

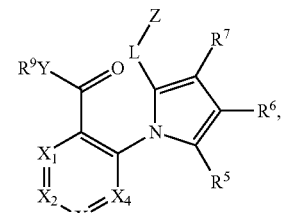

III-B or a pharmaceutically acceptable salt thereof. In some embodiments, for a compound of Formula (III-B), $R^1$, $R^2$, $R^3$, $R^4$, $R^5$, $R^6$, and $R^7$ are not -L-Z.

In certain embodiments, a provided compound is of Formula (III-b):

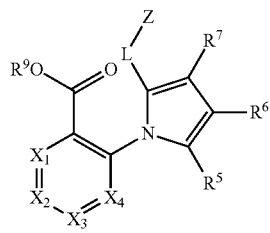

III-b or a pharmaceutically acceptable salt thereof, wherein $X_1$, $X_2$, $X_3$, $X_4$, $R^5$, $R^6$, $R^7$, and $R^9$ are as described herein. In some embodiments, for a compound of Formula (III-b), $R^1$, $R^2$, $R^3$, $R^4$, $R^5$, $R^6$, and $R^7$ are not -L-Z.

In certain embodiments, for a compound of Formula (III-B), Z is Cy to give a compound of Formula (III-B-i):

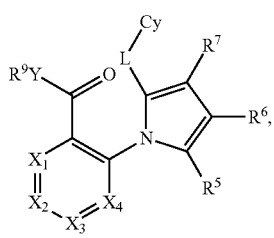

III-B-i or a pharmaceutically acceptable salt thereof. In some embodiments, for a compound of Formula (III-B-i), $R^1$, $R^2$, $R^3$, $R^4$, $R^5$, $R^6$, and $R^7$ are not -L-Cy.

In certain embodiments, for a compound of Formula (III-b), Z is Cy to give a compound of Formula (III-b-i):

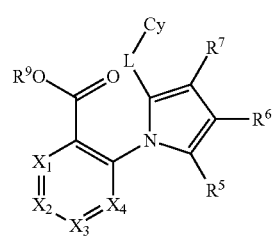

III-b-i or a pharmaceutically acceptable salt thereof. In some embodiments, for a compound of Formula (III-b-i), $R^1$, $R^2$, $R^3$, $R^4$, $R^5$, $R^6$, and $R^7$ are not -L-Cy.

In certain embodiments, a provided compound is of Formula (IV'):

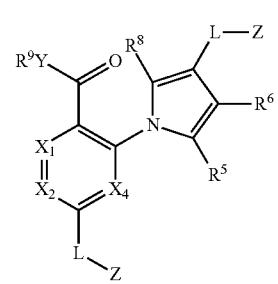

IV' or a pharmaceutically acceptable salt thereof. In some embodiments, for a compound of Formula (IV'), $R^1$, $R^2$, $R^4$, $R^5$, and $R^6$ are not -L-Z.

In certain embodiments, a provided compound is of Formula (IV):

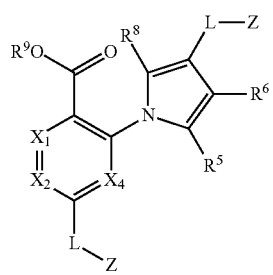

IV or a pharmaceutically acceptable salt thereof, wherein $X_1$, $X_2$, $X_4$, $R^5$, $R^6$, $R^8$, and $R^9$ are as described herein. In some embodiments, for a compound of Formula (IV), $R^1$, $R^2$, $R^4$, $R^5$, and $R^6$ are not -L-Z.

In certain embodiments, for a compound of Formula (IV'), Z is Cy to give a compound of Formula (IV-A):

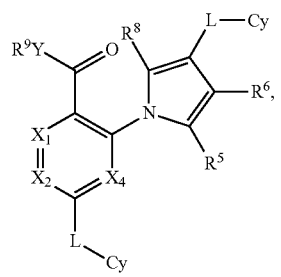

IV-A or a pharmaceutically acceptable salt thereof. In some embodiments, for a compound of Formula (IV-A), $R^1$, $R^2$, $R^3$, $R^4$, $R^5$, $R^6$, and $R^7$ are not -L-Cy.

In certain embodiments, for a compound of Formula (IV), Z is Cy to give a compound of Formula (IV-a):

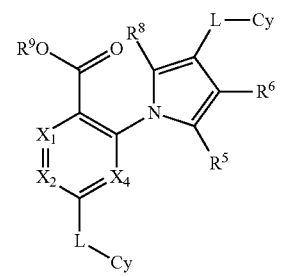

IV-a or a pharmaceutically acceptable salt thereof. In some embodiments, for a compound of Formula (IV-a), $R^1$, $R^2$, $R^3$, $R^4$, $R^5$, $R^6$, and $R^7$ are not -L-Cy.

In certain embodiments, a provided compound is of Formula (V-A), (V-B), (V-C), (V-D), (V-E), or (V-F):

In certain embodiments, a provided compound is of Formula (V-a), (V-b), (V-c), (V-d), (V-e), or (V-f):

V-A
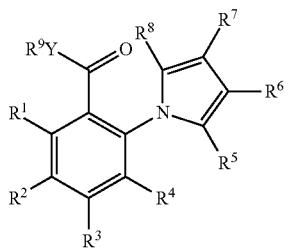

V-a
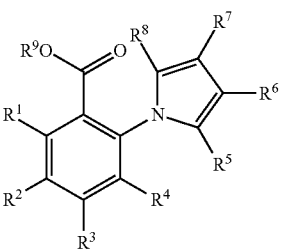

V-B
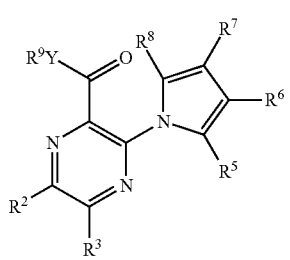

V-b
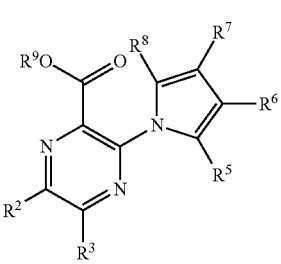

V-C
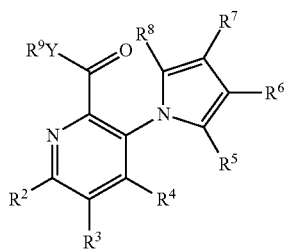

V-c
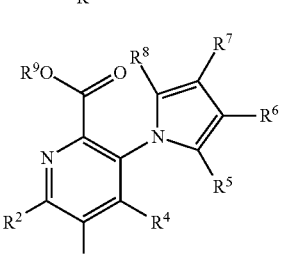

V-D
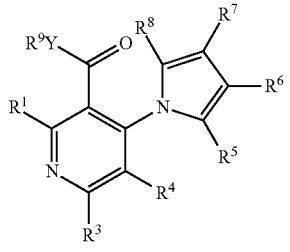

V-d
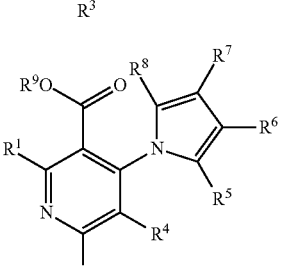

V-E
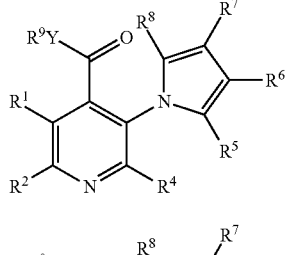

V-e
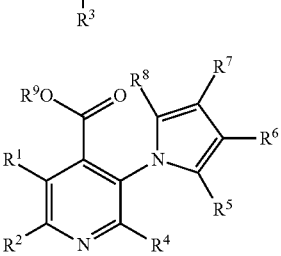

V-F
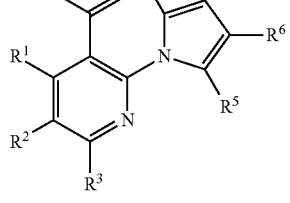

V-f
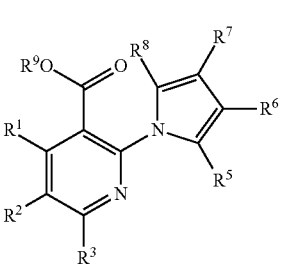

or a pharmaceutically acceptable salt thereof. In some embodiments, for a compound of Formula (V-A), (V-B), (V-C), (V-D), or (V-F), $R^3$ is -L-Z or -L-Cy. In some embodiments, for a compound of Formula (V-A), (V-B), (V-C), (V-D), (V-E), or (V-F), $R^7$ is -L-Z or -L-Cy.

or a pharmaceutically acceptable salt thereof, wherein $R^1$, $R^2$, $R^3$, $R^4$, $R^5$, $R^6$, $R^7$, $R^8$, and $R^9$ are as described herein. In some embodiments, for a compound of Formula (V-a), (V-b), (V-c), (V-d), or (V-f), R³ is -L-Z or -L-Cy. In some embodiments, for a compound of Formula (V-a), (V-b), (V-c), (V-d), (V-e), or (V-f), R⁷ is -L-Z or -L-Cy.

In certain embodiments, a provided compound is of Formula (VI-A), (VI-B), (VI-C), (VI-D), (VI-E), or (VI-F):

VI-A
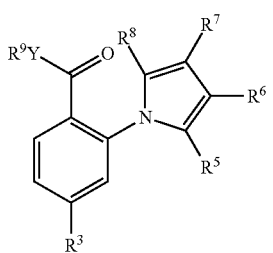

VI-B
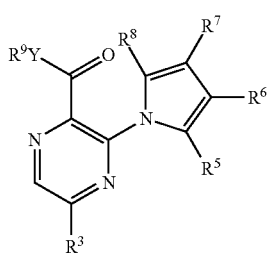

VI-C
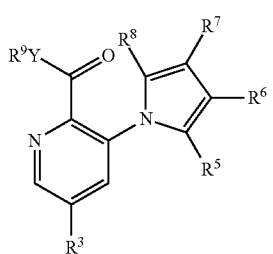

VI-D
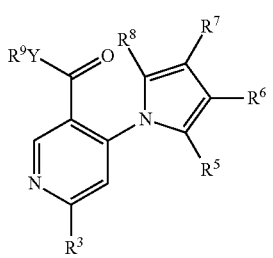

VI-E
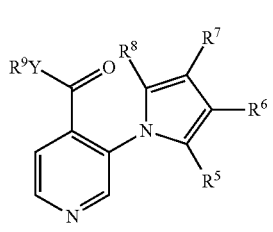

VI-F
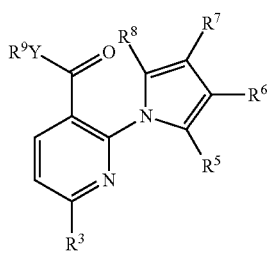

or a pharmaceutically acceptable salt thereof. In some embodiments, for a compound of Formula (VI-A), (VI-B), (VI-C), (VI-D), or (VI-F), R³ is -L-Z or -L-Cy. In some embodiments, for a compound of Formula (VI-A), (VI-B), (VI-C), (VI-D), (VI-E), or (VI-F), R⁷ is -L-Z or -L-Cy.

In certain embodiments, a provided compound is of Formula (VI-a), (VI-b), (VI-c), (VI-d), (VI-e), or (VI-f):

VI-a
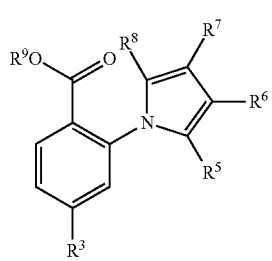

VI-b
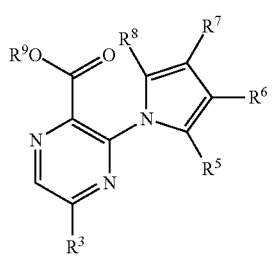

VI-c
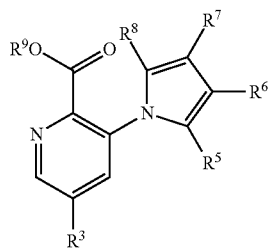

VI-d
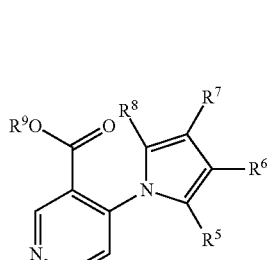

-continued (VI-e)

(VI-f)

or a pharmaceutically acceptable salt thereof, wherein $R^3$, $R^5$, $R^6$, $R^7$, $R^8$, and $R^9$ are as described herein. In some embodiments, for a compound of Formula (VI-a), (VI-b), (VI-c), (VI-d), or (VI-f), $R^3$ is -L-Z or -L-Cy. In some embodiments, for a compound of Formula (VI-a), (VI-b), (VI-c), (VI-d), (VI-e), or (VI-f), $R^7$ is -L-Z or -L-Cy.

As defined generally above, $X_1$ is $CR^1$ or N. In some embodiments, $X_1$ is $CR^1$. In some embodiments, $X_1$ is CH. In some embodiments, $X_1$ is N.

As defined generally above, $X_2$ is $CR^1$ or N. In some embodiments, $X_2$ is $CR^1$. In some embodiments, $X_2$ is CH. In some embodiments, $X_2$ is N.

As defined generally above, $X_3$ is $CR^1$ or N. In some embodiments, $X_3$ is $CR^1$. In some embodiments, $X_3$ is CH. In some embodiments, $X_3$ is N.

As defined generally above, $X_4$ is $CR^1$ or N. In some embodiments, $X_4$ is $CR^1$. In some embodiments, $X_4$ is CH. In some embodiments, $X_4$ is N.

As defined generally above, Y is —O— or —S(=O)$_2$—N($R^N$)—. In certain embodiments, Y is —O—. In certain embodiments, Y is —S(=O)$_2$—N($R^N$)—. When Y is —S(=O)$_2$—N($R^N$)—, the sulfur atom of Y is directly attached to $R^9$. In certain embodiments, Y is —S(=O)$_2$—N($R^N$)—, wherein $R^N$ is hydrogen, optionally substituted $C_{1-6}$ alkyl, or a nitrogen protecting group. In certain embodiments, Y is —S(=O)$_2$—N($R^N$)—, wherein $R^N$ is hydrogen, unsubstituted $C_{1-6}$ alkyl, Bn, BOC, Cbz, Fmoc, trifluoroacetyl, triphenylmethyl, acetyl, or Ts. In certain embodiments, Y is —S(=O)$_2$—NH—.

As defined generally above, $R^1$, $R^2$, $R^3$, and $R^4$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; wherein $R^A$ and $R^B$ are as defined herein.

In some embodiments, $R^1$ is -L-Z. In some embodiments, $R^1$ is -L-Cy. In some embodiments, $R^1$ is hydrogen. In some embodiments, $R^1$ is halo. In some embodiments, $R^1$ is fluoro. In some embodiments, $R^1$ is chloro. In some embodiments, $R^1$ is bromo. In some embodiments, $R^1$ is optionally substituted alkyl, optionally substituted alkenyl, or optionally substituted alkynyl. In some embodiments, $R^1$ is optionally substituted carbocyclyl, optionally substituted aryl, optionally substituted heterocyclyl, or optionally substituted heteroaryl. In some embodiments, $R^1$ is —OR$^A$, —N(R$^B$)$_2$, or —SR$^A$. In certain embodiments, $R^1$ is —OR$^A$. In certain embodiments, $R^1$ is —OH. In certain embodiments, $R^1$ is —OCH$_3$. In some embodiments, $R^1$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, or —SO$_2$N(R$^B$)$_2$.

In some embodiments, $R^2$ is -L-Z. In some embodiments, $R^2$ is -L-Cy. In some embodiments, $R^2$ is hydrogen. In some embodiments, $R^2$ is halo. In some embodiments, $R^2$ is fluoro. In some embodiments, $R^2$ is chloro. In some embodiments, $R^2$ is bromo. In some embodiments, $R^2$ is optionally substituted alkyl, optionally substituted alkenyl, or optionally substituted alkynyl. In some embodiments, $R^2$ is optionally substituted carbocyclyl, optionally substituted aryl, optionally substituted heterocyclyl, or optionally substituted heteroaryl. In some embodiments, $R^2$ is —OR$^A$, —N(R$^B$)$_2$, or —SR$^A$. In certain embodiments, $R^2$ is —OR$^A$. In certain embodiments, $R^2$ is —OH. In certain embodiments, $R^2$ is —OCH$_3$. In some embodiments, $R^2$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, or —SO$_2$N(R$^B$)$_2$.

In some embodiments, $R^3$ is -L-Z. In some embodiments, $R^3$ is -L-Cy. In some embodiments, $R^3$ is hydrogen. In some embodiments, $R^3$ is halo. In some embodiments, $R^3$ is fluoro. In some embodiments, $R^3$ is chloro. In some embodiments, $R^3$ is bromo. In some embodiments, $R^3$ is optionally substituted alkyl, optionally substituted alkenyl, or optionally substituted alkynyl. In some embodiments, $R^3$ is optionally substituted carbocyclyl, optionally substituted aryl, optionally substituted heterocyclyl, or optionally substituted heteroaryl. In some embodiments, $R^3$ is —OR$^A$, —N(R$^B$)$_2$, or —SR$^A$. In certain embodiments, $R^3$ is —OR$^A$. In certain embodiments, $R^3$ is —OH. In certain embodiments, $R^3$ is —OCH$_3$. In some embodiments, $R^3$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, or —SO$_2$N(R$^B$)$_2$.

In some embodiments, $R^4$ is -L-Z. In some embodiments, $R^4$ is -L-Cy. In some embodiments, $R^4$ is hydrogen. In some embodiments, $R^4$ is halo. In some embodiments, $R^4$ is fluoro. In some embodiments, $R^4$ is chloro. In some embodiments, $R^4$ is bromo. In some embodiments, $R^4$ is optionally substituted alkyl, optionally substituted alkenyl, or optionally substituted alkynyl. In some embodiments, $R^4$ is optionally substituted carbocyclyl, optionally substituted aryl, optionally substituted heterocyclyl, or optionally substituted heteroaryl. In some embodiments, $R^4$ is —OR$^A$, —N(R$^B$)$_2$, or —SR$^A$. In certain embodiments, $R^4$ is —OR$^A$. In certain embodiments, $R^4$ is —OH. In certain embodiments, $R^4$ is —OCH$_3$. In some embodiments, $R^4$ is —C(=O)R$^A$, —C(=O)OR$^A$, —C(=O)SR$^A$, —C(=O)N(R$^B$)$_2$, —OC (=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, or —SO$_2$N(R$^B$)$_2$.

As defined generally above, R$^5$, R$^6$, R$^7$, and R$^8$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or R$^5$ and R$^6$ are taken together with their intervening atoms to form an optionally substituted, fused, partially unsaturated or aromatic ring having 0-3 heteroatoms independently selected from nitrogen, oxygen, and sulfur; or R$^6$ and R$^7$ are taken together with their intervening atoms to form an optionally substituted, fused, partially unsaturated or aromatic ring having 0-3 heteroatoms independently selected from nitrogen, oxygen, and sulfur; or R$^7$ and R$^8$ are taken together with their intervening atoms to form an optionally substituted, fused, partially unsaturated or aromatic ring having 0-3 heteroatoms independently selected from nitrogen, oxygen, and sulfur; wherein R$^A$ and R$^B$ are as defined herein.

In some embodiments, R$^5$ is -L-Z. In some embodiments, R$^5$ is -L-Cy. In some embodiments, R$^5$ is hydrogen. In some embodiments, R$^5$ is halo. In some embodiments, R$^5$ is —CN. In some embodiments, R$^5$ is optionally substituted alkyl, optionally substituted alkenyl, or optionally substituted alkynyl. In certain embodiments, R$^5$ is optionally substituted alkyl.

In certain embodiments, R$^5$ is optionally substituted C$_{1-6}$ alkyl. In certain embodiments, R$^5$ is unsubstituted alkyl. In certain embodiments, R$^5$ is unsubstituted C$_{1-6}$ alkyl. In certain embodiments, R$^5$ is methyl. In certain embodiments, R$^5$ is ethyl. In certain embodiments, R$^5$ is propyl. In certain embodiments, R$^5$ is butyl. In some embodiments, R$^5$ is optionally substituted carbocyclyl, optionally substituted aryl, optionally substituted heterocyclyl, or optionally substituted heteroaryl. In some embodiments, R$^5$ is —OR$^A$, —N(R$^B$)$_2$, or —SR$^A$. In some embodiments, R$^5$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, or —SO$_2$N(R$^B$)$_2$.

In some embodiments, R$^6$ is -L-Z. In some embodiments, R$^6$ is -L-Cy. In some embodiments, R$^6$ is hydrogen. In some embodiments, R$^6$ is halo. In some embodiments, R$^6$ is —CN. In some embodiments, R$^6$ is optionally substituted alkyl, optionally substituted alkenyl, or optionally substituted alkynyl. In certain embodiments, R$^6$ is optionally substituted alkyl.

In certain embodiments, R$^6$ is optionally substituted C$_{1-6}$ alkyl. In certain embodiments, R$^6$ is unsubstituted alkyl. In certain embodiments, R$^6$ is unsubstituted C$_{1-6}$ alkyl. In certain embodiments, R$^6$ is methyl. In certain embodiments, R$^6$ is ethyl. In certain embodiments, R$^6$ is propyl. In certain embodiments, R$^6$ is butyl. In some embodiments, R$^6$ is optionally substituted carbocyclyl, optionally substituted aryl, optionally substituted heterocyclyl, or optionally substituted heteroaryl. In some embodiments, R$^6$ is —OR$^A$, —N(R$^B$)$_2$, or —SR$^A$. In some embodiments, R$^6$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$ or —SO$_2$N(R$^B$)$_2$.

In some embodiments, R$^7$ is -L-Z. In some embodiments, R$^7$ is -L-Cy. In some embodiments, R$^7$ is hydrogen. In some embodiments, R$^7$ is halo. In some embodiments, R$^7$ is —CN. In some embodiments, R$^7$ is optionally substituted alkyl, optionally substituted alkenyl, or optionally substituted alkynyl. In certain embodiments, R$^6$ is optionally substituted alkyl. In certain embodiments, R$^6$ is optionally substituted C$_{1-6}$ alkyl. In certain embodiments, R$^6$ is unsubstituted alkyl. In certain embodiments, R$^6$ is unsubstituted C$_{1-6}$ alkyl. In certain embodiments, R$^6$ is methyl. In certain embodiments, R$^6$ is ethyl. In certain embodiments, R$^6$ is propyl. In certain embodiments, R$^6$ is butyl. In some embodiments, R$^7$ is optionally substituted carbocyclyl, optionally substituted aryl, optionally substituted heterocyclyl, or optionally substituted heteroaryl. In some embodiments, R$^7$ is —OR$^A$, —N(R$^B$)$_2$, or —SR$^A$. In some embodiments, R$^7$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$ or —SO$_2$N(R$^B$)$_2$.

In some embodiments, R$^8$ is -L-Z. In some embodiments, R$^8$ is -L-Cy. In some embodiments, R$^8$ is hydrogen. In some embodiments, R$^8$ is halo. In some embodiments, R$^8$ is —CN. In some embodiments, R$^8$ is optionally substituted alkyl, optionally substituted alkenyl, or optionally substituted alkynyl. In certain embodiments, R$^6$ is optionally substituted alkyl. In certain embodiments, R$^6$ is optionally substituted C$_{1-6}$ alkyl. In certain embodiments, R$^6$ is unsubstituted alkyl. In certain embodiments, R$^6$ is unsubstituted C$_{1-6}$ alkyl. In certain embodiments, R$^6$ is methyl. In certain embodiments, R$^6$ is ethyl. In certain embodiments, R$^6$ is propyl. In certain embodiments, R$^6$ is butyl. In some embodiments, R$^8$ is optionally substituted carbocyclyl, optionally substituted aryl, optionally substituted heterocyclyl, or optionally substituted heteroaryl. In some embodiments, R$^8$ is —OR$^A$, —N(R$^B$)$_2$, or —SR$^A$. In some embodiments, R$^8$ is —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$ or —SO$_2$N(R$^B$)$_2$.

In some embodiments, R$^5$, R$^6$, R$^7$, and R$^8$ are not substituted with a guanidinyl group.

In some embodiments, R$^5$ and R$^8$ are the same. In some embodiments, R$^5$ and R$^8$ are hydrogen. In some embodiments, R$^5$ and R$^8$ are methyl. In some embodiments, R$^5$, R$^6$, R$^7$, and R$^8$ are hydrogen. In some embodiments, R$^5$ and R$^8$ are methyl, and R$^6$ and R$^7$ are hydrogen. In some embodiments, R$^5$, R$^6$, and R$^8$ are hydrogen, and R$^7$ is -L-Z or -L-Cy. In some embodiments, R$^5$ and R$^8$ are methyl, R$^6$ is hydrogen, and R$^7$ is -L-Z or -L-Cy.

In some embodiments, R$^3$ and R$^7$ are -L-Z. In some embodiments, R$^3$ and R$^7$ are -L-Cy.

As defined generally above, R$^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom. In certain embodiments, $R^9$ is hydrogen. In certain embodiments, $R^9$ is optionally substituted alkyl, optionally substituted alkenyl, or optionally substituted alkynyl. In certain embodiments, $R^9$ is optionally substituted alkyl. In certain embodiments, $R^9$ is unsubstituted $C_{1-6}$ alkyl. In certain embodiments, $R^9$ is methyl or ethyl. In certain embodiments, $R^9$ is propyl. In certain embodiments, $R^9$ is isopropyl. In certain embodiments, $R^9$ is butyl. In certain embodiments, $R^9$ is pentyl. In certain embodiments, $R^9$ is hexyl. In certain embodiments, $R^9$ is acyloxymethyl. In certain embodiments, $R^9$ is acetoxymethyl. In certain embodiments, $R^9$ is optionally substituted carbocyclyl. In certain embodiments, $R^9$ is optionally substituted, 3- to 7-membered, monocyclic carbocyclyl including zero, one, or two double bonds in the carbocyclic ring system. In certain embodiments, $R^9$ is cyclopropyl. In certain embodiments, $R^9$ is cyclobutyl, cyclopentyl, cyclohexyl, or cycloheptyl. In certain embodiments, $R^9$ is optionally substituted, 5- to 13-membered, bicyclic carbocyclyl including zero, one, two, or three double bonds in the carbocyclic ring system. In certain embodiments, $R^9$ is optionally substituted heterocyclyl. In certain embodiments, $R^9$ is optionally substituted, 3- to 7-membered, monocyclic heterocyclyl including zero, one, or two double bonds in the heterocyclic ring system, wherein one, two, or three atoms in the heterocyclic ring system are independently selected from the group consisting of oxygen, nitrogen, and sulfur. In certain embodiments, $R^9$ is optionally substituted, 5- to 13-membered, bicyclic heterocyclyl including zero, one, two, or three double bonds in the heterocyclic ring system, wherein one, two, three, or four atoms in the heterocyclic ring system are independently selected from the group consisting of oxygen, nitrogen, and sulfur. In certain embodiments, $R^9$ is optionally substituted aryl. In certain embodiments, $R^9$ is optionally substituted, 6- to 14-membered aryl. In certain embodiments, $R^9$ is optionally substituted phenyl. In certain embodiments, $R^9$ is unsubstituted phenyl. In certain embodiments, $R^9$ is optionally substituted heteroaryl. In certain embodiments, $R^9$ is optionally substituted, 5- to 6-membered, monocyclic heteroaryl, wherein one, two, three, or four atoms in the heteroaryl ring system are independently selected from the group consisting of oxygen, nitrogen, and sulfur. In certain embodiments, $R^9$ is optionally substituted, 9- to 10-membered, bicyclic heteroaryl, wherein one, two, three, or four atoms in the heteroaryl ring system are independently selected from the group consisting of oxygen, nitrogen, and sulfur. In certain embodiments, $R^9$ is an oxygen protecting group when attached to an oxygen atom. In certain embodiments, $R^9$ is silyl, TBDPS, TBDMS, TIPS, TES, TMS, MOM, THP, t-Bu, Bn, allyl, acetyl, pivaloyl, or benzoyl when attached to an oxygen atom.

As defined generally above, $R^N$ is hydrogen, optionally substituted alkyl, or a nitrogen protecting group. In certain embodiments, $R^N$ is hydrogen. In certain embodiments, $R^N$ is optionally substituted alkyl. In certain embodiments, $R^N$ is optionally substituted $C_{1-6}$ alkyl. In certain embodiments, $R^N$ is unsubstituted $C_{1-6}$ alkyl. In certain embodiments, $R^N$ is methyl. In certain embodiments, $R^N$ is ethyl, propyl, butyl, pentyl, or hexyl. In certain embodiments, $R^N$ is a nitrogen protecting group. In certain embodiments, $R^N$ is Bn, BOC, Cbz, Fmoc, trifluoroacetyl, triphenylmethyl, acetyl, or Ts.

As defined generally above, each L is independently a bond, —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N═C(R')—, an optionally substituted 3-7 membered cycloalkylene, an optionally substituted 4-7 membered heterocyclylene, an optionally substituted 5-6 membered heteroarylene, an optionally substituted phenylene, or an optionally substituted, straight or branched, $C_{1-6}$ alkylene, $C_{2-6}$ alkenylene, or $C_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N═C(R')—, an optionally substituted 3-7 membered cycloalkylene, an optionally substituted 4-7 membered heterocyclylene, an optionally substituted 5-6 membered heteroarylene, or an optionally substituted phenylene; wherein R and R' are as defined herein.

In some embodiments, L is —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N═C(R')—, an optionally substituted 3-7 membered cycloalkylene, an optionally substituted 4-7 membered heterocyclylene, an optionally substituted 5-6 membered heteroarylene, an optionally substituted phenylene, or an optionally substituted, straight or branched, $C_{1-6}$ alkylene, $C_{2-6}$ alkenylene, or $C_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N═C(R')—, an optionally substituted 3-7 membered cycloalkylene, an optionally substituted 4-7 membered heterocyclylene, an optionally substituted 5-6 membered heteroarylene, or an optionally substituted phenylene.

In some embodiments, L is an optionally substituted, straight or branched, $C_{1-6}$ alkylene, $C_{2-6}$ alkenylene, or $C_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N═C(R')—, an optionally substituted 3-7 membered cycloalkylene, an optionally substituted 4-7 membered heterocyclylene, an optionally substituted 5-6 membered heteroarylene, or an optionally substituted phenylene.

In some embodiments, L is an optionally substituted, straight or branched, $C_3$-6 alkylene, alkenylene, or alkynylene chain wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N═C(R')—, an optionally substituted 3-7 membered cycloalkylene, an optionally substituted 4-7 membered heterocyclylene, an optionally substituted 5-6 membered heteroarylene, or an optionally substituted phenylene.

In some embodiments, L is at least 3 atoms long. One of ordinary skill in the art will understand the phrase "L is at least 3 atoms long" to mean that in certain embodiments L has at least 3 atoms in the main chain, that is, the shortest distance between two points of attachment. In some embodiments, L is at least 4 atoms long. In some embodiments, L is at least 5 atoms long. In some embodiments, L comprises at least one heteroatom in the main chain. In some embodiments, L comprises at least two heteroatoms in the main chain. In some embodiments, L comprises at least three heteroatoms in the main chain.

In certain embodiments, L is —C(O)N(R)N=C(R')—. In some embodiments, L is —C(O)NHN=C(R')—. In certain embodiments, R' is hydrogen. In certain embodiments, R' is optionally substituted aryl or optionally substituted heteroaryl. In certain embodiments, R' is bicyclic heteroaryl. In certain embodiments, R' is 1,8-naphthyridine.

In certain embodiments, L is —C(O)N(R)N(R)C(O)—. In certain embodiments, L is —C(O)NHNHC(O)—. In certain embodiments, L is —C(O)N(R)CH=CH—. In certain embodiments, L is an optionally substituted heteroarylene. In certain embodiments, L is unsubstituted heteroarylene. In certain embodiments, L is a triazole. In certain embodiments, L is 1,2,3-triazole. In certain embodiments, L is oxadiazole. In certain embodiments, L is —C(O)-piperdinyl-. In certain embodiments, L is —C(O)—. In certain embodiments, L is —C(O)N(R)—. In certain embodiments, L is —C(O)NH—. In certain embodiments, L is —C(O)NH-cyclopropyl-. In certain embodiments, L is —C(O)NH(C$_{1-6}$alkyl)-. In certain embodiments, L is —C(O)NHCH$_2$CH$_2$—. In certain embodiments, L is —C(O)NHNHC(O)NH—.

In certain embodiments, L is —C(O)N(R)N(R)C(O)—, and Z is Cy. In certain embodiments, L is —C(O)NHNHC(O)—, and Z is Cy. In certain embodiments, L is —C(O)N(R)CH=CH—, and Z is Cy. In certain embodiments, L is an optionally substituted heteroarylene, and Z is Cy. In certain embodiments, L is unsubstituted heteroarylene, and Z is Cy. In certain embodiments, L is a triazole, and Z is Cy. In certain embodiments, L is 1,2,3-triazole, and Z is Cy. In certain embodiments, L is oxadiazole, and Z is Cy. In certain embodiments, L is —C(O)-piperdinyl-, and Z is Cy. In certain embodiments, L is —C(O)—, and Z is Cy. In certain embodiments, L is —C(O)—, and Z is optionally substituted piperidine. In certain embodiments, L is —C(O)N(R)—, and Z is Cy. In certain embodiments, L is —C(O)NH—, and Z is Cy. In certain embodiments, L is —C(O)NH-cyclopropyl-, and Z is Cy. In certain embodiments, L is —C(O)NH(C$_{1-6}$alkyl)—, and Z is Cy. In certain embodiments, L is —C(O)NHCH$_2$CH$_2$—, and Z is Cy. In certain embodiments, L is —C(O)NHNHC(O)NH—, and Z is Cy.

In some embodiments, L is a bond. In some embodiments, L is not a bond.

In some embodiments, L is —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or —C(O)N(R)N=C(R')—. In some embodiments, L is not —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, or —C(O)N(R)N=C(R')—

As defined generally above, each Z is independently optionally substituted alkyl, optionally substituted alkenyl, optionally substituted alkynyl, or Cy. In certain embodiments, Z is Cy. In certain embodiments, Z is optionally substituted alkyl, optionally substituted alkenyl, or optionally substituted alkynyl.

As defined generally above, each Cy is independently an optionally substituted, monocyclic or bicyclic, saturated, partially unsaturated, or aromatic ring having 0-4 heteroatoms independently selected from nitrogen, oxygen, and sulfur. In certain embodiments, Cy is an optionally substituted, monocyclic or bicyclic heterocyclic ring, wherein 1, 2, 3, or 4 atoms in the heterocyclic ring system are independently selected from the group consisting of nitrogen, oxygen, and sulfur. When Cy is a heterocyclic ring, Cy may be saturated or partially unsaturated. In certain embodiments, when Cy is a heterocyclic ring, Cy includes 0, 1, 2, or 3 double bonds in the heterocyclic ring system. In certain embodiments, Cy is an optionally substituted, 3- to 7-membered, monocyclic heterocyclic ring, wherein 1, 2, or 3 atoms in the heterocyclic ring system are independently selected from the group consisting of nitrogen, oxygen, and sulfur. In certain embodiments, Cy is an optionally substituted, 5- to 13-membered, bicyclic heterocyclic ring, wherein 1, 2, 3, or 4 atoms in the heterocyclic ring system are independently selected from the group consisting of nitrogen, oxygen, and sulfur.

In some embodiments, Cy is optionally substituted aryl. In some embodiments, Cy is optionally substituted, 6- to 14-membered aryl. In some embodiments, Cy is optionally substituted phenyl. In some embodiments, Cy is substituted phenyl. In some embodiments, Cy is monosubstituted phenyl. In some embodiments, Cy is disubstituted phenyl. In some embodiments, Cy is trisubstituted phenyl. In certain embodiments, Cy is phenyl substituted with a carboxylic acid. In certain embodiments, Cy is m-carboxyphenyl. In certain embodiments, Cy is p-carboxyphenyl. In certain embodiments, Cy is unsubstituted phenyl. In certain embodiments, Cy is phenyl substituted with tetrazole. In certain embodiments, Cy is m-tetrazolylphenyl. In certain embodiments, Cy is p-tetrazolylphenyl. In certain embodiments, Cy is phenyl substituted with —SO$_3$H. In certain embodiments, Cy is m-sulfonylphenyl. In certain embodiments, Cy is p-sulfonylphenyl. In certain embodiments, Cy is phenyl substituted with one or more hydroxyl groups. In certain embodiments, Cy is phenyl is substituted with one hydroxyl group. In certain embodiments, Cy is phenyl is substituted with two hydroxyl groups. In certain embodiments, Cy is phenyl is substituted with three hydroxyl groups. In certain embodiments, Cy is phenyl substituted with one or more fluorines.

In certain embodiments, Cy is an optionally substituted 5-6 membered heteroaryl having 1-3 heteroatoms independently selected from nitrogen, oxygen, and sulfur. In certain embodiments, Cy is furan. In certain embodiments, Cy is pyridine. In certain embodiments, Cy is 1,8-naphthyridine. In certain embodiments, Cy is thiophene. In certain embodiments, Cy is pyrrole. In certain embodiments, Cy is quinoline. In certain embodiments, Cy is pyrazole. In certain embodiments, Cy is thiazole. In certain embodiments, Cy is indole. In certain embodiments, Cy is benzothiadiazole. In certain embodiments, Cy is pyrimidinedione. In certain embodiments, Cy is benzofuran. In certain embodiments, Cy is chromene. In certain embodiments, Cy is pyrimidine. In certain embodiments, Cy is quinoxaline. In certain embodiments, Cy is indazole. In certain embodiments, Cy is imidazole. In certain embodiments, Cy is substituted heteroaryl. In certain embodiments, Cy is unsubstituted heteroaryl. In certain embodiments, Cy is substituted heteroaryl. In certain embodiments, Cy is monosubstituted heteroaryl. In certain embodiments, Cy is disubstituted heteroaryl.

In certain embodiments, Cy (e.g., heterocyclyl, aryl (e.g., phenyl), heteroaryl) is substituted with —CO$_2$H. In certain embodiments, Cy is substituted with —SO$_3$H. In certain embodiments, Cy is substituted with an optionally substituted ester. In certain embodiments, Cy is substituted with —C(=O)O(optionally substituted C$_{1-6}$ alkyl). In certain embodiments, Cy is substituted with —C(=O)O(unsubstituted C$_{1-6}$ alkyl). In certain embodiments, Cy is substituted with —C(=O)OBu. In certain embodiments, Cy is substituted with —C(=O)OCH$_2$OC(=O)(optionally substituted C$_{1-6}$ alkyl). In certain embodiments, Cy is substituted with —C(O)OCH$_2$OC(O)CH$_3$. In certain embodiments, Cy is substituted with an optionally substituted sulfonic ester. In certain embodiments, Cy is substituted with —S(O)$_2$OCH$_2$OC(O)CH$_3$. In certain embodiments, Cy is substituted with —C(=O)O(optionally substituted C$_{1-6}$ alkyl); and R$^9$ is optionally substituted C$_{1-6}$ alkyl. In certain embodiments, Cy is substituted with —C(=O)O(unsubstituted C$_{1-6}$ alkyl); and R$^9$ is unsubstituted C$_{1-6}$ alkyl.

In certain embodiments, at least one of R$^1$, R$^2$, R$^3$, R$^4$, R$^5$, R$^6$, R$^7$, and R$^8$ is -L-Z. In certain embodiments, only one of R$^1$, R$^2$, R$^3$, R$^4$, R$^5$, R$^6$, R$^7$, and R$^8$ is -L-Z. In certain embodiments, only two of R$^1$, R$^2$, R$^3$, R$^4$, R$^5$, R$^6$, R$^7$, and R$^8$ are -L-Z.

In certain embodiments, a provided compound is a prodrug. In certain embodiments, In certain embodiments, a provided compound is an ester type prodrug (e.g., Cy is substituted with —C(=O)O(optionally substituted C$_{1-6}$ alkyl), and/or R$^9$ is optionally substituted C$_{1-6}$ alkyl). In certain embodiments, a provided compound is a double ester type prodrug (e.g., Cy is substituted with —C(=O)OCH$_2$OC(=O)(optionally substituted C$_{1-6}$ alkyl), and/or R$^9$ is acyloxymethyl).

In some embodiments, a provided compound is of the formula:

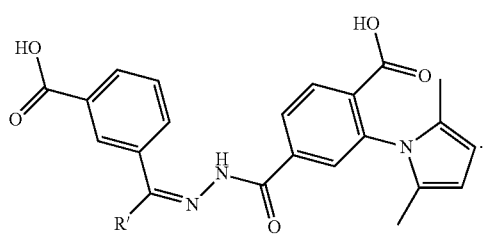

In certain embodiments, R' is

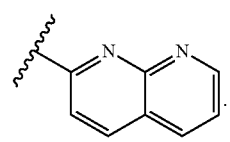 [SMILES: *c1ccc2cccnc2n1]

In certain embodiments, a provided compound is one of the following:

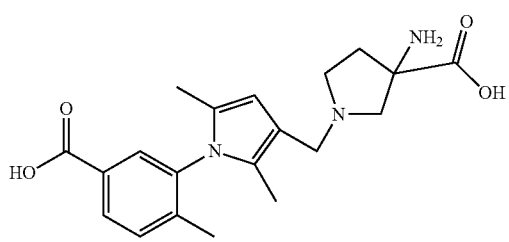

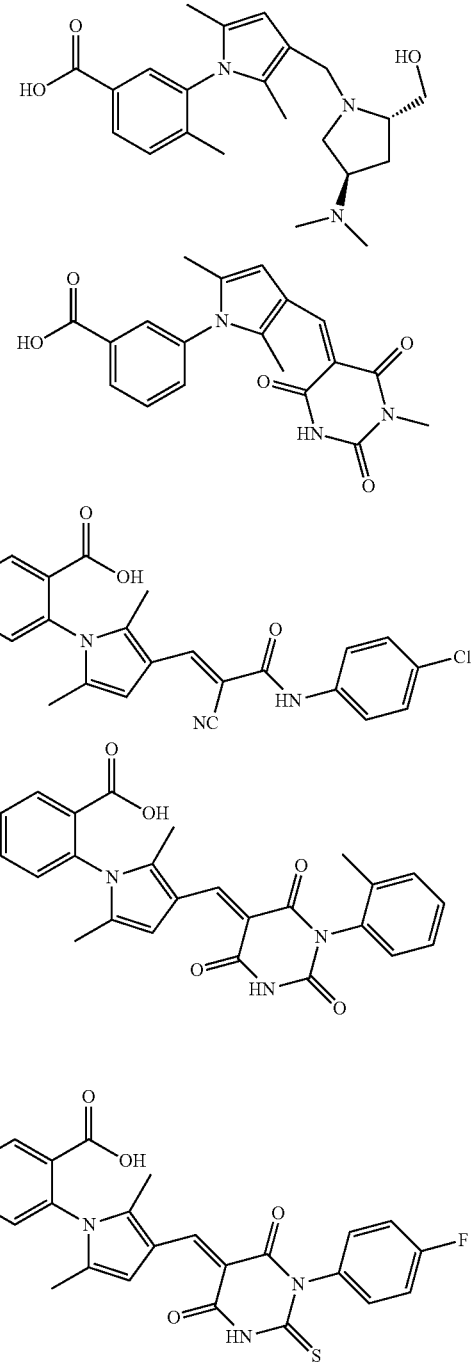

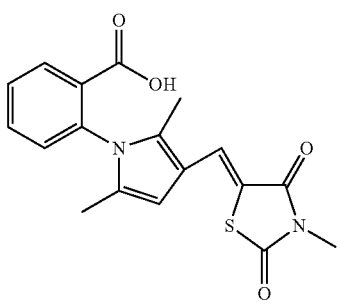

51
-continued
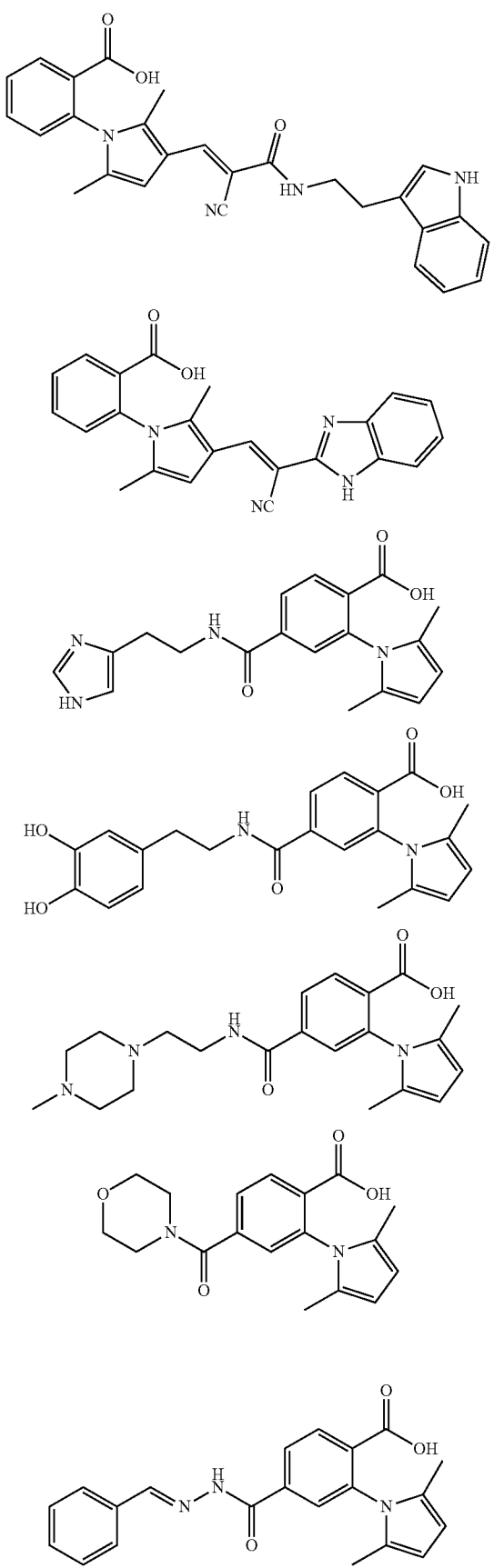
52
-continued
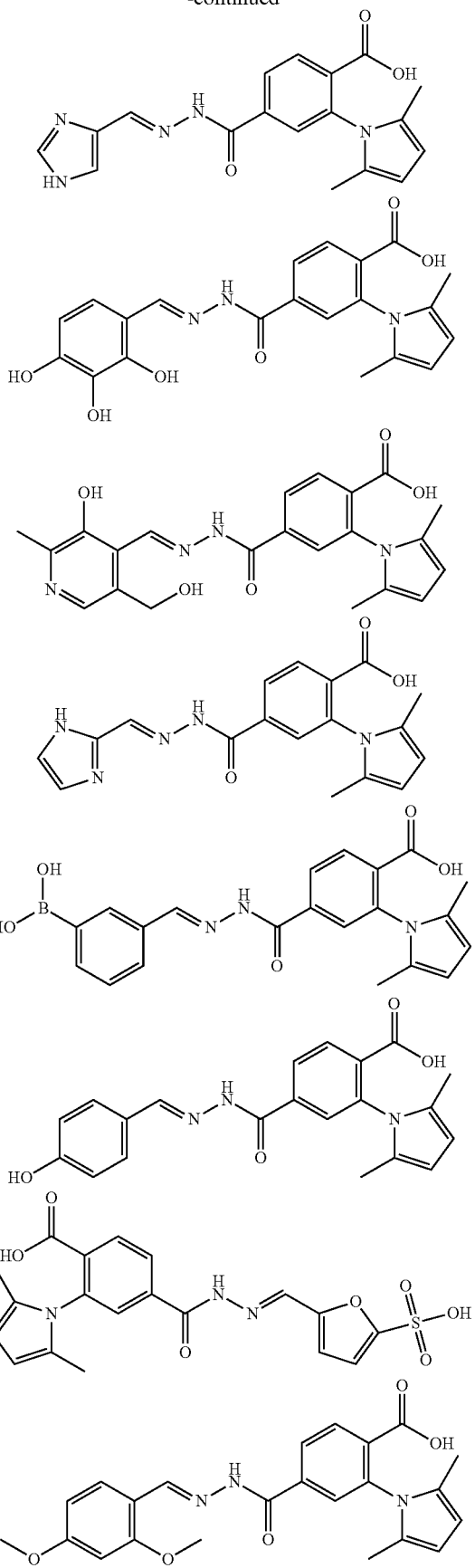

53
-continued
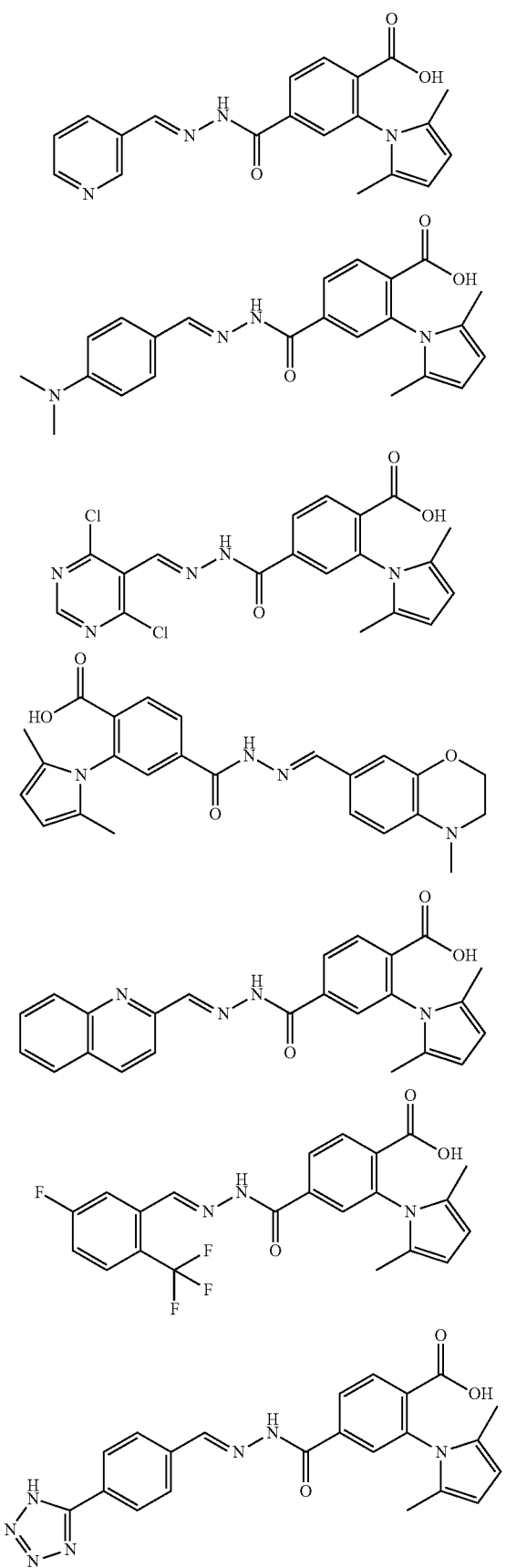
54
-continued
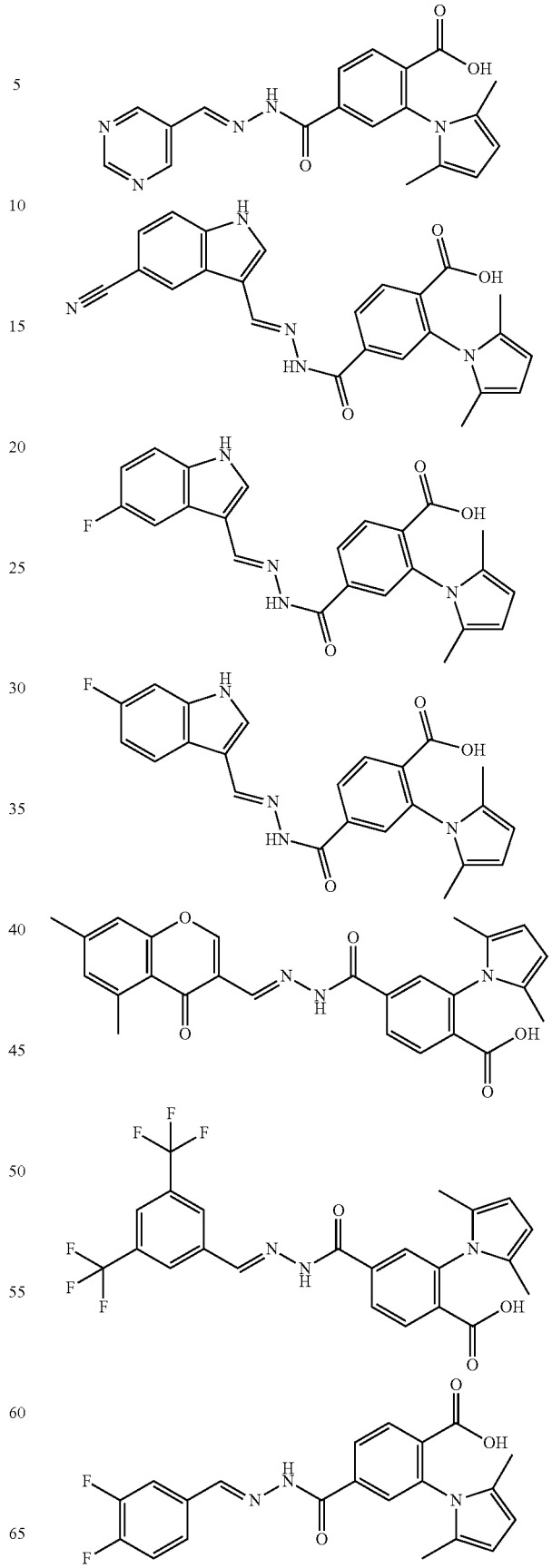

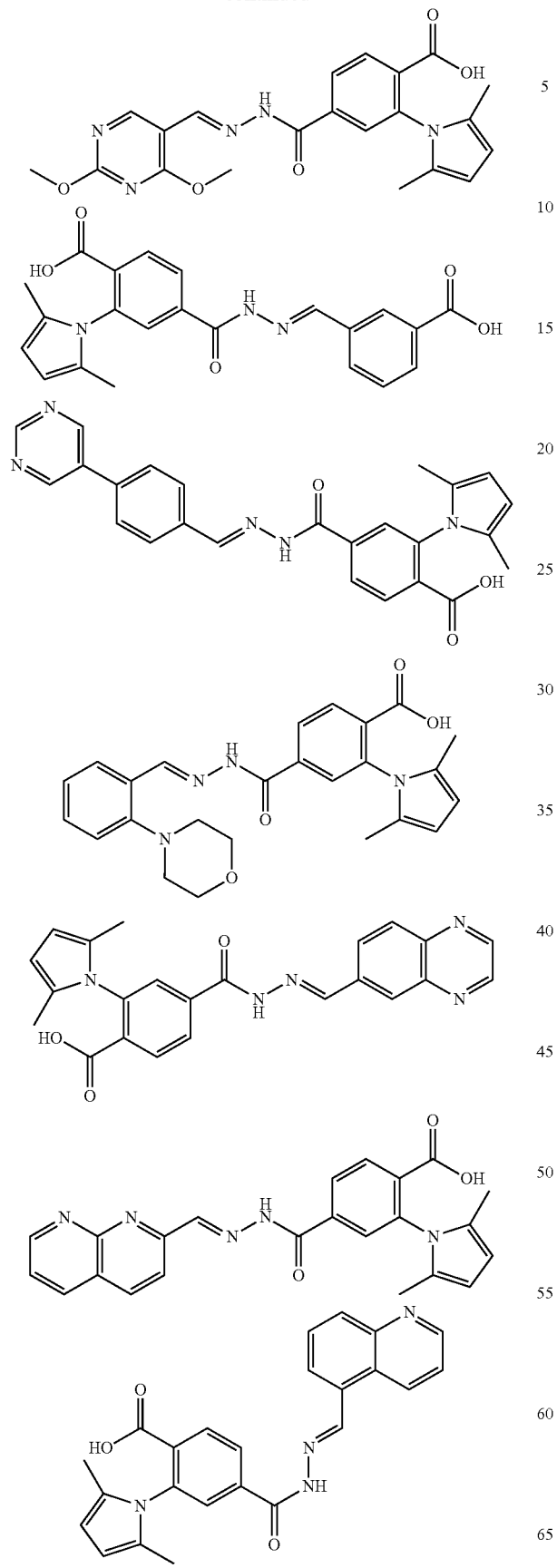
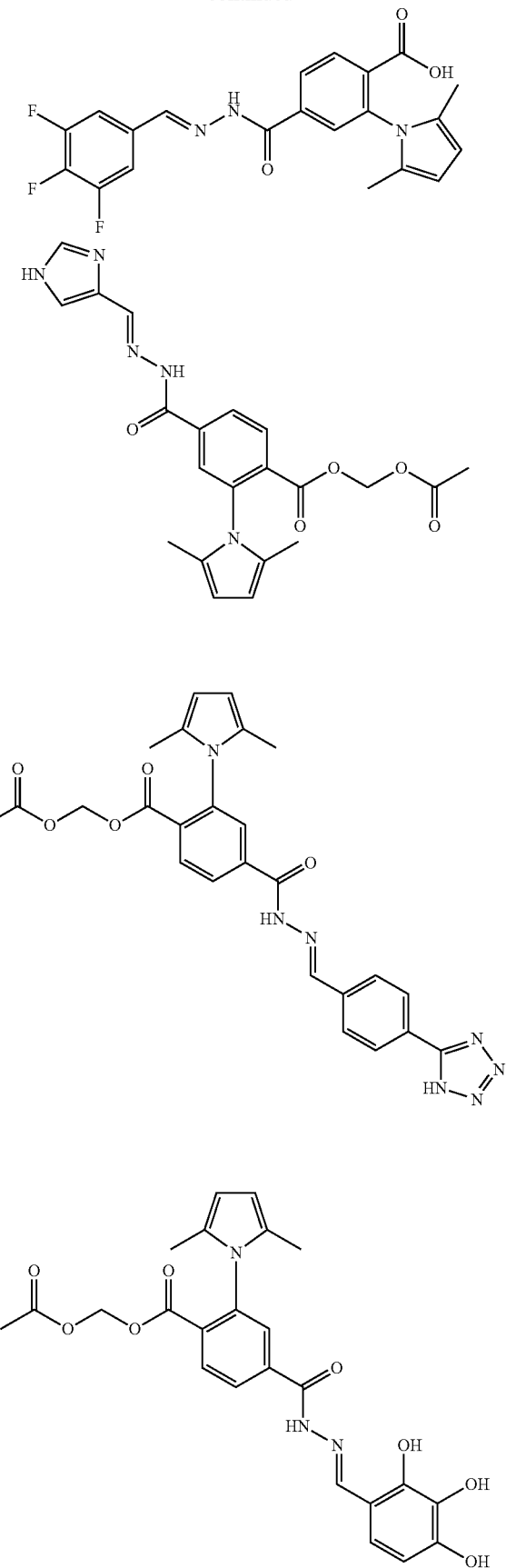

57
-continued
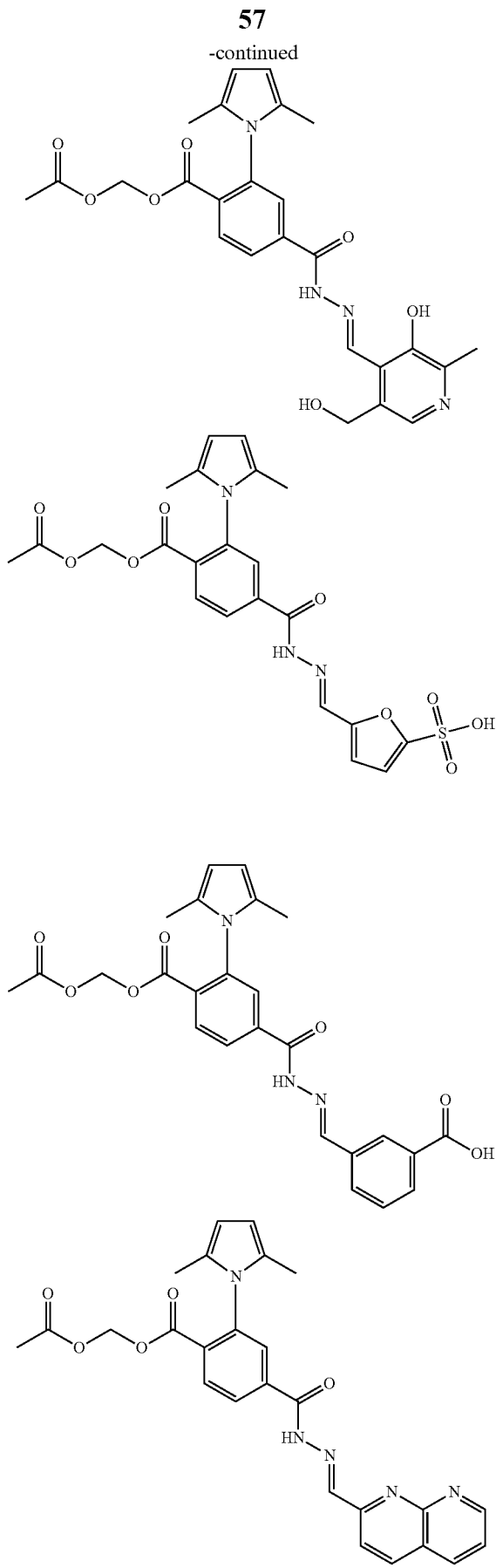
58
-continued
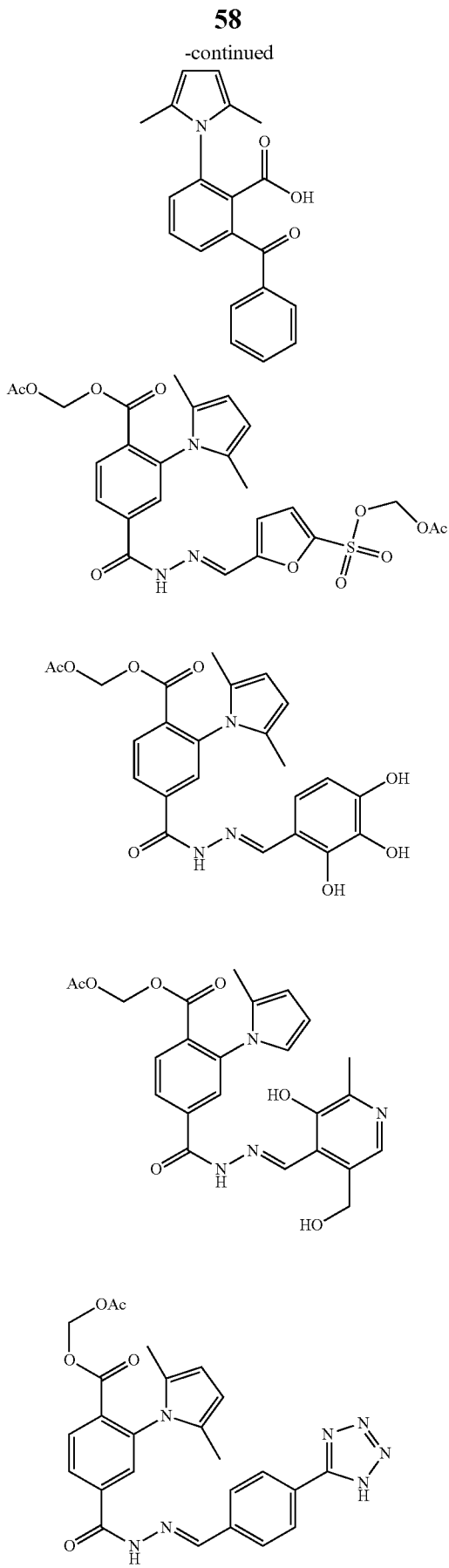

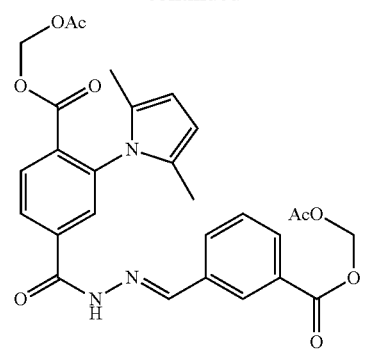
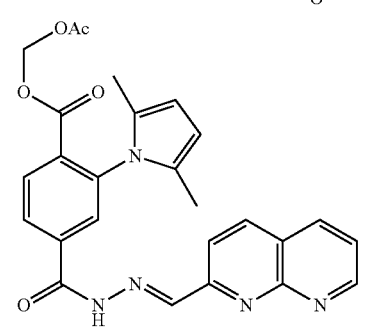
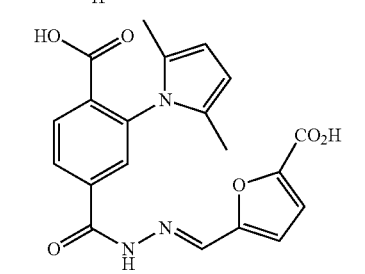
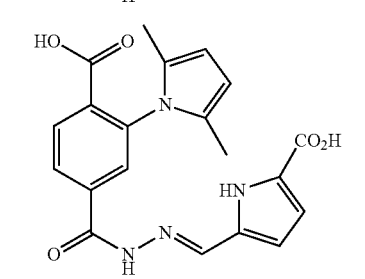
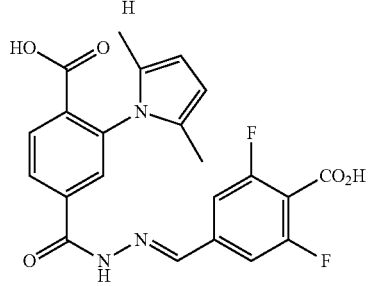
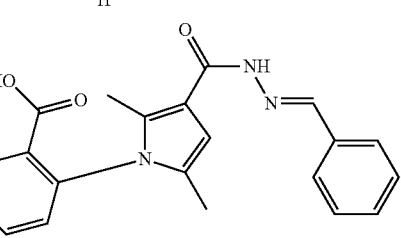
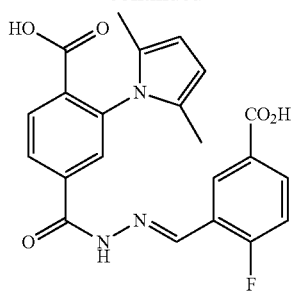
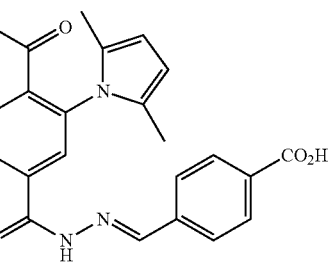
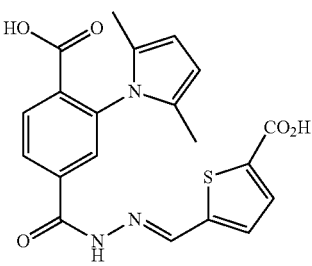
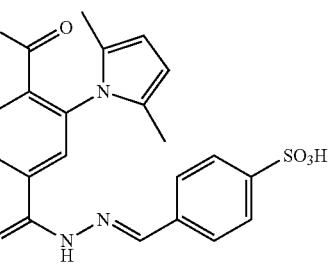
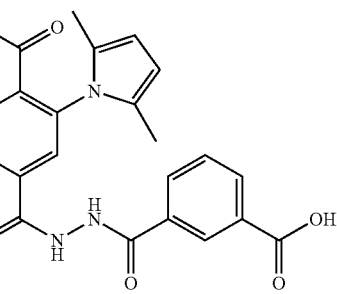

-continued
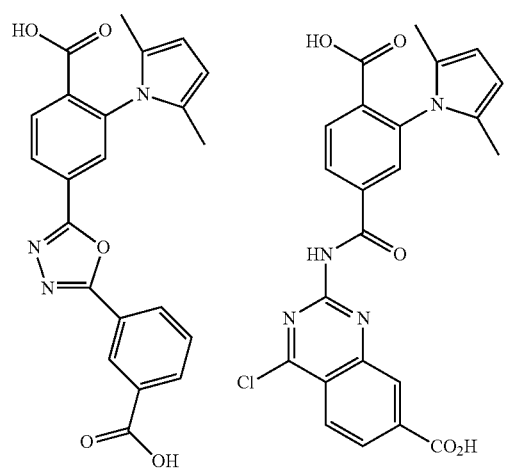
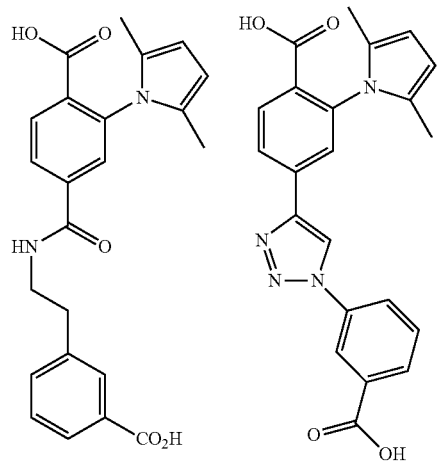
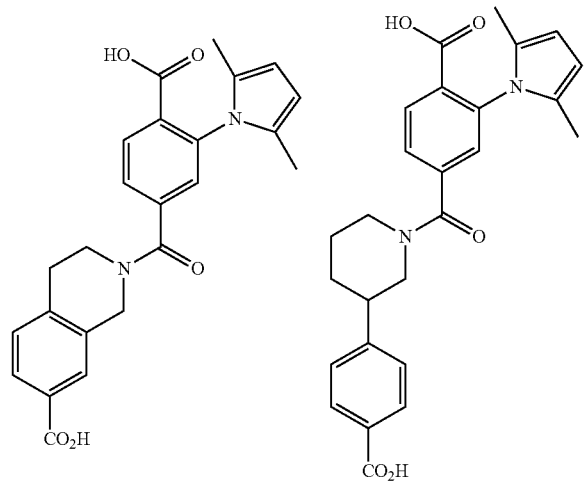
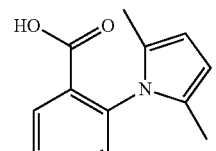
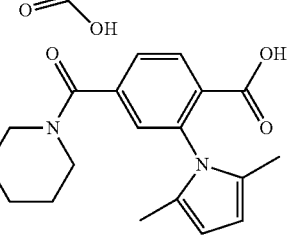
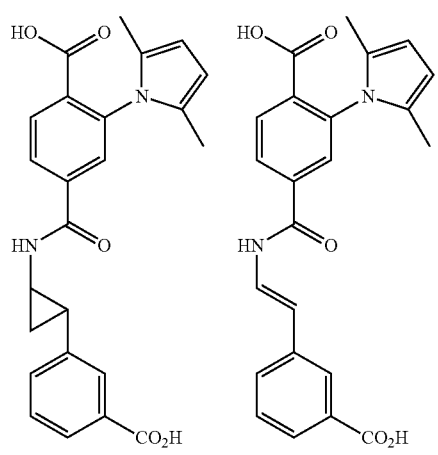
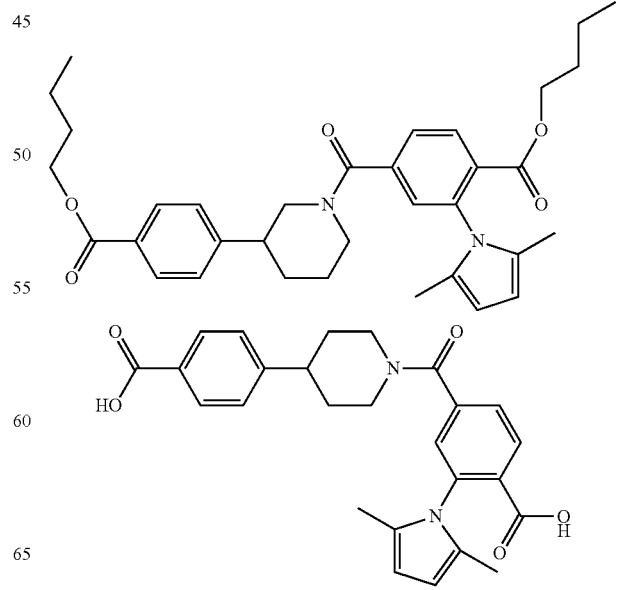

| 63 | 64 |
|---|---|
| -continued | -continued |
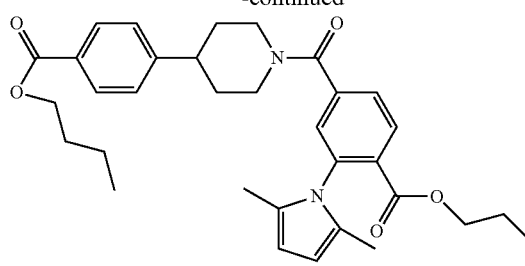
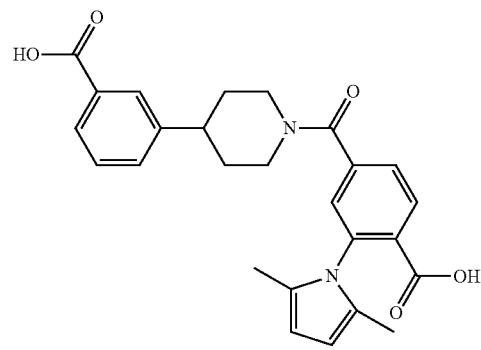
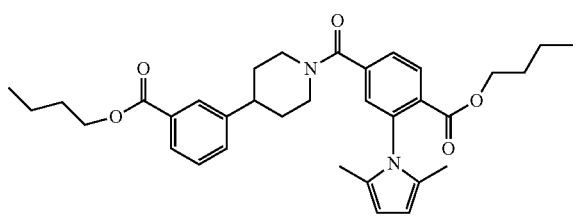
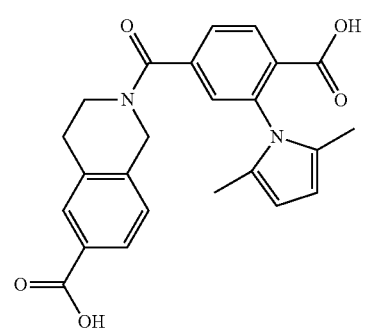
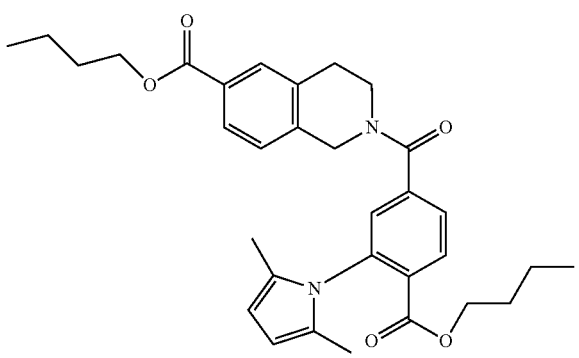
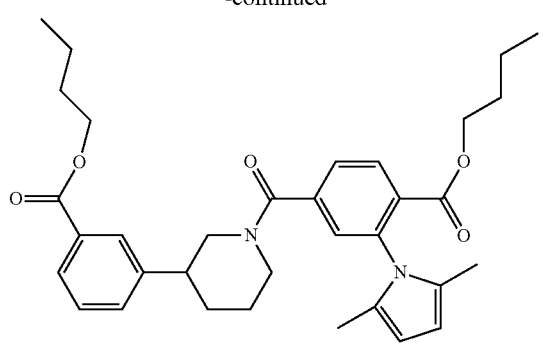
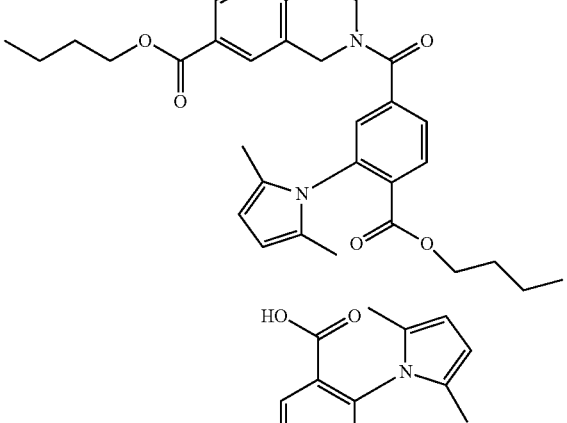
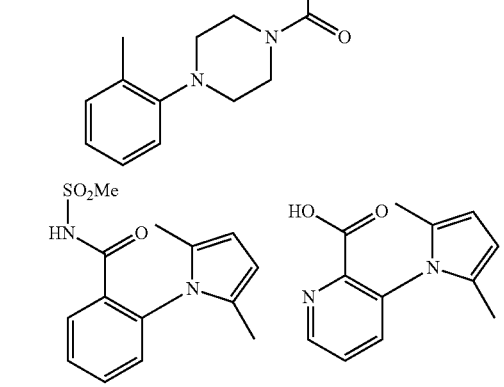
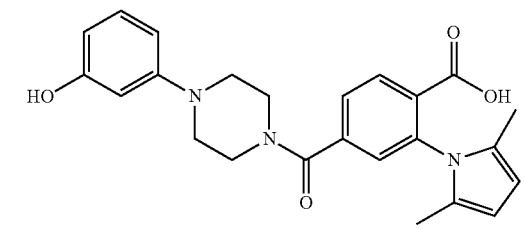
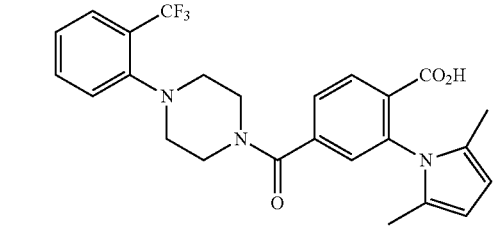

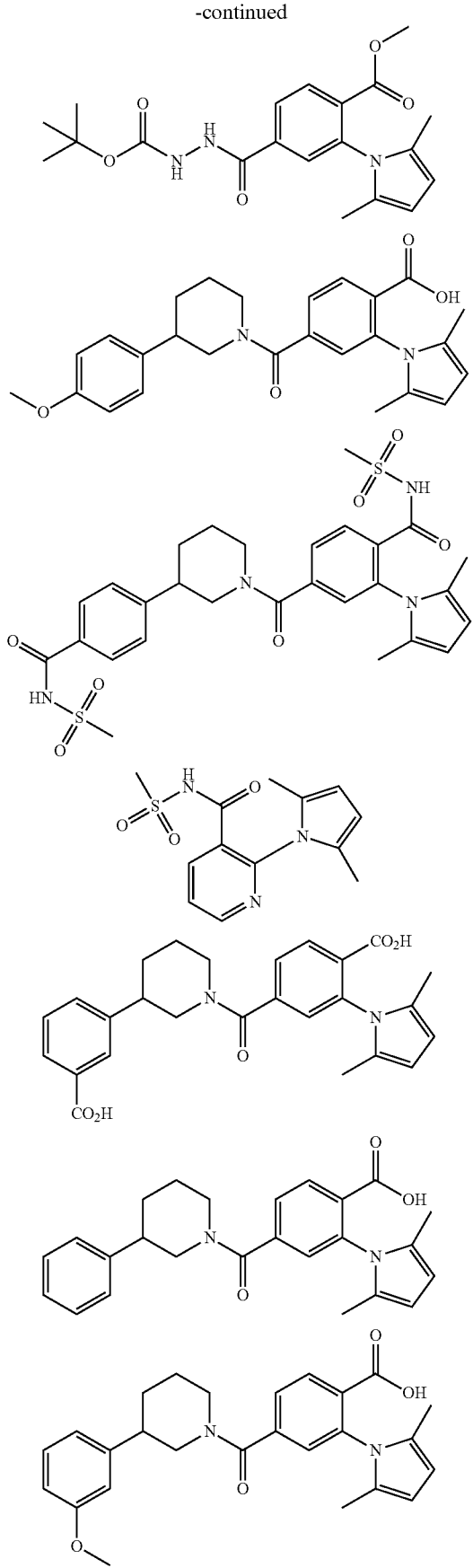
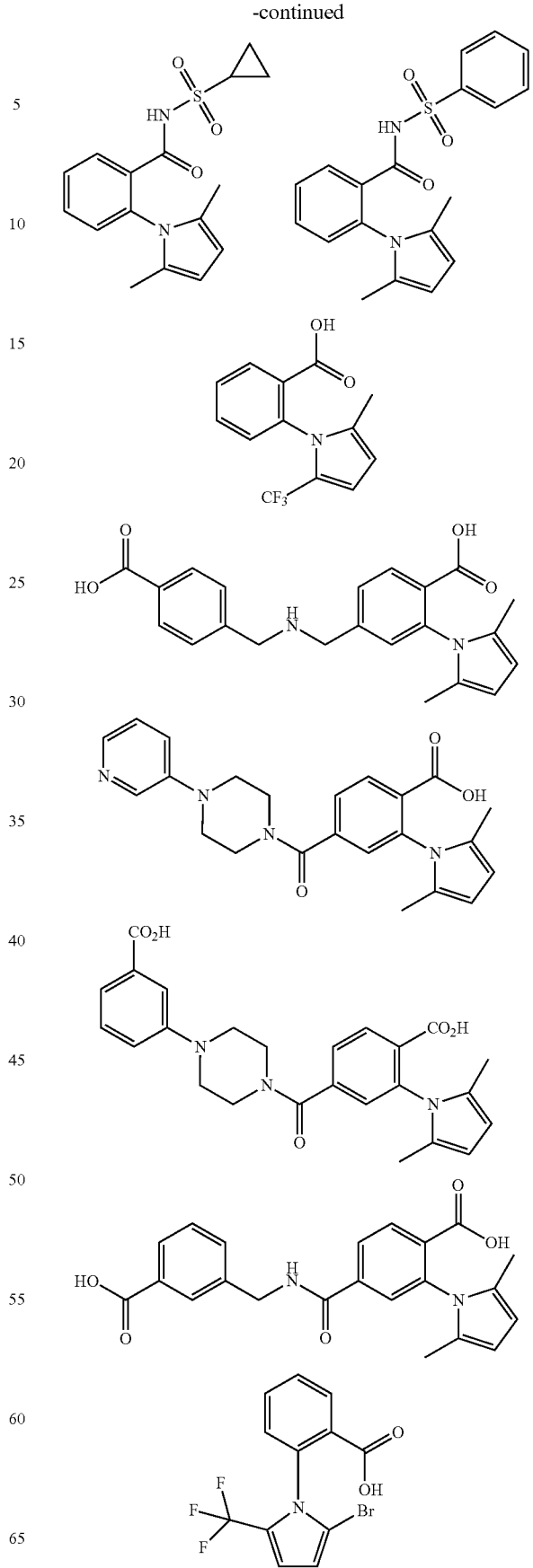

67
-continued
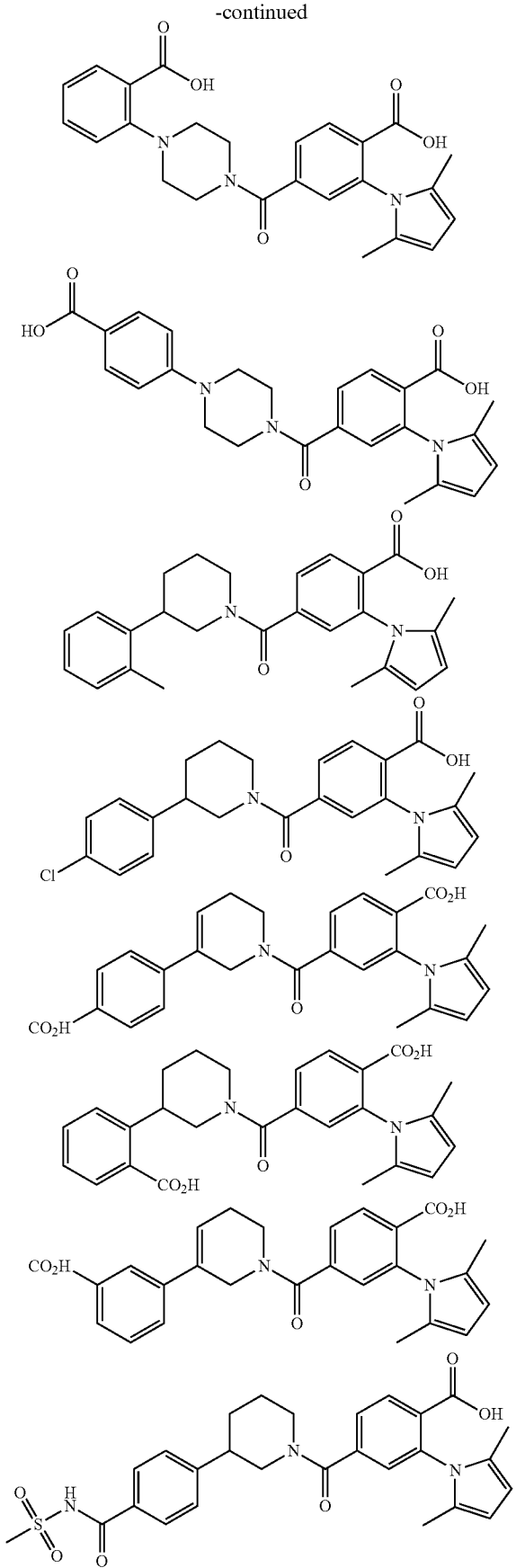
68
-continued
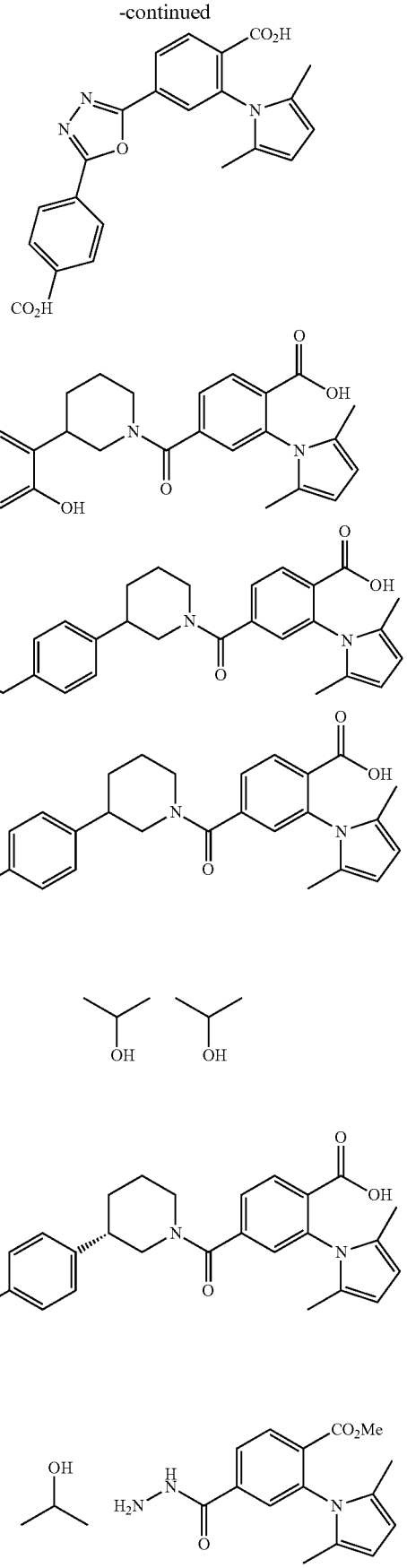

69
-continued
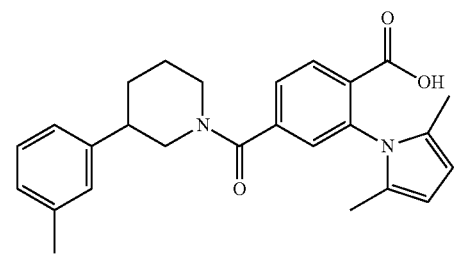
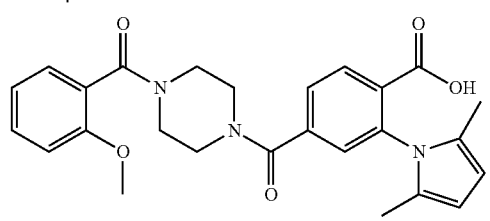
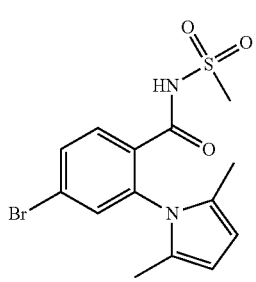
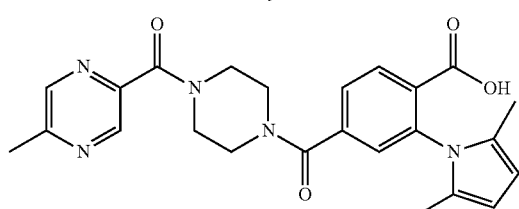
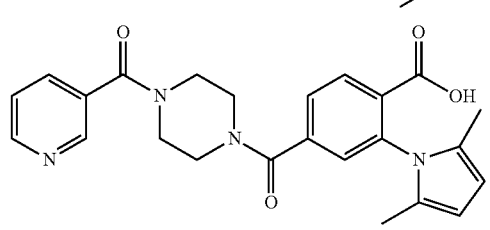
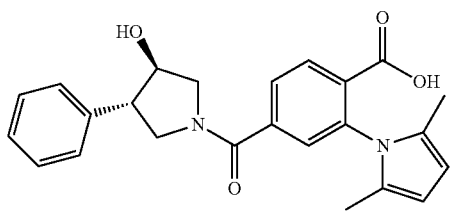
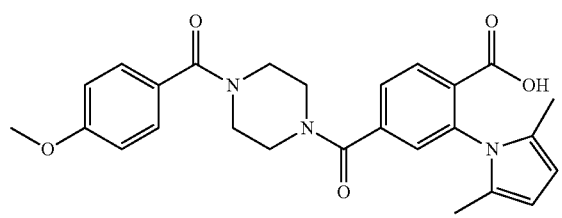
70
-continued
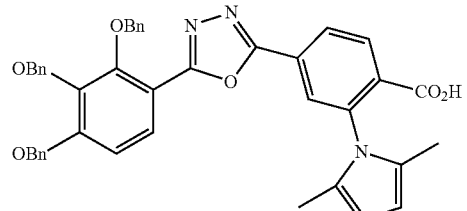
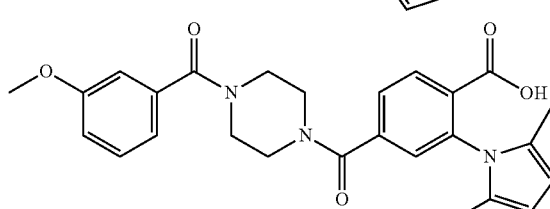
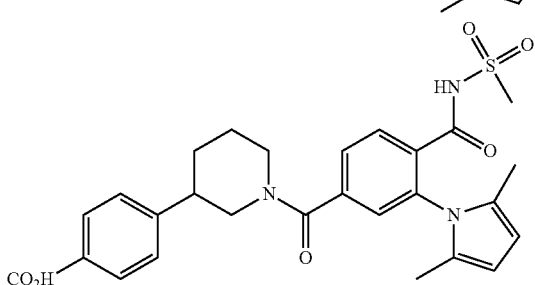
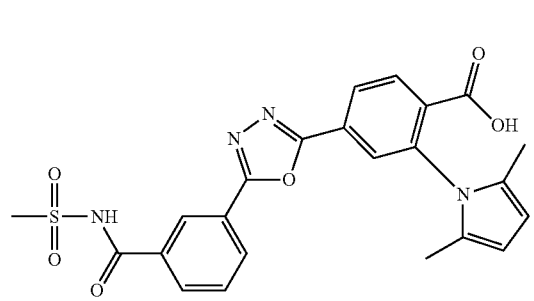
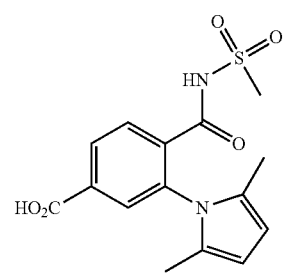
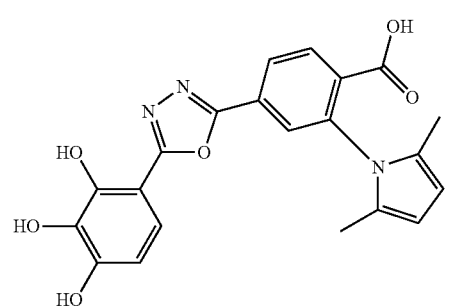

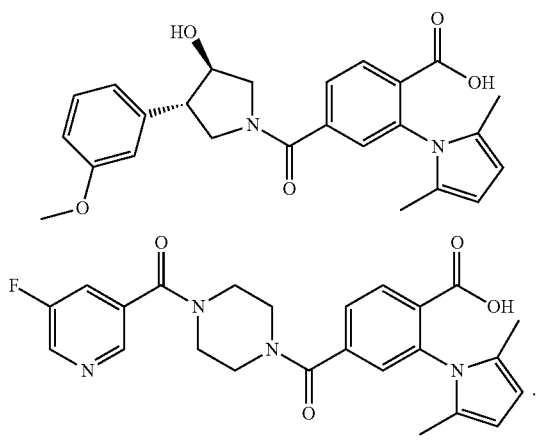
In some embodiments, a provided compound is of the formula:
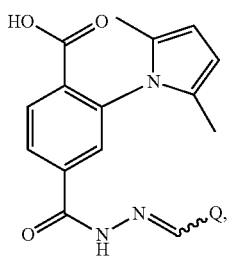
wherein Q is derived from reaction an acyl hydrazine precursor with one of the following aldehyde or ketones:
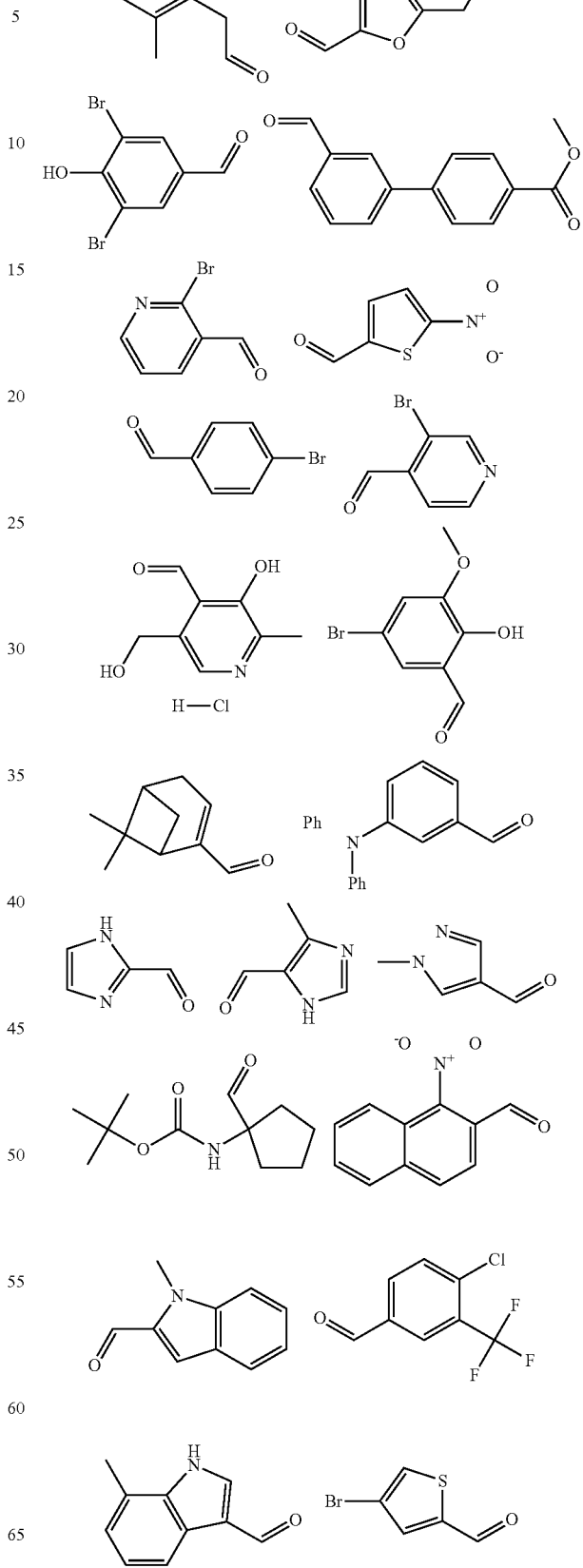

73
-continued
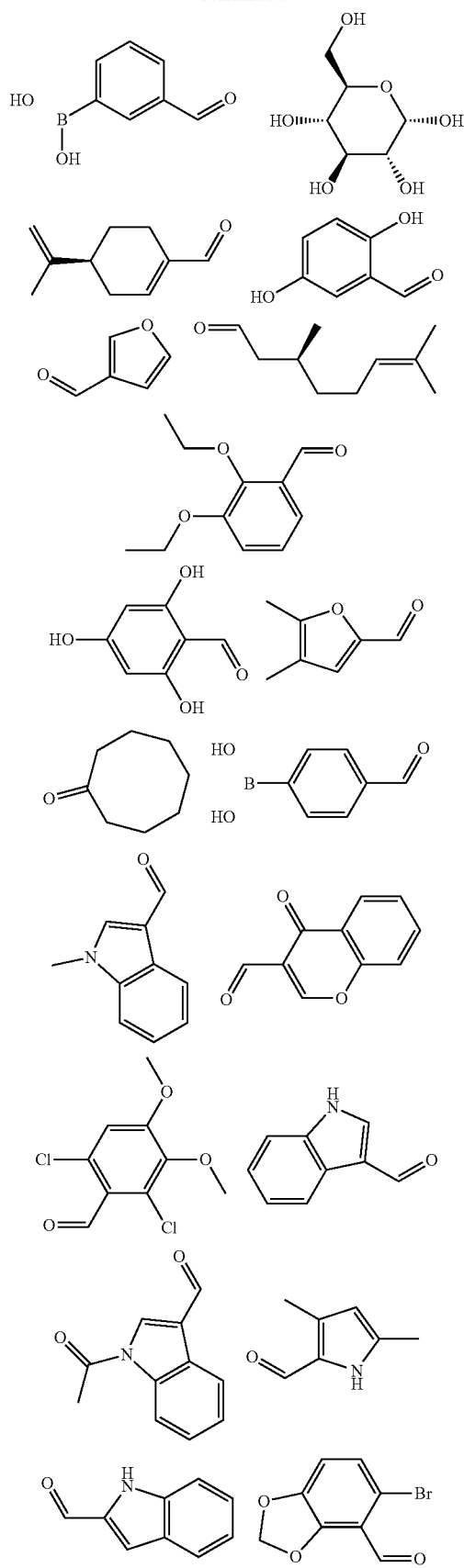
74
-continued
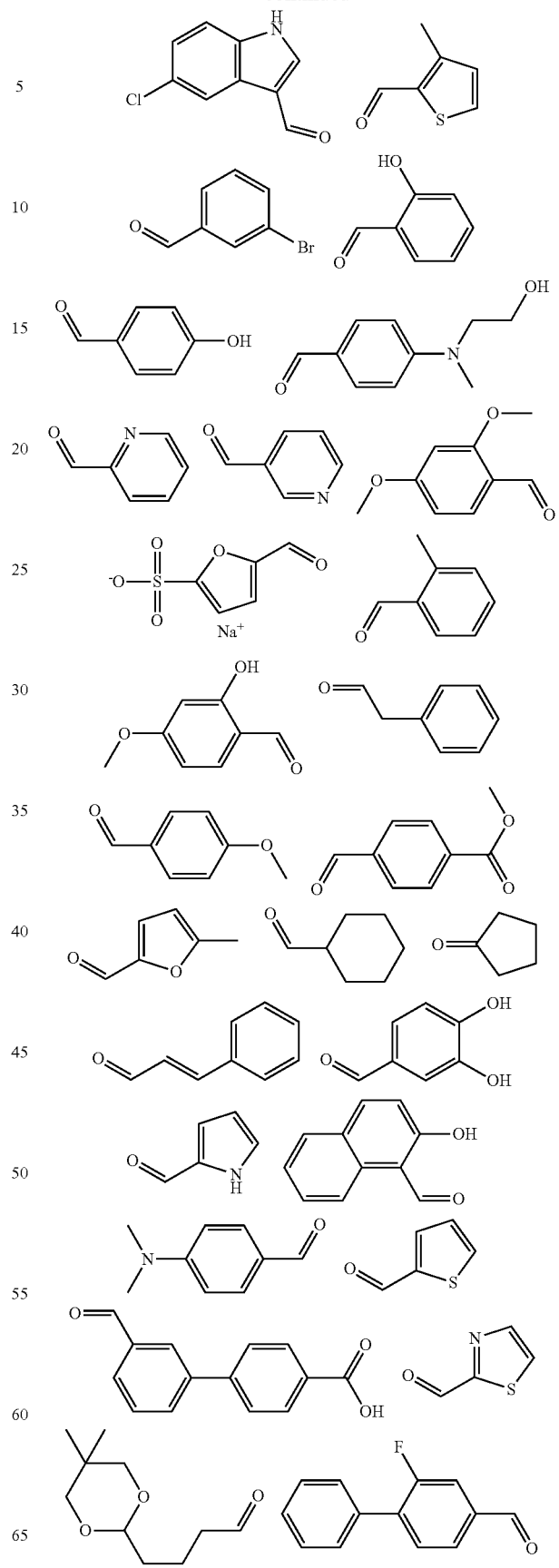

75
-continued
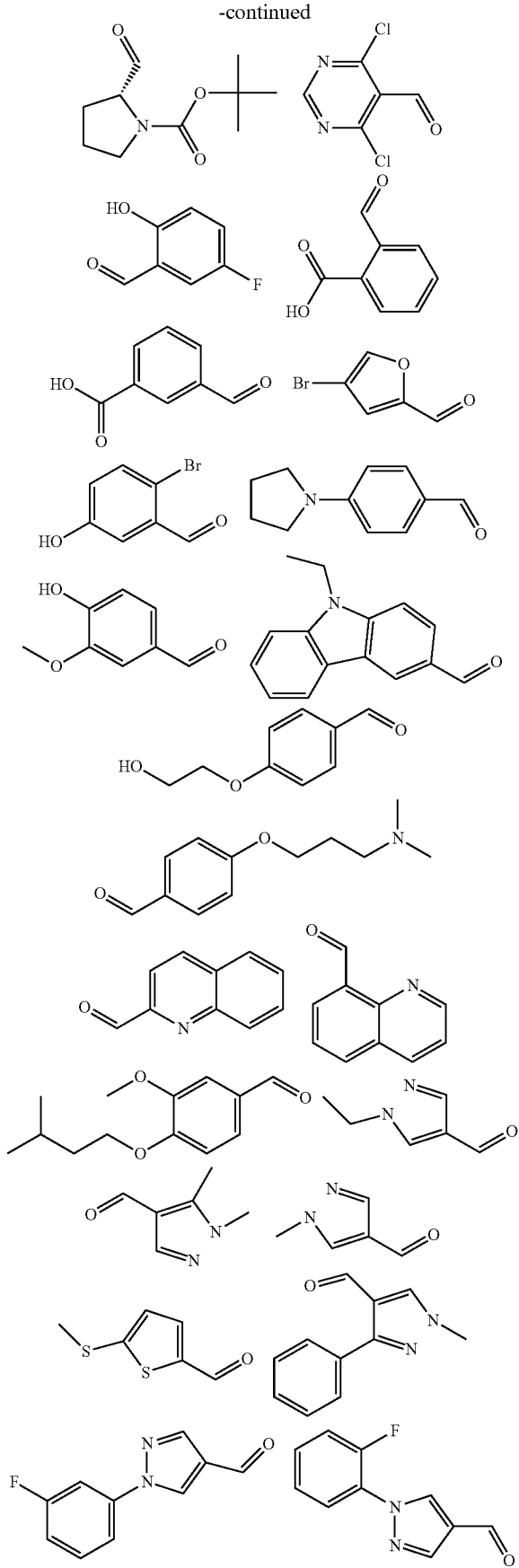
76
-continued
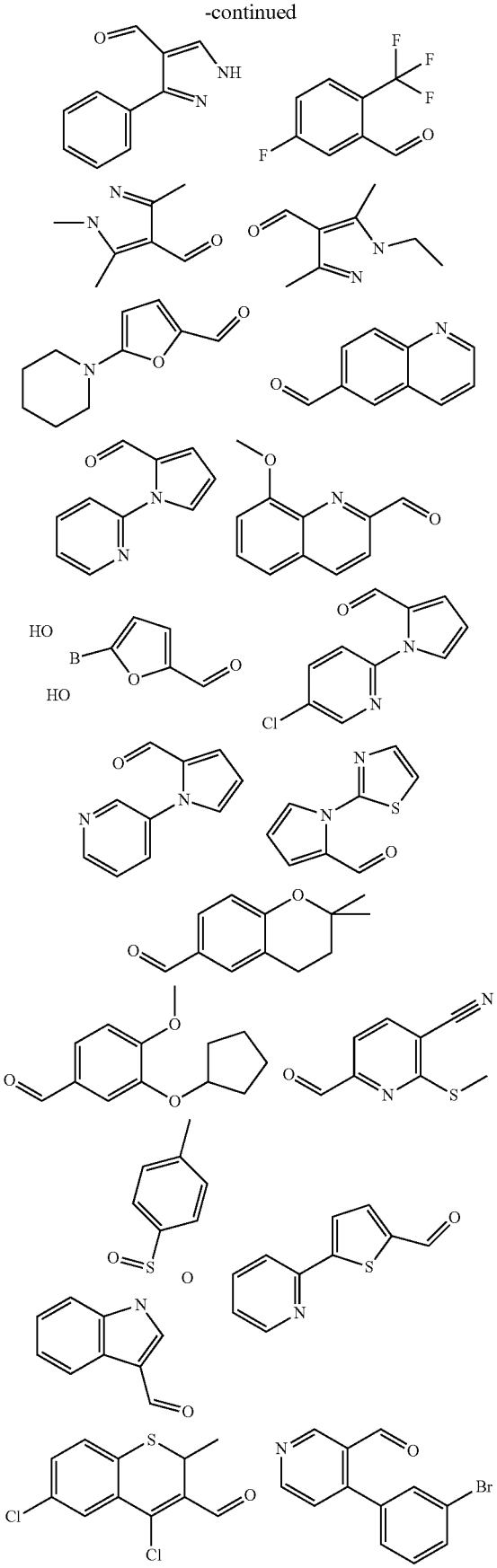

77
-continued
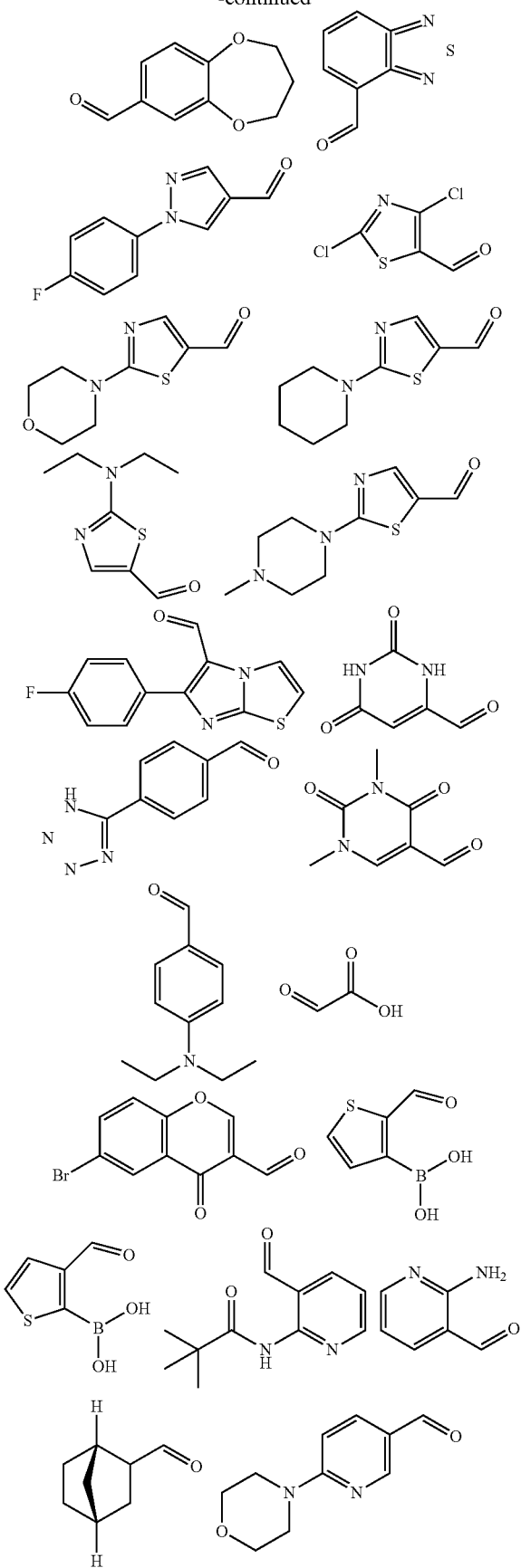
78
-continued
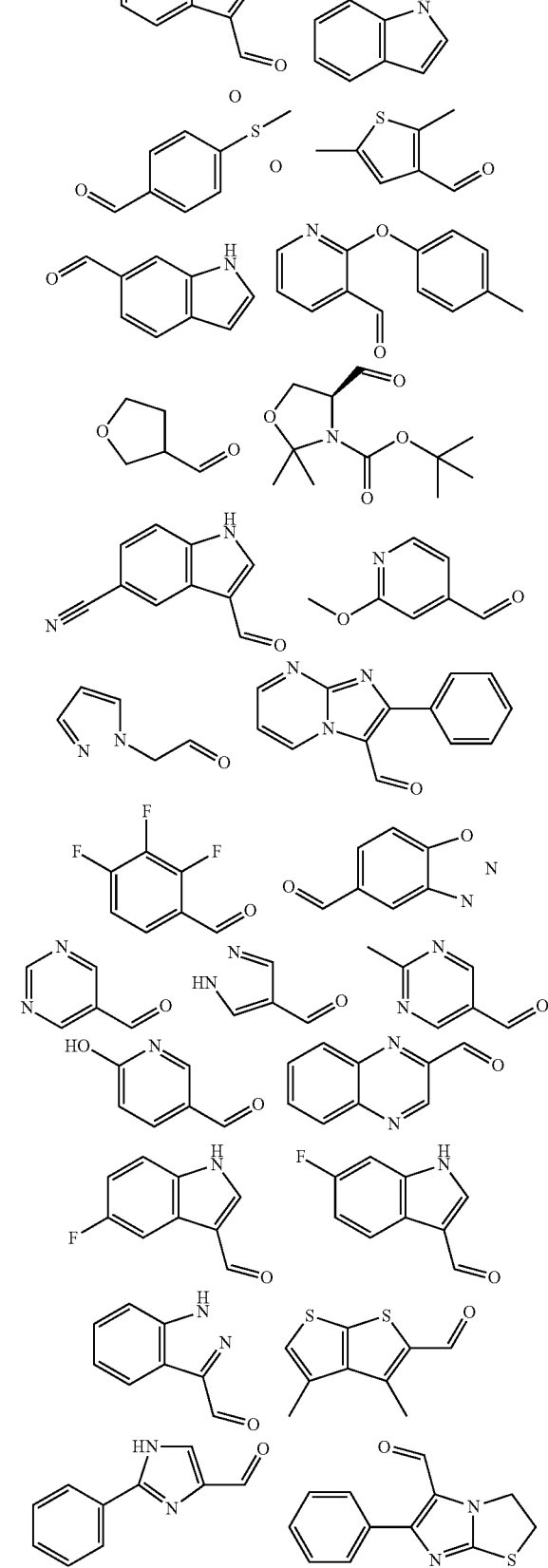

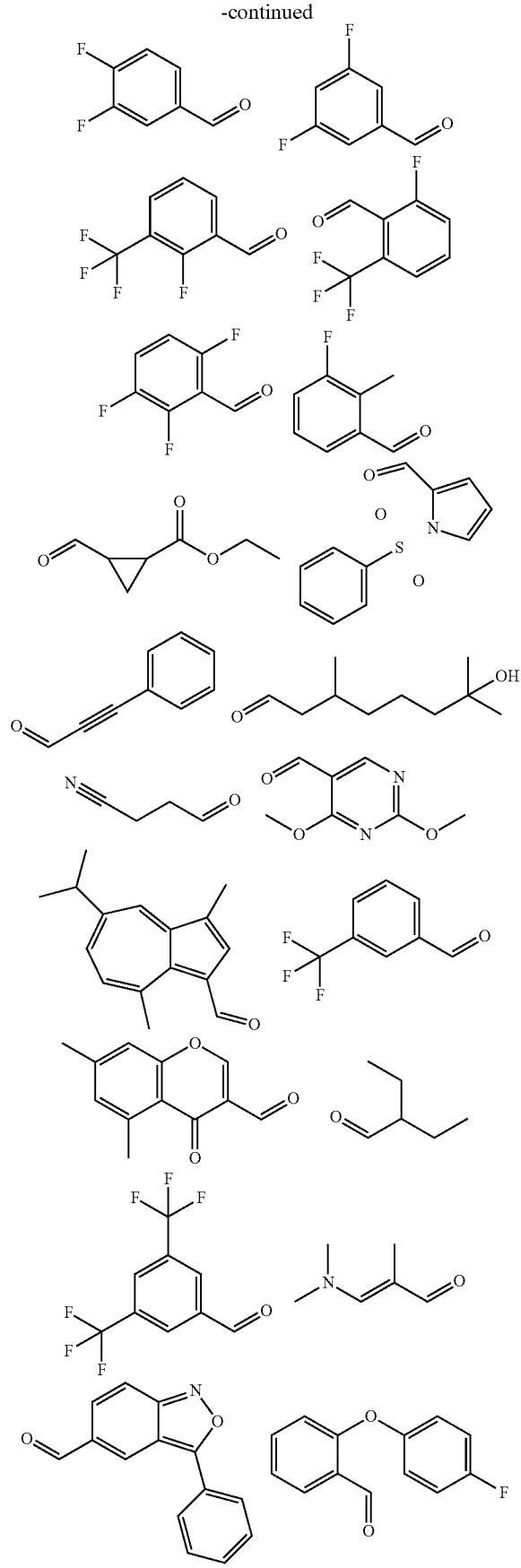
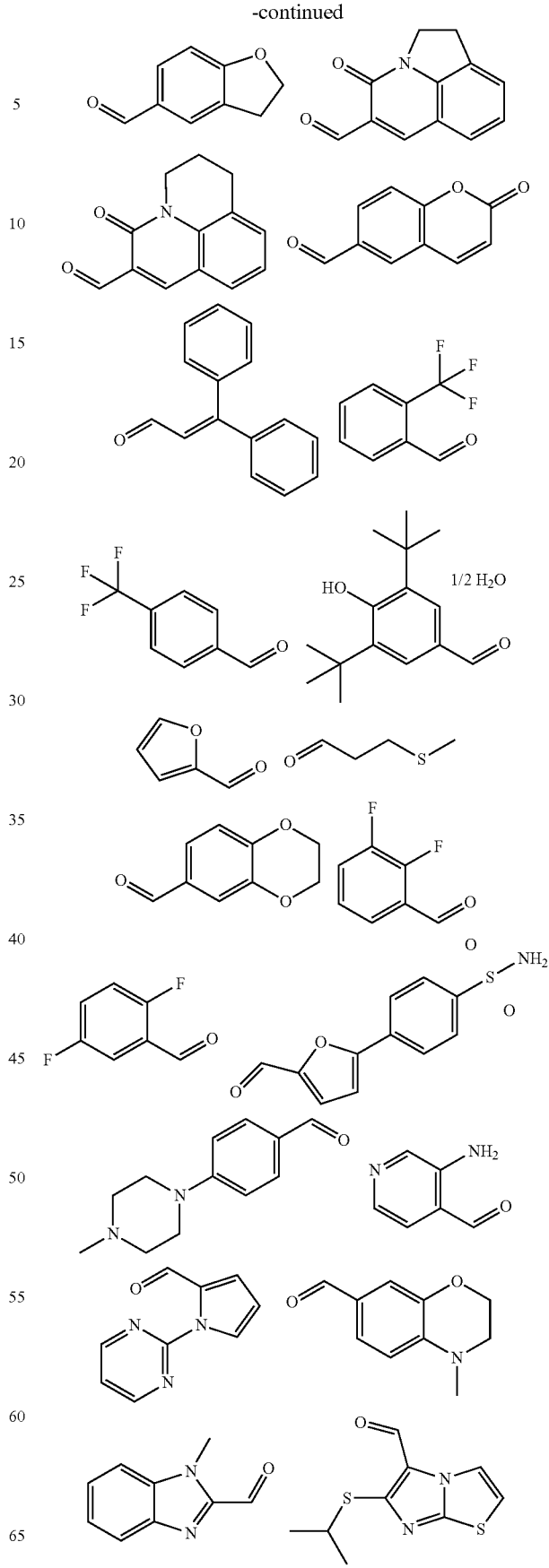

81
-continued
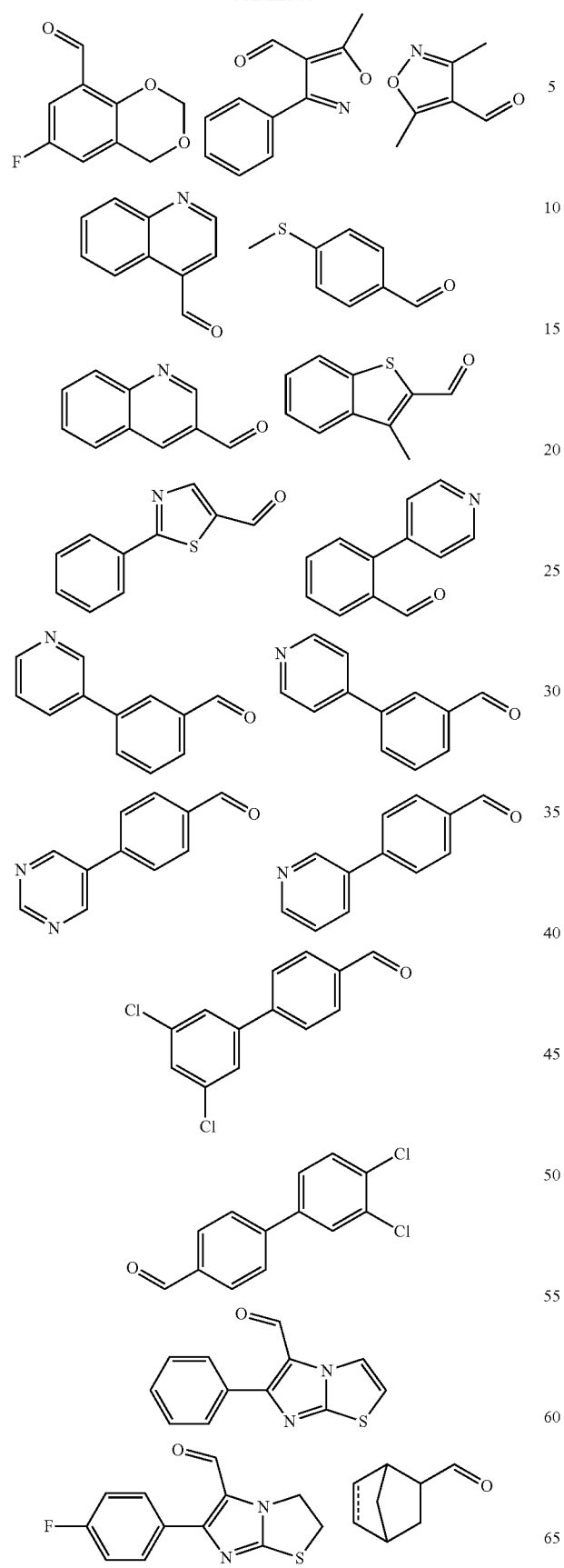
82
-continued
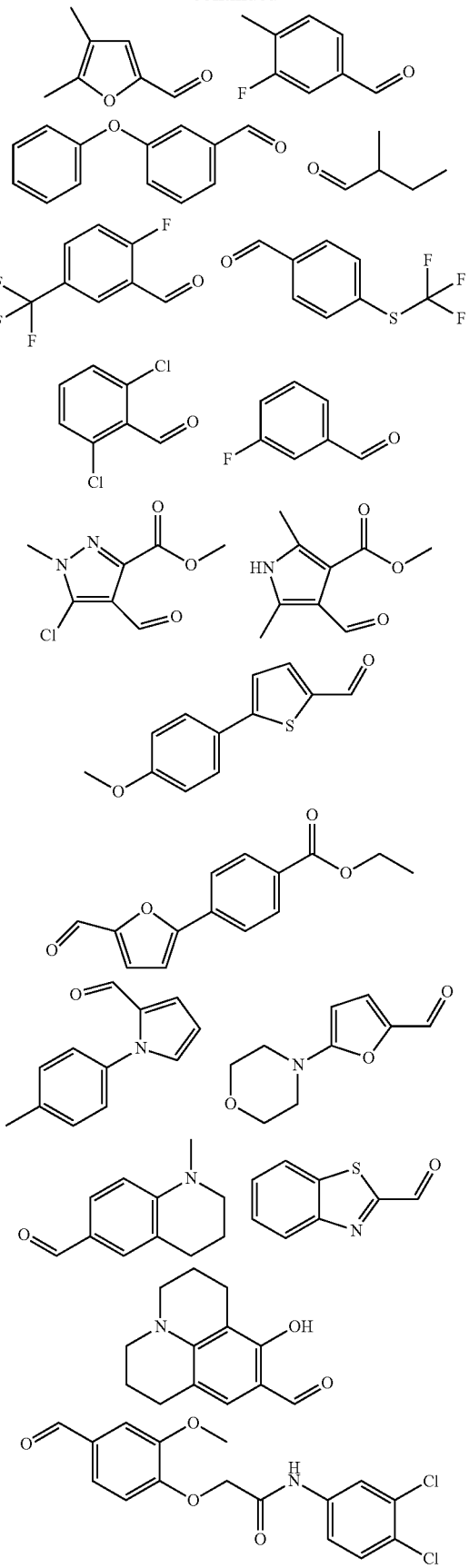

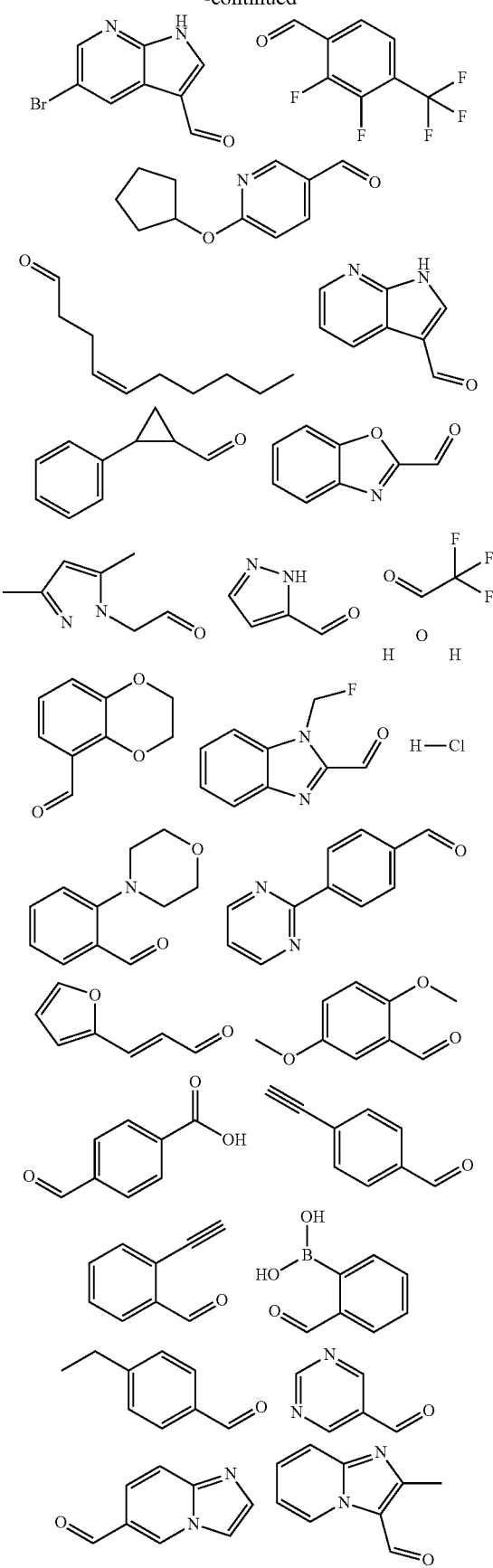
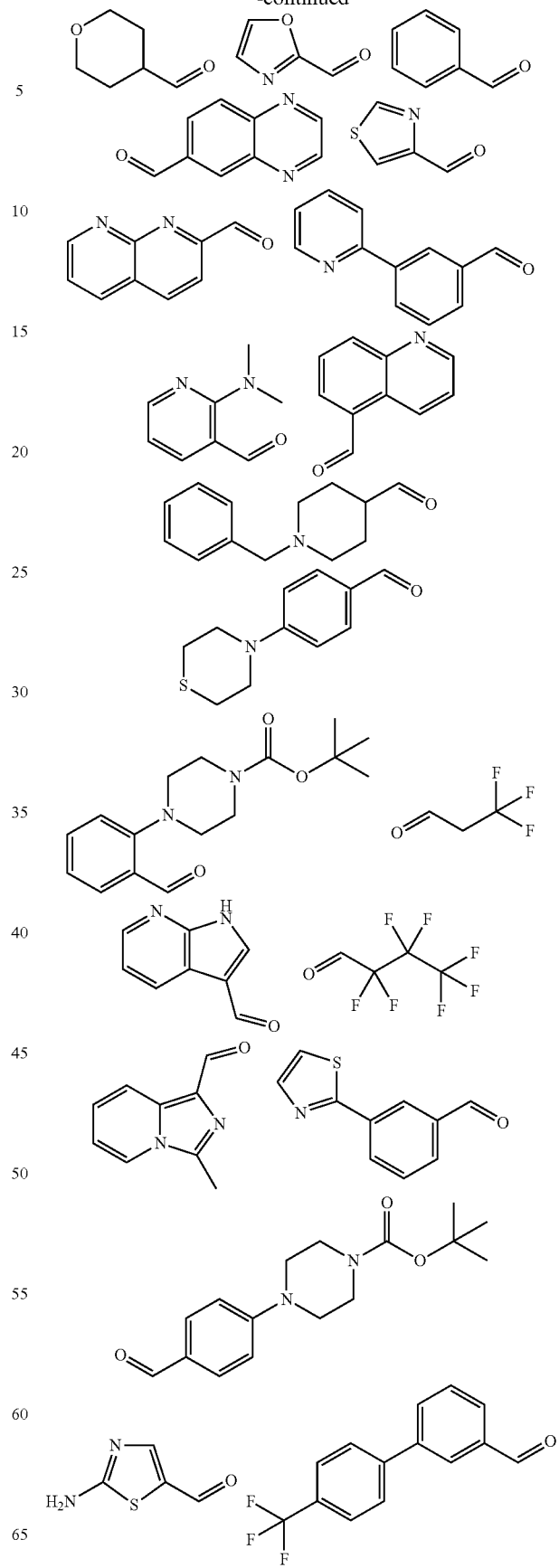

85
-continued
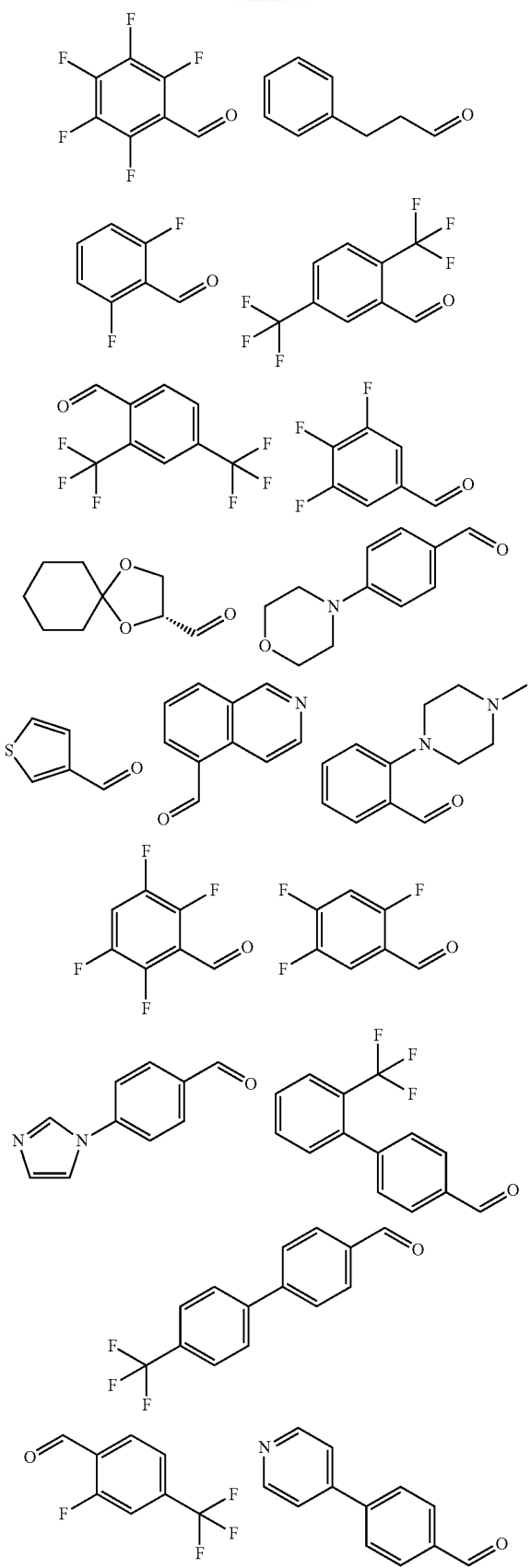
86
-continued
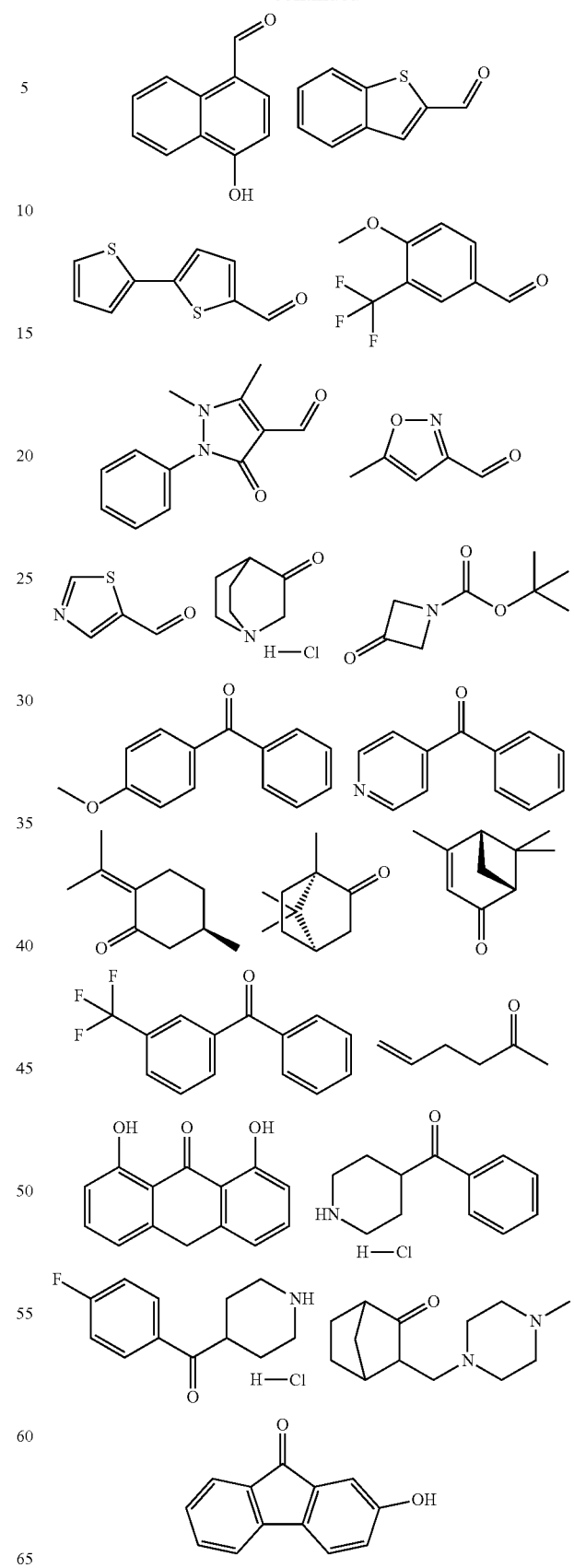

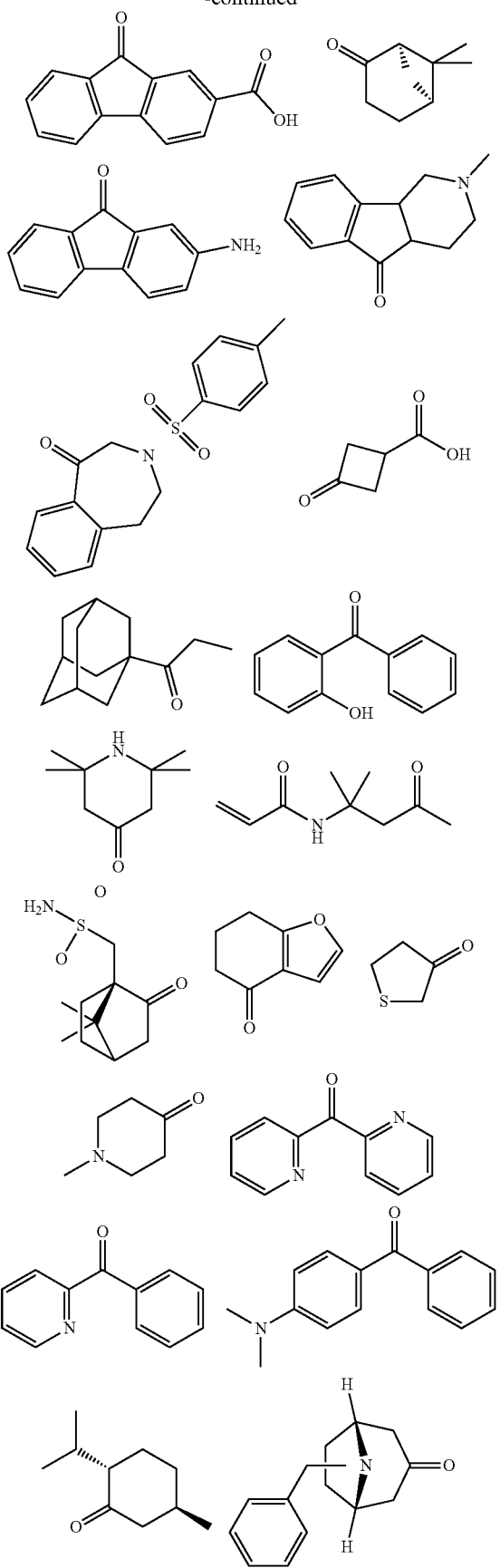
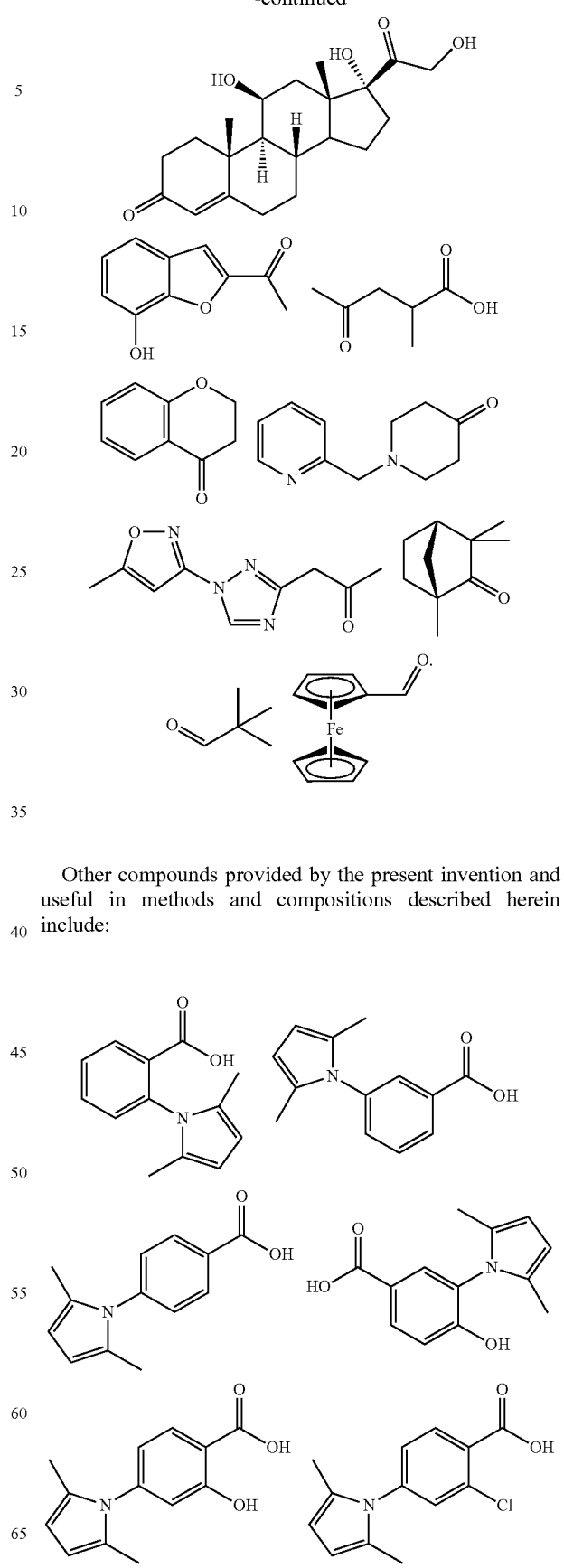
Other compounds provided by the present invention and useful in methods and compositions described herein include:

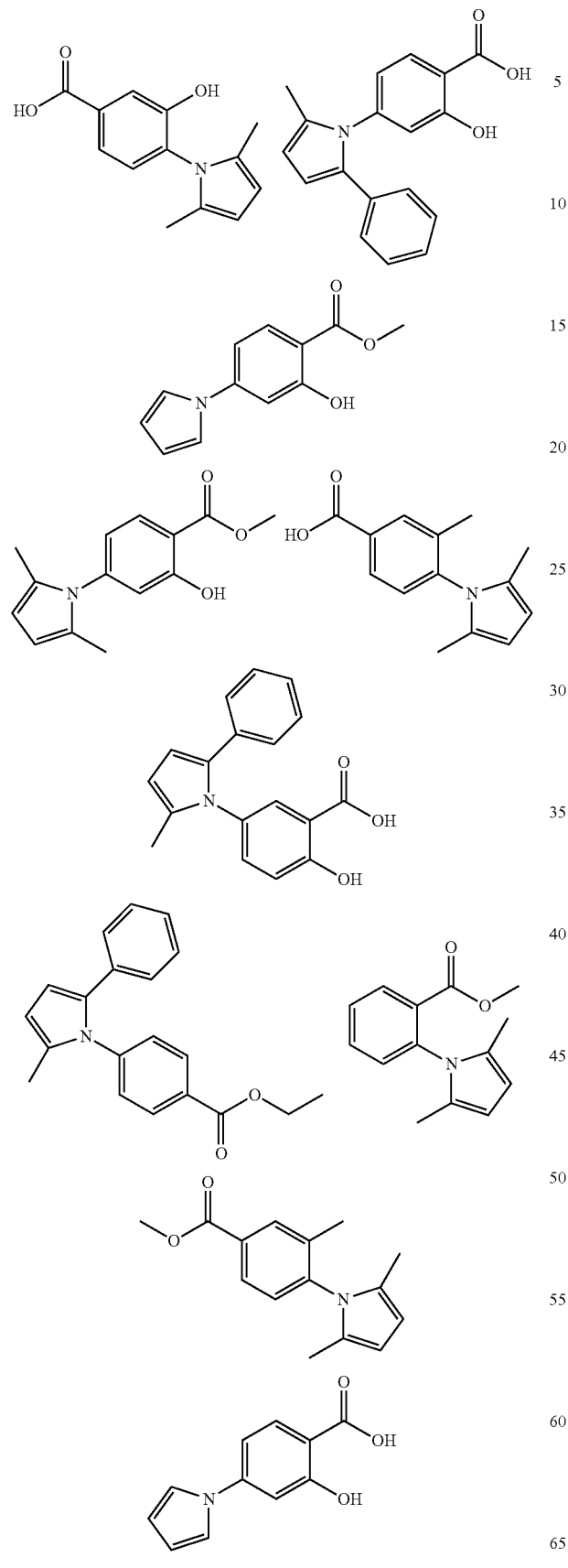
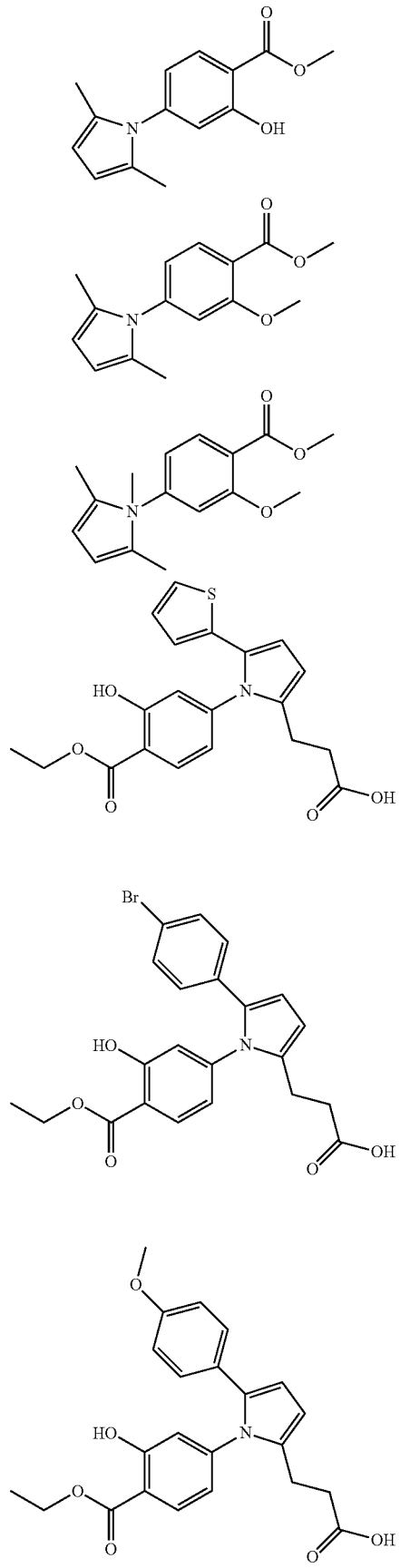

91
-continued
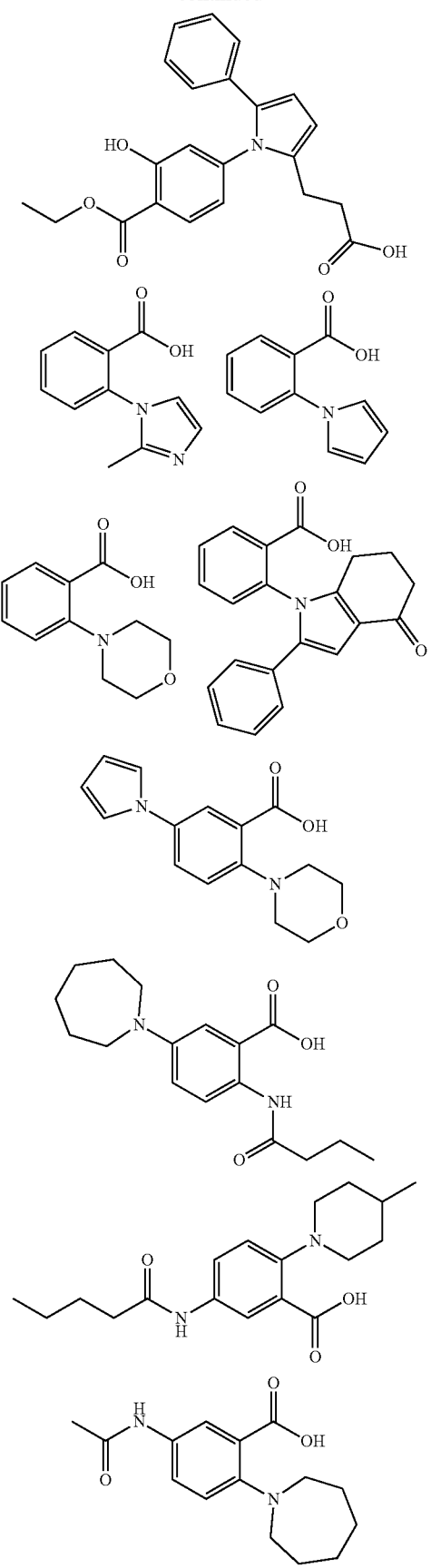
92
-continued
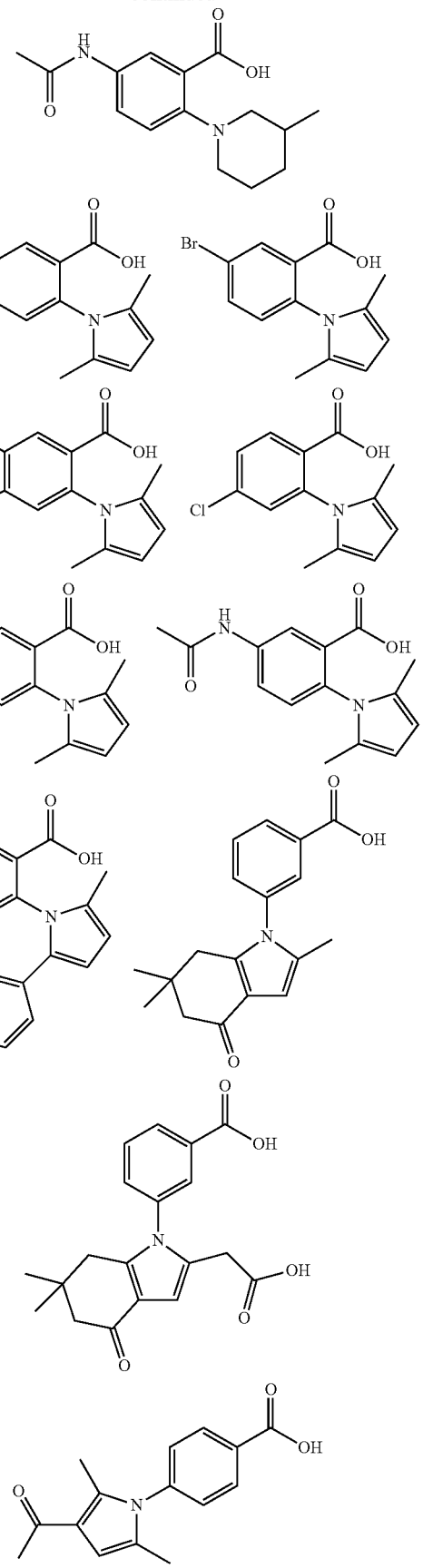

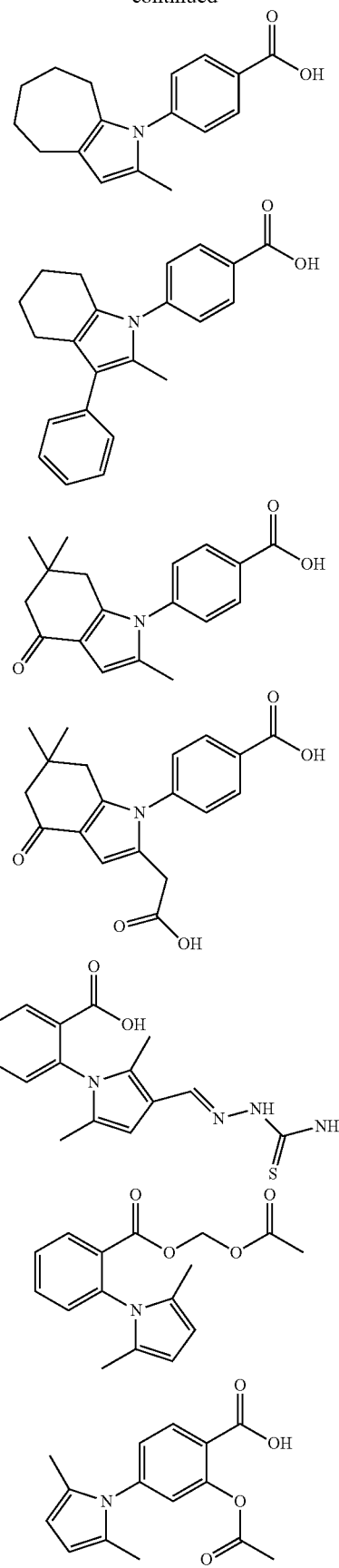
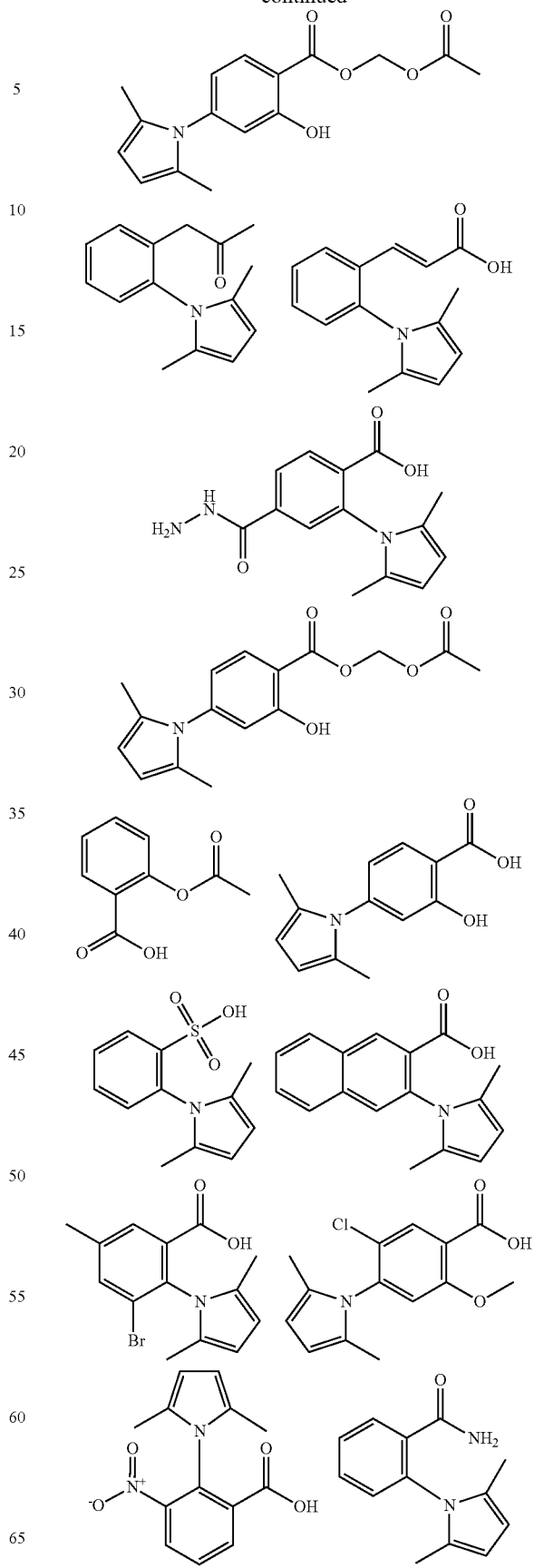

95
-continued
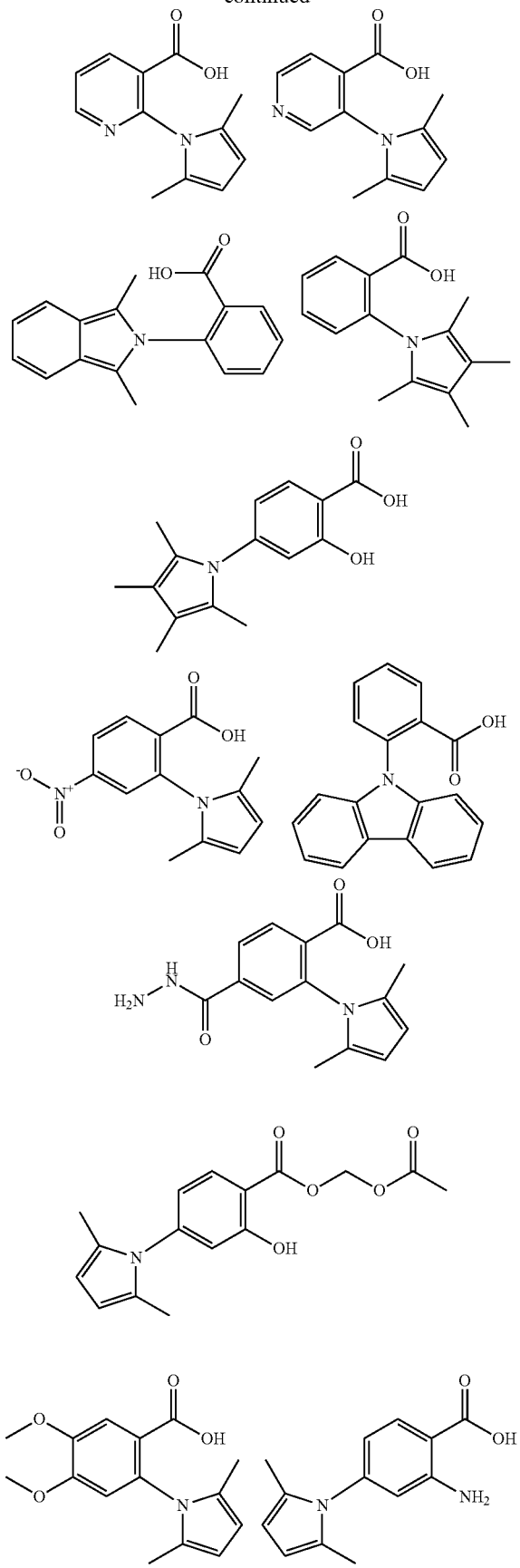
96
-continued
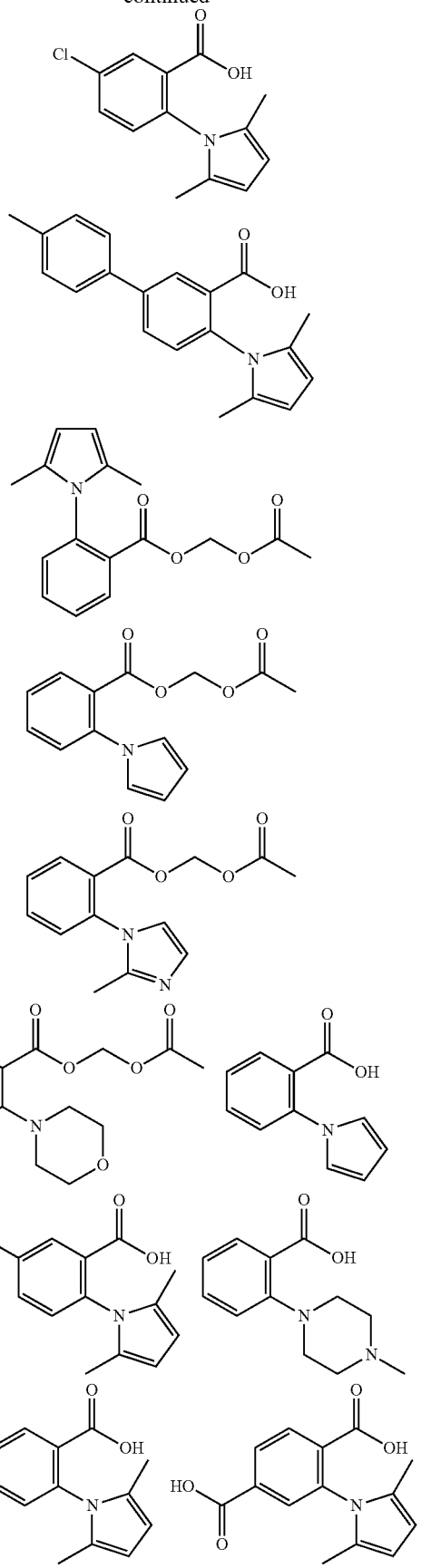

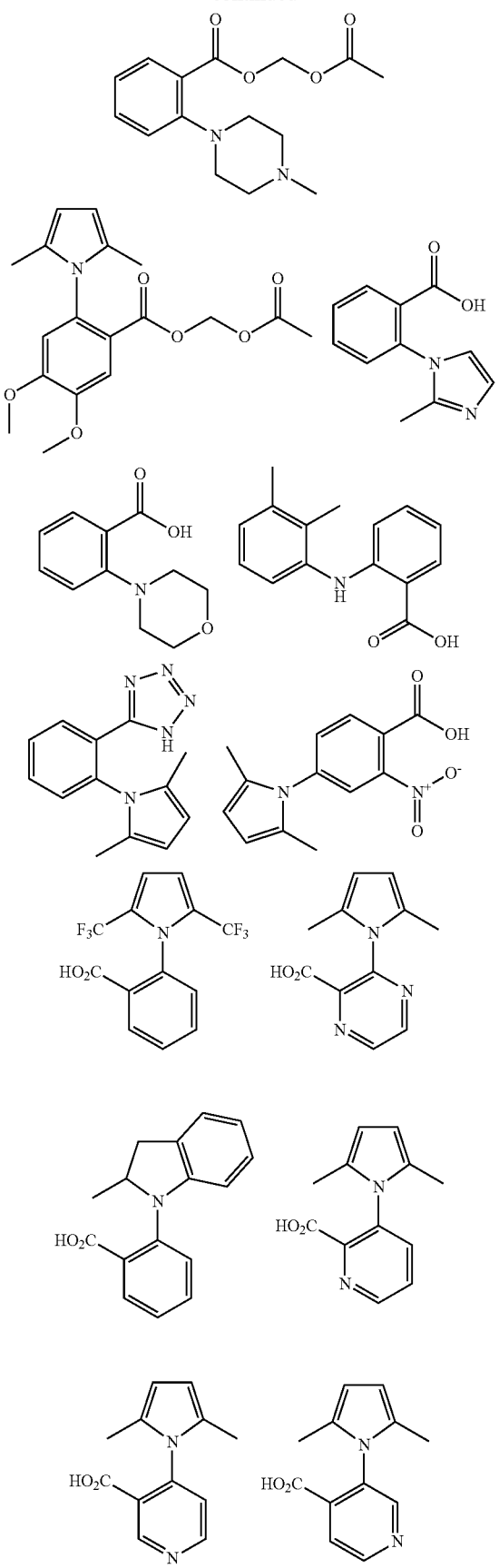
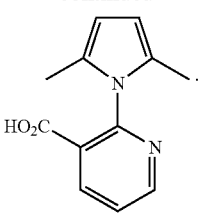
In some embodiments, the compound is not one of the following:

99
-continued
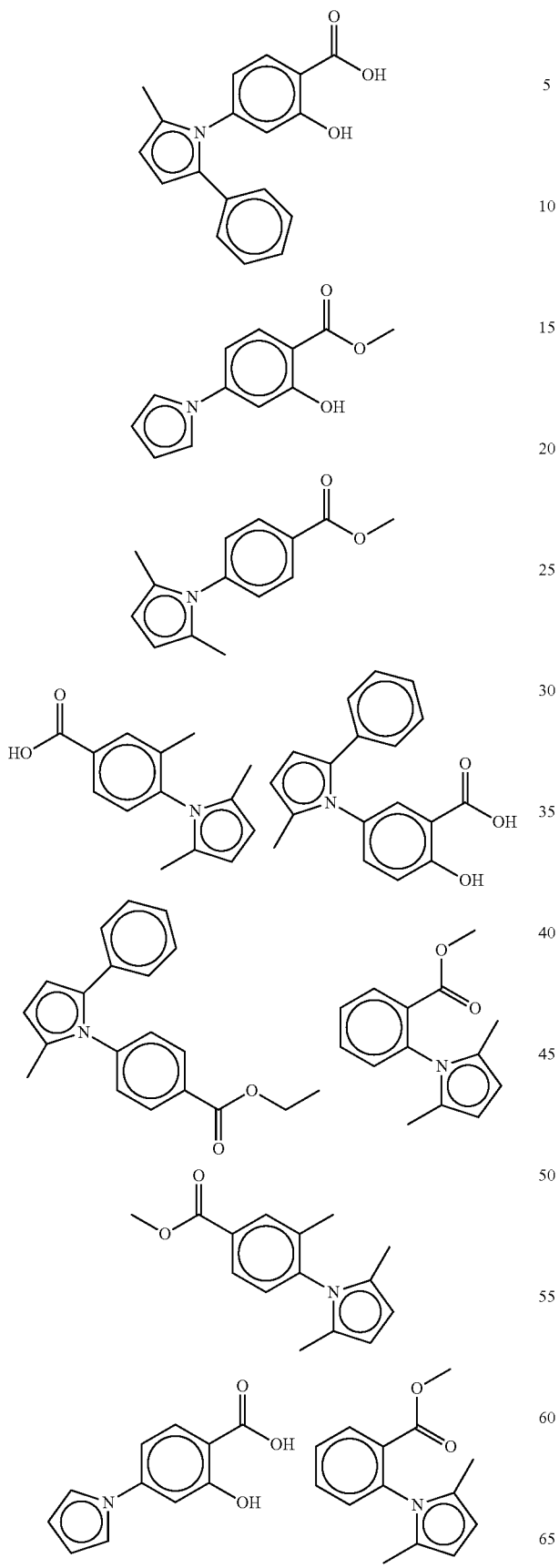
100
-continued
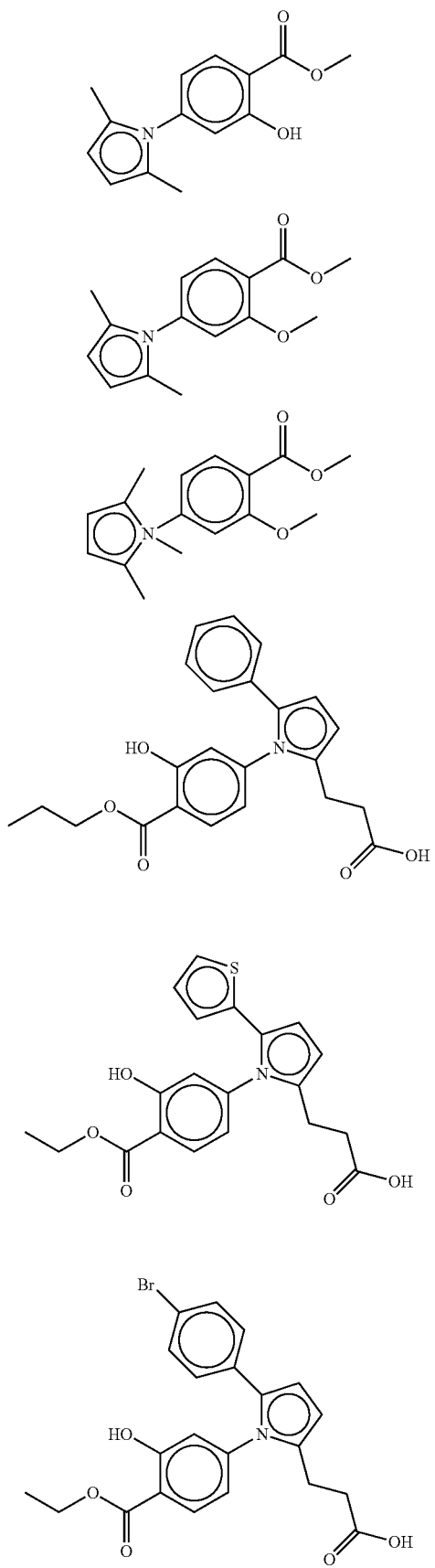

101
-continued
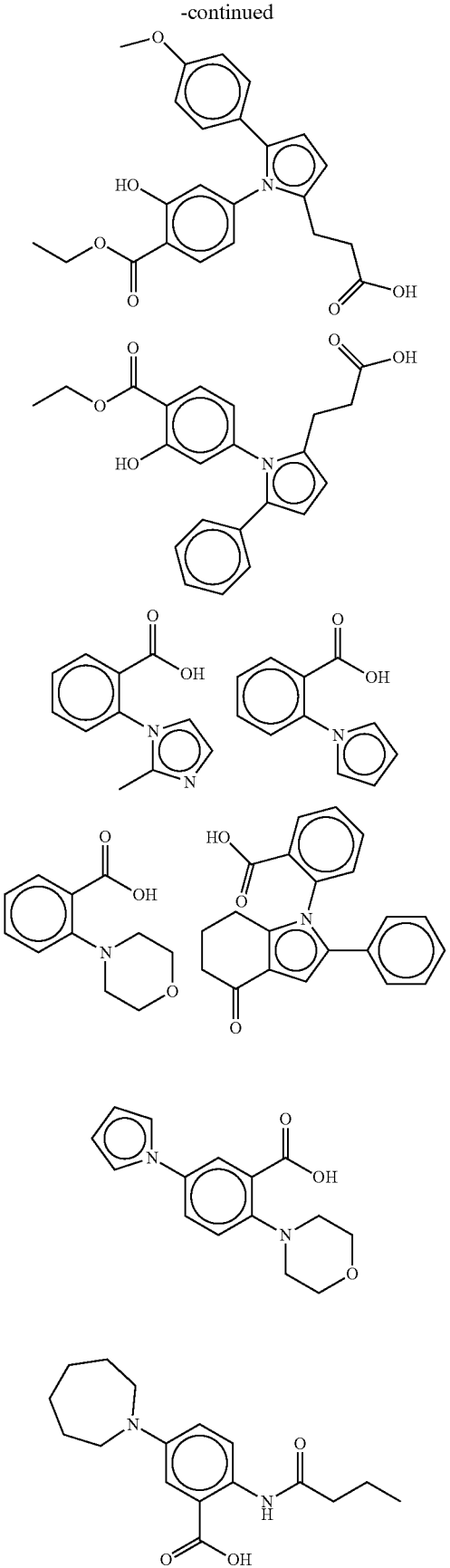
102
-continued
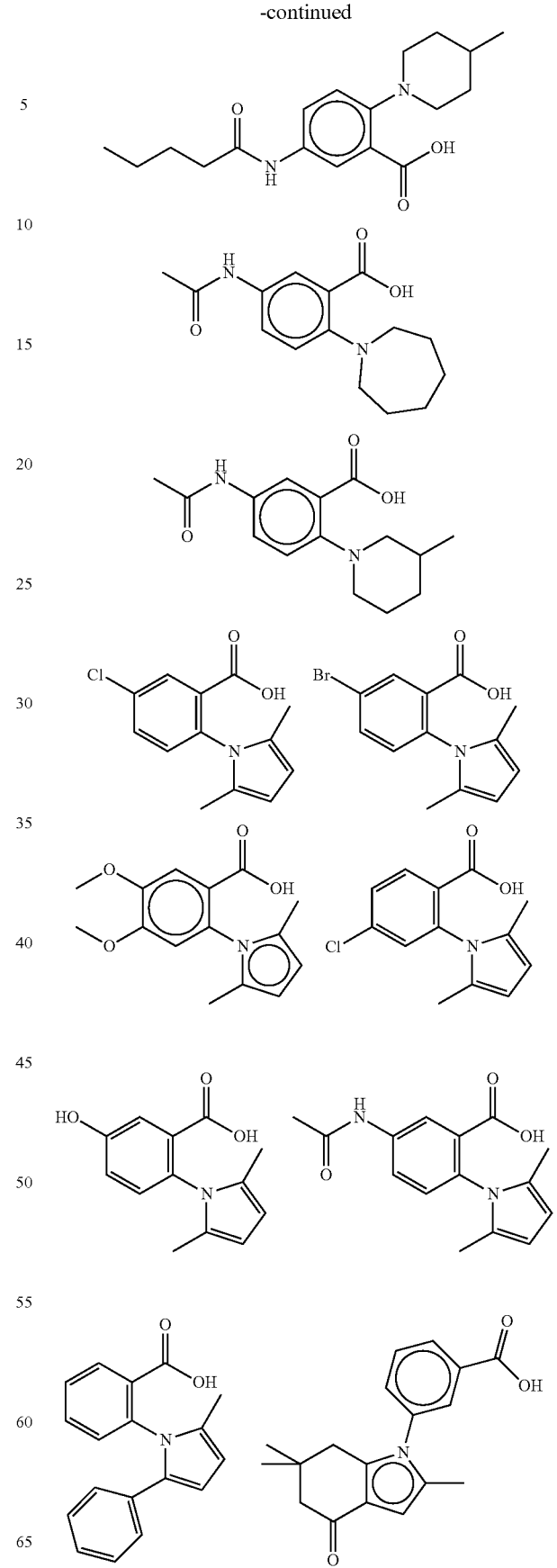

103
-continued
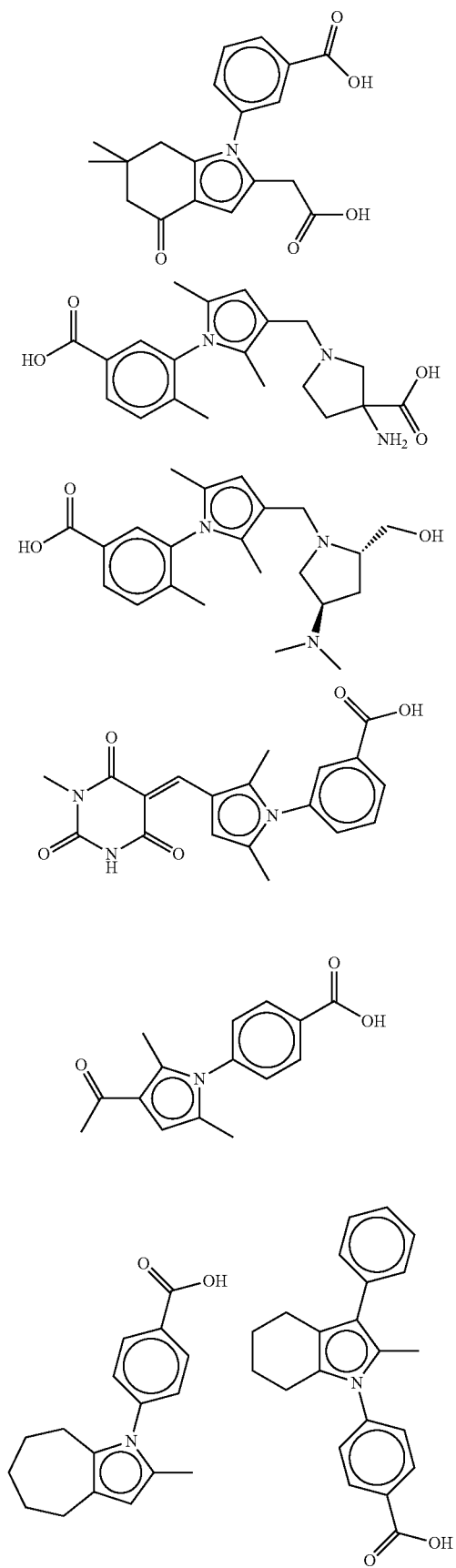
104
-continued
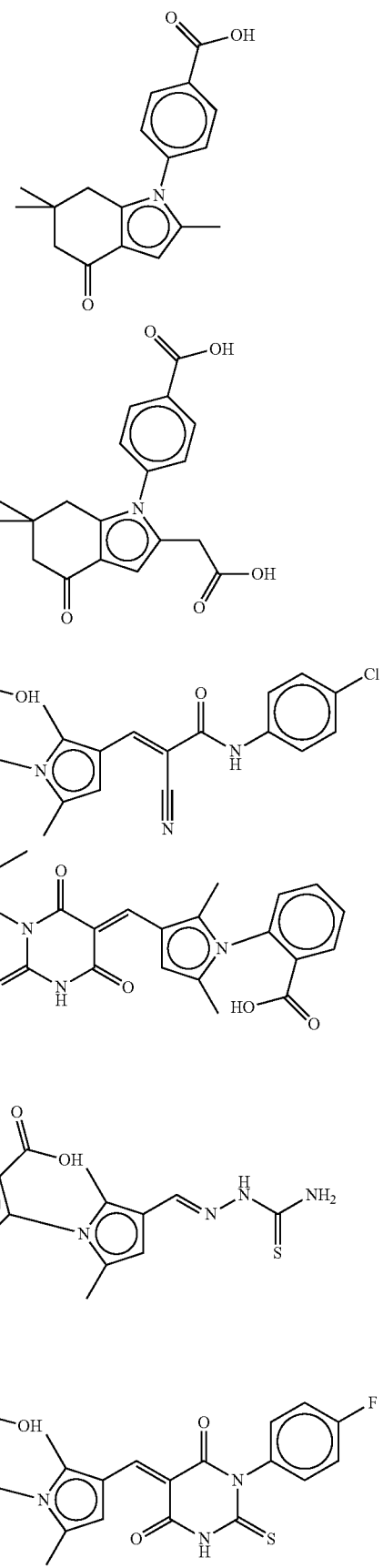

105
-continued

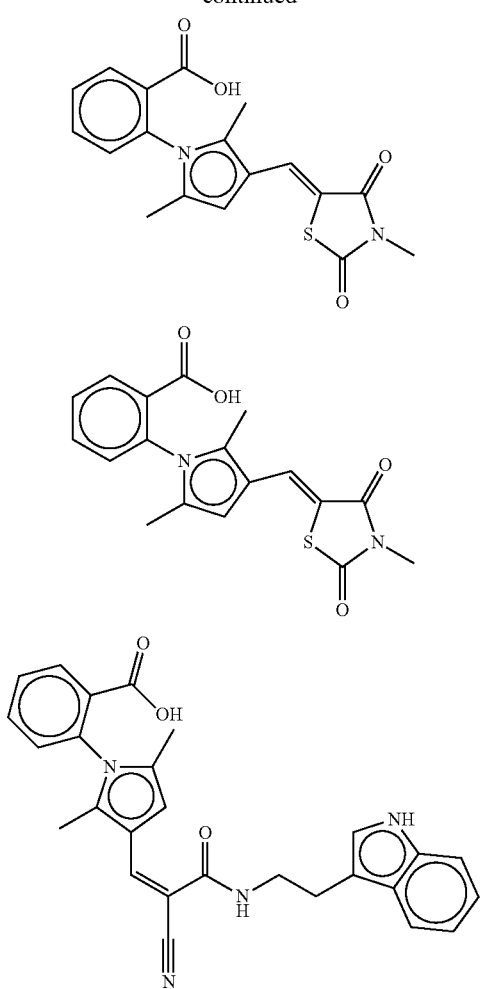

106
-continued

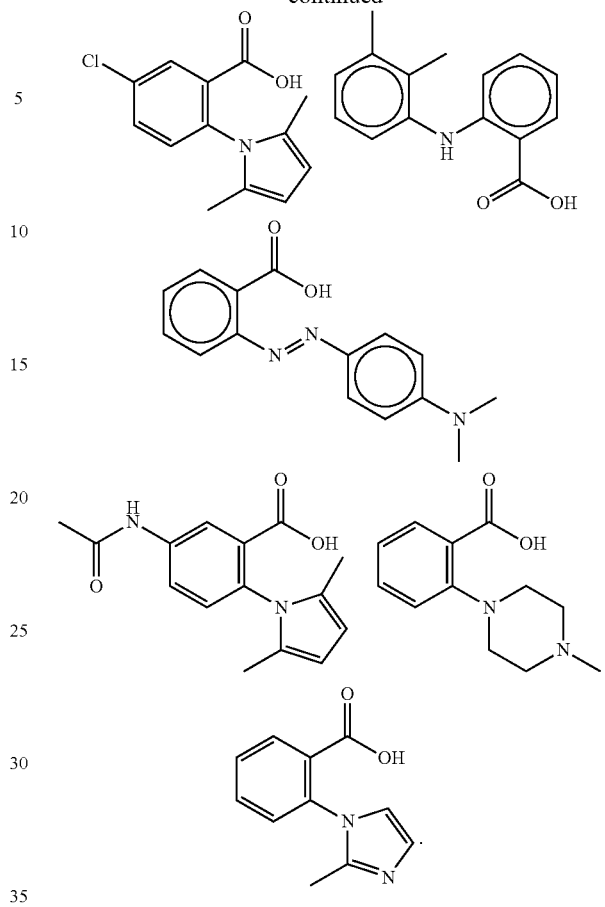

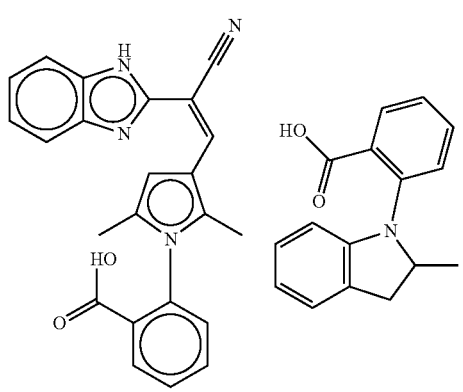

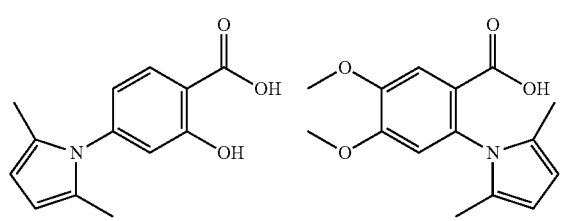

In certain embodiments, a provided compound inhibits Myc, or a mutant or variant thereof. In certain embodiments, a provided compound inhibits c-Myc. In certain embodiments, a provided compound inhibits 1-Myc. In certain embodiments, a provided compound inhibits n-Myc. In certain embodiments, a provided compound inhibits Myc (e.g., c-Myc), e.g., as measured in an assay described herein. In certain embodiments, a provided compound inhibits Myc (e.g., c-Myc) at an $IC_{50}$ less than or equal to 100 µM. In certain embodiments, a provided compound inhibits Myc at an $IC_{50}$ less than or equal to 50 µM. In certain embodiments, a provided compound inhibits Myc at an $IC_{50}$ less than or equal to 10 µM. In certain embodiments, a provided compound inhibits Myc at an $IC_{50}$ less than or equal to 0.5 µM. In certain embodiments, a provided compound inhibits Myc at an $IC_{50}$ less than or equal to 0.1 µM.

Compounds as Research Tools

In some embodiments, the present invention provides compounds for use in investigating the role of Myc, e.g., c-Myc, in various cellular processes and the pathophysiology of various diseases and disorders. In certain embodiments, a provided tool compound is conjugated to a label that allows for capture, purification, imaging, and/or identification.

In certain embodiments, a compound of the present invention is of Formula (VII-A), (VII-B), or (VII-C):

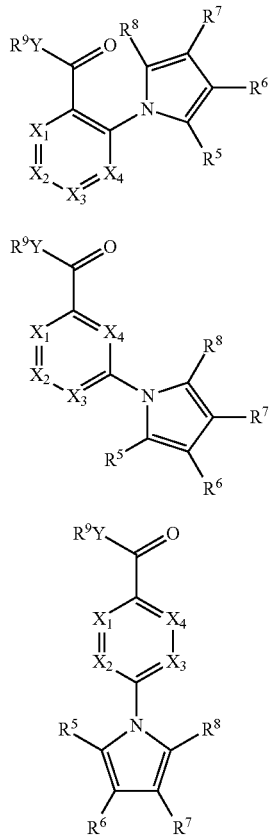

or a pharmaceutically acceptable salt thereof, wherein:
$X_1$ is $CR^1$ or N;
$X_2$ is $CR^2$ or N;
$X_3$ is $CR^3$ or N;
$X_4$ is $CR^4$ or N;
wherein no more than three of $X_1$, $X_2$, $X_3$, and $X_4$ are N;
Y is —O— or —S(=O)$_2$—N($R^N$)—;
$R^1$, $R^2$, $R^3$, and $R^4$ are independently selected from the group consisting of -L$_1$-Tag, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^B$ groups are taken together with their intervening atoms to form an optionally substituted heterocyclic ring;

$R^5$, $R^6$, $R^7$, and $R^8$ are independently selected from the group consisting of -L$_1$-Tag, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or $R^5$ and $R^6$ are taken together with their intervening atoms to form an optionally substituted, fused, partially unsaturated or aromatic ring having 0-3 heteroatoms independently selected from nitrogen, oxygen, and sulfur; or $R^6$ and $R^7$ are taken together with their intervening atoms to form an optionally substituted, fused, partially unsaturated or aromatic ring having 0-3 heteroatoms independently selected from nitrogen, oxygen, and sulfur; or $R^7$ and $R^8$ are taken together with their intervening atoms to form an optionally substituted, fused, partially unsaturated or aromatic ring having 0-3 heteroatoms independently selected from nitrogen, oxygen, and sulfur;

$R^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;

$R^N$ is hydrogen, optionally substituted alkyl, or a nitrogen protecting group;

each L$_1$ is independently an optionally substituted, straight or branched, C$_{1-40}$ alkylene, C$_{2-40}$ alkenylene, or C$_{2-40}$ alkynylene chain wherein one, two, three, four, five, six, seven, eight, nine, or ten methylene units of L$_1$ are optionally and independently replaced by —O—, —S—, —N(R")—, —C(O)—, —C(O)N(R")—, —N(R")C(O)N(R")—, —N(R")C(O)—, —N(R")C(O)O—, —OC(O)N(R")—, —SO$_2$—, —SO$_2$N(R")—, —N(R")SO$_2$—, —OC(O)—, —C(O)O—, —C(O)N(R")N=C(R''')—, an optionally substituted 3-7 membered cycloalkylene, an optionally substituted 4-7 membered heterocyclylene, an optionally substituted 5-6 membered heteroarylene, or an optionally substituted phenylene;

each R" is independently hydrogen, optionally substituted C$_{1-6}$ alkyl, optionally substituted C$_{2-6}$ alkenyl, or optionally substituted C$_{2-6}$ alkynyl;

each R''' is independently hydrogen, optionally substituted alkyl, optionally substituted alkenyl, optionally substituted alkynyl, or an optionally substituted, monocyclic or bicyclic, saturated, partially unsaturated, or aromatic ring having 0-4 heteroatoms independently selected from nitrogen, oxygen, and sulfur; and Tag is a label;

wherein at least one of $R^1$, $R^2$, $R^3$, $R^4$, $R^5$, $R^6$, $R^7$, and $R^8$ is -L$_i$-Tag.

In certain embodiments, a compound of the present invention is of Formula (VII-a), (VII-b), or (VII-c):

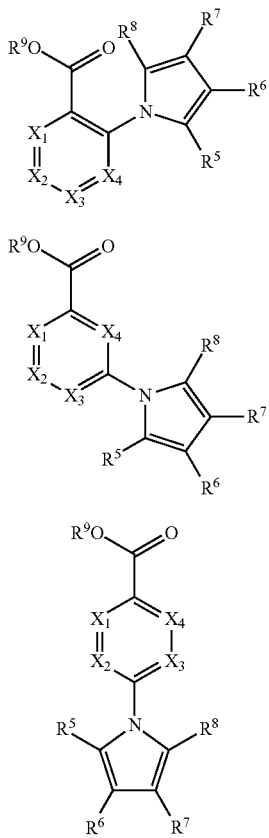

VII-a

VII-b

VII-c or a pharmaceutically acceptable salt thereof,
wherein
$X_1$ is $CR^1$ or N;
$X_2$ is $CR^2$ or N;
$X_3$ is $CR^3$ or N;
$X_4$ is $CR^4$ or N;
wherein no more than three of $X_1$, $X_2$, $X_3$, and $X_4$ are N;
$R^1$, $R^2$, $R^3$, and $R^4$ are independently selected from the group consisting of -$L_1$-Tag, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^B$ groups are taken together with their intervening atoms to form an optionally substituted heterocyclic ring;

$R^5$, $R^6$, $R^7$, and $R^8$ are independently selected from the group consisting of -$L_1$-Tag, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or R$^5$ and R$^6$ are taken together with their intervening atoms to form an optionally substituted, fused, partially unsaturated or aromatic ring having 0-3 heteroatoms independently selected from nitrogen, oxygen, and sulfur; or R$^6$ and R$^7$ are taken together with their intervening atoms to form an optionally substituted, fused, partially unsaturated or aromatic ring having 0-3 heteroatoms independently selected from nitrogen, oxygen, and sulfur; or R$^7$ and R$^8$ are taken together with their intervening atoms to form an optionally substituted, fused, partially unsaturated or aromatic ring having 0-3 heteroatoms independently selected from nitrogen, oxygen, and sulfur;

$R^9$ is hydrogen, optionally substituted alkyl, optionally substituted alkenyl, optionally substituted alkynyl, or an oxygen protecting group;

each $L_1$ is independently an optionally substituted, straight or branched, $C_{1-40}$ alkylene, $C_{2-40}$ alkenylene, or $C_{2-40}$ alkynylene chain wherein one, two, three, four, five, six, seven, eight, nine, or ten methylene units of $L_1$ are optionally and independently replaced by —O—, —S—, —N(R")—, —C(O)—, —C(O)N(R")—, —N(R")C(O)N(R")—, —N(R")C(O)—, —N(R")C(O)O—, —OC(O)N(R")—, —SO$_2$—, —SO$_2$N(R")—, —N(R")SO$_2$—, —OC(O)—, —C(O)O—, —C(O)N(R")N=C(R'")—, an optionally substituted 3-7 membered cycloalkylene, an optionally substituted 4-7 membered heterocyclylene, an optionally substituted 5-6 membered heteroarylene, or an optionally substituted phenylene;

each R" is independently hydrogen, optionally substituted $C_{1-6}$ alkyl, optionally substituted $C_{2-6}$ alkenyl, or optionally substituted $C_{2-6}$ alkynyl;

each R'" is independently hydrogen, optionally substituted alkyl, optionally substituted alkenyl, optionally substituted alkynyl, or an optionally substituted, monocyclic or bicyclic, saturated, partially unsaturated, or aromatic ring having 0-4 heteroatoms independently selected from nitrogen, oxygen, and sulfur; and Tag is a label;
wherein at least one of R$^1$, R$^2$, R$^3$, R$^4$, R$^5$, R$^6$, R$^7$, and R$^8$ is -$L_1$-Tag.

Embodiments of $X_1$, $X_2$, $X_3$, $X_4$, R$^1$, R$^2$, R$^3$, R$^4$, R$^5$, R$^6$, R$^7$, R$^8$, and R$^9$ are described herein.

As described generally above, each $L_1$ is independently an optionally substituted, straight or branched, $C_{1-40}$ alkylene, $C_{2-40}$ alkenylene, or $C_{2-40}$ alkynylene chain wherein one, two, three, four, five, six, seven, eight, nine, or ten methylene units of $L_1$ are optionally and independently replaced by —O—, —S—, —N(R")—, —C(O)—, —C(O)N(R")—, —N(R")C(O)N(R")—, —N(R")C(O)—, —N(R")C(O)O—, —OC(O)N(R")—, —SO$_2$—, —SO$_2$N(R")—, —N(R")SO$_2$—, —OC(O)—, —C(O)O—, —C(O)N(R")N=C(R'")—, an optionally substituted 3-7 membered cycloalkylene, an optionally substituted 4-7 membered heterocyclylene, an optionally substituted 5-6 membered heteroarylene, or an optionally substituted phenylene.

In certain embodiments, each $L_1$ is independently an optionally substituted, straight or branched, $C_{10\text{-}40}$ alkylene, alkenylene, or alkynylene chain wherein one, two, three, four, five, six, seven, eight, nine, or ten methylene units of $L_1$ are optionally and independently replaced by —O—, —S—, —N(R")—, —C(O)—, —C(O)N(R")—, —N(R")C(O)N(R")—, —N(R")C(O)—, —N(R")C(O)O—, —OC(O)N(R")—, —SO$_2$—, —SO$_2$N(R")—, —N(R")SO$_2$—, —OC(O)—, —C(O)O—, —C(O)N(R")N=C(R''')—, an optionally substituted 3-7 membered cycloalkylene, an optionally substituted 4-7 membered heterocyclylene, an optionally substituted 5-6 membered heteroarylene, or an optionally substituted phenylene.

In certain embodiments, each $L_1$ is independently an optionally substituted, straight or branched, $C_{20\text{-}40}$ alkylene, alkenylene, or alkynylene chain wherein one, two, three, four, five, six, seven, eight, nine, or ten methylene units of $L_1$ are optionally and independently replaced by —O—, —S—, —N(R")—, —C(O)—, —C(O)N(R")—, —N(R")C(O)N(R")—, —N(R")C(O)—, —N(R")C(O)O—, —OC(O)N(R")—, —SO$_2$—, —SO$_2$N(R")—, —N(R")SO$_2$—, —OC(O)—, —C(O)O—, —C(O)N(R")N=C(R''')—, an optionally substituted 3-7 membered cycloalkylene, an optionally substituted 4-7 membered heterocyclylene, an optionally substituted 5-6 membered heteroarylene, or an optionally substituted phenylene.

In certain embodiments, each $L_1$ is independently an optionally substituted, straight or branched, $C_{1\text{-}10}$alkylene, $C_{2\text{-}10}$ alkenylene, or $C_{2\text{-}10}$ alkynylene chain wherein one, two, three, four, or five methylene units of $L_1$ are optionally and independently replaced by —O—, —S—, —N(R")—, —C(O)—, —C(O)N(R")—, —N(R")C(O)N(R")—, —N(R")C(O)—, —N(R")C(O)O—, —OC(O)N(R")—, —SO$_2$—, —SO$_2$N(R")—, —N(R")SO$_2$—, —OC(O)—, —C(O)O—, —C(O)N(R")N=C(R''')—, an optionally substituted 3-7 membered cycloalkylene, an optionally substituted 4-7 membered heterocyclylene, an optionally substituted 5-6 membered heteroarylene, or an optionally substituted phenylene.

In some embodiments, $L_1$ comprises ethylene glycol units. In some embodiments, $L_1$ comprises A label may be directly detectable (i.e., it does not require any further reaction or manipulation to be detectable, e.g., a fluorophore or chromophore is directly detectable) or it may be indirectly detectable (i.e., it is made detectable through reaction with or binding to another entity that is detectable, e.g., a hapten is detectable by immunostaining after reaction with an appropriate antibody comprising a reporter such as a fluorophore). Labels suitable for use in the present invention may be detectable by any of a variety of means including, but not limited to, spectroscopic, photochemical, biochemical, immunochemical, electrical, optical, or chemical means. Suitable labels include, but are not limited to, affinity tags, radionuclides (such as, for example, $^{32}$P, $^{35}$S, $^{3}$H, $^{14}$C, $^{125}$I, $^{131}$I, and the like), fluorescent dyes, phosphorescent dyes, chemiluminescent agents (such as, for example, acridinium esters, stabilized dioxetanes, and the like), spectrally resolvable inorganic fluorescent semiconductor nanocrystals (i.e., quantum dots), metal nanoparticles (e.g., gold, silver, copper, and platinum) or nanoclusters, enzymes (such as, for example, those used in an ELISA, i.e., horseradish peroxidase, beta-galactosidase, luciferase, alkaline phosphatase), colorimetric labels (such as, for example, dyes, colloidal gold, and the like), magnetic labels (such as, for example, Dynabeads™), and haptens.

In certain embodiments, the label comprises a fluorescent moiety. Numerous known fluorescent labeling moieties of a wide variety of chemical structures and physical characteristics are suitable for use in the practice of the present invention. Suitable fluorescent dyes include, but are not limited to, fluorescein and fluorescein dyes (e.g., fluorescein isothiocyanine (FITC), naphthofluorescein, 4',5'-dichloro-2', 7'-dimethoxy-fluorescein, 6-carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500,

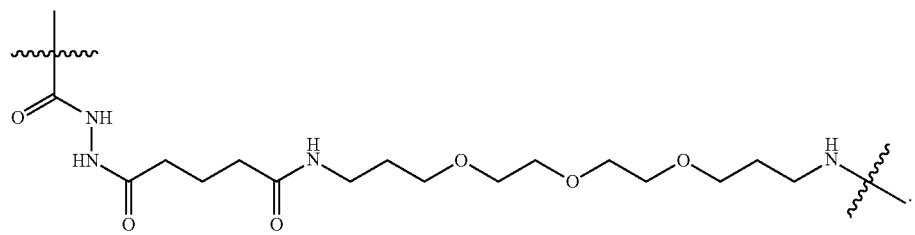 [SMILES: *NCCCOCCOCCOCCCNC(=O)CCCC(=O)NNC(*)=O]

In some embodiments, $L_1$ comprises

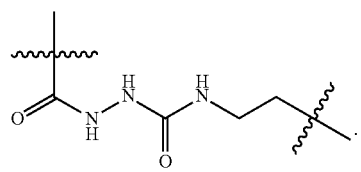 [SMILES: *CCNC(=O)NNC(*)=O]

As described generally above, Tag is a label. The term "label" includes any moiety that allows the compound to which it is attached to be captured, detected, or visualized.

Oregon Green 514), Texas Red, Texas Red-X, Spectrum Red™, Spectrum Green™, cyanine dyes (e.g. Cy-3™, Cy-5™, Cy-3.5™, Cy-5.5™), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R$^6$G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for coupling fluorescent dyes to other chemical entities see, for example, *The Handbook of Fluorescent Probes and Research Products*, 9th Ed., Molecular Probes, Inc., Eugene, Oreg.

The term "luminescence" or "luminescent" means any process of light emission including fluorescence, phosphorescence, scintillation, chemiluminescence, and bioluminescence.

The term "chemiluminescence," "chemiluminescent," or "chemiluminescent substrate" refers to a chemical that produces light as a result of a chemical reaction. Commonly used chemiluminescent substrates include, but are not limited to, luminol (5-amino-2,3-dihydro-1,4-phthalazinedione), lophine (2,4,5-triphenylimidazole), lucigenin (bis-N-methylacridinium), other acridinium esters, luciferin-luciferase, and thioxene derivatives. For example, in the art-recognized ECL™ detection system of Amersham, an acridinium substrate is oxidized by horse radish peroxidase to produce acridinium esters, which react with excess peroxide at an alkaline pH to produce visible chemiluminescence at 430 nm.

In certain embodiments, the label comprises an affinity tag. The term "affinity tag" includes any moiety that takes part in an interaction (e.g., antigen and antibody, enzyme and substrate, receptor and ligand) that facilitates capture and/or purification of the molecule. Examples of such affinity moieties include small chemical compounds (such as biotin and derivatives thereof), short amino acid sequences (e.g., 2 to 20 amino acids in length, 4 to 12 amino acids in length), such as the $(His)_6$ tag, $(Leu)_3$ tag, or FLAG tag. The affinity moiety may also be a fluorous tag, which is a fluorinated alkyl group (e.g., perfluoroalkyl) that allows for recovery of the molecule via its interaction with a fluorous phase (e.g., a fluorous liquid phase, a fluorous solid phase). Other affinity moieties are well known in the art.

In certain embodiments, the affinity moiety is selected from the group consisting of $(His)_6$ tag, $(His)_4$ tag, $(His)_3$ tag, $(His)_2$ tag, $(Leu)_4$ tag, $(Leu)_3$ tag, $(Leu)_2$ tag, HA tag, FLAG tag, VSV-G tag, HSV tag, V5 tag, biotin and derivatives thereof, carbohydrates, and glycans. In certain embodiments, the affinity moiety is $C_4$-$C_{20}$ perfluoralkyl (e.g., $C_6$-$C_{12}$ perfluoroalkyl, $C_6$-$C_8$ perfluoroalkyl, $C_4$ perfluoralkyl, $C_5$ perfluoralkyl, $C_6$ perfluoralkyl, $C_7$ perfluoralkyl, $C_8$ perfluoralkyl, $C_9$ perfluoralkyl, $C_{10}$ perfluoralkyl, $C_{11}$ perfluoralkyl, $C_{12}$ perfluoralkyl, $C_{13}$ perfluoralkyl, $C_{14}$ perfluoralkyl, $C_{15}$ perfluoralkyl, $C_{16}$ perfluoralkyl, $C_{17}$ perfluoralkyl, $C_{18}$ perfluoralkyl, $C_{19}$ perfluoralkyl, or $C_{20}$ perfluoroalkyl). In certain embodiments, the affinity moiety is biotin. In certain embodiments, the affinity moiety is $C_8$ perfluoralkyl.

As described generally above, at least one of $R^1$, $R^2$, $R^3$, $R^4$, $R^5$, $R^6$, $R^7$, and $R^8$ is -$L_1$-Tag. In some embodiments, one of $R^1$, $R^2$, $R^3$, $R^4$, $R^5$, $R^6$, $R^7$, and $R^8$ is -$L_1$-Tag. In some embodiments, more than one of $R^1$, $R^2$, $R^3$, $R^4$, $R^5$, $R^6$, $R^7$, and $R^8$ is -$L_1$-Tag. In some embodiments, $R^1$ is -$L_1$-Tag. In some embodiments, $R^2$ is -$L_1$-Tag. In some embodiments, $R^3$ is -$L_1$-Tag. In some embodiments, $R^4$ is -$L_1$-Tag. In some embodiments, $R^5$ is -$L_1$-Tag. In some embodiments, $R^6$ is -$L_1$-Tag. In some embodiments, $R^7$ is -$L_1$-Tag. In some embodiments, $R^8$ is -$L_1$-Tag.

Exemplary compounds include the following:

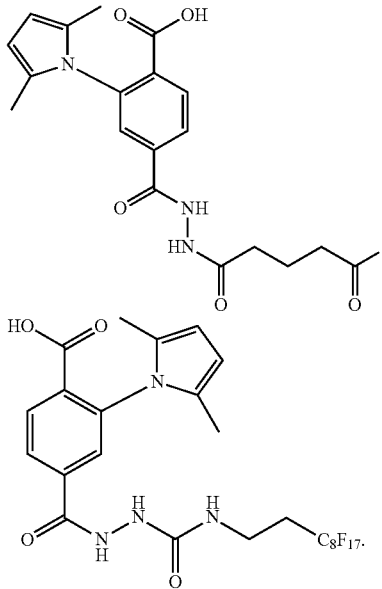
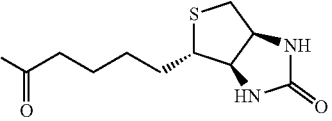

Pharmaceutical Compositions and Administration

The present invention provides pharmaceutical compositions comprising a compound described herein, e.g., a compound of formula I-A, I-B, I-C, I-a, I-b, or I-c, or a pharmaceutically acceptable salt thereof, as described herein, and optionally a pharmaceutically acceptable excipient. It will be understood by one of ordinary skill in the art that the compounds described herein, or salts thereof, may be present as hydrates, solvates, or polymorphs. In certain embodiments, the compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting the activity of Myc (e.g., c-Myc). In certain embodiments, the effective amount is an amount effective for treating a Myc-mediated disorder. In certain embodiments, the effective amount is a prophylactically effective amount. In certain embodiments, the effective amount is an amount effective to prevent a Myc-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. The term "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., *acacia*, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., *acacia*, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and *acacia*, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid composition to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate composition in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antimicrobial agents, antifungal agents, antiparasitic agents, anti-cancer agents, anti-inflammatory agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form.

Methods of Use and Treatment

Compounds and compositions described herein are generally useful for the inhibition of Myc. In some embodiments, compounds and compositions described herein are useful for inhibiting of the activity of c-Myc (e.g., inhibiting c-Myc transcriptional activity). In some embodiments, compounds and compositions described herein are useful for inhibiting 1-Myc. In some embodiments, compounds and compositions described herein are useful for inhibiting n-Myc. In one aspect, methods of treating Myc-mediated disorder in a subject are provided which comprise administering an effective amount of a compound described herein (e.g., a compound of formula I-A, I-B, I-C, I-a, I-b, or I-c), or a pharmaceutically acceptable salt thereof, or a composition thereof, to a subject in need of treatment. In certain embodiments, the effective amount is a therapeutically effective amount. In certain embodiments, the effective amount is a prophylactically effective amount. In certain embodiments, the subject is suffering from a Myc-mediated disorder (e.g., a proliferative disorder). In certain embodiments, the subject is susceptible to a Myc-mediated disorder.

The term "Myc-mediated disorder" (e.g., c-Myc-mediated disorder) means any disease, disorder, or other deleterious condition in which Myc (e.g., c-Myc), or a mutant thereof, is known to play a role. Accordingly, in some embodiments, the present invention relates to treating or lessening the severity of one or more diseases in which Myc is known to play a role. Examples of Myc-mediated diseases include, but are not limited to, a variety of oncogenic and proliferative diseases and disorders including various cancers and benign neoplasms, including but not limited to, leukemias, lymphomas, carcinomas, myelomas, and cardiovascular dieseases.

c-Myc and two of its relatives, n-Myc and 1-Myc, are known to contribute to a wide variety of human cancers. In these cancers, expression of Myc is enhanced relative to the surrounding or normal tissue, implying that there is a selective pressure for increased expression of Myc during cancer (e.g., tumor) development. For example, n-Myc is expressed in a subset of childhood neuroblastoma, correlating with extremely poor prognosis of the affected children (Brodeur et al., (1984) *Science,* 224, 1121-1124.). In other tumors, expression of Myc is increased because mutations occur in the signaling pathway that control its expression. One example includes mutations in the adenomatous polyposis *coli* (APC) pathway that affect c-Myc expression in colorectal carcinomas (van de Wetering et al., *Cell,* 111, 241-250 (2002)).

Elevated or deregulated expression of c-Myc has been detected in a wide range of human cancers and is often associated with aggressive, poorly differentiated tumors. Such cancers include breast, cervical, stomach, small cell lung carcinomas, osteosarcomas, glioblastomas, melanoma, lymphomas, and myeloid leukemias (Pelengaris et al., *Nat Rev Cancer* 2, 764-7 (2002)). c-Myc was first discovered in Burkitt's lymphoma.

Data suggest that even a brief inhibition of Myc expression may be sufficient to permanently stop tumor growth and induce regression of tumors. Jain et al. (*Science* 297, 102-4 (2002)) engineered a conditional transgenic mouse to overexpress Myc, which induced formation of a highly malignant osteogenic sarcoma. A brief loss of Myc overexpression caused the tumor cells to differentiate into mature osteocytes that formed histologically normal bone. Felsher and Bishop, (*Mol. Cell* 4, 199-207 (1999)) showed that transgenic-mice expressing the myc oncogene in hematopoietic cells developed malignant T-cell leukemias and acute myeloid leukemias. However, when this gene was switched off the leukemic cells underwent proliferative arrest, differentiation, and apoptosis. Pelengaris et al. (*Mol. Cell* 3, 565-77 (1999)) targeted expression of an inducible form of the c-Myc-protein to the epidermis of mice and observed formation of angiogenic premalignant skin lesions, which regressed when the c-Myc protein was deactivated.

However, one of ordinary skill in the art will appreciate that Myc (e.g. c-Myc) does not necessarily need to be overexpressed in order for a cancer to be highly dependent upon its activity. A study from Soucek et al. (*Nature* (2008) 455(7213):679-83) shows that tumors that express c-Myc at endogenous levels exhibit tumor regression upon Myc inhibition via a genetically engineered system. Accordingly, in some embodiments, treatment with a Myc inhibitor is not limited to cancers that overexpress Myc. However, in some embodiments, Myc overexpression is used to stratify patients for treatment.

Accordingly, in some embodiments, methods of treating a proliferative disease (e.g., cancer) in a subject are provided which comprise administering an effective amount of a compound described herein (e.g., a compound of formula I-A, I-B, I-C, I-a, I-b, or I-c), or a pharmaceutically acceptable salt thereof, or a composition thereof, to a subject in need of treatment. In certain embodiments, the effective amount is a therapeutically effective amount. In certain embodiments, the effective amount is a prophylactically effective amount. In certain embodiments, the subject is suffering from a proliferative disease (e.g., cancer). In certain embodiments, the subject is susceptible to a proliferative disease (e.g., cancer).

Exemplary proliferative diseases that may be treated with compounds and compositions described herein include cancers and benign neoplasms.

Examples of cancers that may be treated with compounds and compositions described herein include, but are not limited to, solid tumors and hematological cancers. Solid tumors are exemplified by tumors of the breast, bladder, bone, brain, central and peripheral nervous system, colon, connective tissue, endocrine glands (e.g., thyroid and adrenal cortex), esophagus, endometrium, germ cells, head and neck, kidney, liver, lung, larynx and hypopharynx, mesothelioma, muscle, ovary, pancreas, penis, prostate gland, rectum, renal, small intestine, soft tissue, testis, stomach, skin, ureter, vagina, and vulva. Also included are inherited cancers exemplified by retinoblastoma and Wilms' tumor. In addition, primary tumors in said organs are included as well as corresponding secondary tumors in distant organs ("tumor metastases"). In certain embodiments, the cancer that may be treated with compounds and compositions described herein is lung cancer. In certain embodiments, the cancer that may be treated with compounds and compositions described herein is non-small cell lung cancer. Hematological cancers are exemplified by aggressive and indolent forms of leukemia and lymphoma, namely non-Hodgkin's disease, chronic and acute myeloid leukemia (CML/AML), acute lymphoblastic leukemia (ALL), chronic lymphocytic leukemia (CLL), Hodgkin's disease, non-Hodgkin's lymphoma, Burkitt's lymphoma, multiple myeloma, and T-cell lymphoma. Also included are myelodysplastic syndrome, plasma cell neoplasia, paraneoplastic syndromes, cancers of unknown primary site as well as AIDS-related malignancies. In certain embodiments, the cancer that may be treated with compounds and compositions described herein is leukemia. In certain embodiments, the cancer that may be treated with compounds and compositions described herein is AML. In certain embodiments, the cancer that may be treated with compounds and compositions described herein is acute promyelocytic leukemia. In certain embodiments, the cancer that may be treated with compounds and compositions described herein is lymphoma. In certain embodiments, the cancer that may be treated with compounds and compositions described herein is non-Hodgkin lymphoma. In certain embodiments, the cancer that may be treated with compounds and compositions described herein is Burkitt's lymphoma. In certain embodiments, the cancer that may be treated with compounds and compositions described herein is myeloma. In certain embodiments, the cancer that may be treated with compounds and compositions described herein is multiple myeloma.

It will also be appreciated that a cancer as a life-threatening disease process does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Examples of benign neoplasms that may be treated with compounds and compositions described herein include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In some embodiments, the present invention further provides methods of inhibiting Myc comprising contacting Myc with an effective amount of a compound described herein (e.g., a compound of Formula I-A, I-B, I-C, I-a, I-b, or I-c), or a pharmaceutically acceptable salt thereof. In some embodiments, the present disclosure provides methods of inhibiting c-Myc comprising contacting c-Myc with an effective amount of a compound described herein (e.g., a compound of Formula I-A, I-B, I-C, I-a, I-b, or I-c), or a pharmaceutically acceptable salt thereof. In some embodiments, the present invention provides methods of inhibiting l-Myc comprising contacting l-Myc with an effective amount of a compound described herein (e.g., a compound of Formula I-A, I-B, I-C, I-a, I-b, or I-c), or a pharmaceutically acceptable salt thereof. In some embodiments, the present invention provides methods of inhibiting n-Myc comprising contacting n-Myc with an effective amount of a compound described herein (e.g., a compound of Formula I-A, I-B, I-C, I-a, I-b, or I-c), or a pharmaceutically acceptable salt thereof. The Myc may be purified or crude, and may be present in a cell, tissue, or subject. Thus, such methods encompasses both inhibition of in vitro and in vivo activity. In certain embodiments, the method is an in vitro method, e.g., such as an assay method useful as a research tool.

In some embodiments, provided are methods of inhibiting Myc activity in a subject in need thereof (e.g., having a higher Myc activity than normal) comprising administering to the subject an effective amount of a compound described herein (e.g., a compound of Formula I-A, I-B, I-C, I-a, I-b, or I-c), or a pharmaceutically acceptable salt thereof. In some embodiments, provided is a method of inhibiting c-Myc activity in a subject in need thereof (e.g., having a higher c-Myc activity than normal) comprising administering to the subject an effective amount of a compound described herein (e.g., a compound of Formula I-A, I-B, I-C, I-a, I-b, or I-c), or a pharmaceutically acceptable salt thereof.

In some embodiments, provided are methods of cleaving caspase in a subject in need thereof comprising administering to the subject an effective amount of a compound described herein (e.g., a compound of Formula I-A, I-B, I-C, I-a, I-b, or I-c), or a pharmaceutically acceptable salt thereof. In some embodiments, provided are methods of inducing apoptosis in a subject in need thereof comprising administering to the subject an effective amount of a compound described herein (e.g., a compound of Formula I-A, I-B, I-C, I-a, I-b, or I-c), or a pharmaceutically acceptable salt thereof.

In some embodiments, provided are methods of inhibiting gene transcription in a subject in need thereof comprising administering to the subject an effective amount of a compound described herein (e.g., a compound of Formula I-A, I-B, I-C, I-a, I-b, or I-c), or a pharmaceutically acceptable salt thereof. In some embodiments, provided are methods of inhibiting cell proliferation in a subject in need thereof comprising administering to the subject an effective amount of a compound described herein (e.g., a compound of Formula I-A, I-B, I-C, I-a, I-b, or I-c), or a pharmaceutically acceptable salt thereof.

In some embodiments, methods described herein (e.g., methods of inhibiting Myc in vitro or in vivo, methods of inhibiting Myc activity in a subject, methods of treating a proliferative disease, methods of cleaving caspase, methods of inducing apoptosis, methods of inhibiting gene transcription, or methods of inhibiting cell proliferation) are carried out with a compound of formula:

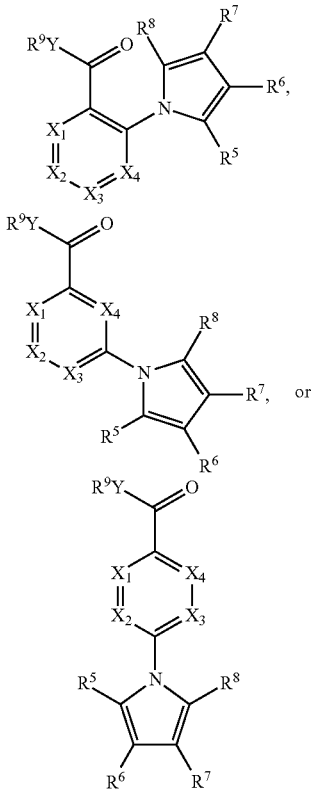

or a pharmaceutically acceptable salt thereof, wherein:
$X_1$ is $CR^1$ or N;
$X_2$ is $CR^2$ or N;
$X_3$ is $CR^3$ or N;
$X_4$ is $CR^4$ or N;
Y is —O— or —S(=O)$_2$—N($R^N$)—;
wherein no more than three of $X_1$, $X_2$, $X_3$, and $X_4$ are N;
$R^1$, $R^2$, $R^3$, and $R^4$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each $R^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^B$ groups are taken together with their intervening atoms to form an optionally substituted heterocyclic ring;

$R^5$, $R^6$, $R^7$, and $R^8$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or $R^5$ and $R^6$ are taken together with their intervening atoms to form an optionally substituted, fused, partially unsaturated or aromatic ring having 0-3 heteroatoms independently selected from nitrogen, oxygen, and sulfur; or $R^6$ and $R^7$ are taken together with their intervening atoms to form an optionally substituted, fused, partially unsaturated or aromatic ring having 0-3 heteroatoms independently selected from nitrogen, oxygen, and sulfur; or $R^7$ and $R^8$ are taken together with their intervening atoms to form an optionally substituted, fused, partially unsaturated or aromatic ring having 0-3 heteroatoms independently selected from nitrogen, oxygen, and sulfur;

$R^9$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group when attached to an oxygen atom;

$R^N$ is hydrogen, optionally substituted alkyl, or a nitrogen protecting group;

each L is independently a bond, —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, an optionally substituted phenylene, or an optionally substituted, straight or branched, $C_{1-6}$ alkylene, $C_{2-6}$ alkenylene, or $C_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocylylene, an optionally substituted 5-6 membered heteroarylene, or an optionally substituted phenylene;

each R is independently hydrogen, optionally substituted $C_{1-6}$ alkyl, optionally substituted $C_{2-6}$ alkenyl, or optionally substituted $C_{2-6}$ alkynyl, or R and an optional substituent on Cy are taken together with their intervening atoms to form a 5-6 membered heterocyclic fused ring;

each R' is independently hydrogen, optionally substituted alkyl, optionally substituted alkenyl, optionally substituted alkynyl, or an optionally substituted, monocyclic or bicyclic, saturated, partially unsaturated, or aromatic ring having 0-4 heteroatoms independently selected from nitrogen, oxygen, and sulfur, or R' and an optional substituent on Cy are taken together with their intervening atoms to form a 5-6 membered carbocyclic or heterocyclic fused ring;

each Z is independently optionally substituted alkyl, optionally substituted alkenyl, optionally substituted alkynyl, or Cy; and each Cy is independently an optionally substituted, monocyclic or bicyclic, saturated, partially unsaturated, or aromatic ring having 0-4 heteroatoms independently selected from nitrogen, oxygen, and sulfur.

In some embodiments, methods described herein (e.g., methods of inhibiting Myc in vitro or in vivo, methods of inhibiting Myc activity in a subject, methods of treating a proliferative disease, methods of cleaving caspase, methods of inducing apoptosis, methods of inhibiting gene transcription, or methods of inhibiting cell proliferation) are carried out with a compound of formula:

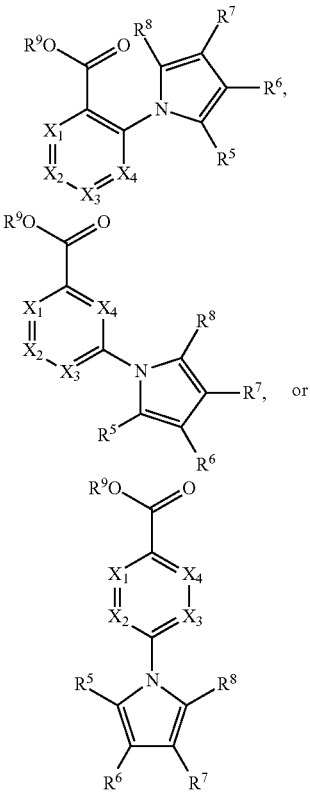

or a pharmaceutically acceptable salt thereof, wherein:
$X_1$ is $CR^1$ or N;
$X_2$ is $CR^2$ or N;
$X_3$ is $CR^3$ or N;
$X_4$ is $CR^4$ or N;
wherein no more than three of $X_1$, $X_2$, $X_3$, and $X_4$ are N;
$R^1$, $R^2$, $R^3$, and $R^4$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each R$^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two R$^B$ groups are taken together with their intervening atoms to form an optionally substituted heterocyclic ring;

$R^5$, $R^6$, $R^7$, and $R^8$ are independently selected from the group consisting of -L-Z, hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; or $R^5$ and $R^6$ are taken together with their intervening atoms to form an optionally substituted, fused, partially unsaturated or aromatic ring having 0-3 heteroatoms independently selected from nitrogen, oxygen, and sulfur; or $R^6$ and $R^7$ are taken together with their intervening atoms to form an optionally substituted, fused, partially unsaturated or aromatic ring having 0-3 heteroatoms independently selected from nitrogen, oxygen, and sulfur; or $R^7$ and $R^8$ are taken together with their intervening atoms to form an optionally substituted, fused, partially unsaturated or aromatic ring having 0-3 heteroatoms independently selected from nitrogen, oxygen, and sulfur;

$R^9$ is hydrogen, optionally substituted alkyl, optionally substituted alkenyl, optionally substituted alkynyl, or an oxygen protecting group;

each L is independently a bond, —O—, —S—, —N(R)—, —C(O)—, —C(O)N(R)—, —N(R)C(O)N(R)—, —N(R)C(O)—, —N(R)C(O)O—, —OC(O)N(R)—, —SO$_2$—, —SO$_2$N(R)—, —N(R)SO$_2$—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, an optionally substituted phenylene, or an optionally substituted, straight or branched, $C_{1-6}$ alkylene, $C_{2-6}$ alkenylene, or $C_{2-6}$ alkynylene chain, wherein one, two, or three methylene units of L are optionally and independently replaced by —O—, —S—, —N(R)—, —C(O)—, —C(O)N(R)—, —N(R)C(O)N(R)—, —N(R)C(O)—, —N(R)C(O)O—, —OC(O)N(R)—, —SO₂—, —SO₂N(R)—, —N(R)SO₂—, —OC(O)—, —C(O)O—, —C(O)N(R)N=C(R')—, an optionally substituted 3-7 membered cycloalkylene, an optionally substituted 4-7 membered heterocyclylene, an optionally substituted 5-6 membered heteroarylene, or an optionally substituted phenylene;

each R is independently hydrogen, optionally substituted $C_{1-6}$ alkyl, optionally substituted $C_{2-6}$ alkenyl, or optionally substituted $C_{2-6}$ alkynyl, or R and an optional substituent on Cy are taken together with their intervening atoms to form a 5-6 membered heterocyclic fused ring;

each R' is independently hydrogen, optionally substituted alkyl, optionally substituted alkenyl, optionally substituted alkynyl, or an optionally substituted, monocyclic or bicyclic, saturated, partially unsaturated, or aromatic ring having 0-4 heteroatoms independently selected from nitrogen, oxygen, and sulfur, or R' and an optional substituent on Cy are taken together with their intervening atoms to form a 5-6 membered carbocyclic or heterocyclic fused ring;

each Z is independently optionally substituted alkyl, optionally substituted alkenyl, optionally substituted alkynyl, or Cy; and each Cy is independently an optionally substituted, monocyclic or bicyclic, saturated, partially unsaturated, or aromatic ring having 0-4 heteroatoms independently selected from nitrogen, oxygen, and sulfur.

Assays

Myc proteins are most closely homologous at the MB1 and MB2 regions in the N-terminal region and at the basic helix-loop-helix leucine zipper (bHLHLZ) motif in the C-terminal region (Osier et al. (2002) Adv Cancer Res 84 81 154; Grandori et al. (2000) Annu Rev Cell Dev Biol 16 653 699. In the human genome, Myc is located on chromosome 8 and is believed to regulate expression of 15% of all gene through binding Enhancer Box sequences (E-boxes) and recruiting histone acetyltransferases (HATs). Myc protein, through its bHLH domain binds DNA, while the leucine zipper domain allows the dimerization with its partner, myc-associated factor X (Max), another bHLH transcription factor. The transcriptionally active Max/Myc dimer promotes cell proliferation as well as apoptosis.

Ever since the identification of MYC as a potential cancer promoting regulator gene in the late 1970s, researches have tried to develop drugs that inhibit its function. However, efforts to target MYC activity have proven largely unsuccessful, in part because the protein product encoded by the MYC oncogene lacks an obvious target-binding site. The absence of a clear ligand binding domain establishes a formidable obstacle toward direct inhibition. High-resolution structures of the Myc/Max complex fail to identify a hydrophobic involution compatible with the positioning of a small molecule. Frequently, previously published Myc inhibitors have shown weak affinity, poor specificity and no in vivo activity. The present invention provide methods and systems for identifying Myc inhibitors that lack these liabilities.

In certain embodiments, compounds of the present invention or those identified by the inventive methods and systems include those which:

exhibit the ability to inhibit Myc activity,
exhibit the ability to block Myc/Max dimerization,
exhibit the ability to trap free Myc,
exhibit the ability to block Myc/Max heterodimer from binding DNA, and/or
exhibit the ability to bind DNA and disrupt binding of Myc/Max binding site.

According to one aspect of the invention, methods for identifying Myc inhibitors are provided. The method is based on the detection of Myc/Max-nucleic acid complex formation which is accomplished by labeling Max and the nucleic acid with luminescent probes, including fluorophores, and chemiluminescent substrates. The physical proximity between the Myc/Max dimer and nucleic acid in the protein-nucleic acid complex provides for a change in fluorescence signal or formation of a chemiluminescent product associated with protein-nucleic acid complex formation, specifically proximity of Max and the nucleic acid. In the presence of a Myc inhibitor, Myc/Max-nucleic acid complex formation is disrupted leading to a corresponding decrease in the expected luminescence detection signal.

The method typically comprises providing a nucleic acid labeled with a fluorescence donor and Max labeled with a fluorescence acceptor, wherein binding of Myc and Max to the nucleic acid is detected by proximity-based luminescence detection; combining the nucleic acid with Myc and Max in presence of a test compound; and identifying the test compound as a Myc inhibitor when the proximity-based luminescence detection signal is decreased in the presence of the test compound relative to the signal in the absence of the test compound. The amount of decrease in measured detection signal necessary for a test compound to be identified as a Myc inhibitor depends upon the type of proximity-based luminescence detection assay used. Generally a 5% or greater decrease relative to an assay performed in the absence of the test compound indicates that the test compound is a Myc inhibitor. In certain embodiments, the test compound stimulates at least a 10%, 25%, 50%, 75% or 100% decrease in detection signal. In certain embodiments, a known Myc inhibitor, such as (but not limited to), (Z,E)-5-(4-Ethylbenzylidine)-2-thioxothiazolidin-4-one is used as a positive control.

Any method of proximity-based luminescence detection can be used in the present invention. Embodiments of proximity based luminescence detection methods include, but are not limited to, fluorescence resonance energy transfer ("FRET") (Stryer, L. *Ann. Rev. Biochem.* 47, 819-846, 1978), luminescence resonance energy transfer ("LRET") (Mathis, G. *Clin. Chem.* 41, 1391-1397, 1995), fluorescence cross-correlation spectroscopy ("FCCS") (Maiti et al. *Proc. Nat'l Acad Sci USA* 94, 11753-11757, 1997), scintillation proximity ("SPA") (Hart and Greenwald, *Molecular Immunology* 16:265-267, 1979; U.S. Pat. No. 4,658,649), direct quenching (Tyagi et al., *Nature Biotechnology* 16, 49-53, 1998), chemiluminescence energy transfer ("CRET") (Campbell, A. K., and Patel, A. *Biochem. J.* 216, 185-194, 1983), bioluminescence energy transfer ("BRET") (Xu, Y., Piston, D. W., Johnson, *Proc. Natl. Acad. Sci.,* 96, 151-156, 1999) and excimer formation (Lakowicz, J. R. *Principles of Fluorescence Spectroscopy*, Kluwer Academic/Plenum Press, New York, 1999). It is understood that the skilled artisan would recognize alternative proximity-based luminescence detection methods that are applicable to the present invention and are useful in the present invention.

The term "luminescence" or "luminescent" means any process of light emission including fluorescence, phosphorescence, scintillation, chemiluminescence, and bioluminescence.

The term fluorescent donor or fluorescence donor refers to a luminescent molecule which emits light that is absorbed by a fluorescence acceptor. The term fluorescent acceptor or fluorescence acceptor refers to either a second luminescent molecule or a quenching molecule which absorbs light emitted from the fluorescence donor. The second fluorophore absorbs the light that is emitted from the fluorescence donor and emits light of different wavelength than the light emitted by the fluorescence donor. The quenching molecule absorbs light emitted by the fluorescence donor. It is envisioned that any luminescent molecule may be used in the practice of this invention.

Examples of fluorophores and quenchers include, but are not limited to, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 650/665, BODIPY TMR-X, BODIPY TR-X, Dialkylaminocoumarin, Cy5.5, Cy5, Cy3.5, Cy3, DTPA (Eu3+)-AMCA and TTHA (Eu3+)-AMCA.

The term "chemiluminescence," "chemiluminescent," or "chemiluminescent substrate" refers to a chemical that produces light as a result of a chemical reaction. Commonly used chemiluminescent substrates include, but are not limited to, luminol (5-amino-2,3-dihydro-1,4-phthalazinedione), lophine (2,4,5-triphenylimidazole), lucigenin (bis-N-methylacridinium), other acridinium esters, luciferinluciferase, and thioxene derivatives. For example, in the art-recognized ECL™ detection system of Amersham, an acridinium substrate is oxidized by horse radish peroxidase to produce acridinium esters, which react with excess peroxide at an alkaline pH to produce visible chemiluminescence at 430 nm.

In some embodiments, the art-recognized AlphaLISA TruHits Kit of PerkinElmer is used. This kit includes AlphaLISA BSA-biotin Acceptor beads and Streptavidin Alpha Donor beads which interact together to generate an AlphaLISA signal. The excitation of the Donor beads provokes the release of singlet oxygen molecules that triggers a cascade of energy transfer in the Acceptor beads, resulting in a sharp peak of light emission at 615 nm.

It is understood that the skilled artisan would recognize that any compatible fluorescence donor-acceptor pair will work in the present invention and that the aforementioned fluorophores and quenchers are exemplary and not limiting.

In one embodiment, the labeled nucleic acid and/or Max are in solution and free to diffuse in all directions. In another embodiment, the labeled nucleic acid and/or Max are affixed to a solid phase substrate, such as, a microtiter plate, microarray slide, membrane or microsphere. In some embodiments, the nucleic acid and/or Max are linked to the solid substrate via a covalent or non-covalent interaction, e.g., biotin/avidin interaction.

Candidate test compounds useful in accordance with the invention encompass numerous chemical classes, although typically they are small organic compounds. The term "small molecule" is used to refer to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. In certain embodiments, small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§330.5, 331 through 361, and 440 through 460, incorporated herein by reference; drugs for veterinary use are listed by the FDA under 21 C.F.R. §§500 through 589, incorporated herein by reference. All listed drugs are considered acceptable for use in accordance with the present invention.

Candidate test compounds comprise functional chemical groups necessary for structural interactions with proteins and/or nucleic acids, and typically include at least an amine, carbonyl, hydroxyl or carboxyl group, preferably at least two of the functional chemical groups and more preferably at least three of the functional chemical groups. The candidate test compounds can comprise cyclic carbon or heterocyclic structure and/or aromatic or polyaromatic structures substituted with one or more of the above-identified functional groups. Candidate test compounds also can be biomolecules such as peptides, saccharides, fatty acids, sterols, isoprenoids, purines, pyrimidines, and derivatives or structural analogs of the above, or combinations thereof and the like.

Candidate test compounds are obtained from a wide variety of sources including libraries, (such as, but not limited to, commercial libraries, historical libraries/collections) of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the reaction mixture. These include reagents such as salts, buffers, proteins (e.g., albumin), detergents, and polymers, which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be determined by one of skill in the art. Such experimentation typically involves optimization of the assay parameters, not the fundamental composition of the assay. Incubation temperatures typically are between 4° C. and 40° C. Incubation times preferably are minimized to facilitate rapid, high throughput screening, and can be between 0.1 and 10 hours.

The instant invention is also directed to kits and compositions comprising labeled Max and/or nucleic acid. The kit can contain other compounds, such as enzymes, and/or buffers, for performing the methods of the present invention.

The kit can also include instructions for performing the inventive methods to identify Myc inhibitors as described here. Kits may also include a package housing one or more containers comprising one or more reagents for performing the method(s) of the present invention.

In certain embodiments, the method to identify Myc inhibitors comprises performing a high-throughput proximity-based luminescence detection assay to identify compounds having potential Myc inhibitory activity; re-testing the identified potential Myc inhibitor compounds by proximity-based luminescence detection assay using different concentrations of the potential Myc inhibitors, thereby identifying at least a subset of compounds having potential Myc inhibitory activity; and performing secondary and tertiary assays to confirm the ability of the identified compounds to inhibit Myc-induced transcription and optionally to determine the mode of action of the identified compounds. In certain embodiments, the secondary assays are cell-based and/or biochemical assays.

In some embodiments, cellular assays can compliment the biochemical analyses to measure the cellular potency of compounds to induce cellular phenotypes expected as a result of loss of transcription factor function. This includes gene expression analysis, chromatin immunoprecipitation (ChIP) analysis, cellular proliferation analysis, and cell state analysis. Gene expression analysis can be performed using, for example, qRT-PCR, Nanostring technology, microarray technology, or RNA-seq technology to study transcript changes following treatment with compound. In some embodiments, ChIP analysis is performed on the factor of interest to study if compound treatment alters its genomic occupancy. In some embodiments, cellular proliferation or cell state analysis can indicate if the compound alters cell cycle progression or cellular identity.

In some embodiments, the cell based assays are performed using Myc-dependent human cancer cell lines, such as, MM1S, CA-46, BL2, H2171, H82, HL60, and U87. The assays are performed to determine the effects of a test compound on cellular viability. Cell viability may be determined by, for example, ATPLite® (PerkinElmer) assay (Cree I. A., and Andreotti P. E., 1997, Measurement of cytotoxicity by ATP-based luminescence assay in primary cell cultures and cell lines. *Toxicology in vitro*, 11, 553-556).

In some embodiments, the biochemical assays are selected from the group consisting of gel shift assays (Garner M M, Revzin A (July 1981). "A gel electrophoresis method for quantifying the binding of proteins to specific DNA regions: application to components of the *Escherichia coli* lactose operon regulatory system". *Nucleic Acids Res.* 9 (13): 3047-60; Fried M, Crothers D M (December 1981). "Equilibria and kinetics of lac repressor-operator interactions by polyacrylamide gel electrophoresis". *Nucleic Acids Res.* 9 (23): 6505-25), NanoString transcript analysis (U.S. Pat. No. 7,473,767; incorporated herein by reference), chromatin immunoprecipitation assays (Kuo, M. H., Allis, C. D. *Methods,* 19:425-433, 1999; Bernstein, B. E., Humphrey, E. L., Liu, C. L., Schreiber, S. L., *Methods Enzymol,* 376:349-360, 2004), flow cytometry (U.S. Pat. No. 6,890,487; incorporated herein by reference), and quantitative real time reverse transcription polymerase chain reaction (qRT-PCR) (Donaldson et al., 2002 *Water Res.* 36:2505-2514; Kageyama et al., 2003 *J Clin Microbiol* 41:1548-1557; Kojima et al., 2002 *J Virol Methods* 100:107-114; Richards et al., 2004 *J Virol Methods* 116:63-70). The assays are performed to investigate the mode of action, and selectivity of the identified Myc inhibitors. For example, gel shift assays may be performed to study protein-DNA interactions to confirm:

(i) the test compound's Myc/Max/nucleic acid biochemical inhibitory activity and potency,
(ii) to determine the effect of the test compound on Myc/Max/nucleic acid complex formation, and/or
(iii) to identify DNA intercalators.

Chromatin immunoprecipitation assays may be performed to investigate protein:DNA interactions in a cellular context, while NanoString transcript analysis may be performed to determine transcriptional output of Myc target genes.

EXAMPLES

In order that the invention described herein may be more fully understood, the following examples are set forth. It should be understood that these examples are for illustrative purposes only and are not to be construed as limiting this invention in any manner.

A High Throughput Technology to Screen for Inhibitors of c-Myc/Max Dimerization and DNA Binding Methods described herein (e.g., in vitro high throughput screening technology) can be used to identify inhibitors, including small molecular weight inhibitors, peptides, and RNA aptamers that block transcription factor function. In some embodiments, the primary screening technology uses AlphaScreen technology (Perkin Elmer), a bead-based proximity assay, purified biological components, nucleotide polymers containing protein binding sites, and candidate inhibitors. An exemplary assay uses full-length human c-Myc and Max proteins and monitors formation of the c-Myc/Max/Ebox DNA ternary complex using singlet oxygen transfer between AlphaScreen beads resulting in production of luminescent signal that results in a reduction in signal intensity. Assays based on this system can use a variety of different tags, truncated proteins, fusion proteins or proteins from non-human species. Protein can be purified from *E. coli*, mammalian cells or other sources. Assays described herein can use any nucleotide polymer (DNA or RNA) containing a binding site of interest. These assays are amenable to miniaturization, automation (automated plate filling and compound pin transfer) and high throughput screening as we use it in 96-, 384- or 1536-well plate formats.

Assays described herein are superior to alternative methodologies for measuring protein:protein interactions such as FRET or FP for a variety of reasons. In some embodiments, the cost per well for protein is reduced by using protein concentrations in the tens of nanomolar or lower which is significantly lower than alternatives such as thermal melt or FP. In some embodiments, low concentration of protein components is important for detection of low affinity ligands that are often identified in high throughput and fragment screening. In some embodiments, the assay is unaffected by molecular orientation or proximity which can have a large impact on FRET. This enables the sensitive interrogation of large multi-component complexes. In some embodiments, AlphaScreen effectively displays an anti-Stokes shift which minimizes the impact of intrinsically fluorescent molecules on the assay. Since the transfer of energy is mediated by singlet oxygen, the readout wavelength can be blue-shifted relative to the excitation wavelength and time resolved, which is avoids interference from autoflourescence. In some embodiments, the relatively long signal distance of 200 nm that singlet oxygen can travel allows reporting on full protein complexes and not just single target binding. In some embodiments, assays described herein are amenable to miniaturization with and can be scaled down to smaller volumes with relative ease. In some embodiments, neither the small molecules being assayed nor the target protein, c-Myc, need to be chemically, conformationally or behaviorally altered by tethering them to a surface or reporter which can induce artifacts. Assays described herein have the option of having c-Myc free in solution (as it is inside a cell) and having Max and DNA bound to a bead. In some embodiments, assays described herein have the flexibility of alternative configuration where c-Myc and DNA are bound to a bead and Max is free in solution. In certain embodiments, assays described herein allow for various configurations depending on the protein target or pair.

Assay Development and Validation

Figure 8:
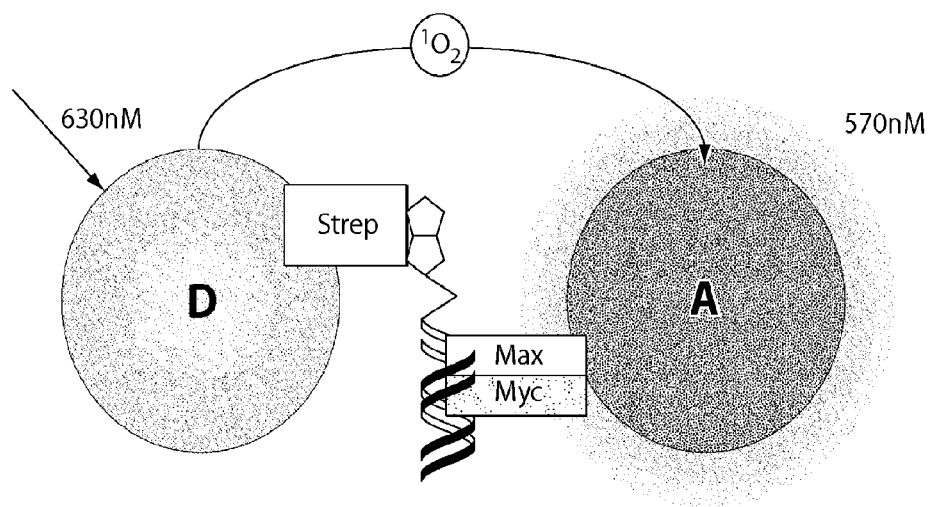
FIG. 8 shows an exemplary alpha assay configuration for monitoring c-Myc/Max/Ebox DNA complex formation.

Two complimentary assays were developed to monitor c-Myc/Max/Ebox DNA complex formation. The AlphaScreen assay (Perkin Elmer) is comprised of an acceptor and a donor bead in solution (FIG. 8). The donor bead is illuminated at 680 nm, which generates a singlet $O_2$ molecule. If the acceptor bead is within 200 nm within 4 msec of illumination ($O_2$ half-life), it will transfer the energy and generate luminescent signal at a wavelength of 520-620 nm.

Biotinylated Ebox DNA ([Biotin-triethyleneglycol] GGAAGCAGACCACGTGGTCT GCTTCC) was used in conjunction with strepavidin donor bead in the assay shown in FIG. 8. $His_6$-Max was used with $Ni^{++}$ acceptor beads. Free c-Myc (purified as $his_6$-cMyc, followed by a thrombin cleavage reaction to remove the $his_6$ tag) was added free in solution. A reciprocal assay (not shown in FIG. 8) used biotinylated Ebox DNA with strepavidin donor beads. $His_6$-cMyc was used in conjunction with the $Ni^{++}$ acceptor bead. Recombinant free Max (purified as $his_6$-Max followed by thrombin cleavage of the $his_6$ tag) was added free in solution. The different assay set-ups offer flexibility in which components are bound to beads or free in solution.

All reagents were diluted in reaction buffer (20 mM HEPES, 150 mM KCl, 0.1% w/v BSA, 0.01% w/v Tween20, 20 µg/ml glycogen, 1 mM DTT, pH 8.0 and allowed to equilibrate to room temperature, where glycogen and DTT are added immediately prior to use). The composition of the reaction buffer can vary and be optimized depending on the complex of interest. It was found that adjusting the pH from 7.4 to 8.0 better mimics the nuclear conditions and favours Myc/Max heterodimer formation over Max/Max homodimer formation. Also, the BSA and Tween20 concentrations were optimized to reduce background, non-specific associations and aggregation. DTT was added to mimic the reducing conditions of the cellular interior and improves signal magnitude. Without wishing to be bound by theory, it was also thought that BSA reduces background signal by sequestering errant singlet oxygen. Early attempts to use automation were confounded by a gradient of signal across the plate, in the direction of plate filling, which was reasoned to be caused by adsorption of oligos onto polypropylene tubing. It was discovered that the addition of glycogen, serving as a carrier, corrected the defect in assay automation. The ability to fully automate can be important when screening compound libraries and therefore, this was a modification that was found to have a profound effect on assay performance.

The Myc/Max/Ebox DNA assay is scalable to 96-, 384- or 1536-well plate formats. Reaction volumes for 96-well based formats include 50 µL total reaction volume, 384-well format includes 20 µL total reaction volume and 1536-well format includes 8 µL total reaction volume. Individual pipetting or liquid-handling robotics can be used to add reaction components. For 384-well plate formats, a 2× solution of components with final concentrations of cMyc at 25 nM, Ni-coated Acceptor Bead at 25 µg/ml, and 10 nM biotinylated oligo with the Myc/Max Ebox binding region is added in 10 µL 384-well plates (AlphaPlate-384, PerkinElmer, USA). After addition of Alpha beads to master solutions all subsequent steps were performed in low light conditions.

Addition to wells was performed with either a multichannel pipet or a Biotek EL406 liquid handler. After a 1 minute 1000 rpm spin-down, 100 nL of compounds from stock plates were added by pin transfer using a Janus Workstation (PerkinElmer, USA). In the current assay setups, DMSO is not allowed to exceed 2% v/v of the assay. A second 2× solution with final concentrations of Max at 1.25 nM and Donor Bead at 25 µg/ml was prepared separately for two symmetric liquid delivery steps. Following this addition, the plates were sealed with foil to block light exposure and to prevent evaporation. The plates were centrifuged at 1000 rpm for 1 minute. Next, the plates were incubated in the room with the plate reader (for temperature equilibration) for 2 hours prior to reading the assay. AlphaScreen measurements were performed on an Envision 2104 (PerkinElmer, USA) utilizing the manufacturer's protocol. For 1536-well plate format, all procedures were done as above in 1536-AlphaPlates from PerkinElmer. The total reaction volume was 8 µL with additions of 4 µL for the first solution containing acceptor beads and 4 µL for the second containing donor beads.

Figure 2:
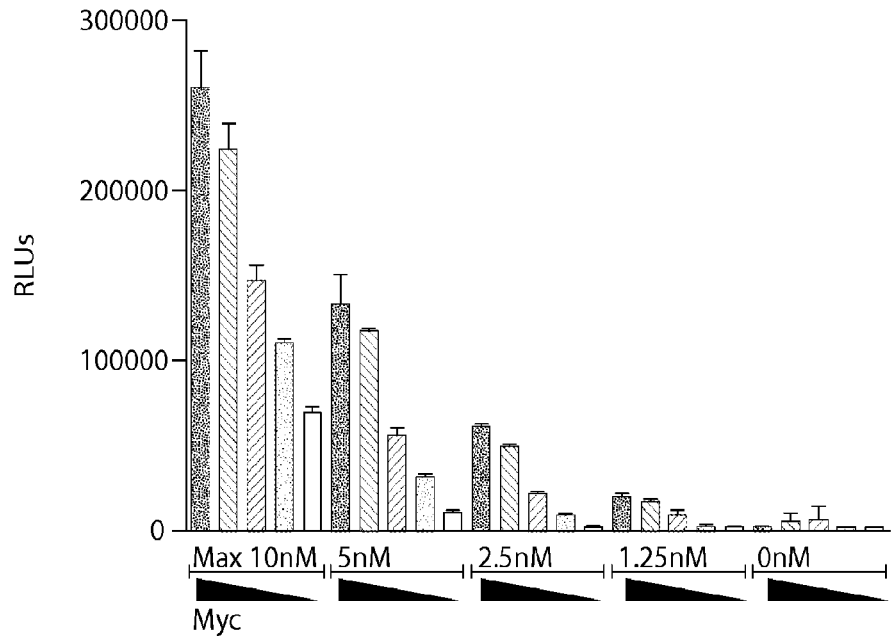
FIG. 2 (left) depicts high throughput assay optimization for c-Myc-dependent signal. Signal (RLUs) of bead proximity is dependent on c-Myc and Max protein concentrations. A fixed DNA concentration was used.
Figure 2:
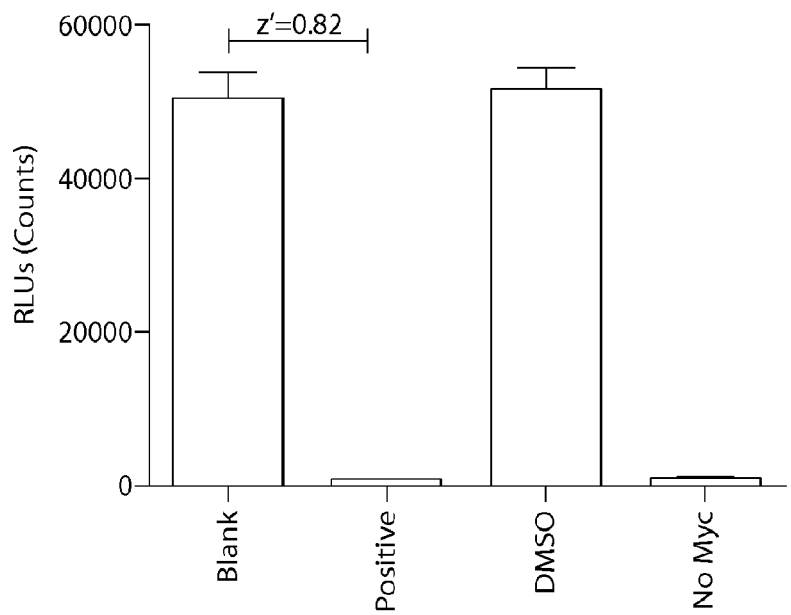
Figure 3:
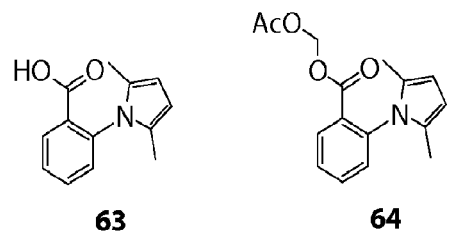
FIG. 3 illustrates how Compound 64 (squares), an acetoxymethyl ester prodrug version of the free acid Compound 63 (circles), has increased cellular activity as measured in a cellular proliferation assay of the MYC-dependent human small cell lung carcinoma line H2171 and human multiple myeloma line MM1.S.
Figure 3:
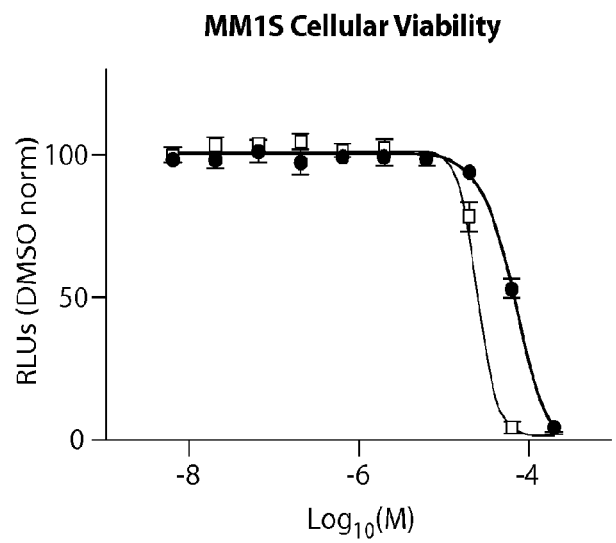
Figure 3:
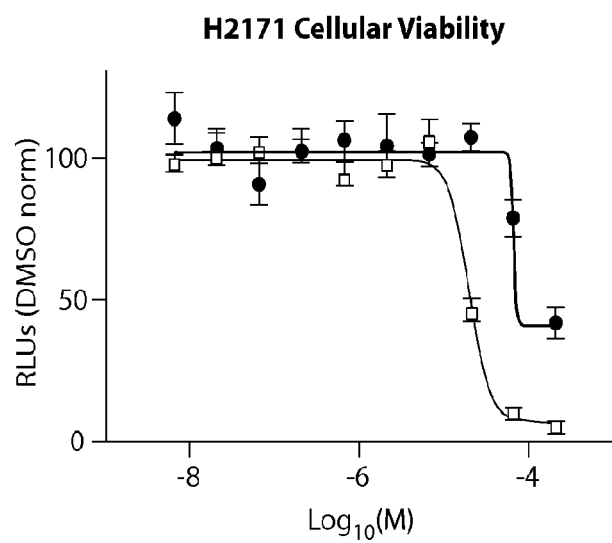
Figure 4:
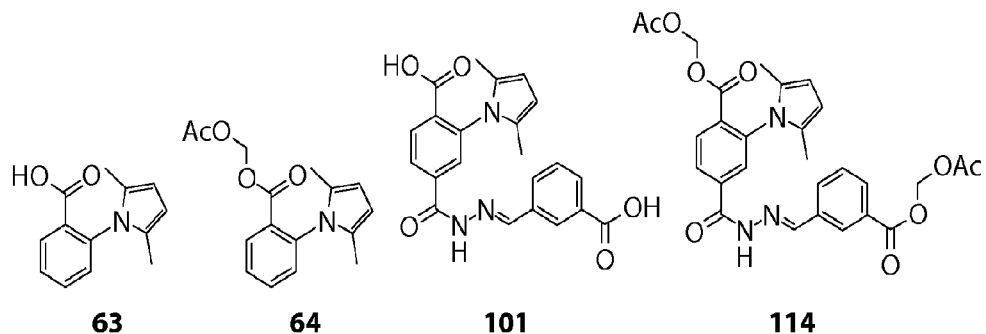
FIG. 4 details the increased biochemical activity of Compound 101 (triangles), as measured by a c-Myc/Max/Ebox DNA AlphaScreen assay. Generating an acetomoxymethyl ester prodrug (inverted triangles) increases cellular potency of the compound, as measured in a cellular proliferation assay of the MYC-dependent human multiple myeloma line MM1.S.
Figure 4:
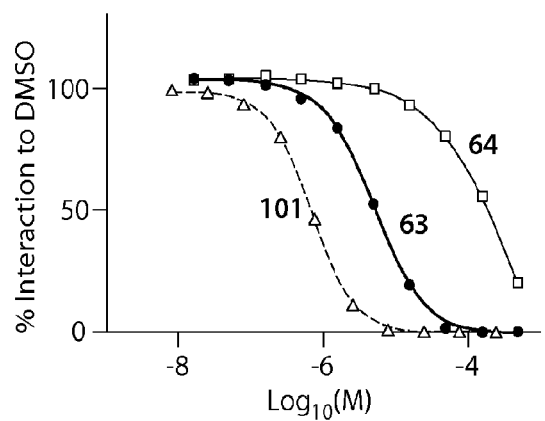
Figure 4:
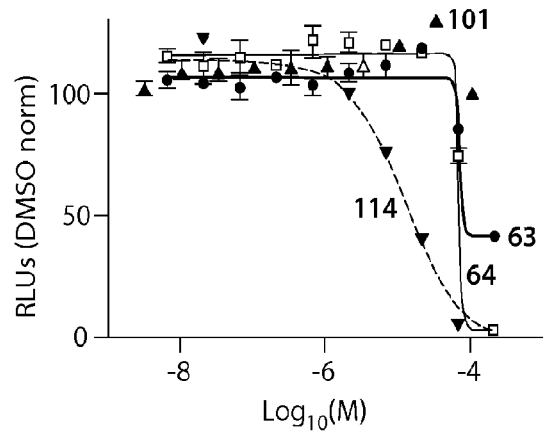

The concentration of each component can be an important variable in the success of the assay and the production of component-specific signal. For example, the ability of a protein to homodimerize under certain conditions produce signal that is independent of each component. For Assay 1, using c-Myc at 25 nM, Max at 1.25 nM and biotinylated Ebox at 10 nM gave robust component-specific signal (FIG. 2, left). For Assay 2, using c-Myc at 50 nM, Max at 25 nM and biotinylated Ebox at 25 nM gave robust component-specific signal (FIG. 2, right). Factor-specific signal was not limited to only the indicated concentrations as additional combinations can also produce robust signal. This is a consideration when optimizing different transcription factors and protein batches. These assays can be performed in the nanomolar concentration range of protein components.

The High Throughput Technology is Adaptable to Other Dimeric Transcription Factors and their Interaction with Nucleotide Polymers Transcription factors are key drivers of cell state specification through regulating the gene expression program of the cell. Therefore, targeting transcription factors in a disease state when the gene expression program is deregulated is highly desirable. The c-Myc/Max/Ebox DNA AlphaScreen assay described above recapitulates the mechanism that c-Myc utilizes to bind its DNA binding site to regulate transcription and induce oncogenic transformation. This allows for the identification of biologically relevant inhibitors of a key event that causes many human cancers. Because the assay uses purified components, it can be applied for the investigation and identification of inhibitors of any step of a transcriptional regulatory pathway. Of particular interest are Max/Max homodimer formation and MITF complex formation as it is implicated in skin cancers.

To demonstrate this, this technology has been adapted to develop a high throughput-screening assay for the oncogenic transcription factor MITF. MITF can homodimerize or heterodimerize with three binding partners, TFEB, TFEC and TFE3, to associate with DNA. Assays were developed to monitor formation of MITF/TFEB/DNA and MITF/TFE3/DNA complexes. The MITF assays were performed similarly to the c-Myc/Max/Ebox DNA assay described above except the protein components were different. Thus, this high throughput-screening strategy is amenable to screen for inhibitors of other transcription factor/nucleotide binding events. Follow-up secondary and tertiary assays for the transcription factors of interest can be used to report on biochemical, and cellular activity.

Secondary and Tertiary Assays to Validate and Optimize Hits Against Transcription Factors of Interest Inhibitors discovered from the assays described above were validated using biochemical and cellular assays. Established biochemical, cell biological and in vivo models can be used to explore selectivity, potency, and mechanism of action. These assays are used for validating hits, identifying AlphaScreen assay artifacts, and investigating cellular potency and on-target activity. In some embodiments, this approach utilizing the sensitive biochemical high throughput screening technology with secondary and tertiary assays supported by iterative rounds of medicinal chemistry can serve as a platform for discovering transcription factor inhibitors through assaying focused libraries with structurally similar transcription factor, such as different basic helix-loop-helix transcription factors.

Figure 5:
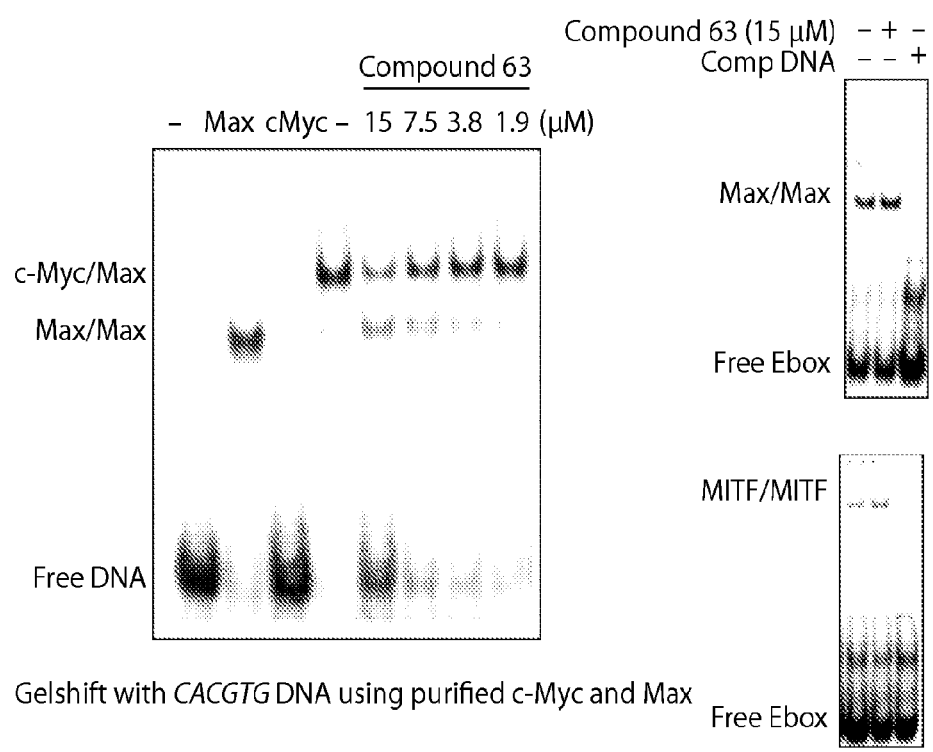
FIG. 5 describes validation of Compound 63 activity using an orthogonal biochemical assay. Compound 63 inhibits c-Myc/Max/Ebox DNA complex formation (top band) in a dose dependent manner in a gelshift assay. Decreasing amounts of 63 was added to purified c-Myc, Max and biotinylated Ebox DNA. Biotinylated Ebox DNA complexed with protein (either c-Myc/Max or Max/Max) or free (bottom band) was assayed using a 6% retardation gel, transferred to a membrane and detected using straptavidin-HRP. Compound 63 displays selectivity towards c-Myc/Max at tested doses.
Figure 6:
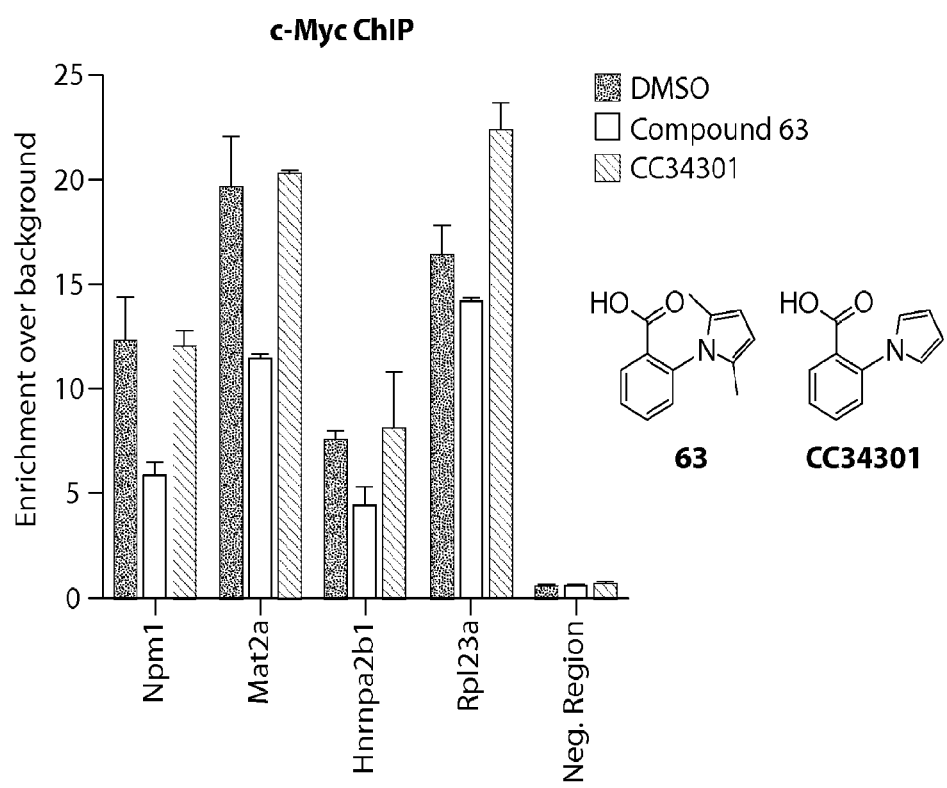
FIG. 6 depicts a c-Myc chromatin immunoprecipitation assay to investigate c-Myc genomic occupancy in H2171 cells treated with DMSO, Compound 63 (100 µM) or CC34301 (100 µM) for 4 hours. Standard chromatin immunoprecipitation procedures were followed using an antibody specific to c-Myc (Santa Cruz, catalogue number sc-764). Quantitative PCR analysis was performed on four c-Myc binding sites (Npm1, Mat2a, Hnrnpa2b1, and Rp123a) and one non-binding site (Neg region) and normalized to a background region to determine the fold enrichment over background. Treatment with 63 for 4 hours reduced c-Myc occupancy at these binding sites compared to DMSO or CC34301 treatment. Max genomic occupancy was largely unchanged at these sites. c-Myc protein levels were unchanged under these conditions.
Figure 7:
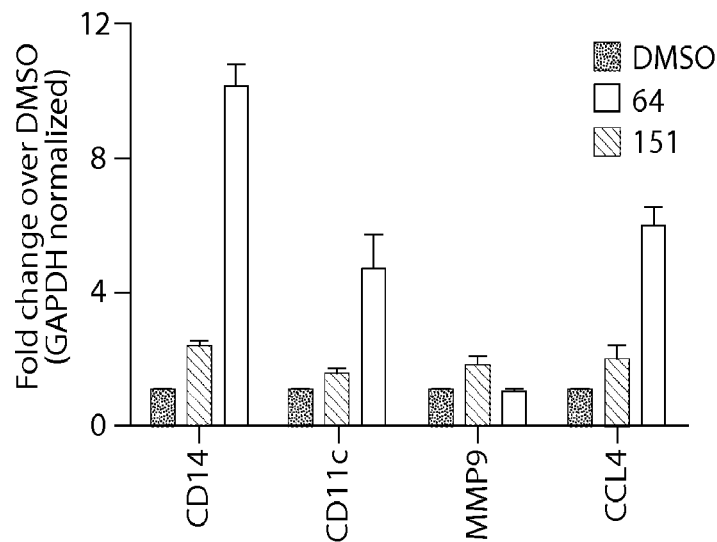
FIG. 7 depicts the assessment of on-target activity versus general toxicity. HL-60 promyelocytic leukemia cells express high levels of c-Myc to maintain a proliferative and undifferentiated cell state. Loss of c-Myc function results in loss of cellular proliferation and induction of cellular differentiation. HL-60 cells were treated with DMSO, 64 (12.5 μM or 25 μM), or 151 (25 μM) for four days.
Figure 7:
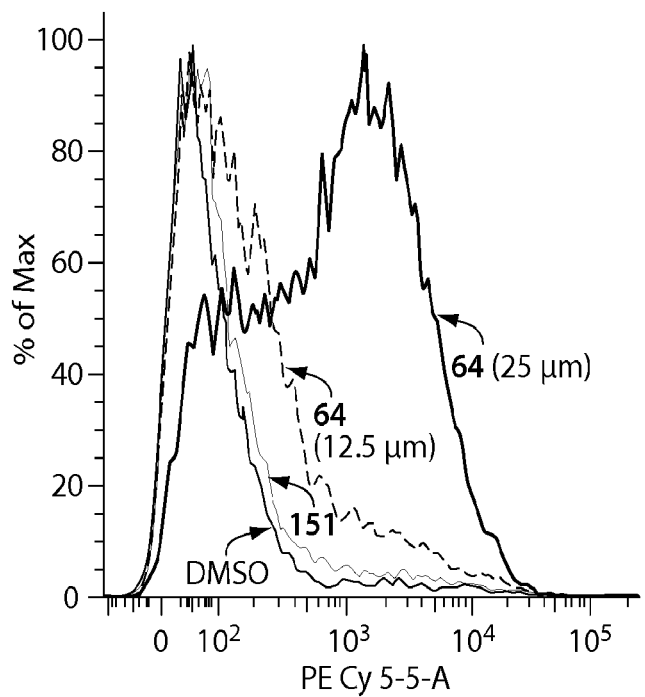
Figure 9:
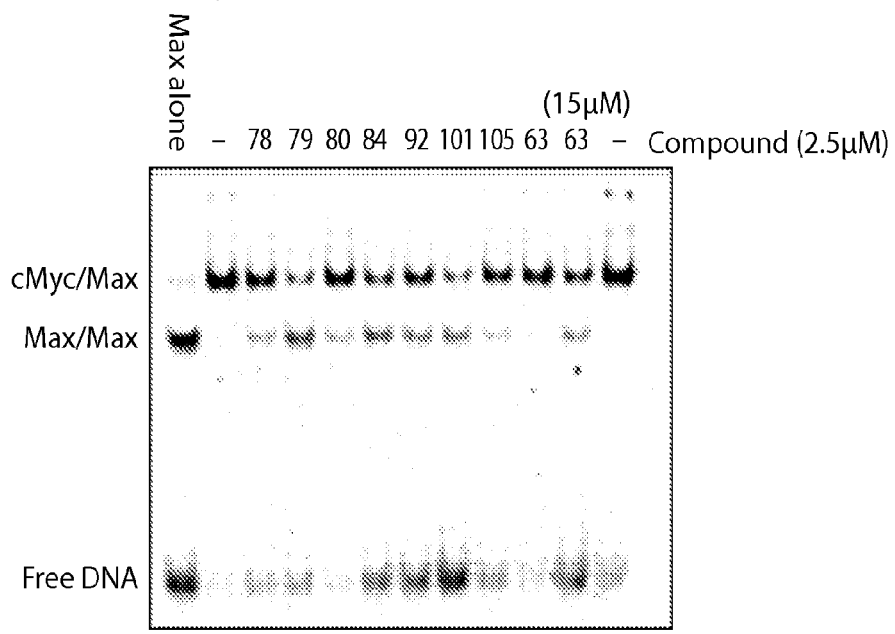
FIG. 9 shows that compounds can be developed that display different potency and selectivity profiles against different transcription factor:DNA complexes. Compounds tested at 2.5 μM for their inhibitory activity against c-Myc/Max/Ebox DNA, Max/Max/Ebox DNA and MITF/MITF/Ebox DNA complex formation using gelshift assays.
Figure 1:
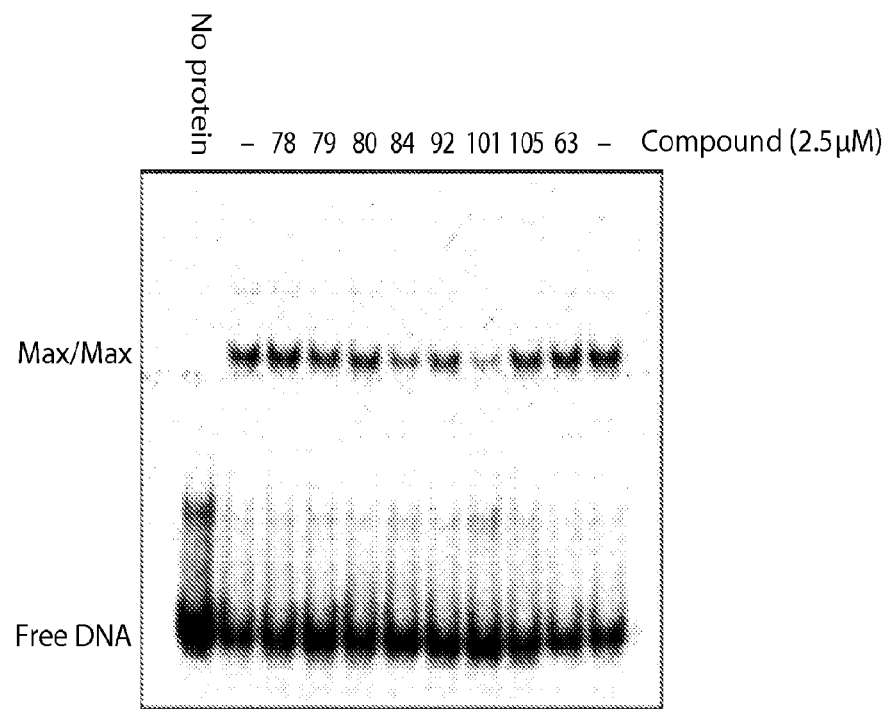
Figures 2, 9:
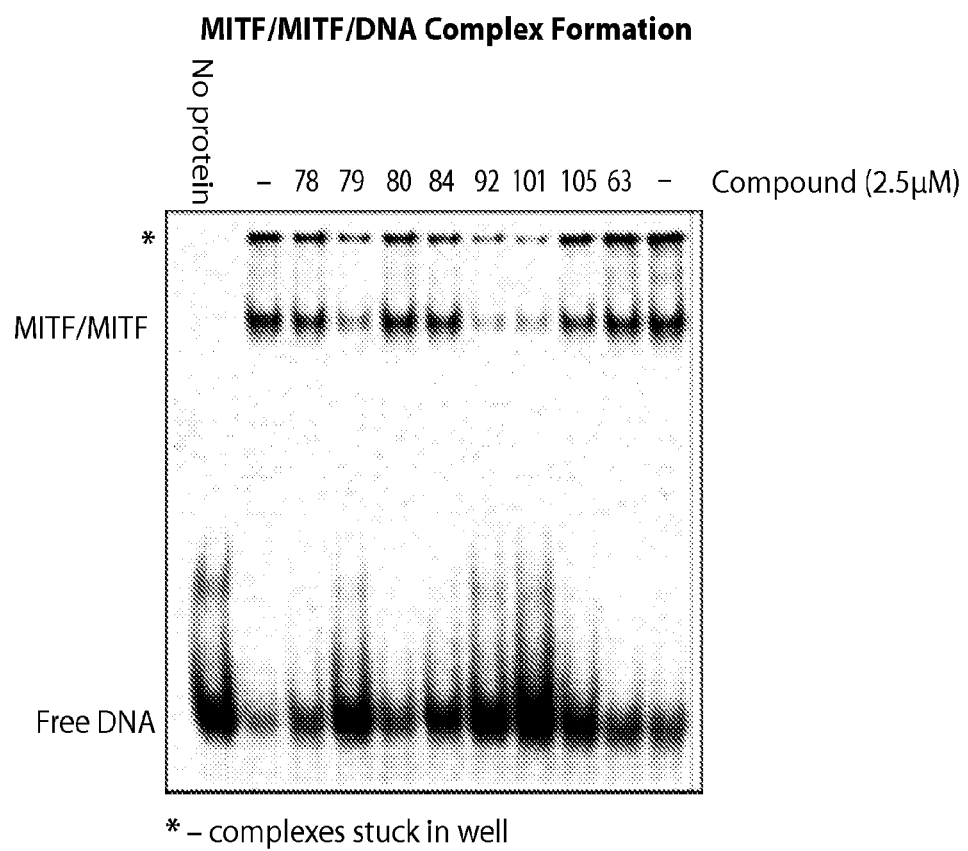
Figure 10:
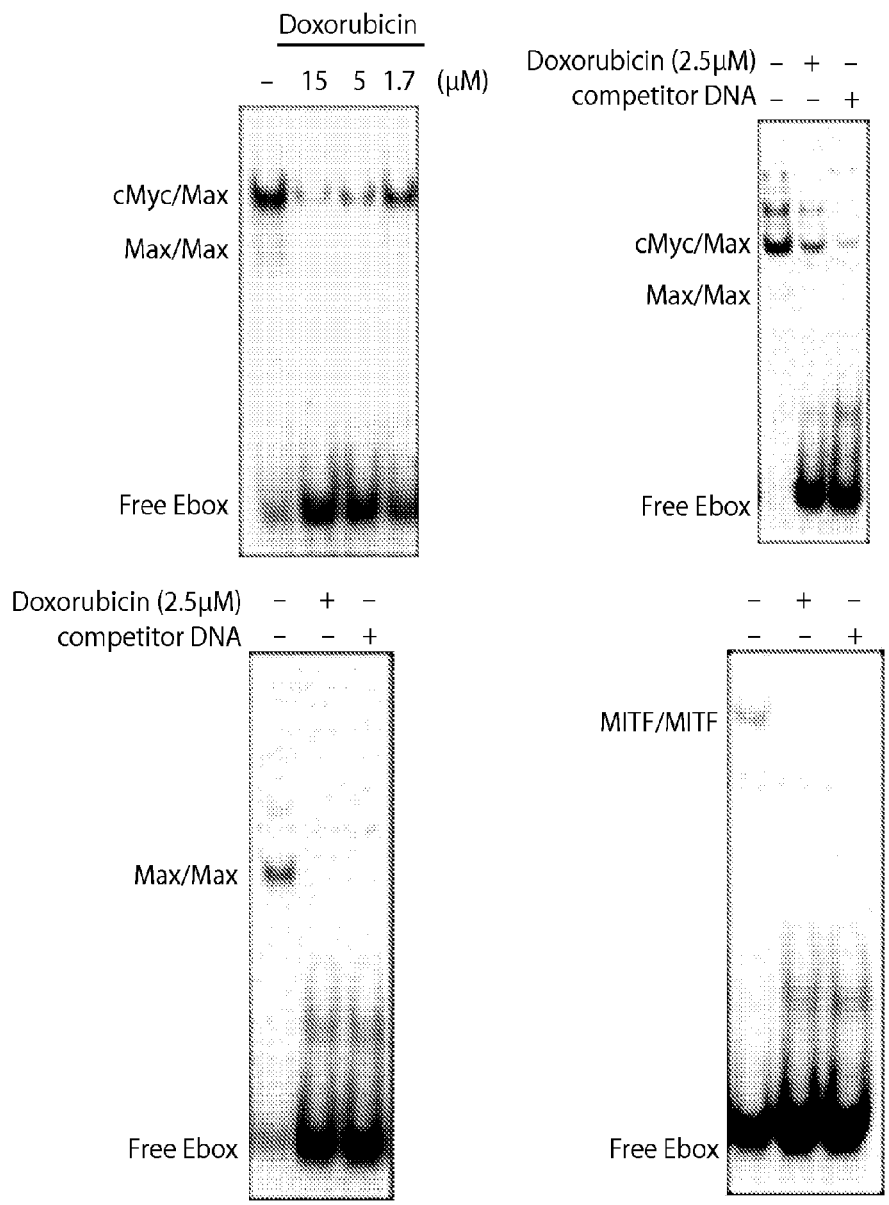
FIG. 10 demonstrates that comparative biochemical analyses with inhibitors with known mechanisms of action provide insights into mechanism of action. A DNA intercalator, doxorubicin, non-specifically disrupts protein:DNA complex formation, which is different than 63 and related compounds.

AlphaScreen hits can be validated using orthogonal biochemical assays such as a gelshift assay (also called an electrophoretic mobility shift assay) with purified components or cellular lysates. FIG. 5 (left) illustrates how the AlphaScreen hit 63 was validated using a gelshift assay with purified c-Myc, Max and Ebox DNA. Compound 63 reduced c-Myc/Max/Ebox DNA complex formation in a dose-dependent manner. Compounds and analogs were then examined for potency and selectivity against structurally similar transcription factor:DNA complexes, such as Max/Max/Ebox DNA and MITF/MITF/Ebox DNA. Data in FIG. 9 show how analogs can be tested for potency against structurally similar transcription factors and how medicinal chemistry optimization can drive potency and selectivity against different transcription factor:DNA complexes. For example, Compound 101 potently disrupted c-Myc/Max/Ebox DNA, Max/Max/Ebox DNA and MITF/MITF/Ebox DNA complex formation relative to DMSO at 2.5 mM. Compound 79 disrupted c-Myc/Max/Ebox DNA and MITF/MITF/Ebox DNA complex formation but not Max/Max/Ebox DNA complexes at the tested dose. Compound 92 appeared most potent of the compounds tested against MITF/MITF/Ebox DNA complexes. The selectivity among structurally similar transcription factors can also provide insights into compound mechanism of action. For example, DNA intercalators such as doxorubicin will non-specifically disrupt all protein:DNA interactions supporting a model that the compounds described above do not function as DNA intercalators. Cellular assays can compliment the biochemical analyses to measure the cellular potency of compounds to induce cellular phenotypes expected as a result of loss of transcription factor function. This includes gene expression analysis, chromatin immunoprecipitation (ChIP) analysis, cellular proliferation analysis and cell state analysis. Gene expression analysis can be performed using qRT-PCR, Nanostring technology, microarray technology, or RNA-seq technology to study transcript changes following treatment with compound. ChIP analysis can be performed on the factor of interest to study if compound treatment alters its genomic occupancy. Cellular proliferation and cell state analysis can indicate if the compound alters cell cycle progression or cellular identity. Thus, the approach using biochemical and cellular assays with large chemical libraries or focused libraries of hits identified in high throughput screens can serve as a platform to develop inhibitors of transcription factor function.

c-Myc/Max/Ebox DNA AlphaScreen Assay Conditions

Figure 11A:
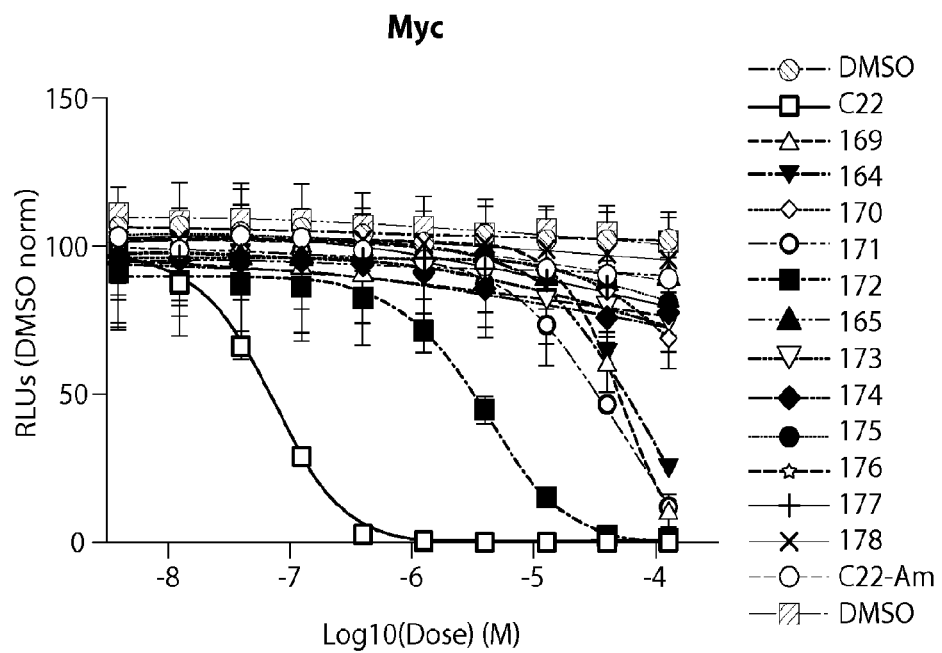
FIG. 11 shows exemplary biochemical data of exemplary compounds of the invention in c-Myc/Max/Ebox DNA AlphaScreen assays.
Figure 11A:
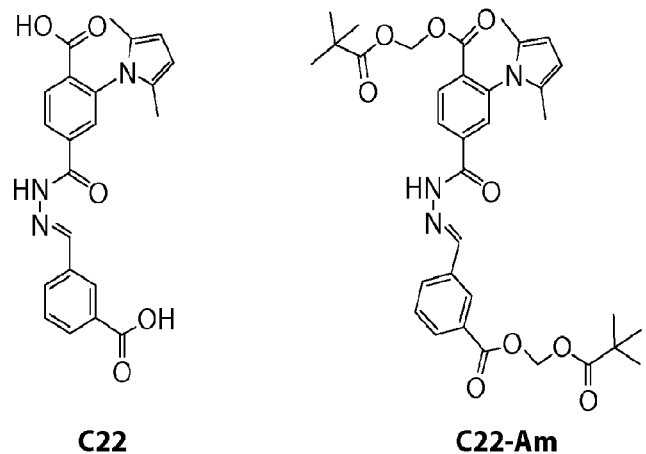
Figure 11B:
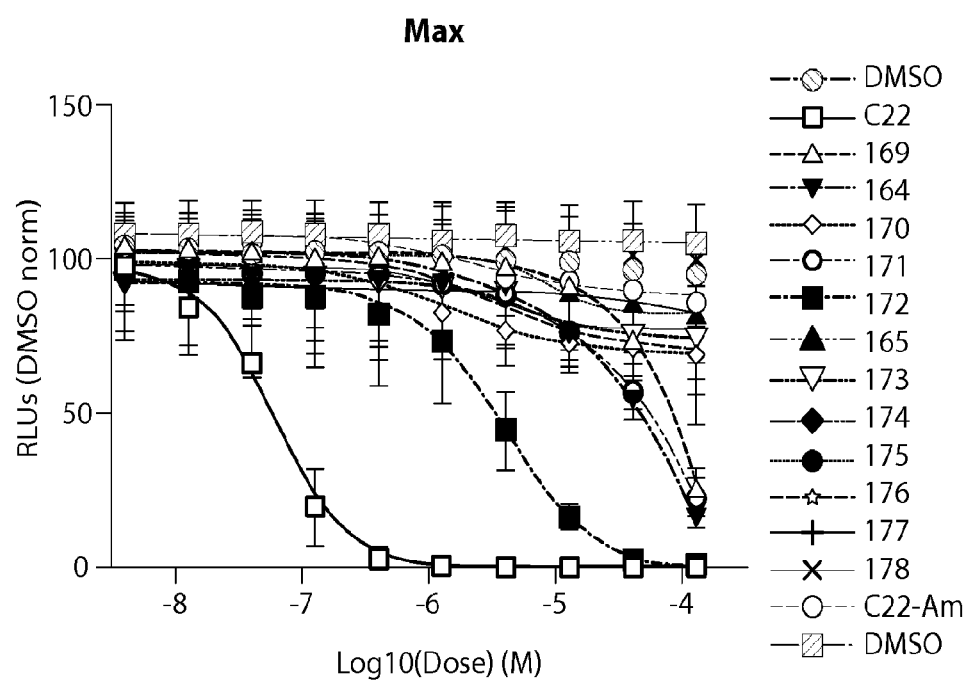
Figure 12A:
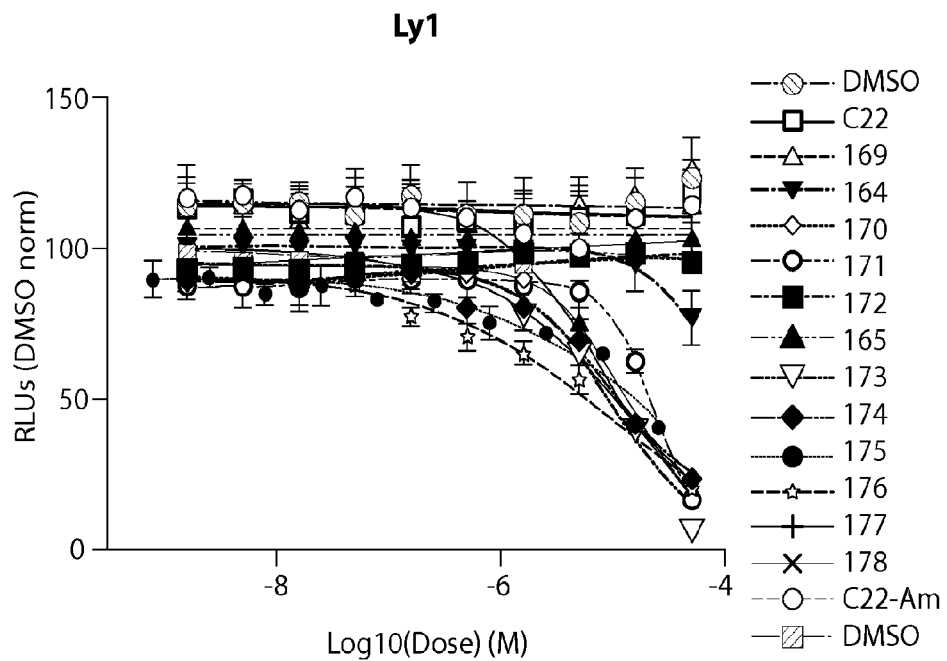
FIG. 12 shows exemplary data of exemplary compounds of the invention in cell viability assays of select MYC-dependent human cell lines (e.g., Ly1 (FIG. 12A), Ly4 (FIG. 12B), H2172 (FIG. 12C), and CA-46 (FIG. 12D)).
Figure 12B:
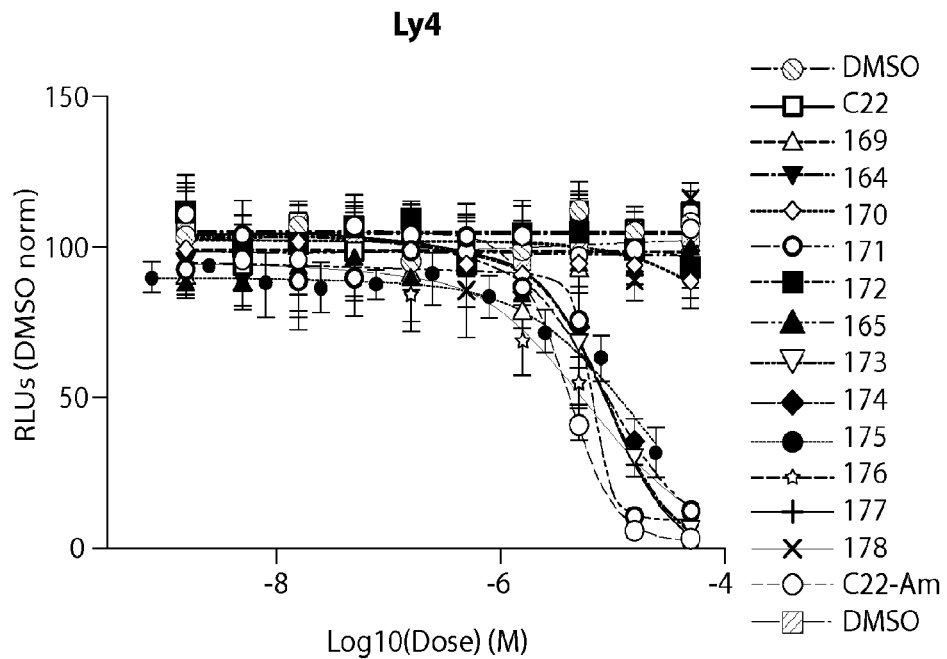
Figure 12C:
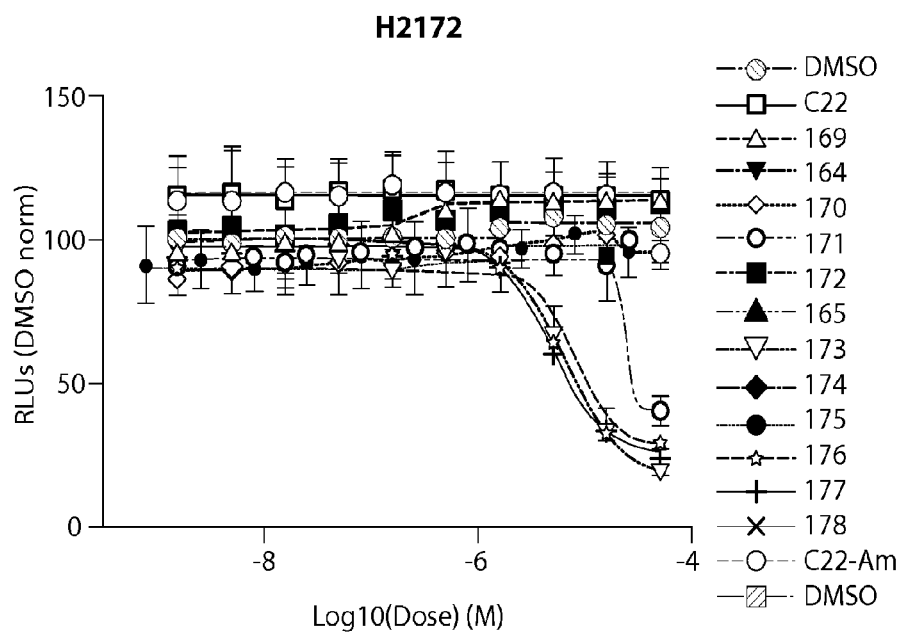
Figure 12D:
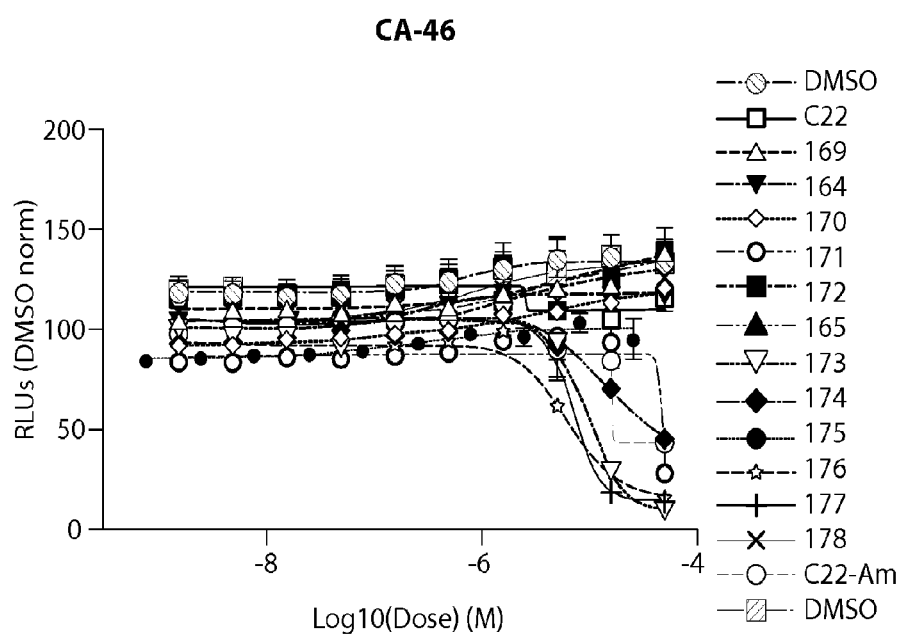

This protocol was used to generate the biochemical data in Table 2 and FIG. 11. The primary AlphaScreen assay is amenable to 384-well and 1536-well plate formats for HTS. Human his6-c-Myc and his6-Max were used with biotinylated DNA containing a single Ebox sequence (biotinG-GAAGCAGACCACGTGGTCTGCTTCC) purchased from MWG Operon. Free c-Myc was generated from his6-c-Myc through thrombin cleavage of the his6 tag. For 384-well plate assays, 10 μL of a 2× solution of free c-Myc (25 nM final), Ni++-coated Acceptor Bead (25 μg/ml final), and biotinylated Ebox oligo (10 nM final) were added to 384-well plates with a Biotek EL406 liquid handler. 100 nL of compounds from stock plates were added by pin transfer using a Janus Workstation (PerkinElmer), allowing the compounds to interact with c-Myc prior to c-Myc binding with Max. In the current assay, DMSO was not allowed to exceed 2% v/v of the assay. 10 μl of 2× master mix containing streptavidin-coated donor beads (25 μg/ml final) and his6-Max (1.25 nM final) were added. AlphaScreen measurements were performed on an Envision 2104 (PerkinElmer) utilizing the manufacturer's protocol. The assay can also be performed in 1536-plate format with 8 μL total volume using two 4 μL additions (instead of 20 μL and 10 μL respectively).

Assays are performed with minor modifications from the manufacturer's protocol (PerkinElmer). Both master mixes were made in room temperature assay buffer (50 mM HEPES, 150 mM NaCl, 0.2% w/v BSA, 0.02% w/v Tween20, 40 μg/ml glycogen, 500 μM DTT, pH 8.0, DTT and glycogen added fresh). Alpha beads were added to respective master solutions and wrapped in foil. All subsequent steps were performed in low light conditions. Solution 1: 2× solution of components with final concentrations of cMyc (25 nM), Ni-coated Acceptor Bead (25 μg/ml), and biotinylated Ebox oligo (10 nM). Solution 2: 2× solution of streptavidin-coated donor beads (25 μg/ml final) and his6-Max (1.25 nM final). 10 L Solution 1 were added to 384-well plate (AlphaPlate-384, PerkinElmer) with Biotek EL406 liquid handler and the plates were centrifuged at 1000 rpm for 1 minute. 100 nL of compounds from stock plates were added by pin transfer using a Janus Workstation. 10 μL Solution 2 were added with the liquid handler. Plates were sealed with foil to block light exposure and prevent evaporation. Plates were centrifuged at 1000 rpm for 1 minute followed by 2 hour incubation. AlphaScreen measurements were performed on an Envision 2104 utilizing the manufacturer's protocol. Excitation was at 680 nm for donor bead release of singlet oxygen and emission was read with a bandpass filter from 520-620 nm. Glycogen: Roche Diagnostics #10901393001. Plate 1536: Perkin Elmer, 6004350. Plate 384: Perkin Elmer, 6005350. Nickel-His Alpha Beads: 6760619R.

Cell Viability Assay

This assay was used for the H2171 and MM1S cell data shown in Table 2, and for the Jurkat (an immortalized line of human T lymphocyte cells), Ly1 (OCI-Ly1 human non-Hodgkin lymphoma cell line), Ly4 (OCI-Ly4 human non-Hodgkin lymphoma cell line), H2172 (NCI-H2172 human non-small cell lung cancer cell line), and CA-46 (a human Burkitt's lymphoma cell line) cell data shown in Table 3 and FIG. 12. Cells were counted and adjusted to 60,000 cells/mL. Using a Biotek EL406, 50 μL of cells are media were distributed into 384 well white plates from Thermo. Immediately after plating, compound in DMSO was distributed to plates. For large plate sets, cells were returned to 37° C. incubator while not in use.

Compounds were added to plates using a 100 nL 384 well pin transfer manifold on a Janus workstation. Stocks were arrayed in 10 point quadruplicate dose response in DMSO stock in 384 well Greiner compound plates. After addition of compound, plates were incubated for three days in a 37° C. incubator.

Cell viability was read out using ATPlite from Perkin Elmer. Plates were removed from the incubator and brought to room temperature prior to use. Lyophilized powder was resuspended in lysis buffer and diluted 1:2 with DI water. 25 µL of this solution was added to each well using the Biotek liquid handler. Plates were sealed with adherent aluminum seals prior to vortexing and spinning down at 1000 g for 1 minute. Plates were incubated for 15 minutes at room temperature before signal was read on an Envision Plate Reader.

Synthetic Methods

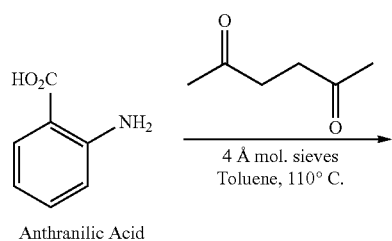

Anthranilic Acid

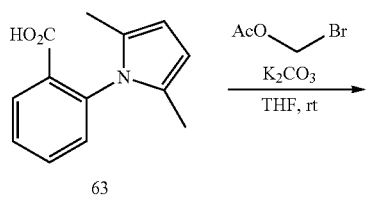

63

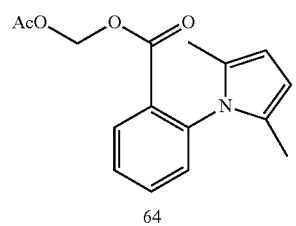

64

Compound 63 was prepared through Paal-Knorr pyrrole synthesis by refluxing anthranilic acid in toluene with 1.5 molar equivalents of 2,5-hexanedione in the presence of 200 wt % molecular sieves or can be purchased from Maybridge as catalog number CC39901 (Compound 1).

Compound 64 was generated by treatment of a solution of 63 in THF with 3 equivalents potassium carbonate at room temperature followed by addition of 1.5 molar equivalents acetoxymethyl bromide.

Alternate ester prodrugs can be prepared in an analogous fashion using appropriate halides such as chloromethyl pivalate, chloromethyl isopropyl carbonate, or 1-chloroethyl isopropyl carbonate.

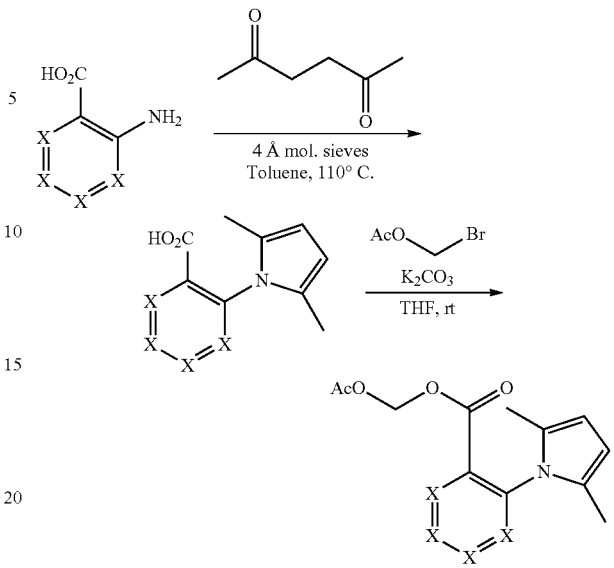

Substituted 2-(2,5-dimethylpyrrolyl) aryl or heteroaryl acids were prepared according to the procedure for Compound 63 and their AM esters generated analogously to Compound 64.

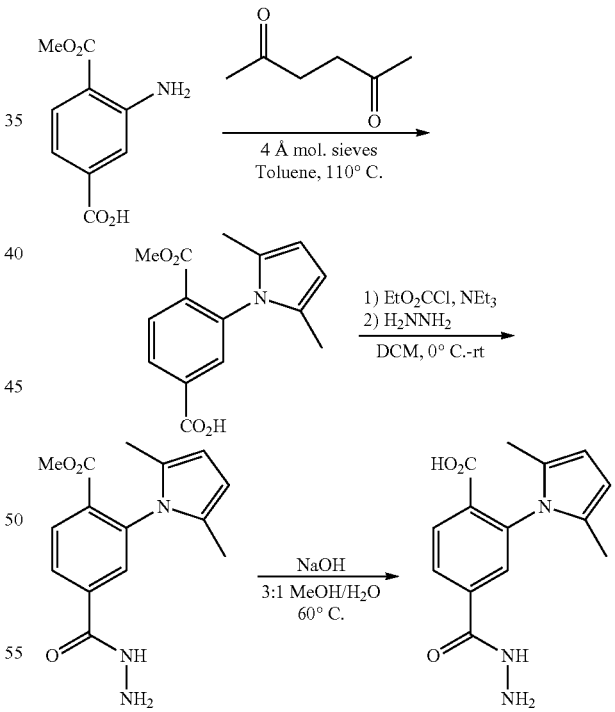

3-(2,5-dimethyl-1H-pyrrol-1-yl)-4-(methoxycarbonyl) benzoic acid was prepared according to the general procedure. Treatment of this compound with ethylchloroformate and triethylamine, followed by hydrazine methyl 2-(2,5-dimethyl-1H-pyrrol-1-yl)-4-(hydrazinecarbonyl)benzoate which may be used directly in further reactions or hydrolyzed with sodium hydroxide to afford the free carboxylic acid.

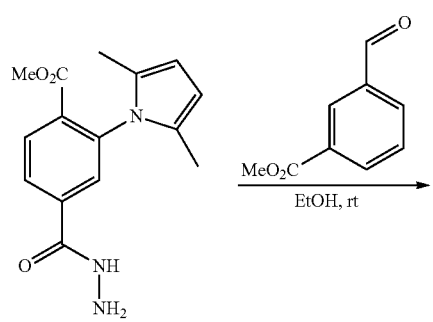

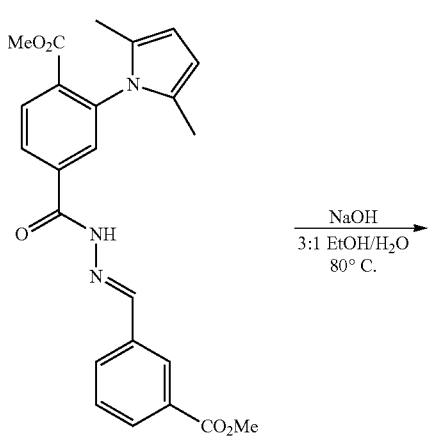

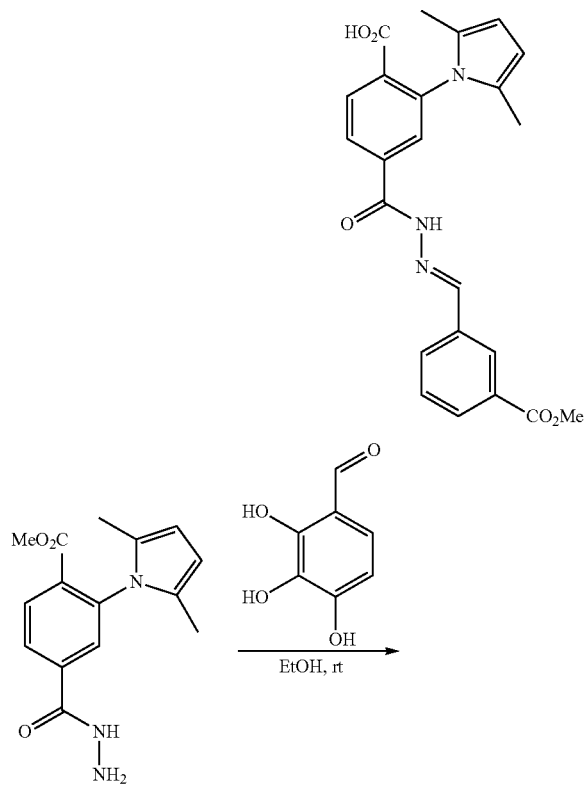

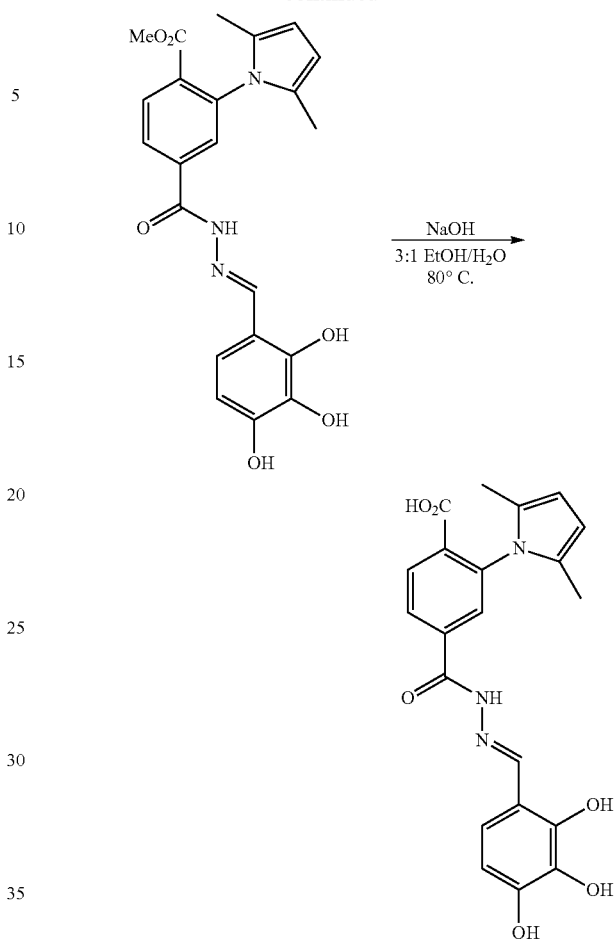

Two specific examples include preparation of compounds 79 and 101. Methyl 2-(2,5-dimethyl-1H-pyrrol-1-yl)-4-(hydrazinecarbonyl)benzoate was stirred with an equimolar amount of the respective aldehyde in ethanol at room temperature. Upon completion of the reaction, 1M NaOH was then added and the mixture was heated to reflux to provide the free carboxylic acid.

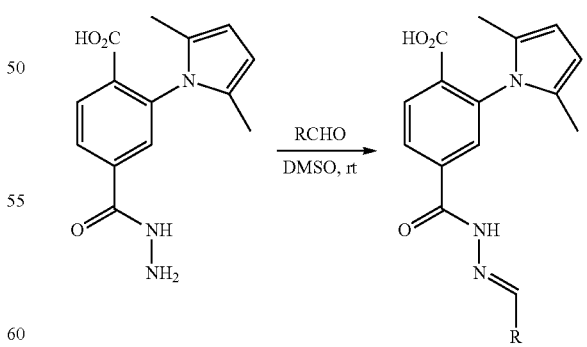

For library synthesis, 2-(2,5-dimethyl-1H-pyrrol-1-yl)-4-(hydrazinecarbonyl)benzoic acid may be dissolved in DMSO and mixed with an equimolar amount of an appropriate aldehyde as a stock solution in the same solvent. The reactions may be performed in a sealed microtiter plate by shaking at ambient temperature to provide stock solutions appropriate for screening in biochemical assays as evidenced by LC/MS analysis.

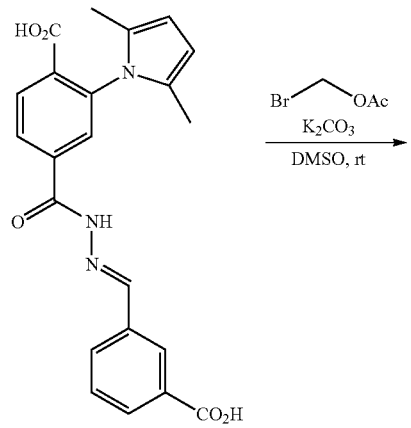

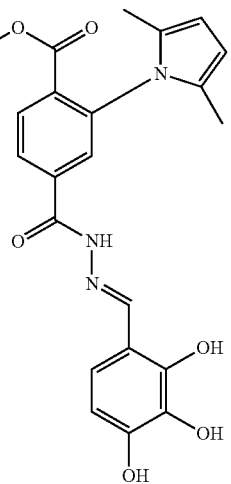

Selected hydrazides may be converted to their AM ester prodrugs in an analogous procedure to that used for Compound 64.

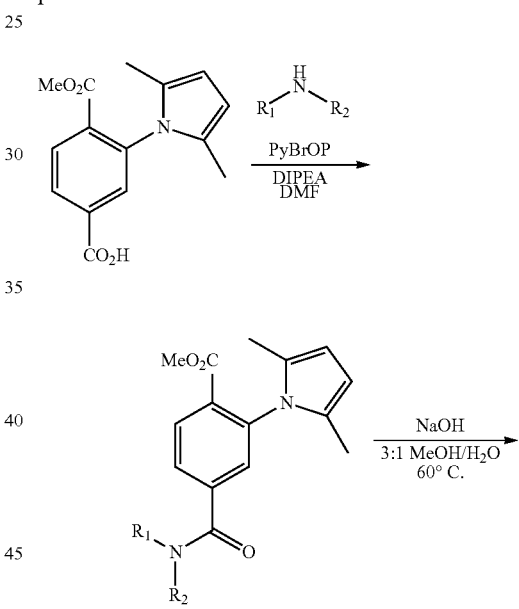

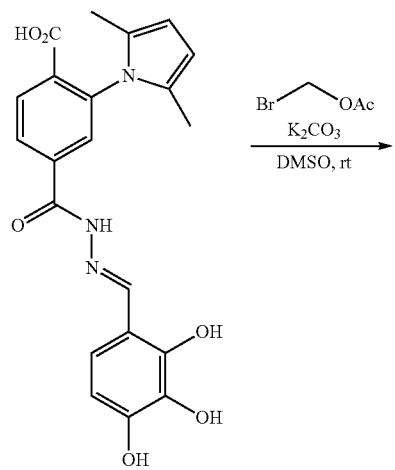

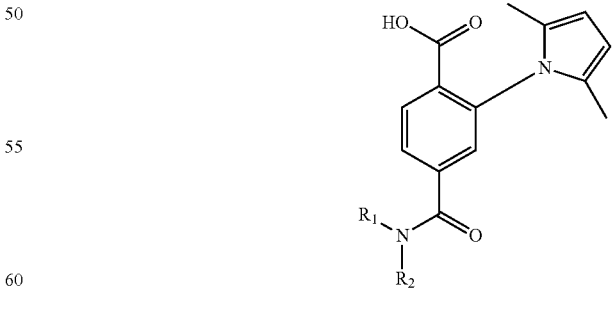

Alternately, amides may be prepared from the 3-(2,5-dimethyl-1H-pyrrol-1-yl)-4-(methoxycarbonyl)benzoic acid intermediate by PyBrOP activation in the presence of DIPEA in DMF. Hydrolysis of the resulting methyl esters then affords the free carboxylic acid functionality.

147
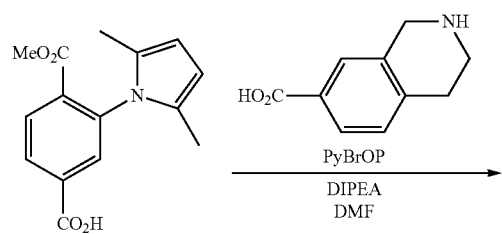 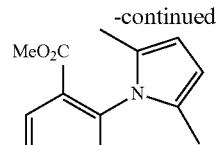
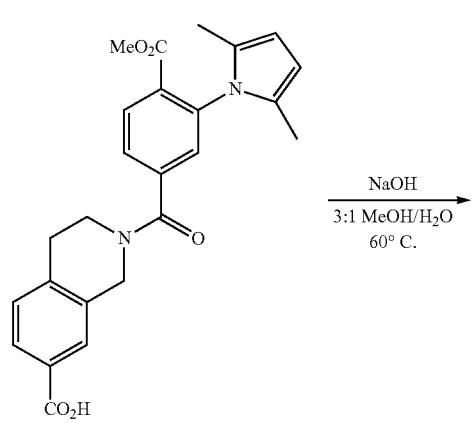 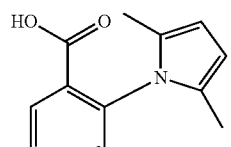
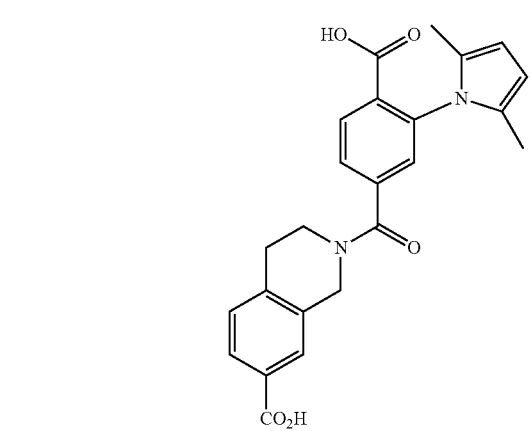
148
-continued
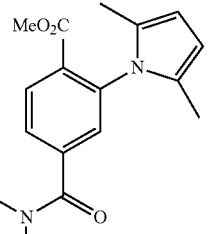
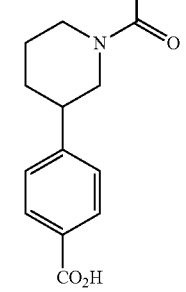
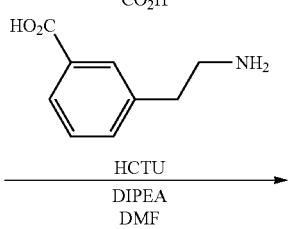
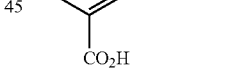
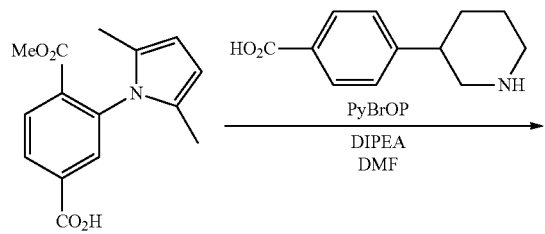 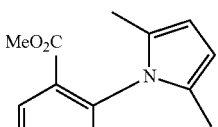
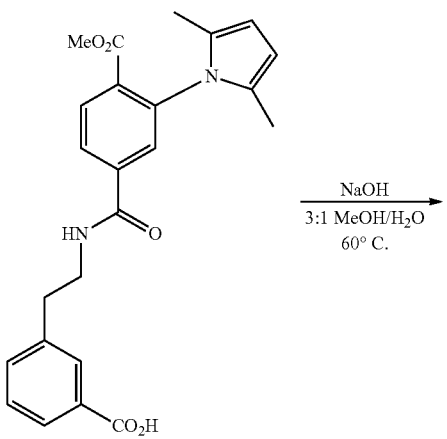

149
-continued
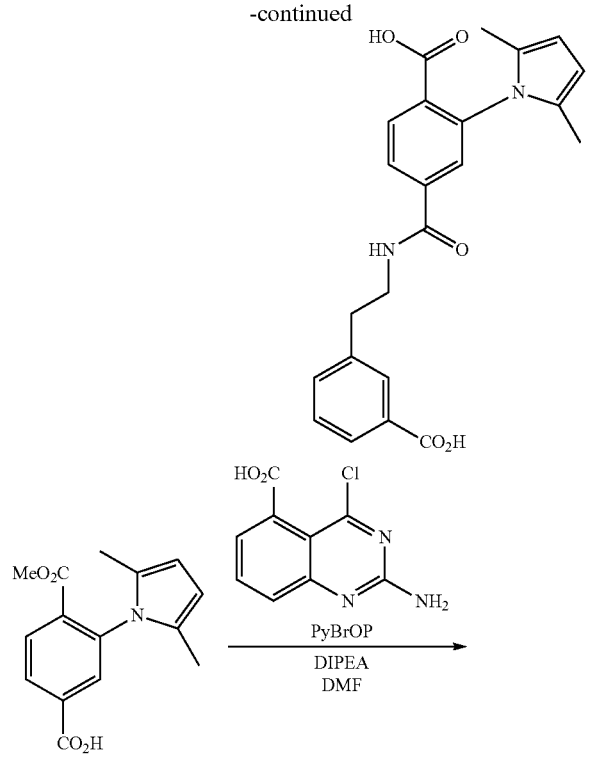
150
-continued
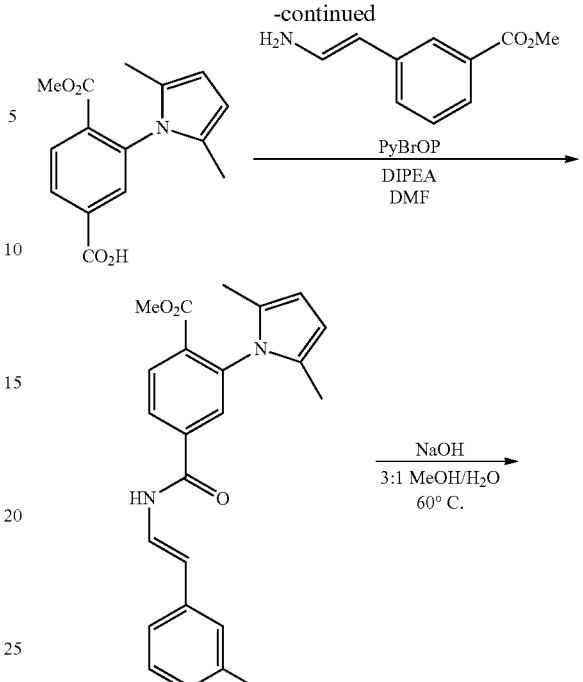
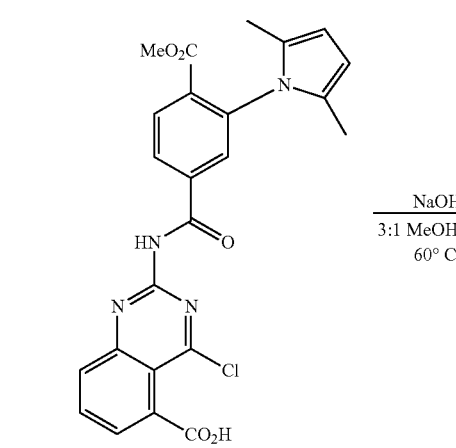
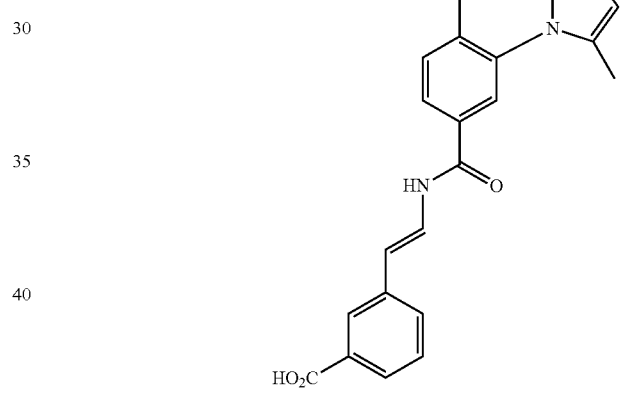
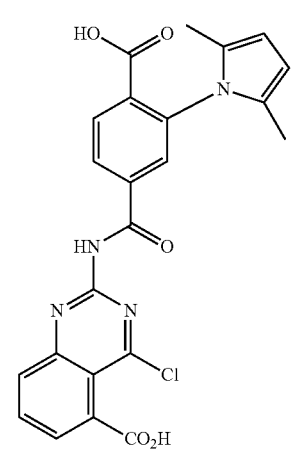
Specific examples may be prepared according to this general procedure by utilizing, primary and secondary amines or anilines.
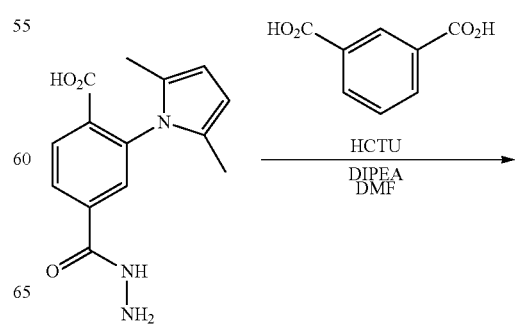

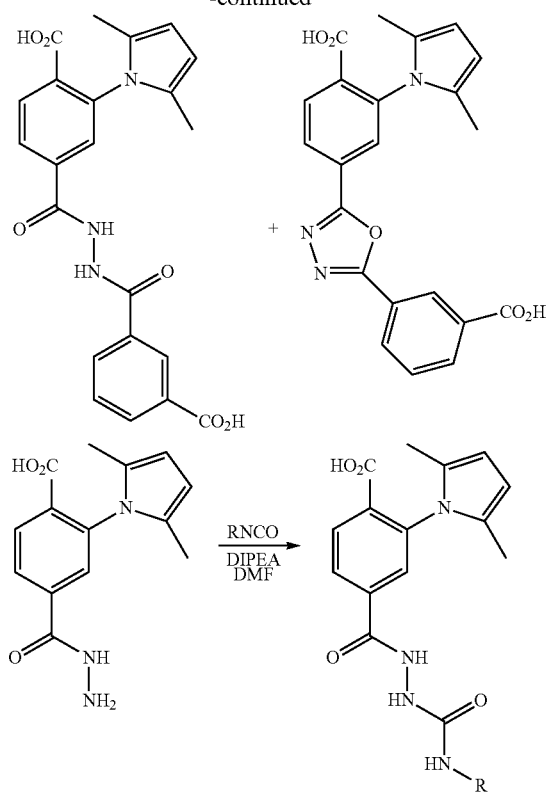

The hydrazides can also be functionalized by acylation using appropriately activated carboxylic acids or isocyanates in the presence of base. Bisacyl hydrazides can be cyclized to afford oxadiazoles in situ or using dehydrating reagents such as POCl₃.

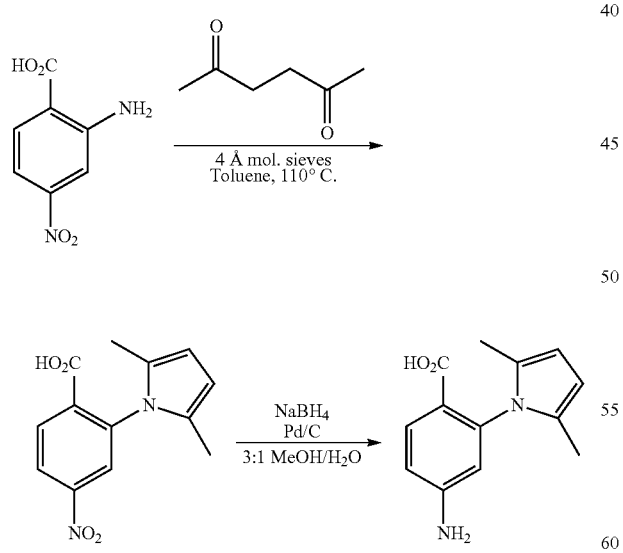

2-2,5-dimethylpyrrolyl-4-nitrobenzoic acid prepared as described may be reduced using sodium borohydride and palladium on carbon to afford an aniline derivative.

This aniline can then be acylated by activated carboxylic acids or isocyanates to afford a range of amide and urea-linked analogs.

Aryl halides based on this core scaffold can participate in Suzuki coupling with appropriate boronic acids to afford biaryl derivatives.

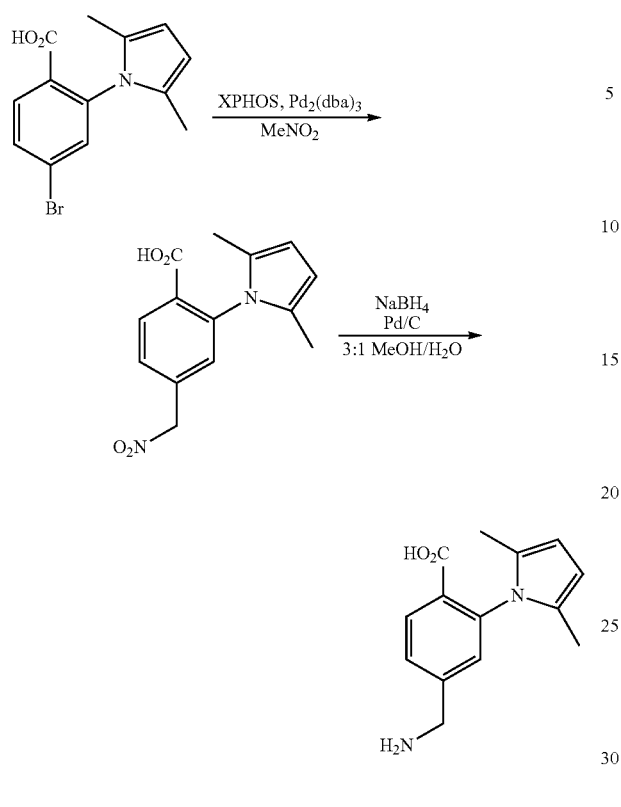

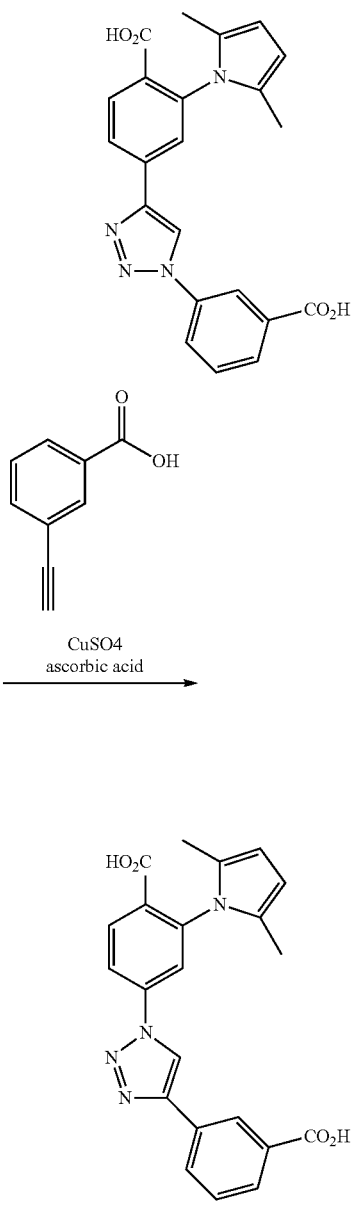

Nitromethylation or cyanation of these halides provides access to the appropriate benzylamines, which may be acylated to afford a homologated series of amides and ureas.

Preparation of 4-alkynyl and 4-ethynyl 2-(2,5-dimethyl-pyrrolyl)benzoic acids enables Huisgen cycloadditions with appropriate alkynes and azides to afford triazole linked analogs.

Experimental Procedures

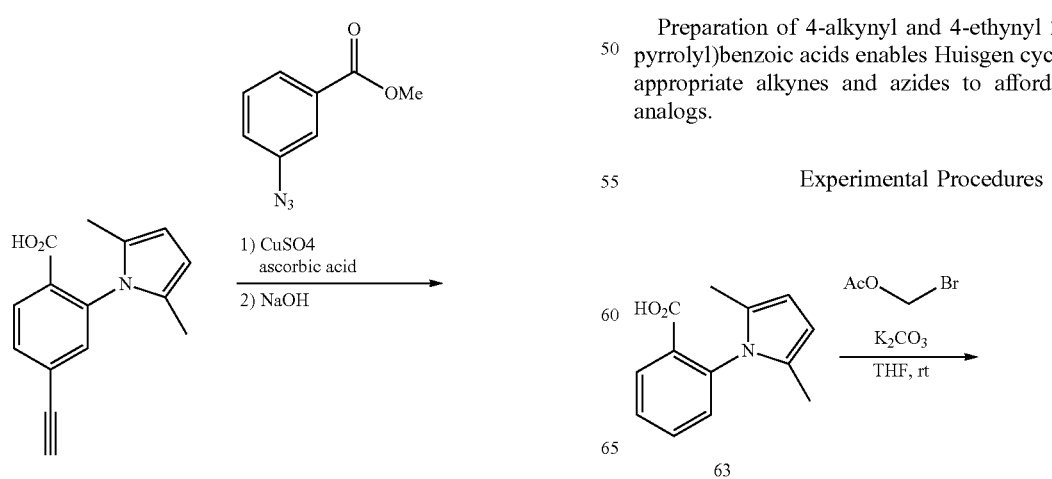

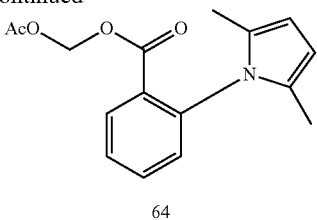

Compound 64: 2-(2,5-dimethylpyrrolyl)benzoic acid (1 g, 4.65 mmol, 1 equiv) was dissolved in anhydrous tetrahydrofuran (0.2 M). Potassium carbonate (1.92 g, 13.95 mmol, 3 equiv) was added, followed by acetoxymethyl bromide (1.06 mL, 6.98 mmol, 1.5 equiv) and the reaction was stirred at room temperature overnight. The reaction was partitioned into ethyl acetate and water and then extracted with ethyl acetate. Combined organics were washed with brine, dried over sodium sulfate and concentrated. The crude residue was purified by MPLC (ISCO) on a 40 g silica gel cartridge, eluting with a gradient from 0-100% ethyl acetate in hexanes. 982 mg (74%) of 64 was isolated as an off-white solid. $^1$H NMR (400 MHz, Methanol-$d_4$) δ 7.92 (dd, J=7.8, 1.6 Hz, 1H), 7.70 (td, J=7.7, 1.6 Hz, 1H), 7.57 (td, J=7.6, 1.2 Hz, 1H), 7.25 (dd, J=7.8, 1.2 Hz, 1H), 5.76 (s, 2H), 5.69 (s, 2H), 2.04 (d, J=13.8 Hz, 3H), 1.87 (s, 6H). $^{13}$C NMR (100 MHz, Methanol-d4) δ 171.20, 170.84, 166.38, 139.96, 134.40, 131.99, 131.85, 129.89, 129.80, 106.92, 80.60, 20.87, 12.90. LC/MS: RT=2.46 min, m/z=288.106.

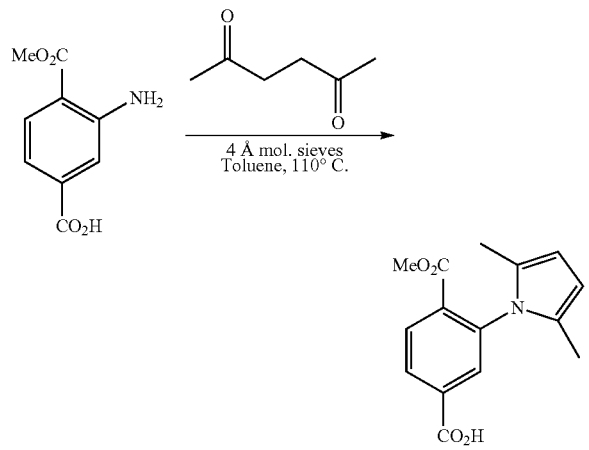

3-(2,5-dimethyl-1H-pyrrol-1-yl)-4-(methoxycarbonyl) benzoic acid: 1-methyl-2-aminoterephthalate (3.9 g, 20 mmol, 1 equiv) was dissolved in anhydrous toluene (0.2 M). 4 Å molecular sieves (7.8 g, 200 wt %) were added, followed by 2,5-hexanedione (4.6 mL, 20 mmol, 2 equiv) and the reaction was heated to reflux for 40 hours. The reaction was allowed to cool to room temperature, filtered and concentrated. The crude residue was purified by MPLC on a 40 g silica gel cartridge, eluting with a gradient from 0-100% ethyl acetate in hexanes, to afford 3.47 g of 3-(2,5-dimethyl-1H-pyrrol-1-yl)-4-(methoxycarbonyl)benzoic acid (64%) of an off white solid. $^1$H NMR (400 MHz, Methanol-$d_4$) δ 8.15 (dd, J=8.0, 1.6 Hz, 1H), 7.93 (d, J=8.0 Hz, 1H), 7.84 (d, J=1.6 Hz, 1H), 5.79 (s, 1H), 3.63 (s, 3H), 1.88 (s, 6H). $^{13}$C NMR (100 MHz, Methanol-d4) δ 167.90, 167.80, 139.71, 136.81, 135.95, 132.50, 131.57, 130.60, 130.01, 107.17, 107.08, 53.23, 53.21, 12.88, 12.85. LC/MS: RT=2.22 min, m/z=274.142.

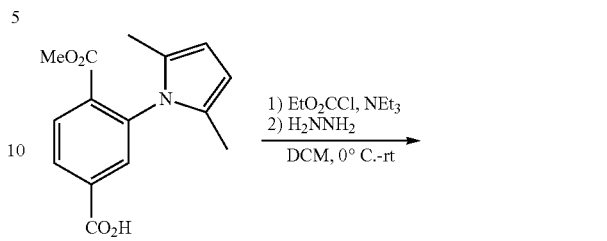

Methyl 2-(2,5-dimethyl-1H-pyrrol-1-yl)-4-(hydrazinecarbonyl)benzoate: 3-(2,5-dimethyl-1H-pyrrol-1-yl)-4-(methoxycarbonyl)benzoic acid (3.0 g, 10.98 mmol, 1 equiv) was dissolved in anhydrous dichloromethane (0.2 M) and cooled to 0° C. under an inert atmosphere. Triethylamine (4.75 mL, 32.9 mmol, 3 equiv) was added dropwise via syringe, followed by ethyl chloroformate (1.09 mL, 13.2 mmol, 1.2 equiv) and the reaction was stirred at 0° C. for 3 hours. Anhydrous hydrazine (457 □L, 14.3 mmol, 1.3 equiv) was added and the reaction stirred at 0° C. for 2 additional hours. The reaction was concentrated under reduced pressure and the crude residue was purified by MPLC on a 40 g silica gel cartridge, eluting with a gradient from 0-100% ethyl acetate in hexanes, to afford 1.59 g (50%) of the title compound as a yellow solid. $^1$H NMR (400 MHz, Methanol-$d_4$) δ 7.96 (d, J=1.1 Hz, 2H), 7.68 (t, J=1.1 Hz, 1H), 5.79 (s, 2H), 3.64 (s, 3H), 1.89 (s, 9H). $^{13}$C NMR (100 MHz, Methanol-d4) δ 167.79, 167.54, 139.95, 138.26, 135.59, 131.76, 130.41, 130.08, 128.30, 107.12, 53.22, 53.20, 15.10, 12.87. LC/MS: RT=1.73 min, m/z=289.515.

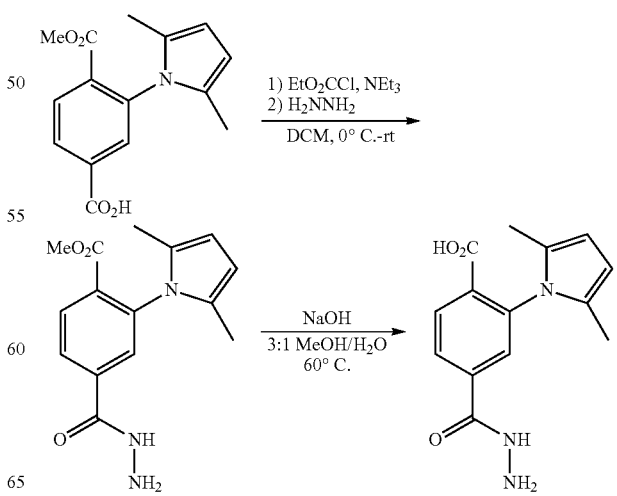

2-(2,5-dimethyl-1H-pyrrol-1-yl)-4-(hydrazinecarbonyl) benzoic acid: 3-(2,5-dimethyl-1H-pyrrol-1-yl)-4-(methoxycarbonyl)benzoic acid (563 mg, 2 mmol, 1 eq) was dissolved in anhydrous dichloromethane (0.2 M) and cooled to 0° C. under an inert atmosphere. Triethylamine (865 □L, 6 mmol, 3 equiv) was added dropwise via syringe, followed by ethyl chloroformate (199 □L, 2.4 mmol, 1.2 equiv) and the reaction was stirred at 0° C. for 3 hours. Anhydrous hydrazine (83 □L, 2.6 mmol, 1.3 equiv) was added and the reaction stirred at 0° C. for 2 additional hours. The reaction was concentrated under reduced pressure and the crude residue re-dissolved in a 3:1 mixture of methanol and water (0.1M). Sodium hydroxide (400 mg, 10 mmol, 5 equiv was added and the reaction heated to 60° C. for 1 hour. The methanol was removed under reduced pressure and the mixture acidified with hydrochloric acid. As the hydrazide is relatively unstable in solution, it was filtered and directly purified by preparative HPLC on a 21.5 mm×250 mm 150 Å C18 column eluting with 5-95% acetonitrile in water and 0.1% TFA. Lyophilization afforded 221 mg (41%) of the title compound as a red-orange powder. LC/MS: RT=1.00 min, m/z=274.136.

Hydrazone Library Synthesis: 2-(2,5-dimethyl-1H-pyrrol-1-yl)-4-(hydrazinecarbonyl)benzoic acid was dissolved in DMSO to a stock concentration of 11.1 mM. 36 μL of this stock was dispensed into each well of four 96-well deep well storage plates using a multichannel pipette. 4 μL of a 100 mM stock of 371 diverse aldehydes were then dispensed in the same manner into the four plates. Plates were sealed and shaken overnight at room temperature. LC/MS indicated complete reaction to provide 10 mM stocks of the hydrazone library suitable for biochemical screening.

4-bromo-2-(2,5-dimethyl-1H-pyrrol-1-yl)benzoic acid: 2-amino-4-bromobenzoic acid (mg, 0.1 mmol, 1 equiv.) was dissolved in toluene (0.1 M) in a 4 mL vial equipped with a magnetic stirbar. 4 Å molecular sieves (mg, 200 wt %) were added, followed by 2,5-hexanedione (17.6 μL, 0.15 mmol, 1.5 equiv), the vial was sealed and the mixture heated to 110° C. for 16 hours. The reaction mixture was then cooled, filtered, washing with methanol, and concentrated. Crude residue was purified by silica gel flash chromatography on a 4 g ISCO silica gel cartridge and eluting with a gradient of 0-10% methanol in dichloromethane to afford 16.5 mg (56%) of the desired product as an orange film. LC/MS: RT=1.57 min, m/z=295.826.

Compound 140: 2-amino-4-nitrobenzoic acid (mg, 0.3 mmol, 1 equiv.) was dissolved in toluene (0.1 M) in a 4 mL vial equipped with a magnetic stirbar. 4 Å molecular sieves (mg, 200 wt %) were added, followed by 2,5-hexanedione (17.6 μL, 0.15 mmol, 1.5 equiv), the vial was sealed and the mixture heated to 110° C. for 16 hours. The reaction mixture was then cooled, filtered, washing with methanol, and concentrated. Crude residue was purified by silica gel flash chromatrography on a 4 g ISCO silica gel cartridge and eluting with a gradient of 0-10% methanol in dichloromethane to afford 52 mg (67%) of the desired product as a yellow film. LC/MS: RT=1.61 min, m/z=260.92.

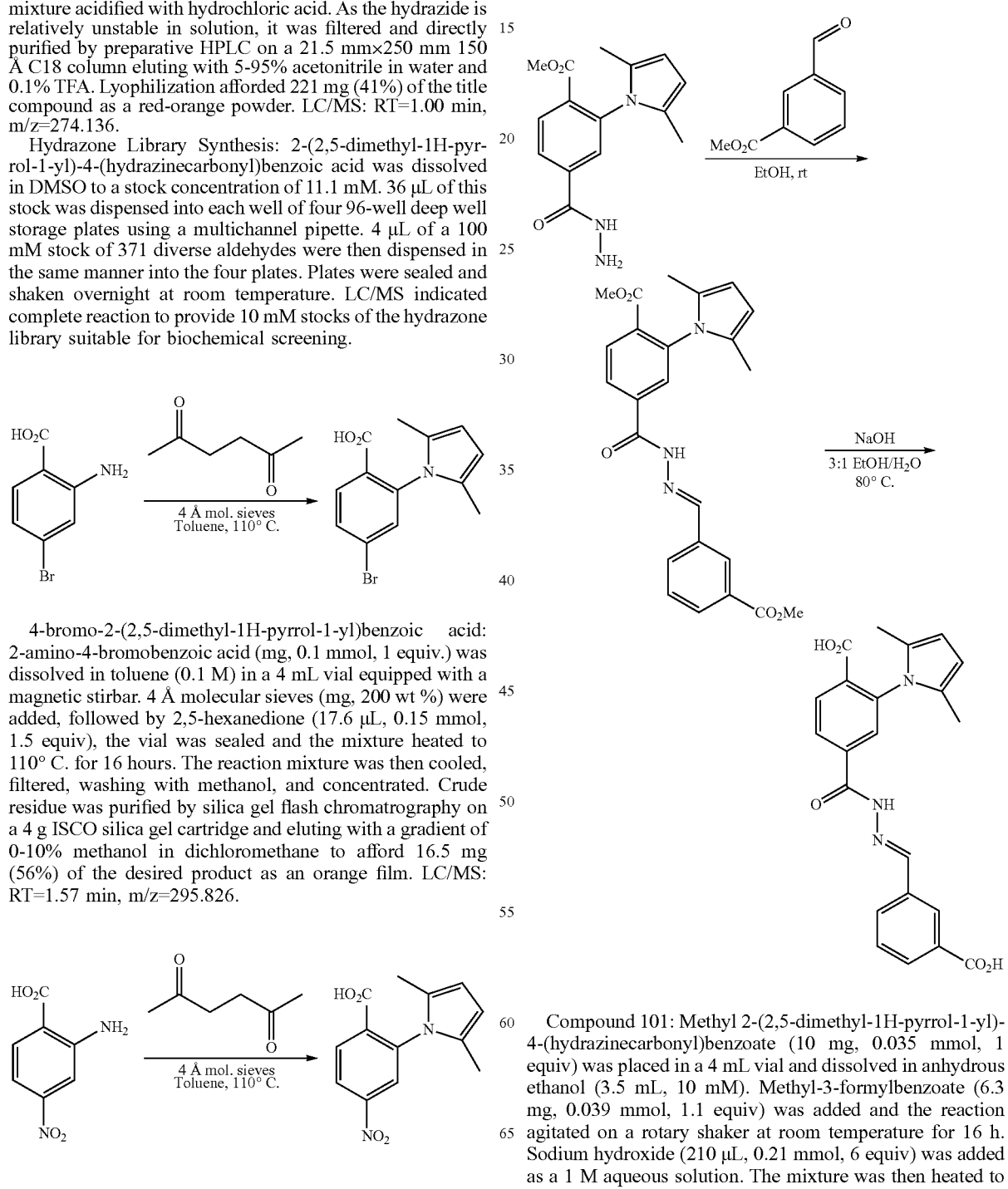

Compound 101: Methyl 2-(2,5-dimethyl-1H-pyrrol-1-yl)-4-(hydrazinecarbonyl)benzoate (10 mg, 0.035 mmol, 1 equiv) was placed in a 4 mL vial and dissolved in anhydrous ethanol (3.5 mL, 10 mM). Methyl-3-formylbenzoate (6.3 mg, 0.039 mmol, 1.1 equiv) was added and the reaction agitated on a rotary shaker at room temperature for 16 h. Sodium hydroxide (210 μL, 0.21 mmol, 6 equiv) was added as a 1 M aqueous solution. The mixture was then heated to 80° C. in the sealed vial for 3 hours. The mixture was acidified with 1 M aqueous hydrochloric acid and concentrated. The crude residue was purified by silica gel flash column chromatography eluting with a gradient of 0-10% Acetic acid in 2-propanol to afford 4.5 mg of a red solid (32%). LC/MS: RT=1.39 min, m/z=405.828.

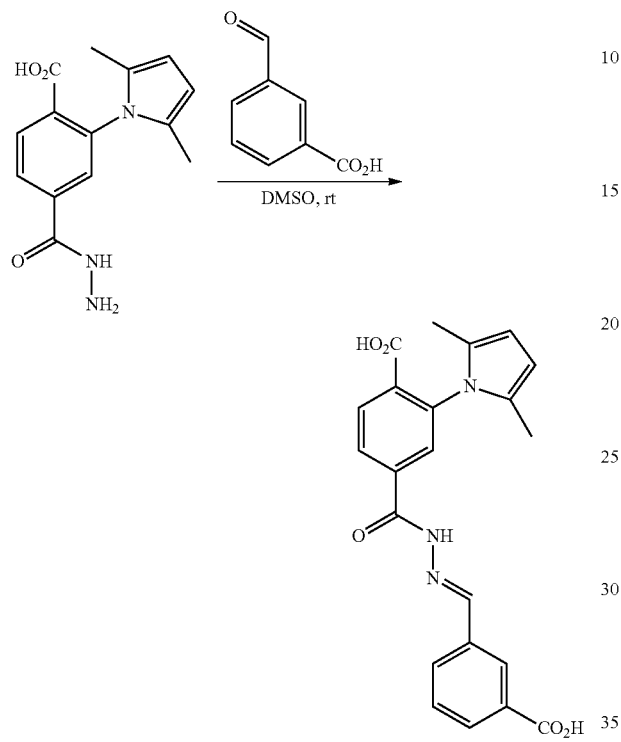

Alternately, a preparative version of the general library synthesis could be conducted where a 11.1 mM stock solution of 2-(2,5-dimethyl-1H-pyrrol-1-yl)-4-(hydrazinecarbonyl)benzoic acid (1.8 mL) in dimethyl sulfoxide could be mixed with a 100 mM stock solution of 3-formylbenzoic acid (200 μL) in the same solvent and incubated for hours to afford a 10 mM stock solution of the crude hydrazide. This material could be purified by reverse phase preparative HPLC to afford 3.7 mg of 101 as a pale orange powder (46%). $^1$H NMR (400 MHz, Methanol-$d_4$) δ 8.48-8.41 (m, 2H), 8.21-8.05 (m, 3H), 7.91-7.85 (m, 1H), 7.83 (d, J=1.7 Hz, 1H), 7.59 (dd, J=8.7, 6.9 Hz, 2H), 5.84-5.74 (m, 2H), 1.96 (d, J=14.3 Hz, 6H). $^{13}$C NMR (100 MHz, cd$_3$od) δ 218.42, 191.90, 167.06, 134.78, 133.42, 132.92, 131.81, 131.31, 131.13, 131.05, 130.34, 129.05, 129.00, 128.65, 127.83, 127.69, 127.13, 115.68, 113.07, 109.99, 38.99, 38.98.

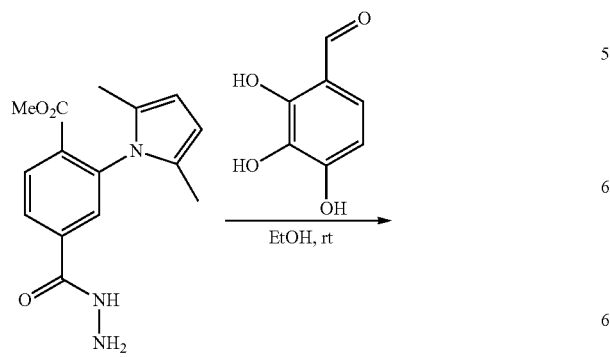

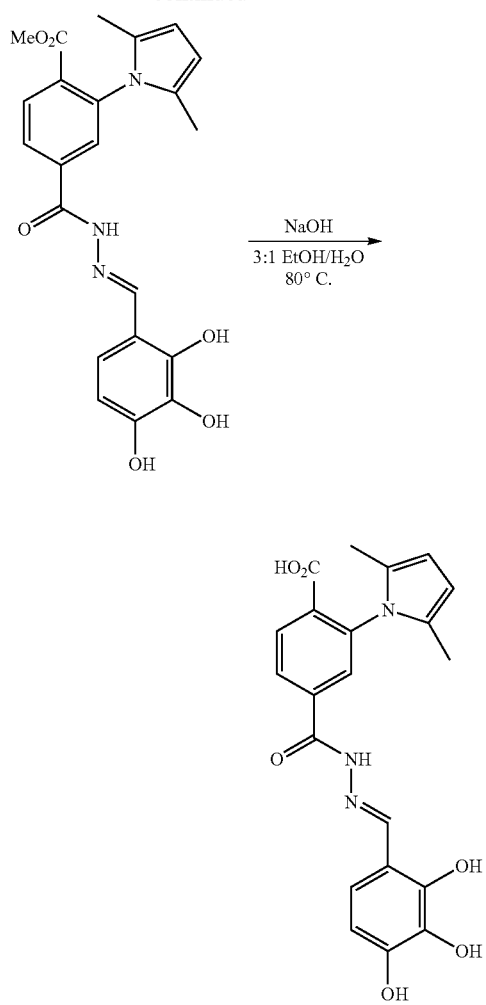

Compound 79: Methyl 2-(2,5-dimethyl-1H-pyrrol-1-yl)-4-(hydrazinecarbonyl)benzoate (10 mg, 0.035 mmol, 1 equiv) was placed in a 4 mL vial and dissolved in anhydrous ethanol (3.5 mL, 10 mM). 2,3,4-trihydroxybenzaldehyde (5.9 mg, 0.39 mmol, 1.1 equiv) was added and the reaction agitated on a rotary shaker at room temperature for 16 h. Sodium hydroxide (210 μL, 0.21 mmol, 6 equiv) was added as a 1 M aqueous solution. Then, the mixture was heated to 80° C. in the sealed vial for 3 hours. The mixture was acidified with 1 M aqueous hydrochloric acid and concentrated. The crude residue was purified by silica gel flash column chromatography eluting with a gradient of 0-10% Acetic acid in 2-propanol to afford 2.8 mg of a red solid (20%). LC/MS: RT=1.31 min, m/z=409.829.

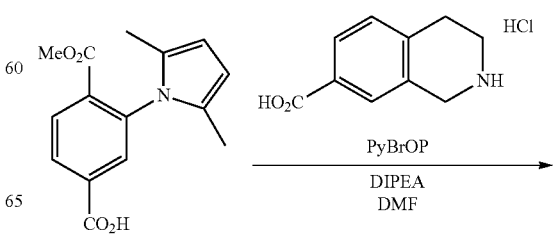

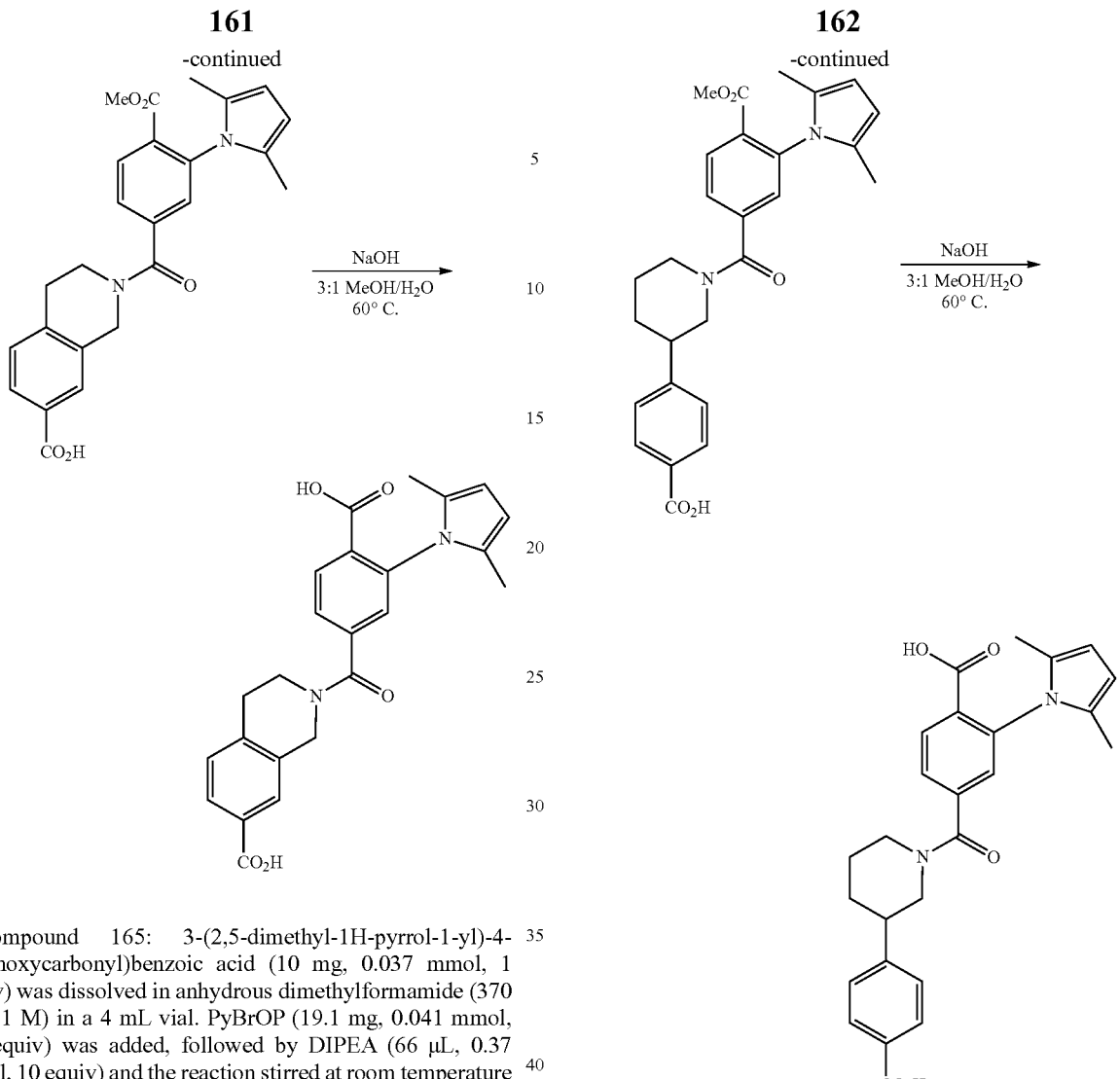

Compound 165: 3-(2,5-dimethyl-1H-pyrrol-1-yl)-4-(methoxycarbonyl)benzoic acid (10 mg, 0.037 mmol, 1 equiv) was dissolved in anhydrous dimethylformamide (370 µl, 0.1 M) in a 4 mL vial. PyBrOP (19.1 mg, 0.041 mmol, 1.1 equiv) was added, followed by DIPEA (66 µL, 0.37 mmol, 10 equiv) and the reaction stirred at room temperature in the sealed vial for 1 hour. 1,2,3,4-tetrahydroisoquinoline-7-carboxylic acid hydrochloride (8.8 mg, 0.041 mmol, 1.1 equiv) was added and the mixture heated to 80° C. for 3 hours in the sealed vial. The reaction was quenched by addition of water and partitioned into 10 mL each of water and ethyl acetate. The aqueous layer was extracted twice more with ethyl acetate and the combined organics washed with 30 mL brine, dried over sodium sulfate, filtered and concentrated. The crude residue was dissolved in 3:1 methanol:water (370 µL, 0.1 M) and sodium hydroxide was added (7.5 mg, 0.19 mmol, 5 equiv.). The reaction was heated to 60° C. for 3 hours. Upon completion of the reaction (as judged by LC/MS), the reaction was acidified by addition of concentrated hydrochloric acid and purified by preparative HPLC. LC/MS: RT=1.81 min, m/z=419.046.

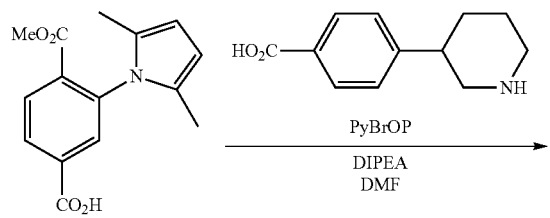

Compound 164: 3-(2,5-dimethyl-1H-pyrrol-1-yl)-4-(methoxycarbonyl)benzoic acid (10 mg, 0.037 mmol, 1 equiv) was dissolved in anhydrous dimethylformamide (370 µl, 0.1 M) in a 4 mL vial. PyBrOP (19.1 mg, 0.041 mmol, 1.1 equiv) was added, followed by DIPEA (33 µL, 0.185 mmol, 5 equiv) and the reaction stirred at room temperature in the sealed vial for 1 hour. 4-(piperidin-3-yl)benzoic acid (6.2 mg, 0.041 mmol, 1.1 equiv) was added and the mixture heated to 80° C. for 3 hours in the sealed vial. The reaction was quenched by addition of water and partitioned into 10 mL each of water and ethyl acetate. The aqueous layer was extracted twice more with ethyl acetate and the combined organics washed with 30 mL brine, dried over sodium sulfate, filtered and concentrated. The crude residue was dissolved in 3:1 methanol:water (370 µL, 0.1 M) and sodium hydroxide was added (7.5 mg, 0.19 mmol, 5 equiv.). The reaction was heated to 60° C. for 3 hours. Upon completion of the reaction (as judged by LC/MS), the reaction was acidified by addition of concentrated hydrochloric acid and purified by preparative HPLC. LC/MS: RT=1.74 min, m/z=447.063.

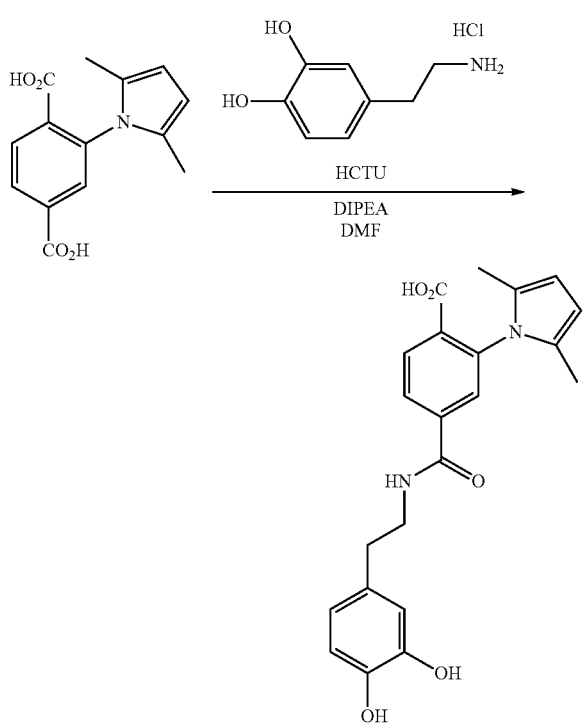

Compound 73: 2-(2,5-dimethyl-1H-pyrrol-1-yl)terephthalic acid (11 mg, 0.0403 mmol, 1 equiv) was added to a 4 mL vial, followed by HCTU (18 mg, 0.044 mmol, 1.1 equiv) and the solids dissolved in anhydrous dimethylformamide (403 µL, 0.1 M). DIPEA (36 µL, 0.20 mmol, 5 equiv) was added and the reaction was stirred for 5 minutes. Dopamine hydrochloride (15 mg, 0.081 mmol, 2 equiv) was added and the reaction stirred for 24 hours at room temperature. Reaction mixture was purified by silica gel flash chromatography on a 4 g ISCO silica gel cartridge, eluting with 0-10% methanol in dichloromethane to afford 2.4 mg of a red solid (16%). LC/MS: RT=1.29 min, m/z=394.873.

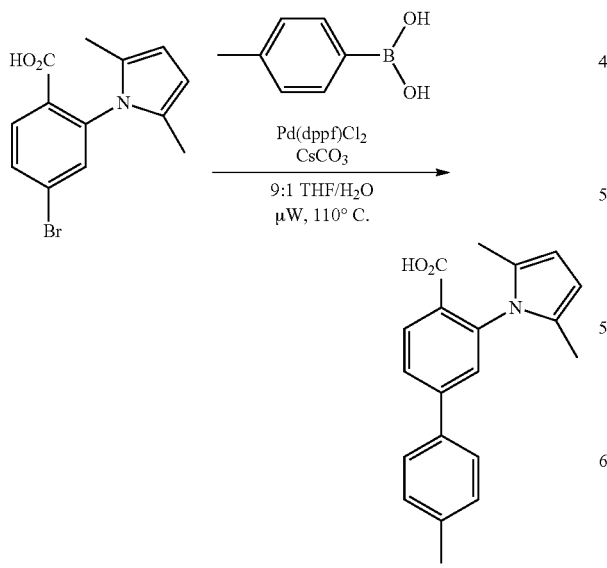

Compound 148: 4-bromo-2-(2,5-dimethyl-1H-pyrrol-1-yl)benzoic acid (10 mg, 0.034 mmol, 1 equiv) was added to a microwave vial followed by 4-methyl-phenylboronic acid (9 mg, 0.068 mmol, 2 equiv), cesium carbonate (22 mg, 0.068 mmol, 2 equiv.) and [1,1'-Bis(diphenylphosphino)ferrocene]dichloropalladium (II) dichloromethane complex (5.6 mg, 0.0068 mmol, 0.2 equiv). The vial was capped with a septum and purges with inert atmosphere. Solid reagents were dissolved in a degassed mixture of 9:1 tetrahydrofuran:water and the reaction heated to 110° C. in a microwave for 10 minutes. The reaction was cooled and partitioned between ethyl acetate and water. The aqueous layer was extracted 3 times with ethyl acetate. Combined organics were washed with brine, dried over sodium sulfate and concentrated. The crude residue was purified by silica gel flash chromatography on a 4 g ISCO silica gel cartridge, eluting with 0-10% methanol in dichloromethane to afford 2.5 mg pale yellow oil (24%). LC/MS: RT=1.88 min, m/z=305.839.

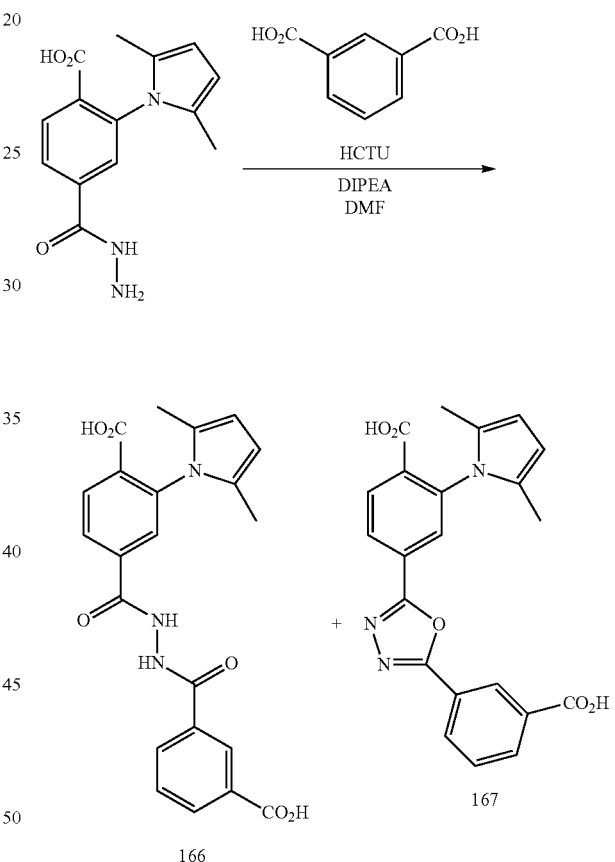

Compounds 166 and 167: Isophtalic acid (6 mg, 0.037 mmol, 1 equiv.) was placed in a 4 mL vial followed by HCTU (15 mg, 0.037 mmol, 1 equiv.). The reagents were dissolved in anhydrous dimethylformamide and DIPEA (33 µL, 0.185 mmol, 5 equiv.) was added. The reaction was stirred for 10 minutes and then 2-(2,5-dimethyl-1H-pyrrol-1-yl)-4-(hydrazinecarbonyl)benzoic acid (10 mg, 0.037 mmol, 1 equiv) was added and the reaction stirred for 24 hours at room temperature. The reaction mixture was purified by reverse phase preparative HPLC to afford 0.8 mg 166 (LC/MS: RT=1.72 min, m/z=421.947) as a red powder (5%) and 167 (LC/MS: RT=1.59 min, m/z=403.955) as a red powder 0.9 mg (6%).

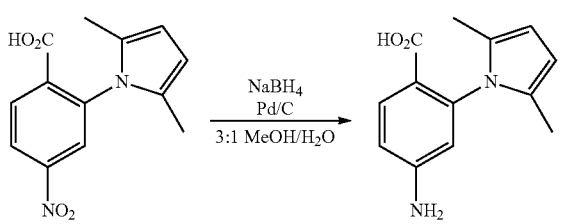 [SMILES: Cc1ccc(C)n1-c1cc([N+](=O)[O-])ccc1C(=O)O ; "NaBH4Pd/C" ; Cc1ccc(C)n1-c1cc(N)ccc1C(=O)O]

4-amino-2-(2,5-dimethyl-1H-pyrrol-1-yl)benzoic acid: 2-(2,5-dimethyl-1H-pyrrol-1-yl)-4-nitrobenzoic acid (52 mg, 0.2 mmol, 1 equiv) was placed in a round bottom flask and dissolved in a 3:1 mixture of methanol:water. 10% Palladium on charcoal (21.2 mg, 0.02 mmol, 0.1 equiv) was added to the solution and the solution was cooled to 0° C. Sodium borohydride (30.3 mg, 0.8 mmol, 4 equiv) was added and the reaction stirred loosely capped for 4 hours while warming to room temperature. The reaction was filtered through a plug of cotton and the filter washed with methanol. The filtrate was concentrated and purified by silica gel flash chromatography on a 4 g ISCO cartridge eluting with 0-10% methanol in dichloromethane to afford 33.2 mg (72%) of the desired product as an off white solid. LC/MS: RT=1.215 min, m/z=231.163.

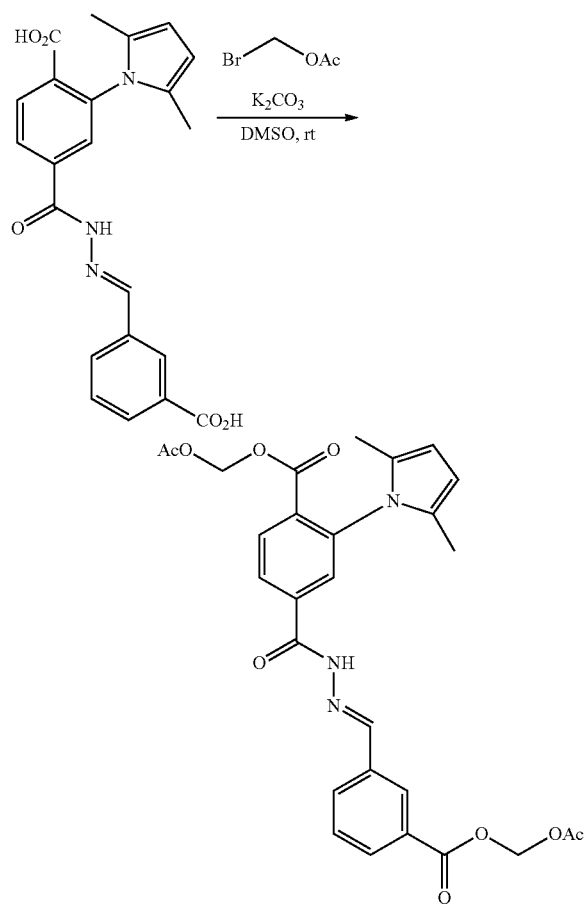

AM diester (in situ): To a 10 mM screening stock of the (E)-4-(2-(3-carboxybenzylidene)hydrazinecarbonyl)-2-(2,5-dimethyl-1H-pyrrol-1-yl)benzoic acid (20 µL, 0.002 mmol, 1 equiv.), was added acetoxymethyl bromide (0.1 µL, 0.006 mmol, 3 equiv.). Potassium carbonate (1.38 mg, 0.01 mmol, 5 equiv.) was added and the reaction was shaken at room temperature for 1 hour. After completion of the reaction as judged by LC/MS (20 min), the stock removed from residual solid by centrifugation and aspiration with a pipette. The resulting stock solution could be utilized directly in biochemical and cellular experiments.

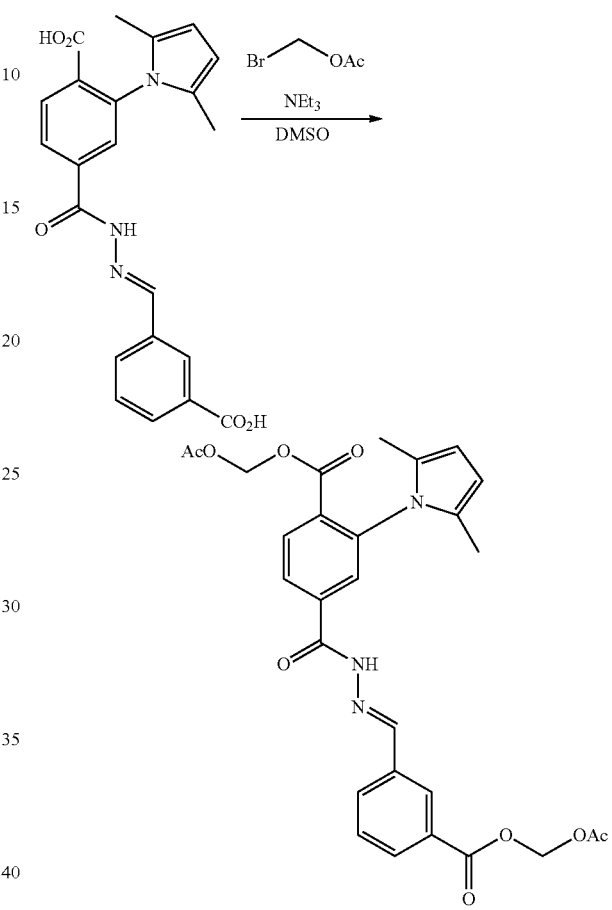

AM diester: To a 10 mM stock of (E)-4-(2-(3-carboxybenzylidene)hydrazinecarbonyl)-2-(2,5-dimethyl-1H-pyrrol-1-yl)benzoic acid (2 mL, 0.02 mmol, 1 equiv.), was added acetoxymethyl bromide (6.1 µL, 0.04 mmol, 2 equiv.). When the reaction was judged complete by LC/MS (20 min), the reaction mixture was purified by preparative reverse phase HPLC to afford 0.7 mg of the title compound as a pale orange powder (6%). LC/MS: RT=1.78 min, m/z=549.529 $^1$H NMR (400 MHz, Methanol-$d_4$) δ 8.47-8.38 (m, 2H), 8.23-8.04 (m, 4H), 7.88-7.79 (m, 1H), 7.58 (dt, J=15.4, 7.8 Hz, 2H), 6.02-5.82 (m, 2H), 5.75 (s, 4H), 2.13-2.03 (m, 6H), 1.90 (d, J=9.4 Hz, 6H).

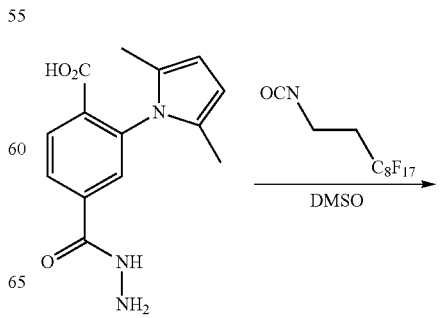

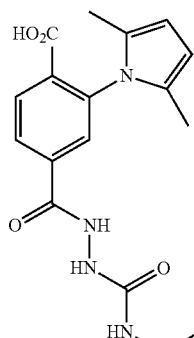

Compound 168: To a 20 mM stock of the hydrazide (25 μL, 0.005 mmol, 1 equiv.) in a polypropylene Eppendorf tube was added a 20 mM stock of perfluorooctylethylisocyanate (25 μL, 0.005 mmol, 1 equiv.) and the reaction was incubated overnight at room temperature to afford a 10 mM stock solution of the acyl semicarbazide which was suitable for use in biochemical assays. LC/MS: RT=1.72 min, m/z=762.645

Synthesis of Compounds T1, T1-2, T2, and T4 to T8

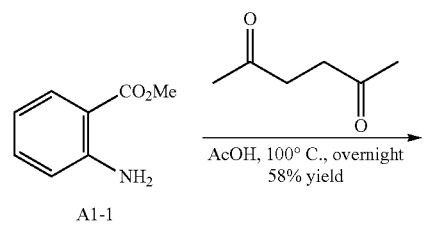

A1-1

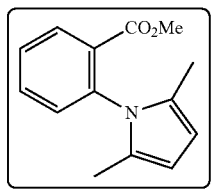

T1-2

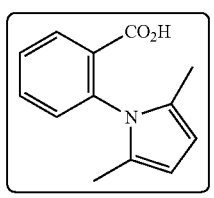

T1

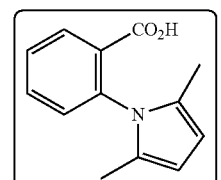

T1

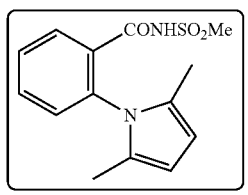

T2

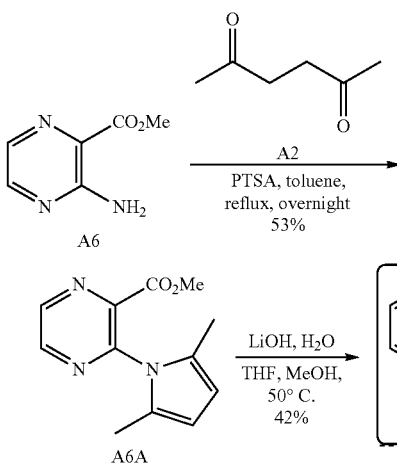

A6 → A6A → T4

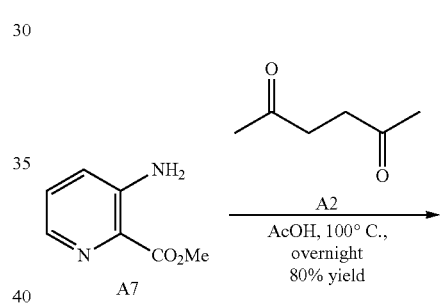

A7 → A7-1

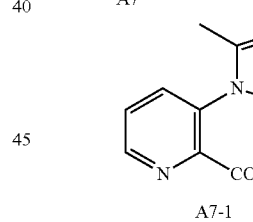

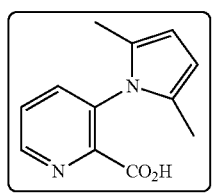

T5

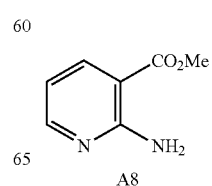

A8

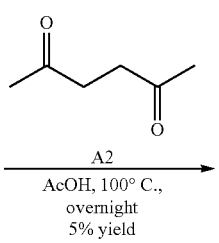

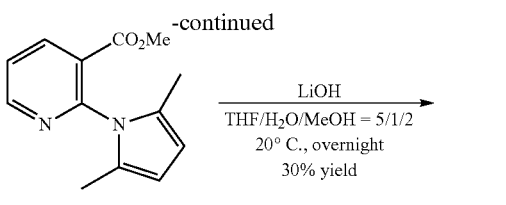

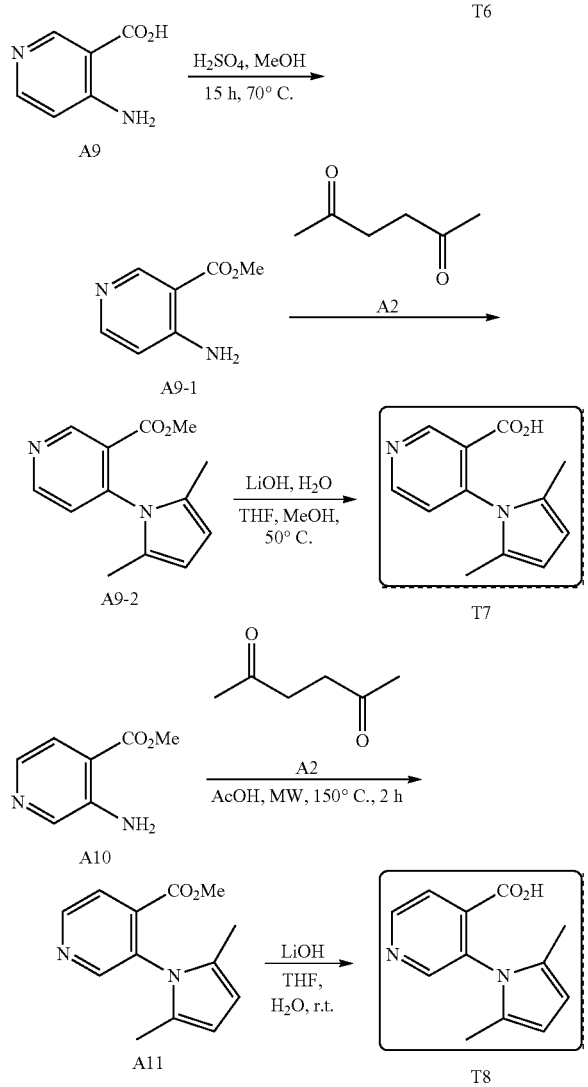

1H), 7.53-7.49 (m, 1H), 7.30 (d, J=8.0 Hz, 1H), 5.90 (s, 2H), 3.70 (s, 3H), 1.94 (s, 6H) ppm.

To a solution of compound T1-2 (300 mg, 1.31 mmol) in THF/H$_2$O/MeOH (8 mL) was added LiOH (126 mg, 5.24 mmol). The mixture was stirred at 20° C. overnight. TLC showed the reaction was completed. The mixture was dissolved with EA and water. The solution was adjusted to pH6 by 1N HCl solution, extracted with EA. The organic layer was dried over Na$_2$SO$_4$ and evaporated in vacuo to afford T1 (260 mg, 70% yield). LCMS: (M+H$^+$): 216. $^1$H NMR (CDCl$_3$; 400 MHz) δ 8.11 (d, J=7.2 Hz, 1H), 7.66 (d, J=7.2 Hz, 1H), 7.54 (t, J=7.2 Hz, 1H), 7.28 (d, J=5.2 Hz, 1H), 5.92 (s, 2H), 1.96 (s, 6H) ppm.

To a solution of T1 (100 mg, 0.465 mmol) in DCM (3 mL) was added MeSO$_2$NH$_2$ (53 mg, 0.558 mmol), TEA (94 mg, 0.93 mmol) and HATU (194 mg, 0.512 mmol) under N$_2$. The mixture was stirred at r.t. overnight. LCMS showed the reaction was completed. The mixture was evaporated in vacuo. The residue was purified by pre-HPLC to afford T2 (4 mg, 3% yield). LCMS: (M+H$^+$): 293. $^1$H NMR (CDCl$_3$; 400 MHz) δ 8.19 (d, J=8 Hz, 1H), 7.73 (t, J=7.6 Hz, 1H), 7.63 (t, J=7.6 Hz, 1H), 6.90 (s, 1H), 6.12 (s, 2H), 3.22 (s, 3H), 1.99 (s, 6H) ppm.

Compound A6 (0.5 g, 3.26 mmol) in toluene (8 mL) was added Compound A2 (0.59 g, 5.17 mmol) and PTSA (0.06 g, 0.31 mmol) at r.t., then the mixture was heated to 130° C. and stirred overnight. TLC showed there was about 50% SM remained. The mixture was concentrated under vacuo to get the crude product. The crude was purified by column (PE/EA=5:1) to get the Compound A6A (0.41 g, purity: 90% on TLC) as yellow solid. $^1$H NMR (400 M; CDCl$_3$) δ 8.678 (dd, J=2.4 Hz, 2 H), 5.856 (s, 2 H), 3.767 (s, 3 H), 1.93 (s, 6 H) ppm.

To a mixture of compound A6A(0.4 g, 1.73 mmol) in THF (5 mL), MeOH (2 mL) and H$_2$O (1 mL) was added LiOH.H$_2$O (0.36 g, 8.65 mmol), then the mixture was stirred at r.t. for one hour. TLC showed the reaction was completed, the solvent was removed under vacuo, the residue was dissolved in water and extracted with EA (ethyl acetate), the organic layer was separated and putted off, the water phase was acidized and extracted with EA three times, the organic phase was washed with water and brine, dried over Na$_2$SO$_4$, evaporated to get the T4 (0.15 g, purity: 95% on LCMS) as yellow solid. LCMS (M+H$^+$): 218. $^1$H NMR (400 M; DMSO) δ 8.86 (d, J=6.4 Hz, 2H), 5.79 (s, 2H), 1.91 (s, 6H) ppm.

To a solution of compound A7 (1 g, 6.5 mmol) in AcOH (10 mL) was added hexane-2,5-dione (0.9 g, 8 mmol) under N$_2$. The mixture was stirred at 100° C. overnight. TLC showed the reaction was completed. The mixture was concentrated in vacuo. The residue was purified by column chromatography on silica gel to afford compound A7-1(1.2 g, 80% yield).

To a solution of compound A7-1 (100 mg, 0.44 mmol) in THF/H$_2$O/MeOH (8 mL) was added LiOH (52 mg, 1.3 mmol). The mixture was stirred at 20° C. overnight. TLC showed the reaction was completed. The mixture was dissolved with EA and water. The solution was adjusted to pH 6 by 1N HCl solution, extracted with EA. The organic layer was dried over Na$_2$SO$_4$ and evaporated in vacuo to afford T5 (70 mg, 70% yield). LCMS (M+H$^+$): 217. $^1$H NMR (CDCl$_3$; 400 MHz) δ 8.74 (d, J=1.6 Hz, 1H), 7.77 (m, 2H), 5.99 (m, 2H), 1.94 (s, 6H) ppm.

To a solution of compound A8 (2 g, 13 mmol) in AcOH (10 mL) was added hexane-2,5-dione (1.8 g, 16 mmol) under N$_2$. The mixture was stirred at 100° C. overnight. TLC showed the conversion ratio is about 10%. The mixture was To a solution of compound A1-1 (2 g, 13.2 mmol) in AcOH (10 mL) was added hexane-2,5-dione (1.81 g, 15.8 mmol) under N$_2$. The mixture was stirred at 100° C. overnight. TLC showed the reaction was completed. The mixture was concentrated in vacuo. The residue was purified by column chromatography on silica gel to afford compound T1-2 (1.75 g, 58% yield). LCMS: (M+H$^+$): 230. $^1$H NMR (CDCl$_3$; 400 MHz) δ 7.97 (d, J=7.6 Hz, 1H), 7.65-7.61 (m, concentrated in vacuo. The residue was purified by column chromatography on silica gel to afford compound A8-1 (0.15 g, 5% yield).

To a solution of compound A8-1 (150 mg, 0.65 mmol) in THF/H$_2$O/MeOH (8 mL) was added LiOH.H$_2$O (100 mg, 2.6 mmol). The mixture was stirred at 20° C. overnight. TLC showed the reaction was completed. The mixture was dissolved with EA and water. The solution was adjusted to pH 6 by 1N HCl solution, extracted with EA. The organic layer was dried over Na$_2$SO$_4$ and evaporated in vacuo to afford T6 (26 mg, 20% yield). LCMS (M+H$^+$): 217. $^1$H NMR (CDCl$_3$; 400 MHz) δ 8.66 (d, J=2.4 Hz, 1H), 8.36 (m, 1H), 7.60 (m, 1H), 5.75 (m, 2H), 1.96 (s, 6H) ppm.

Compound A9 (3 g, 21.72 mmol) in MeOH (50 mL) was cooled to 0° C. and H$_2$SO$_4$ was added dropwise, after the addition, the mixture was stirred at 0° C. for 30 min, then the mixture was heated to 80° C. overnight. TLC showed the reaction was completed, the mixture was acidized to pH 8 with NaHCO$_3$, then the solution was extracted with EA three times, the organic layer was washed with water and brine, dried over Na$_2$SO$_4$, evaporated to get the product A9-1 (3 g, purity: 90% on TLC) without further purification. $^1$H NMR (400 M, DMSO) δ 8.66 (s, 2 H), 8.07 (d, J=6 Hz, 1H), 7.27 (s, 2 H), 6.68 (d, J=5.6 Hz, 1H), 3.81 (s, 3H) ppm.

To a mixture of Compound A9-1 (1 g, 6.6 mmol) in AcOH (5 mL) was added Compound A2 (1.12 g, 9.8 mmol), the mixture was heated to 130° C. under M.W. for 10 h, TLC showed there was SM (starting material) remained, the solvent was removed under vacuo, the crude was purified by pre-TLC to obtain the product A9-2 (0.008 g, 90% purity on TLC).

To a mixture of compound A9-2 (0.018 g, 0.08 mmol) in THF (5 mL), MeOH (2 mL) and H$_2$O (1 mL) was added LiOH.H$_2$O (0.017 g, 0.41 mmol), then the mixture was stirred at r.t. for one hour. TLC showed the reaction was completed, the solvent was removed under vacuo, the residue was dissolved in water and extracted with EA, the organic layer was separated and putted off, the water phase was acidized and extracted with EA three times, the organic phase was washed with water and brine, dried over Na$_2$SO$_4$, evaporated to get the crude product, the crude product was purified by pre-HPLC to obtain T7 (0.006 g, purity: 95% on LCMS). LCMS (M+H$^+$): 217. $^1$H NMR (400 M, DMSO) δ 9.08 (s, 1 H), 8.47 (d, J=8 Hz, 1H), 7.38 (d, d, J=8 Hz, 1H), 5.84 (s, 2H), 2.09 (s, 6 H) ppm.

Compound A10 (0.5 g, 3.3 mmol) in AcOH (5 mL) was added Compound A2 (0.56 g, 4.9 mmol), then the mixture was heated to 130° C. under M.W. (microwave) for 2 h. TLC showed there was about 50% SM remained. The mixture was concentrated under vacuo to get the crude product. The crude was purified by column (PE (petroleum ether)/EA=5:1) to get the Compound A11 (0.4 g, purity: 90% on TLC) as yellow solid. $^1$H NMR (400 M; CDCl$_3$) δ 8.77 (d, J=4.8 Hz, 1 H), 8.59 (s, 1 H), 7.75 (d, J=4.8 Hz, 1 H), 5.88 (s, 2 H), 3.70 (s, 3 H), 1.90 (s, 6 H) ppm.

To a mixture of compound A11 (0.4 g, 1.7 mmol) in THF (5 mL), MeOH (2 mL) and H$_2$O (1 mL) was added LiOH.H$_2$O (0.36 g, 8.7 mmol), then the mixture was stirred at r.t. (room temperature) for one hour. TLC showed the reaction was completed, the solvent was removed under vacuo, the residue was dissolved in water and extracted with EA, the organic layer was separated and putted off, the water phase was acidized and extracted with EA three times, the organic phase was washed with water and brine, dried over Na$_2$SO$_4$, evaporated to get the T8 (0.25 g, purity: 95% on LCMS) as yellow solid. LCMS (M+H$^+$): 217. $^1$H NMR (400 M; DMSO) δ 13.59 (s, 1 H), 8.80 (d, J=4.8 Hz, 1 H), 8.56 (s, 1 H), 7.78 (d, J=4.8 Hz, 1 H), 5.78 (s, 2 H), 1.87 (s, 6 H) ppm.

Synthesis of Compounds TX1 to TX19

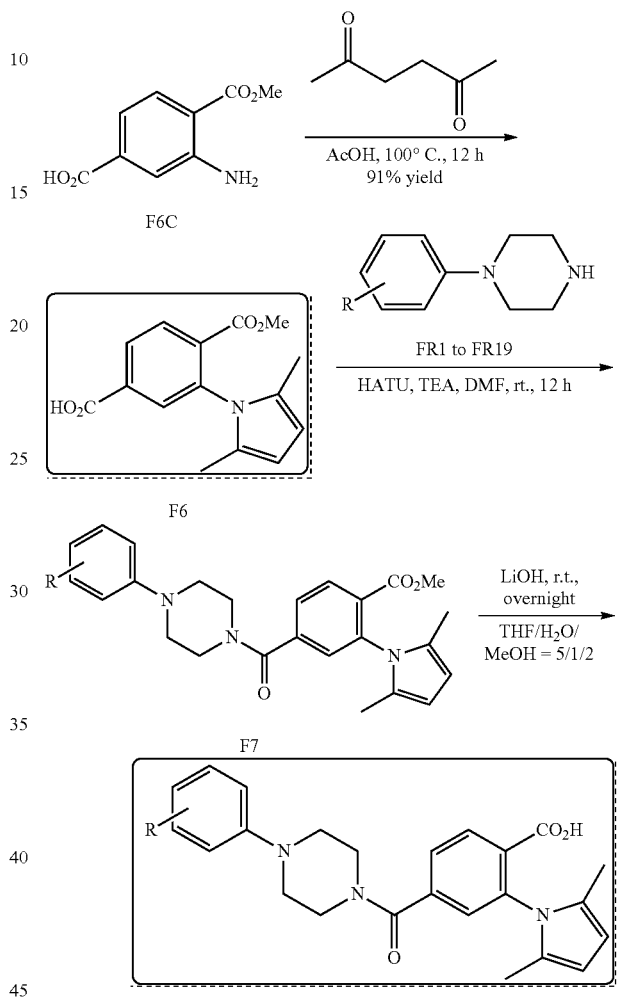

To a solution of compound F6C (25 g, 128 mmol) in AcOH (250 mL) was added hexane-2,5-dione (18.9 g, 166 mmol) under N$_2$. The mixture was stirred and heated to 100° C. overnight. TLC showed the reaction was completed. The mixture was evaporated in vacuo. The residue was washed with MTBE and PE, concentrated in vacuo to afford compound F6 (32 g, 91% yield). $^1$H NMR (CDCl$_3$; 400 MHz) δ 8.23 (d, J=8.0 Hz, 1H), 8.05-8.02 (m, 2H), 5.91 (s, 2H), 3.72 (s, 3H), 1.95 (s, 6H), 2.03 (s, 6H).

To a solution of compound F6 (200 mg, 0.733 mmol) in DMF (5 mL) was added compound FR1 (where R is hydrogen; 131 mg, 0.806 mmol), HATU (306 mg, 0.806 mmol) and TEA (148 mg, 1.466 mmol) with stirred at r.t. for 12 h. TLC showed the reaction was completed. The mixture was concentrated in vacuo. The residue was purified by column chromatography on silica gel to afford compound F7 (200 mg, 66% yield). LCMS: (M+H$^+$): 418.

To a solution of compound F7 (200 mg, 0.48 mmol) in H$_2$O/MeOH (4 mL) was added LiOH.H$_2$O (60 mg, 1.44 mmol). The mixture was stirred at r.t. overnight. TLC showed the reaction was completed. The mixture was dissolved with brine, adjusted to pH4~6, extracted with EA. The organic layer was dried over $Na_2SO_4$ and concentrated in vacuo at 20° C. The residue was purified by pre-HPLC to afford TX1 (44 mg, 23% yield). LCMS (M+H$^+$): 404. $^1$H NMR (CDCl$_3$; 400 MHz) δ 8.18 (d, J=8.0 Hz, 1H), 7.63 (d, J=8.0 Hz, 1H), 7.33-7.28 (m, 3H), 6.96-6.94 (m, 3H), 5.94 (s, 2H), 3.96 (s, 2H), 3.59 (s, 2H), 3.29 (s, 2H), 3.16 (s, 2H), 1.98 (s, 6H) ppm.

As unlimiting examples, compounds TX2 to TX19 were synthesized using a method similar to the method of preparing compound TX1 (Table 1A).

TABLE 1A

Yields of compounds TX2 to TX19.

| No. | TX2 | TX3 |
|---|---|---|
| Structure | [structure] | [structure] |
| yield | 30% | 14% |
| No. | TX6 | TX7 |
| Structure | [structure] | [structure] |
| yield | 20% | 30% |
| No. | TX10 | TX11 |
| Structure | [structure] | [structure] |
| yield | 25% | 34% |
| No. | TX14 | TX15 |
| Structure | [structure] | [structure] |
| yield | 30% | 13% |
| No. | TX18 | TX19 |

TABLE 1A-continued

Yields of compounds TX2 to TX19.

| Structure | | |
|---|---|---|
| yield | 23% | 20% |
| No. | TX4 | TX5 |
| Structure | | |
| yield | 42% | 23% |
| No. | TX8 | TX9 |
| Structure | | |
| yield | 31% | 27% |
| No. | TX12 | TX13 |
| Structure | | |
| yield | 25% | 28% |
| No. | TX16 | TX17 |
| Structure | | |
| yield | 31% | 15% |

Synthesis of compound K4

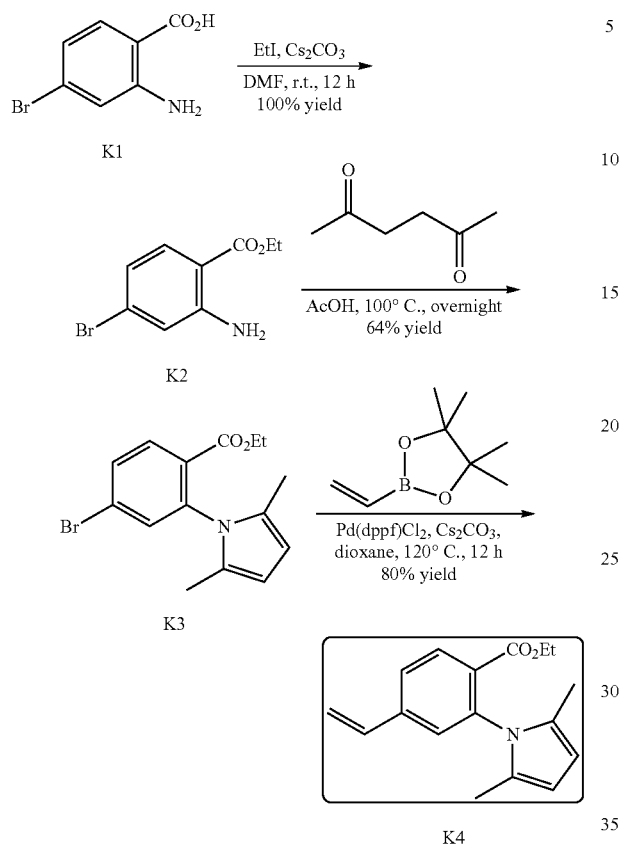

To a solution of compound K1 (10 g, 46.5 mmol) and Cs$_2$CO$_3$ (30.3 g, 93 mmol) in DMF (100 mL) was added iodoethane (8.7 g, 55.8 mmol) under N$_2$. The mixture was stirred at r.t. for 12 h. TLC showed the reaction was completed. The mixture was dissolved with water and extracted with EA. The organic layer was dried over Na$_2$SO$_4$ and evaporated in vacuo to afford compound K2 (12.4 g, 100% yield). $^1$H NMR (CDCl$_3$; 400 MHz) δ 7.69 (d, J=8.8 Hz, 1H), 6.83 (s, 1H), 6.73 (d, J=8.4 Hz, 1H), 5.83 (s, 2H), 4.33-4.28 (m, 2H), 1.36 (t, J=7.2 Hz, 3H) ppm.

To a solution of compound K2 (12.4 g, 50.8 mmol) in AcOH (100 mL) was added hexane-2,5-dione (6.98 g, 61.2 mmol) under N$_2$. The mixture was stirred and heated to 100° C. overnight. TLC showed the reaction was completed. The mixture was evaporated in vacuo. The residue was purified by column chromatography on silica gel to afford compound K3 (10.44 g, 64% yield). $^1$H NMR (CDCl$_3$; 400 MHz) δ 7.84 (d, J=8.8 Hz, 1H), 7.65 (d, J=8.0 Hz, 1H), 7.47 (s, 1H), 5.87 (s, 2H), 4.15-4.09 (m, 2H), 1.94 (s, 6H), 1.12 (t, J=7.2 Hz, 3H) ppm.

To a solution of compound K3 (5 g, 15.6 mmol) in dioxane (100 mL) was added BpinCH=CH$_2$ (2.64 g, 17.1 mmol), Pd(dppf)Cl$_2$ (1.14 g, 1.56 mmol) and Cs$_2$CO$_3$ (10.2 g, 31.2 mmol) under N$_2$. The mixture was stirred and heated to 120° C. for 12 h. LCMS showed the reaction was completed. The mixture was filtered and the filtrate was evaporated in vacuo. The residue was purified by pre-HPLC to afford compound K4 (2.5 g, 80% yield). LCMS (M+H$^+$): 270. $^1$H NMR (CDCl$_3$; 400 MHz) δ 7.95 (d, J=8 Hz, 1H), 7.51 (d, J=8.0 Hz, 1H), 7.32 (s, 1H), 6.79-6.72 (m, 1H), 5.89 (t, J=10.4 Hz, 3H), 5.44 (d, J=10.8 Hz, 1H), 4.15-4.10 (m, 2H), 1.96 (s, 6H), 1.13 (t, J=7.2 Hz, 3H) ppm.

Synthesis of Compounds T10a and T10

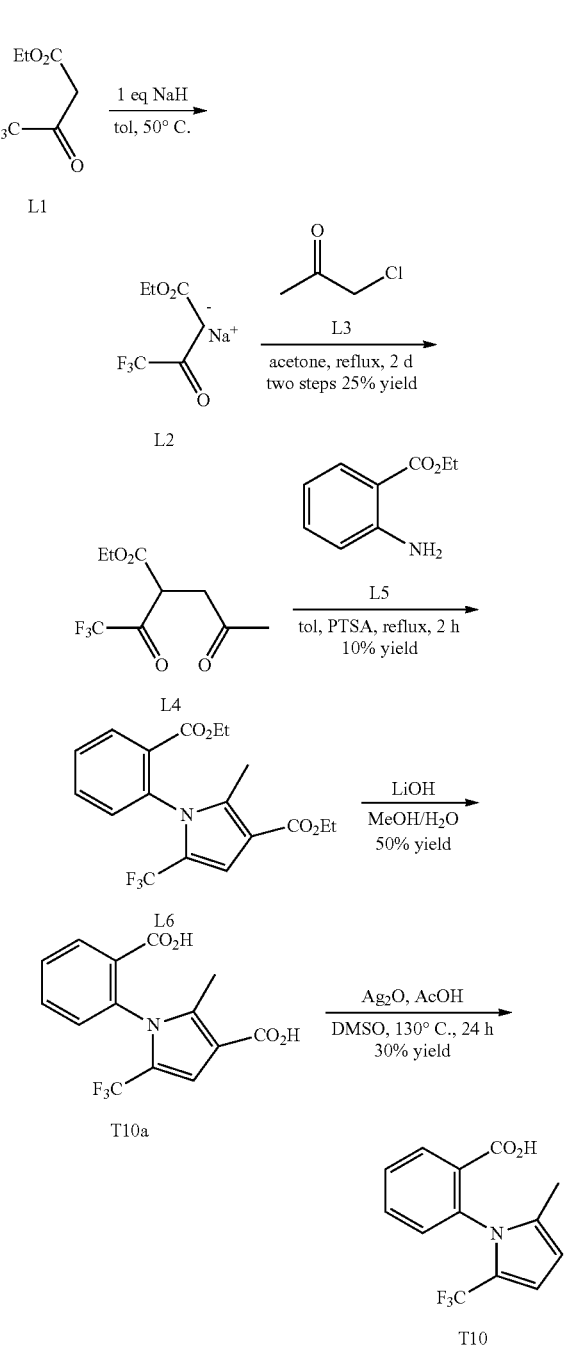

To a solution of compound L1 (18.4 g, 0.1 mol) in toluene (200 ml) was added NaH (3 g, 0.1 mol) portionwise with stirred at r.t. after 1 h, the solution was evaporated to afford the solid compound L2; then the compound L2 was added to the solution of compound L3. Then the whole solution was refluxed two days. The solvent was removed by concentration. The crude compound was acidified with 1N aq HCl, extract with DCM. The DCM was removed by concentration. Then the crude oil was distilled by oil pump to afford the compound L4 (6 g, 25% yield).

A mixture of compound L5 (500 mg, 3 mmol) and compound L4 (870 mg, 3.6 mmol) in tol (toluene, 10 mL) was added Cat (catalytic amount) PTSA (50 mg, 0.3 mmol) and stirred at reflux for 4 h. TLC showed the reaction was worked. The mixture was evaporated. The residue was purified by pre-TLC (PE:EA=3:1) to afford compound L6 (110 mg, 10% yield).

A mixture of compound L6 (100 mg, 0.27 mmol) and LiOHH$_2$O (57 mg) in EtOH/H$_2$O (1.5/0.5 mL) was stirred 0° C. for 2 h. TLC showed the reaction was completed. The mixture was partitioned between H$_2$O and EA, the organic layer was concentrated to afford compound T10a (42 mg, 50% yield). LCMS: t=2.48 min; purity: 87.5%; MS cal.: 313.0; MS found: [M+H]314.0. $^1$H NMR (MeOD; 400 MHz) δ 8.12 (d, J=1.2 Hz, 1H), 7.72~7.70 (m, 1H), 7.66~7.62 (m, 1H), 6.45 (s, 1H), 1.99 (s, 3H) ppm.

A mixture of T10a (80 mg, 0.32 mmol), Ag$_2$O (23 mg) and AcOH (6 mg, 0.1 mmol) in DMSO (2 mL) was stirred 130° C. for 24 h. TLC showed the reaction was completed. The mixture was purified by pre-HPLC to afford compound T10 (20 mg, 30% yield). LCMS: t=2.83 min; purity: 99.7%; MS cal.:269.0; MS found: [M+H]270. $^1$H NMR: (MeOD; 400 MHz) δ 8.17 (m, 1H), 7.72~7.69 (m, 1H), 7.62~7.59 (m, 1H), 7.38~7.37 (m, 1H), 6.64 (d, J=1.6 Hz, 1H), 6.03 (d, J=1.6 Hz, 1H), 1.99 (s, 3H) ppm.

Synthesis of Compound T20

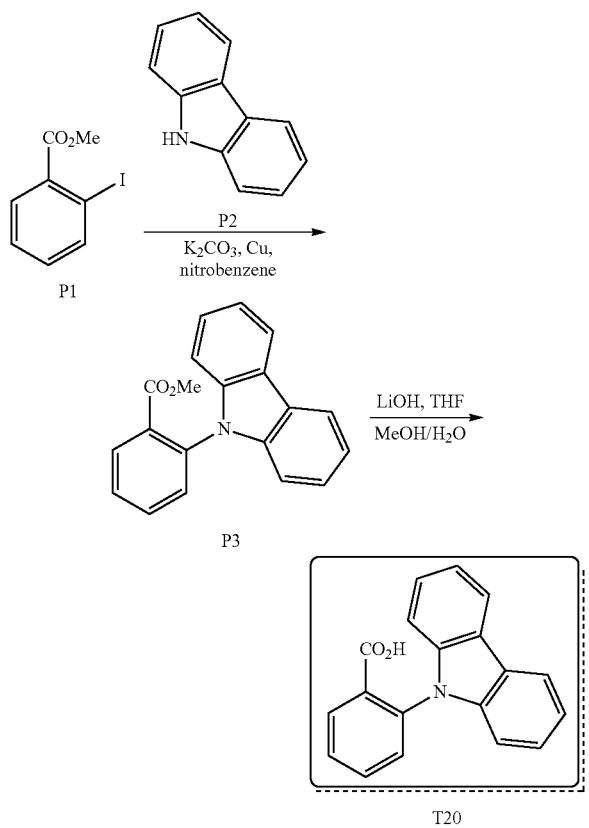

A mixture of Compound P1 (0.5 g, 1.91 mmol), Compound P2 (0.32 g, 1.91 mmol), and K$_2$CO$_3$ (0.39 g, 2.82 mmol), Cu (6.06 mg, 0.09 mmol) in nitrobenzene (5 mL) was heated at 160° C. for 10 h. TLC showed there was about 50% SM remained. After cooling, a 1:1 mixture of water and chloroform was added and the two layers were separated. The aqueous layer was extracted twice with chloroform. The organic layer was washed with brine, dried over Na$_2$SO$_4$, evaporated to get the crude product. The crude product was purified by column to obtain the Compound P3 (0.1 g, 90% TLC purity).

To a mixture of compound P3 (100 mg, 0.33 mmol) in THF (5 mL), MeOH (2 mL), and H$_2$O (1 mL) was added LiOH.H$_2$O (69.62 mg, 1.66 mmol). Then the mixture was stirred at r.t. overnight. TLC showed the reaction was completed. the solvent was removed under vacuo, the residue was dissolved in water and extracted with EA. the organic layer was separated and discarded, the water phase was acidized and extracted with EA (20 ml×3). The organic phase was washed with water and brine, dried over Na$_2$SO$_4$, evaporated to get the T20 (20 mg, 96% LCMS purity). $^1$H NMR (400 M; DMSO) δ ppm 12.61 (s, 1 H), 8.18 (d, J=7.2 Hz, 2 H), 8.03 (dd, J=7.6 Hz 1 H), 7.82 (td, J=7.6 Hz, 1 H), 7.64-7.70 (m, 1 H), 7.59 (d, J=8.0 Hz, 1 H), 7.32-7.38 (m, 2 H), 7.19-7.24 (m, 2 H), 7.05 (d, J=8.0 Hz, 1 H) ppm.

Synthesis of Compound T1-A

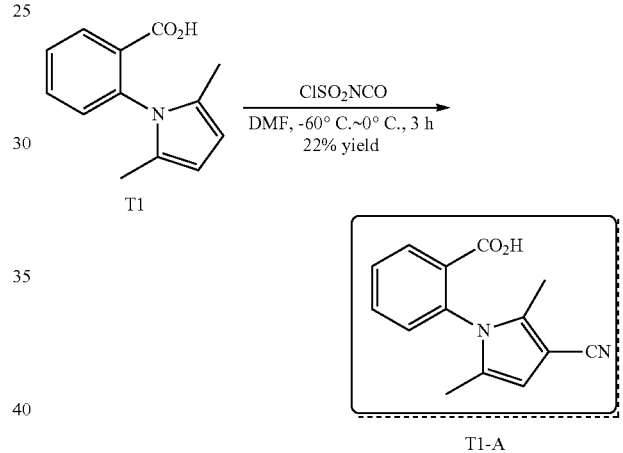

Under N$_2$ to a solution of T1 (100 mg, 0.465 mmol) in DMF (2.5 mL), cooled to −60° C., was added a solution of ClSO$_2$NCO (66 mg, 0.465 mmol) in ACN (1.5 mL) dropwise. The mixture was stirred at −60° C. to 0° C. for 2 h. TLC showed most of starting material was consumed. The mixture was concentrated in vacuo. The residue was purified by pre-TLC to afford T1-A (25 mg, 22% yield). LCMS (M+H$^+$): 241. $^1$H NMR (MeOD; 400 MHz) δ 7.91 (d, J=7.2 Hz, 1H), 7.62-7.57 (m, 2H), 7.22 (d, J=7.6 Hz, 1H), 6.10 (s, 1H), 2.09 (s, 3H), 1.93 (s, 3H) ppm.

Synthesis of Compound T18

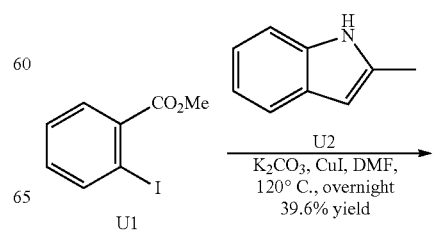

A mixture of compound U1 (1 g, 7.62 mmol), compound U2 (2 g, 7.62 mmol), K₂CO₃ (2.11 g, 15.25 mmol), and CuI (145 mg, 0.762 mmol) in DMF (15 mL) with stirred at 120° C. under N₂ atmosphere overnight (neat reaction). TLC showed the reaction was completed. The mixture was partitioned between H₂O and EA. The organic layer was dried and concentrated. The residue was purified by silica gel column (PE:EA=40:1) to afford compound U3 (800 mg, 39.6% yield). ¹H NMR (MeOD; 400 MHz) δ 8.10 (d, J=1.2 Hz, 1H), 8.08 (t, J=7.2 Hz, 1H), 7.59 (t, J=7.6 Hz, 1H), 7.41 (t, J=7.6 Hz, 1H), 7.11-7.07 (m, 2H), 6.85 (d, J=8 Hz, 1H), 6.44 (s, 1H) ppm.

A mixture of compound U3 (6 g, 21.6 mmol) and LiOH.H₂O (395 mg, 9.42 mmol) in THF/H₂O (4/2 mL) was stirred at r.t. for 6 h. TLC showed the reaction was completed. The solution was adjusted to pH=2 with 1N HCl. The mixture was partitioned between H₂O and EA. the organic layer was dried and concentrated to afford compound T18 (80 mg, 17% yield). ¹H NMR (CDCl₃; 400 MHz) 8.13 (d, J=8 Hz, 1H), 7.72 (t, J=1.2 Hz, 1H), 7.56 (t, J=7.6 Hz, 2H), 7.36 (t, J=4 Hz, 1H), 7.08-7.05 (m, 2H), 6.82 (d, J=8 Hz, 1H), 6.40 (s, 1H), 2.18 (s, 3H) ppm.

Synthesis of Compounds TL×2 and TL×3

A mixture of Compound V1 (3.0 g, 10.8 mmol) in THF (30 mL) was cooled to 0° C. and BH₃.THF (33 mL, 33 mmol) was added dropwise. After the addition, the mixture was stirred at rt (room temperature) overnight. TLC showed the reaction was completed. The reaction mixture was poured into ice water, and the solution was extracted with EA, the organic layer was washed with water and brine, dried over Na₂SO₄, concentrated under vacuo and purified by column to afford the Compound V2 (1.5 g, purity: 90% on TLC).

A mixture of Compound V2 (1 g, 3.8 mmol) in DCM (15 mL) was added MnO₂ (3.4 g, 39.1 mmol) at r.t., after the addition, the mixture was stirred at r.t. for two days. TLC showed the reaction was completed, the reaction mixture was filtered and the filtrate was concentrated. The crude product was purified by column to afford the Compound V3 (0.34 g, purity: 90% on TLC). ¹H NMR (400 M; CDCl₃) δ ppm 10.13 (s, 1 H), 8.09 (d, J=8 Hz, 1 H), 8.04-8.02 (m, 1 H), 7.81 (s, 1 H), 3.73 (s, 3 H), 1.96 (s, 6 H) ppm.

A mixture of compound V3 (50 mg, 0.20 mmol) and compound V5-2 (47 mg, 0.25 mmol) in MeOH (5 mL) was added NaOAc (31.85 mg, 0.40 mmol), the mixture was stirred at r.t. for 2 h, then NaBH₃CN (24.40 mg, 0.40 mmol) was added. After the addition the mixture was stirred for another 1 h. TLC showed the reaction was completed, the mixture was filtered. The filtrate was concentrated under vacuo and purified by pre-TLC to afford the compound V4-2 (60 mg, purity: 90% on TLC). Compound V4-3 was similarly synthesized using compound V5-3.

A mixture of compound V4-2 (60 mg, 0.14 mmol) in THF (5 mL), MeOH (2 mL), and H$_2$O (1 mL) was added LiOH H$_2$O (30.96 mg, 0.74 mmol) at r.t. Then the mixture was stirred at rt overnight. LCMS showed the reaction was completed, the mixture was concentrated and purified by pre-HPLC to afford TLx2 (5 mg, purity: 90% on LCMS) $^1$H NMR (400 MHz; MeOD) δ ppm 8.19 (s, 1 H), 8.11 (d, J=7.6 Hz, 1 H), 8.00 (d, J=8 Hz, 2 H), 7.71 (d, J=7.2 Hz, 1 H), 7.66 (d, J=9.6 Hz, 1 H), 7.59 (t, J=7.6 Hz, 1 H), 7.38 (s, 1 H), 5.77 (s, 2 H), 4.38 (d, J=6 Hz, 2 H), 1.92 (s, 6 H) ppm. Compound TLx3 was similarly synthesized using compound V4-3 at a 53.57% yield.

Synthesis of Compound T10

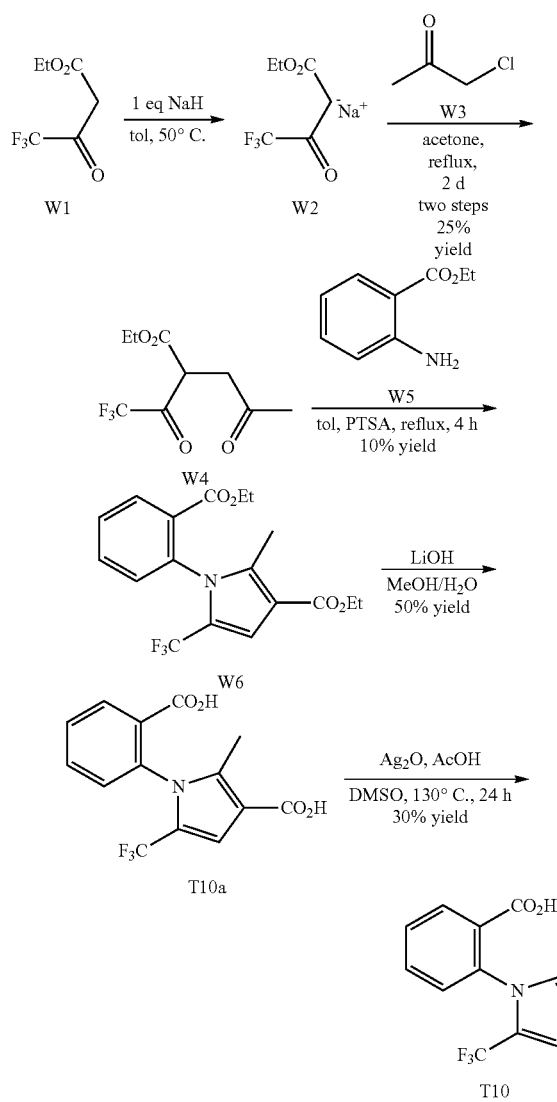

To a solution of compound W1 (18.4 g, 0.1 mol) in toluene (200 ml) was added NaH (3 g, 0.1 mol) portionwise with stirred at r.t. after 1 h, the solution was evaporated to afford the solid compound W2; then the compound W2 was added to the solution of compound W3. Then the whole solution was refluxed two days. The solvent was removed by concentration. The crude compound was acidified with 1N aq HCl, extract with DCM. The DCM was removed by concentration. Then the crude oil was distilled by oil pump to afford the compound W4 (6 g, 25% yield).

A mixture of compound W5 (500 mg, 3 mmol) and compound W4 (870 mg, 3.6 mmol) in tol (10 mL) was added Cat PTSA (50 mg, 0.3 mmol) and stirred at reflux for 4 h. TLC showed the reaction was worked. The mixture was evaporated. The residue was purified by pre-TLC (PE: EA=3:1) to afford compound W6 (110 mg, 10% yield).

A mixture of compound W6 (100 mg, 0.27 mmol) and LiOHH$_2$O (57 mg) in EtOH/H$_2$O (1.5/0.5 mL) was stirred 0° C. for 2 h. TLC showed the reaction was completed. The mixture was partitioned between H$_2$O and EA, the organic layer was concentrated to afford compound T10a (42 mg, 50% yield). LCMS: t=2.48 min; purity: 87.5%; MS cal.: 313.0; MS found: [M+H]314.0. $^1$H NMR: (MeOD; 400 MHz) δ 8.12 (d, J=1.2 Hz, 1H), 7.72~7.70 (m, 1H), 7.66~7.62 (m, 1H), 6.45 (s, 1H), 1.99 (s, 3H) ppm.

A mixture of T10a (80 mg, 0.32 mmol), Ag$_2$O (23 mg) and AcOH (6 mg, 0.1 mmol) in DMSO (2 mL) was stirred 130° C. for 24 h. TLC showed the reaction was completed. The mixture was purified by pre-HPLC to afford T10 (20 mg, 30% yield). LCMS: t=2.83 min; purity: 99.7%; MS cal.:269.0; MS found: [M+H]270. $^1$H NMR (MeOD; 400 MHz) δ 8.17 (m, 1H), 7.72~7.69 (m, 1H), 7.62~7.59 (m, 1H), 7.38~7.37 (m, 1H), 6.64 (d, J=1.6 Hz, 1H), 6.03 (d, J=1.6 Hz, 1H), 1.99 (s, 3H) ppm.

Synthesis of Compound T24

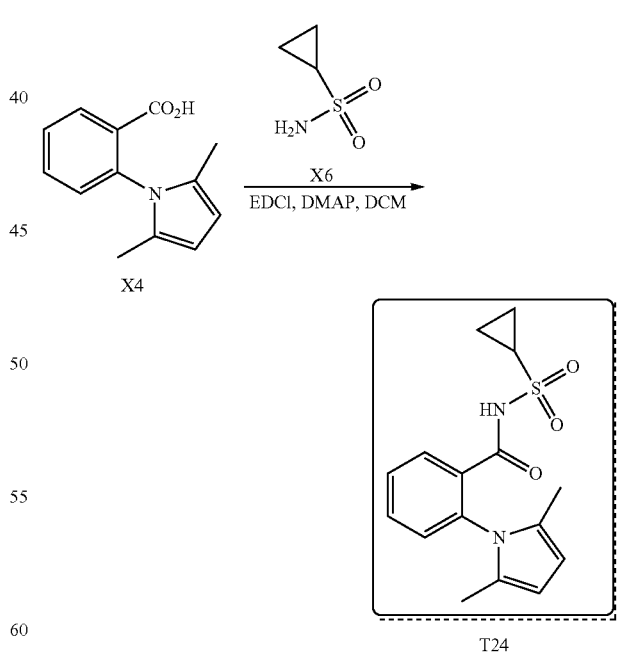

A mixture of Compound X4 (1 g, 4.65 mmol) and Compound X6 (0.67 g, 5.57 mmol) in DCM (10 mL) was added EDCI (1.18 g, 6.18 mmol) and DMAP (1.56 g, 12.78 mmol) at r.t., then the mixture was stirred at room temperature overnight. LCMS showed the reaction was completed, the mixture was diluted with DCM, washed with 1N/L HCl solution and water, dried over Na$_2$SO$_4$, concentrated to afford the T24 (0.5 g, purity: 95% on LCMS) $^1$H NMR (400 MHz; CDCl$_3$) δ ppm 8.25 (d, J=1.2 Hz, 1 H), 7.73-7.69 (m, 1 H), 7.64-7.60 (m, 1 H), 7.33-7.10 (m, 1 H), 6.93 (s, 1 H), 6.10 (s, 2 H), 3.02-2.96 (m, 1 H), 1.99 (s, 6 H), 1.33-1.30 (m, 2 H), 1.06-1.04 (m, 2 H) ppm.

Synthesis of Compound T25

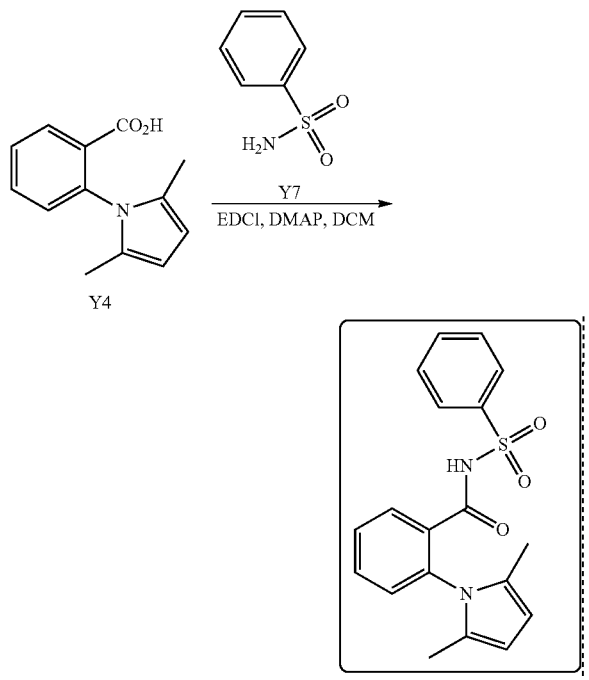

A mixture of Compound Y4 (1 g, 4.65 mmol) and Compound Y7 (0.87 g, 5.57 mmol) in DCM (10 mL) was added EDCI (1.18 g, 6.18 mmol) and DMAP (1.56 g, 12.78 mmol) at r.t., then the mixture was stirred at room temperature overnight. LCMS showed the reaction was completed, the mixture was diluted with DCM, washed with 1N/L HCl solution and water, dried over Na$_2$SO$_4$, concentrated to afford T25 (0.5 g, purity: 95% on LCMS). 11H NMR (400 MHz; CDCl$_3$) δ ppm 8.10 (d, J=7.6 Hz, 1 H), 8.01 (d, J=1.6 Hz, 2 H), 7.64-7.61 (m, 2 H), 7.55-7.49 (m, 3 H), 7.25 (s, 1 H), 7.04 (s, 2 H), 6.13 (s, 2 H), 1.78 (s, 6 H) ppm.

Synthesis of Compound TL4X8

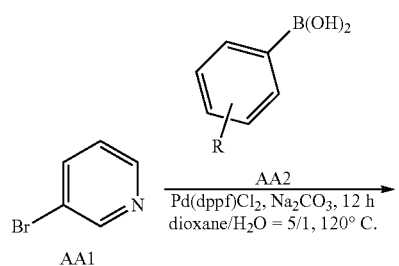

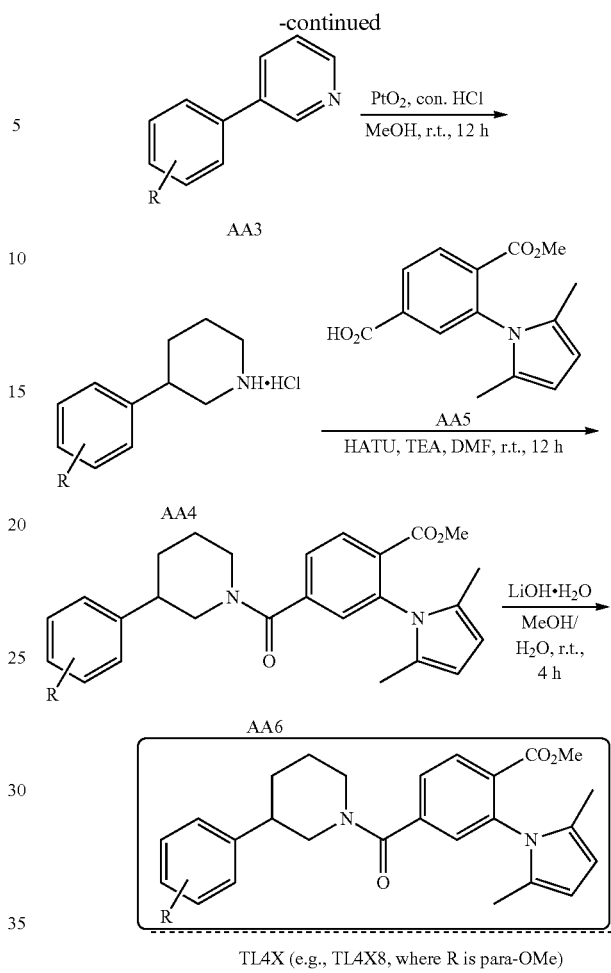

To a solution of compound AA1 (17.4 g, 110 mmol) in dioxane/H$_2$O (180 mL) was added compound AA2 (20 g, 132 mmol), Pd(dppf)Cl$_2$ (8.05 g, 11 mmol) and Na$_2$CO$_3$ (23.32 g, 220 mmol) under N$_2$. The mixture was stirred at 120° C. for 12 h. LCMS showed the reaction was completed. The mixture was filtered and the filtrate was concentrated in vacuo. The residue was purified by column chromatography on silica gel to afford compound AA3 (18.97 g, 93% yield). $^1$H NMR (CDCl$_3$; 400 MHz) δ 8.81 (d, J=2.0 Hz, 1H), 8.54 (t, J=3.2 Hz, 1H), 7.84-7.82 (m, 1H), 7.53-7.51 (m, 4H), 7.34 (d, J=4.4 Hz, 1H), 7.02-7.00 (m, 1H), 3.85 (s, 3H) ppm.

To a solution of compound AA3 (2 g, 10.8 mmol) in MeOH (25 mL) were added PtO$_2$ (0.2 g) and con. HCl (2 mL). The mixture was stirred at 50 psi overnight. TLC showed the reaction was completed. The mixture was filtered and the filtrate was concentrated in vacuo to afford compound AA4 (2.5 g, 100% yield). LCMS: (M-35): 192.

To a solution of compound AA4 (1 g, 4.39 mmol) in DMF (10 mL) was added compound AA5 (1 g, 3.66 mmol), HATU (1.39 g, 3.66 mmol) and TEA (1.11 g, 10.98 mmol). The mixture was stirred at r.t. for 12 h. TLC showed the reaction was completed. The mixture was concentrated in vacuo. The residue was purified by column chromatography on silica gel to afford compound AA6 (0.64 g, 40% yield). LCMS: (M+H$^+$): 447.

To a solution of compound AA6 (640 mg, 1.43 mmol) in MeOH/H$_2$O (16 mL) was added LiOH.H$_2$O (180 mg, 4.29 mmol). The mixture was stirred at r.t. for 4 h. TLC showed the reaction was completed. The mixture was adjusted to Ph 6~7, extracted with EA. The organic layer was dried over Na₂SO₄ and concentrated. The residue was purified by pre-HPLC to afford TL4X8 (230 mg, 37% yield). LCMS: (M+H⁺): 433. ¹H NMR (DMSO; 400 MHz) δ 7.91-7.87 (m, 1H), 7.57 (d, J=7.2 Hz, 1H), 7.30-7.21 (m, 2H), 7.02 (d, J=8.4 Hz, 1H), 6.91-6.79 (m, 2H), 5.75 (s, 2H), 4.54-4.45 (m, 1H), 3.73-3.68 (m, 4H), 3.15-3.13 (m, 1H), 2.78-2.69 (m, 2H), 1.88-1.66 (m, 10H) ppm. Compounds including a R group different from the para-OMe as in TL4X8 can be similarly synthesized.

Synthesis of Compound TL4X19

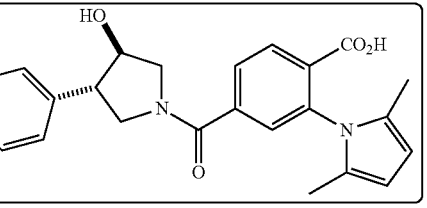

TL4X19

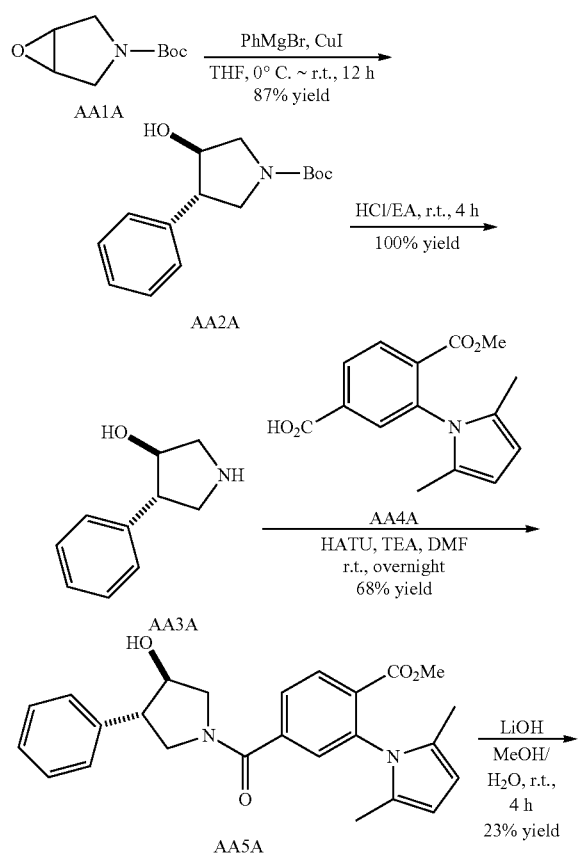

To a solution of compound AA1A (1 g, 5.4 mmol) and CuI (51 mg, 0.27 mmol) in THF (10 mL) under N₂, cooled to 0° C., was added PhMgBr (2.97 mL, 5.94 mmol) dropwise. The mixture was stirred at 0° C.~r.t. for 3 h. TLC showed the reaction was completed. The mixture was quenched by sat. NH₄Cl solution, extracted with EA. The organic layer was dried over Na₂SO₄ and concentrated in vacuo. The residue was purified by column chromatography on silica gel to afford compound AA2A (1.24 g, 87% yield).

To a solution of compound AA2A (400 mg, 1.52 mmol) in DCM (5 mL) was added HCl/EA (15 mL). The mixture was stirred at r.t. for 2 h. TLC showed the reaction was completed. The mixture was concentrated in vacuo to afford compound AA3A (300 mg, 100% yield). LCMS (M+H⁺): 164.

To a solution of compound AA4A (418 mg, 1.53 mmol) in DMF (10 mL) was added compound AA3A (300 mg, 1.84 mmol), HATU (580 mg, 1.53 mmol), TEA (309 mg, 3.06 mmol). The mixture was stirred at r.t. overnight. TLC showed the reaction was completed. The mixture was concentrated in vacuo. The residue was purified by column chromatography on silica gel to afford compound AA5A (440 mg, 68% yield). LCMS: (M+H⁺): 419.

To a solution of compound AA5A (440 mg, 1.05 mmol) in MeOH/H₂O (6 mL) was added LiOH.H₂O (130 mg, 3.15 mmol). The mixture was stirred at r.t. for 4 h. TLC showed the reaction was completed. The mixture was adjusted to pH 5~6, extracted with EA. The organic layer was dried over Na₂SO₄ and concentrated in vacuo. The residue was purified by pre-HPLC to afford TL4X19 (105 mg, 23% yield). LCMS (M+H⁺): 405. ¹H NMR (CDCl₃; 400 MHz) δ 8.09 (d, J=8.0 Hz, 1H), 7.41 (d, J=6.4 Hz, 1H), 7.38-7.29 (m, 5H), 7.16 (s, 1H), 5.87 (s, 2H), 4.47-3.36 (m, 6H), 1.93-1.89 (m, 6H) ppm.

Compounds listed in Table 1B can be similarly synthesized as described herein.

TABLE 1B

Yields of exemplary compounds of the invention

| No. | TL4X1 | TL4X2 |
|---|---|---|
| Structure | (structure) | (structure) |
| yield | 30% | 35% |
| No. | TL4X5 | TL4X6 |

TABLE 1B-continued

Yields of exemplary compounds of the invention

| | | |
|---|---|---|
| Structure | (structure) | (structure) |
| yield | 43% | 20% |
| No. | TL4X9 | TL4X10 |
| Structure | (structure) | (structure) |
| yield | 42% | |
| No. | TL4X13 | TL4X14 |
| Structure | (structure) | (structure) |
| yield | 20% | |
| No. | TL4X17 | TL4X18 |
| Structure | (structure) | (structure) |
| yield | 3% | |
| No. | TL4Y5A | TL4Y5B |
| Structure | (structure) | (structure) |
| yield | 5% | |
| No. | TL4X3 | TL4X4 |

TABLE 1B-continued
Yields of exemplary compounds of the invention
| Structure |  |  |
|---|---|---|
| yield | 68% | 52% |
| No. | TL4X7 | TL4Y5 |
| Structure |  | 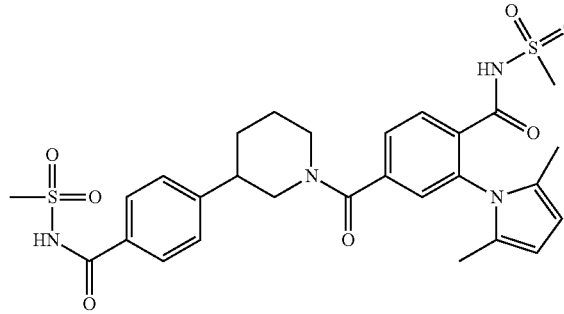 |
| yield | 26.5% | 11% |
| No. | TL4X11 | TL4X12 |
| Structure |  | 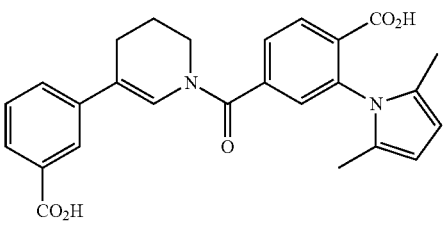 |
| yield | | |
| No. | TL4X15 | TL4X16 |
| Structure |  | 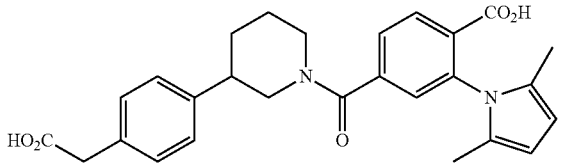 [SMILES: Cc1ccc(C)n1-c1cc(C(=O)N2CCCC(c3ccc(CC(=O)O)cc3)C2)ccc1C(=O)O] |
| yield | 20% | 16% |
| No. | TL4X21 | |
| Structure |  | |

Synthesis of Compound AB2

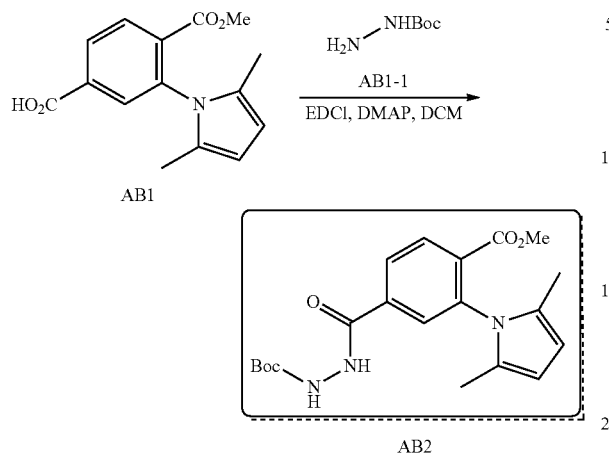

To a stirred solution of Compound AB1 (0.5 g, 1.83 mmol) and Compound AB1-1 (0.29 g, 2.19 mmol) in DCM (15 mL) was added EDCI (0.49 g, 2.55 mmol) and DMAP (0.31 g, 2.55 mmol) at r.t., then the mixture was stirred at r.t. for 3 h. TLC showed the reaction was completed. The reaction mixture was concentrated and purified by column to afford the Compound AB2 (0.5 g, purity: 90% on TLC). $^1$H NMR (400 MHz; CDCl$_3$) δ ppm 8.41 (s, 1 H), 7.99 (d, J=8 Hz, 1 H), 7.93 (d, J=8 Hz, 1 H), 7.74 (s, 1 H), 5.88 (s, 2 H), 3.70 (s, 3 H), 1.91 (s, 6 H), 1.49 (s, 9 H) ppm.

Synthesis of Compound AB3

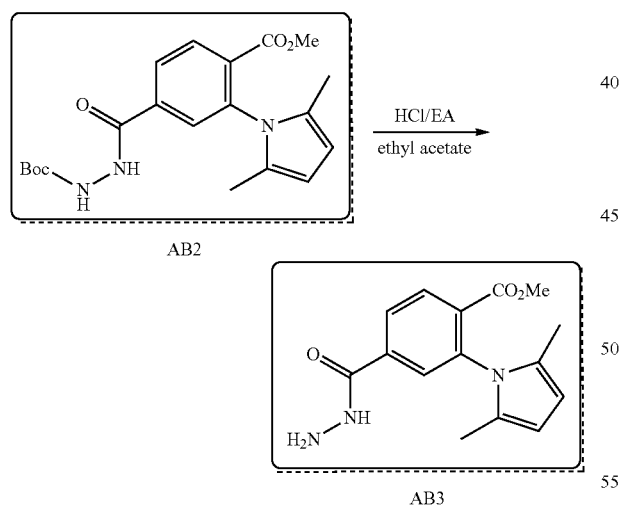

To a stirred solution of Compound AB2 (0.1 g, 0.26 mmol) in EA (5 mL) was added HCl/EA (5 mL) at 0° C. Then the mixture was stirred at r.t. for 0.5 h. TLC showed the reaction was completed. The mixture was neutralized with NaHCO$_3$ to pH 8 and extracted with DCM, the organic layers were washed with brine, dried over Na$_2$SO$_4$, concentrated to afford the Compound AB3 (50 mg, purity: 90% on TLC). $^1$H NMR (400 MHz; CDCl$_3$) δ ppm 8.02 (d, J=8 Hz, 1 H), 7.88-7.86 (m, 1 H), 7.66 (s, 1 H), 7.45 (s, 1 H), 5.89 (s, 2 H), 4.14 (s, 2 H), 3.71 (s, 3 H), 1.93 (s, 6 H) ppm.

Synthesis of Compound TL5X3

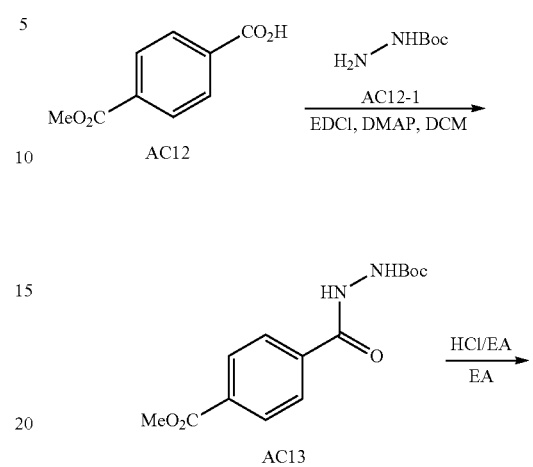

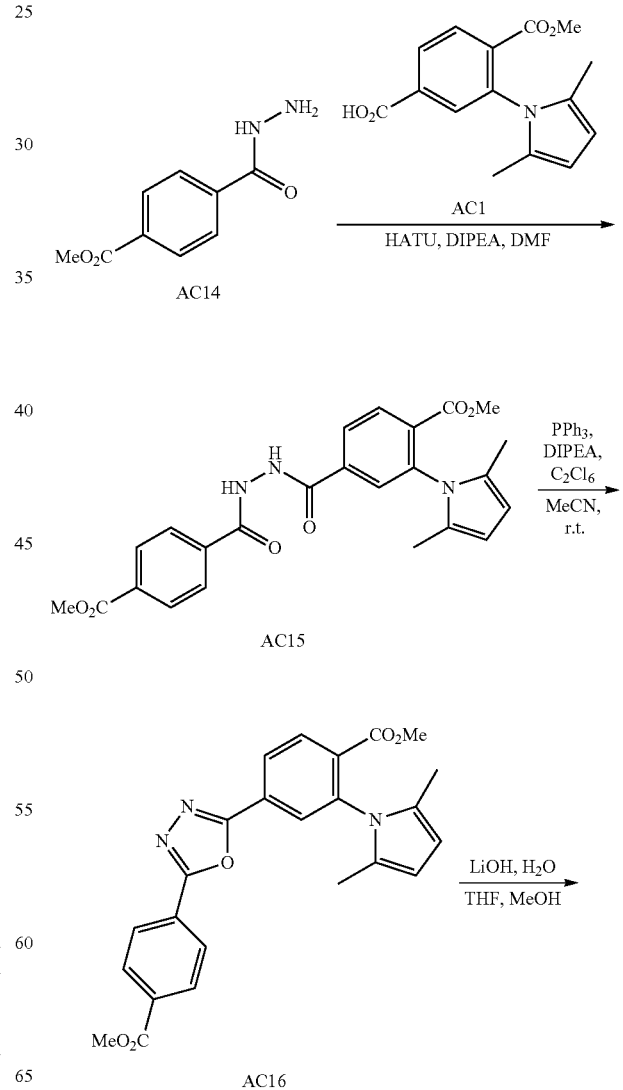

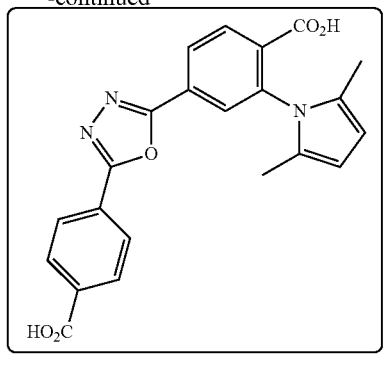

TL5X3

To a stirred solution of Compound AC12 (1 g, 5.55 mmol) and Compound AC12-1 (0.88 g, 6.66 mmol) in DCM (15 mL) was added EDCI (1.49 g, 7.77 mmol) and DMAP (0.95 g, 7.77 mmol) in one portion at r.t., then the mixture was stirred at r.t. for 3 h. TLC showed the reaction was completed. The reaction mixture was concentrated and purified by column to afford the Compound AC13 (1.2 g, purity: 90% on TLC). $^1$H NMR (400 MHz; CDCl$_3$) δ ppm 8.31 (s, 1 H), 8.06 (d, J=8.4 Hz, 2 H), 7.84 (d, J=8.4 Hz, 2 H), 6.80 (s, 1 H), 3.93 (s, 3 H), 1.49 (s, 9 H) ppm.

To a stirred solution of Compound AC13 (0.7 g, 2.38 mmol) in EA (10 mL) was added HCl/EA (20 mL) at 0° C. Then the mixture was stirred at r.t. for 2 h. TLC showed the reaction was completed. The mixture was neutralized with NaHCO$_3$ to pH 8 and extracted with DCM, the organic layers were washed with brine, dried over Na$_2$SO$_4$, concentrated to afford the Compound AC14 (0.4 g, purity: 90% on TLC).

A mixture of Compound AC1 (0.87 g, 3.18 mmol), HATU (1.33 g, 3.50 mmol) and DIPEA (0.82 g, 6.37 mmol) in DMF (10 mL) was stirred at r.t. for 10 min, then Compound AC14 (0.68 g, 3.50 mmol) was added. The reaction mixture was stirred at r.t. overnight. TLC showed the reaction was completed. The mixture was diluted with water, extracted with EA three times. The organic layers were washed with water and brine, dried over Na$_2$SO$_4$, concentrated to afford the Compound AC9 (0.5 g, purity: 90% on TLC). 1H NMR (400 MHz; CDCl$_3$) δ ppm 9.69 (s, 1 H), 9.60 (s, 1 H), 8.04 (d, J=8.0 Hz, 2 H), 7.95-7.90 (m, 2 H), 7.84 (d, J=8.0 Hz, 2 H), 7.75 (s, 1 H), 5.81 (s, 2 H), 3.89 (s, 3 H), 3.64 (s, 3 H), 1.84 (s, 6 H) ppm.

A mixture of Compound AC15 (0.25 g, 0.56 mmol), PPh$_3$ (0.29 g, 1.11 mmol) and DIPEA (0.43 g, 3.34 mmol) in MeCN (5 mL) was stirred at r.t. for 10 min, then a solution of C$_2$Cl$_6$ (0.20 g, 0.83 mmol) in MeCN was added dropwise at r.t. After the addition, the mixture was stirred at r.t. for another 2 h. TLC showed the reaction was completed. The reaction mixture was concentrated and purified by column to afford the Compound AC16 (0.17 g, purity: 90% on TLC). $^1$H NMR (400 MHz; CDCl$_3$) δ ppm 8.27-8.25 (m, 1 H), 8.15 (s, 4 H), 8.06 (d, J=8.0 Hz, 1 H), 7.99 (s, 1 H), 5.87 (s, 2 H), 3.91 (s, 3 H), 3.67 (s, 3 H), 1.91 (s, 6 H).

Compound AC16 (0.15 g, 0.35 mmol) was dissolved in the mixed solvent of THF (5 mL), MeOH (2 mL) and H$_2$O (1 mL), then LiOH·H$_2$O (0.07 g, 1.74 mmol) was added. The reaction mixture was stirred at r.t. for 1 h. TLC showed the reaction was completed. The solvent was removed and water was added, the solution was extracted with MTBE three times. The aqueous phase was acidified by 1N/L HCl solution to pH 3 and extracted with ethyl acetate three times, the organic layer was washed with water and brine, dried over Na$_2$SO$_4$, concentrated to afford the TL5X3 (50 mg, purity: 97% on LCMS). $^1$H NMR: (400 MHz; DMSO) δ ppm 8.33-8.29 (m, 3 H), 8.12 (d, J=8.0 Hz, 2 H), 8.06 (d, J=8.0 Hz, 1 H), 8.01 (s, 1 H), 5.78 (s, 2 H), 1.91 (s, 6 H) ppm.

Synthesis of Compound TL5X4

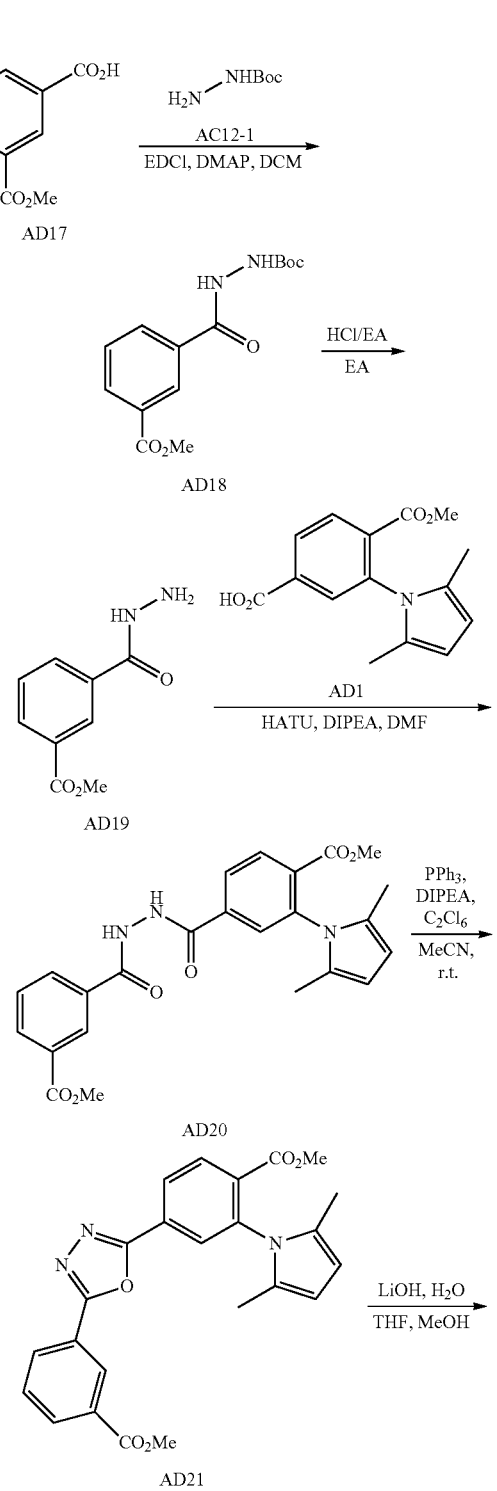

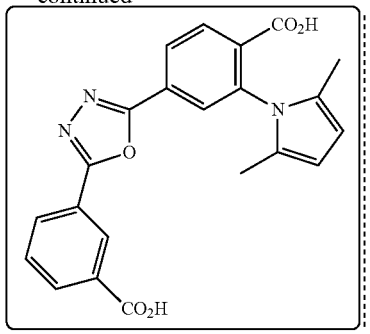

TL5X4

To a stirred solution of Compound AD17 (4 g, 22.2 mmol) and Compound AD12-1 (0.3.52 g, 26.64 mmol) in DCM (50 mL) was added EDCI (5.11 g, 26.64 mmol) and DMAP (3.25 g, 26.64 mmol) in one portion at r.t., then the mixture was stirred at r.t. for 1 h. TLC showed the reaction was completed. The reaction mixture was concentrated and purified by column to afford the Compound AD18 (5.9 g, purity: 90% on TLC).

To a stirred solution of Compound AD18 (7.8 g, 26.50 mmol) in EA (20 mL) was added HCl/EA (50 mL) at 0° C. Then the mixture was stirred at r.t. for 2 h. TLC showed the reaction was completed. The mixture was neutralized with NaHCO$_3$ to pH 8 and extracted with DCM, the organic layers were washed with brine, dried over Na$_2$SO$_4$, concentrated to afford the Compound AD19 (3.5 g, purity: 90% on TLC).

A mixture of Compound AD1 (0.80 g, 2.93 mmol), HATU (1.22 g, 3.22 mmol) and DIPEA (0.75 g, 2.85 mmol) in DMF (10 mL) was stirred at r.t. for 10 min, then Compound AD19 (0.62 g, 3.22 mmol) was added. The reaction mixture was stirred at r.t. overnight. TLC showed the reaction was completed. The mixture was diluted with water, extracted with EA three times. The organic layers were washed with water and brine, dried over Na$_2$SO$_4$, concentrated to afford the crude. The crude product was purified by column to obtain the Compound AD9 (1 g, purity: 90% on TLC).

A mixture of Compound AD20 (1 g, 2.22 mmol), PPh$_3$ (1.17 g, 4.45 mmol) and DIPEA (1.73 g, 13.35 mmol) in MeCN (10 mL) was stirred at r.t. for 10 min, then a solution of C$_2$Cl$_6$ (0.79 g, 3.34 mmol) in MeCN was added dropwise at r.t. After the addition, the mixture was stirred at r.t. for another 2 h. TLC showed the reaction was completed. The reaction mixture was concentrated and purified by column to afford the Compound AD21 (0.5 g, purity: 90% on TLC).

Compound AD21 (0.45 g, 1.04 mmol) was dissolved in the mixed solvent of THF (10 mL), MeOH (4 mL) and H$_2$O (2 mL), then LiOH.H$_2$O (0.22 g, 5.22 mmol) was added. The reaction mixture was stirred at r.t. for 2 h. TLC showed the reaction was completed. The solvent was removed and water was added, the solution was extracted with MTBE three times. The aqueous phase was acidified by 1N/L HCl solution to pH 3 and extracted with ethyl acetate three times, the organic layer was washed with water and brine, dried over Na$_2$SO$_4$, concentrated to afford the TL5X4 (0.4 g, purity: 95% on LCMS). $^1$H NMR: (400 MHz; DMSO) δ ppm 8.64 (s, 1 H), 8.42 (d, J=8.0 Hz, 1 H), 8.32 (dd, J=8.0 Hz, 1 H), 8.17 (d, J=8.0 Hz, 1 H), 8.06 (d, J=8.0 Hz, 1 H), 8.01 (d, J=4.0 Hz, 1 H), 7.75 (t, J=8.0 Hz, 1 H), 5.78 (s, 2 H), 1.91 (s, 6 H) ppm.

Synthesis of Compound AE11

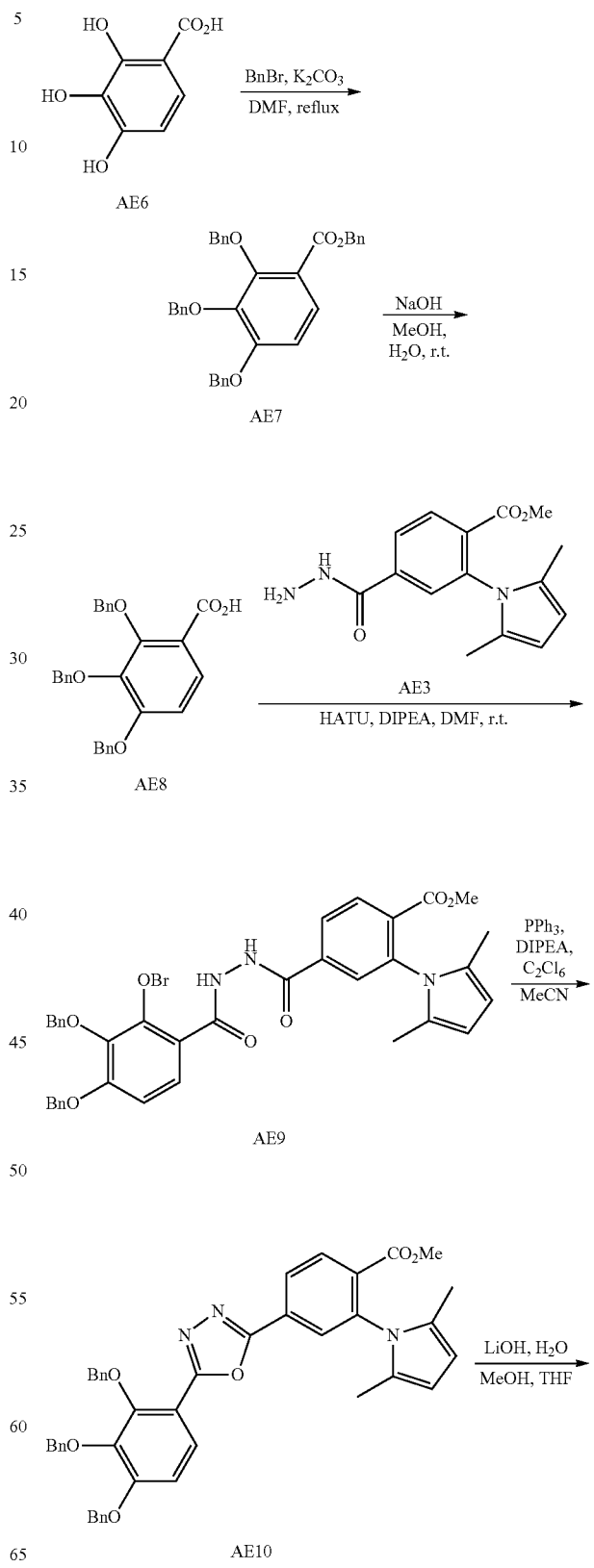

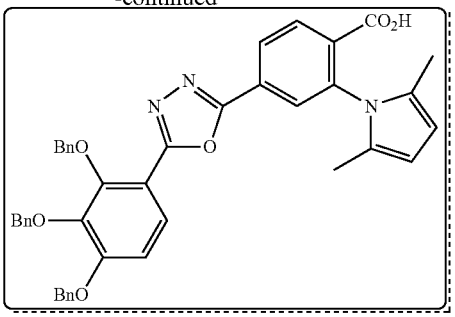

AE11

A mixture of Compound AE6 (2 g, 11.76 mmol) and BnBr (9.65 g, 56.43 mmol) in DMF (30 mL) was added $K_2CO_3$ (8.12 g, 58.78 mmol) at r.t., then the mixture was heated to 120° C. and stirred overnight. LCMS showed the reaction was completed. After the mixture was cooled to r.t., it was filtered and the filtrate was concentrated under vacuo to give the crude product. The crude product was purified by column to afford the Compound AE7 (6 g, purity: 90% on TLC). $^1$H NMR 400 MHz; $CDCl_3$) δ ppm 7.57 (d, J=8.8 Hz, 1 H), 7.32-7.19 (m, 20 H), 5.23 (s, 2 H), 5.05-4.94 (m, 6 H) ppm.

A mixture of Compound AE7 (1 g, 1.88 mmol) and NaOH (3.61 mL, 21.67 mmol) in MeOH (10 mL) was stirred at r.t. overnight. TLC showed the reaction was completed. The mixture was concentrated under vacuo. The residual was dissolved in $H_2O$, and the solution was extracted with DCM three times, the organic layer was discarded. The aqueous phase was acidified with 1 N/L HCl solution to pH 3 and extracted with ethyl acetate. The organic layer was washed with water and brine, dried over $Na_2SO_4$, concentrated to afford the Compound AE8 (0.78 g, purity: 90% on TLC). $^1$H NMR (400 MHz; DMSO) δ ppm 12.61 (s, 1 H), 7.51-7.04 (m, 17 H), 5.20 (s, 2 H), 4.97 (d, J=13.2 Hz, 4 H) ppm.

A mixture of Compound AE8 (0.4 g, 0.91 mmol), HATU (0.38 g, 0.99 mmol) and DIPEA (0.29 g, 2.27 mmol) in DMF (8 mL) was stirred at r.t. for 10 min, then Compound AE3 (0.27 g, 0.95 mmol) was added. The reaction mixture was stirred at r.t. overnight. TLC showed the reaction was completed. The mixture was diluted with water, extracted with EA three times. The organic layers were washed with water and brine, dried over $Na_2SO_4$, concentrated to afford the Compound AE9 (0.5 g, purity: 90% on TLC). $^1$H NMR: (400 MHz; $CDCl_3$) δ ppm 10.63 (d, J=3.6 Hz, 1 H), 9.55 (d, J=4.8 Hz, 1 H), 7.91-7.72 (m, 4 H), 7.35-7.21 (m, 15 H), 6.78 (d, J=9.2 Hz, 1 H), 5.81 (s, 2 H), 5.24 (s, 2 H), 5.09 (s, 2 H), 4.98 (s, 2 H), 3.63 (s, 3 H), 1.85 (s, 6 H) ppm.

A mixture of Compound AE9 (0.6 g, 0.84 mmol), $PPh_3$ (0.44 g, 1.69 mmol) and DIPEA (0.65 g, 5.07 mmol) in MeCN (10 mL) was stirred at r.t. for 10 min, then a solution of $C_2Cl_6$ (0.30 g, 1.27 mmol) in MeCN was added dropwise at r.t. After the addition, the mixture was stirred at r.t. for another 2 h. TLC showed the reaction was completed. The reaction mixture was concentrated and purified by column to afford the Compound AE10 (0.4 g, purity: 90% on TLC). $^1$H NMR (400 MHz; $CDCl_3$) δ ppm 8.04-8.00 (m, 2 H), 7.94 (s, 1 H), 7.80 (d, J=8.0 Hz, 1 H), 7.49-7.40 (m, 9 H), 7.33-7.32 (m, 3 H), 7.27-7.25 (m, 3 H), 6.95 (d, J=8.0 Hz, 1 H), 5.94 (s, 2 H), 5.25 (s, 2 H), 5.22 (s, 2 H), 5.15 (s, 2 H), 3.74 (s, 3 H), 1.97 (s, 6 H) ppm.

Compound AE10 (0.4 g, 0.58 mmol) was dissolved in the mixed solvent of THF (5 mL), MeOH (2 mL) and $H_2O$ (1 mL), then $LiOH.H_2O$ (0.12 g, 2.89 mmol) was added. The reaction mixture was stirred at r.t. for 2 h. TLC showed the reaction was completed. The solvent was removed and water was added, the solution was extracted with MTBE three times. The aqueous phase was acidified by 1N/L HCl solution to pH 3 and extracted with ethyl acetate three times, the organic layer was washed with water and brine, dried over $Na_2SO_4$, concentrated to afford the Compound AE11 (0.3 g, purity: 90% on TLC). $^1$H NMR: (400 MHz; DMSO) δ ppm 8.06-8.03 (m, 1 H), 7.96 (d, J=8.0 Hz, 1 H), 7.81 (d, J=8.0 Hz, 1 H), 7.72 (s, 1 H), 7.51 (d, J=8.0 Hz, 2 H), 7.45-7.33 (m, 7 H), 7.29-7.18 (m, 7 H), 5.78 (s, 2 H), 5.27 (s, 2 H), 5.12 (s, 2 H), 5.06 (s, 2 H), 1.87 (s, 6 H) ppm.

Synthesis of Compound TL5X1

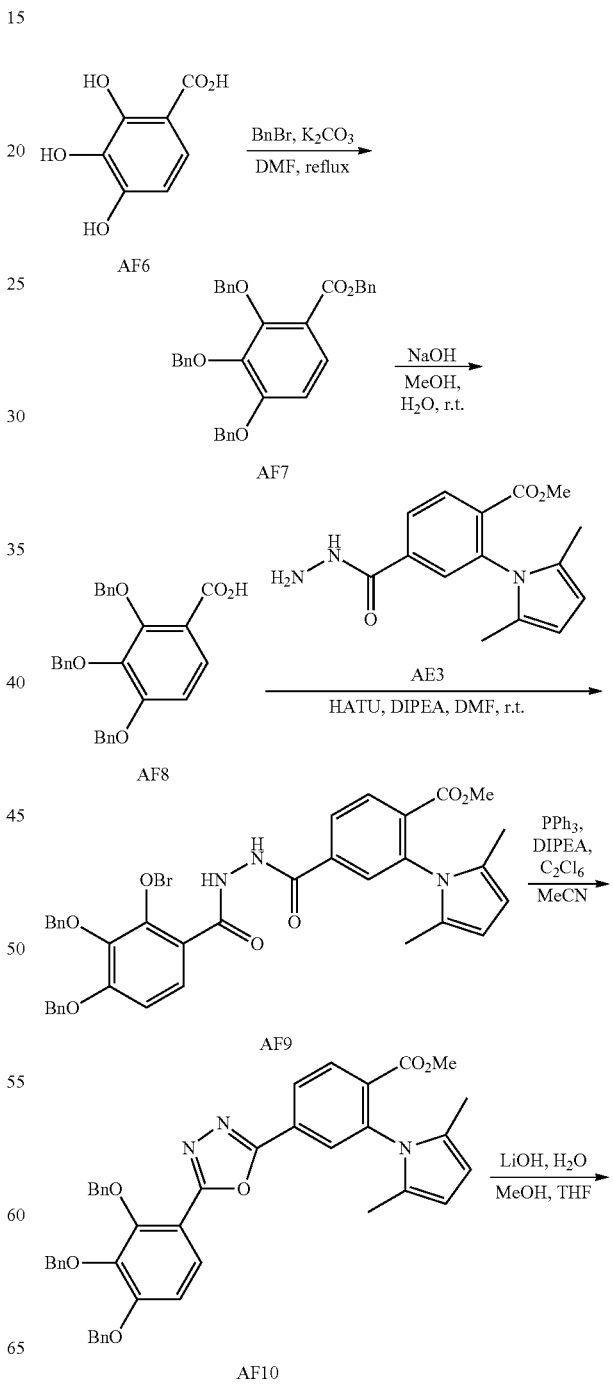

-continued

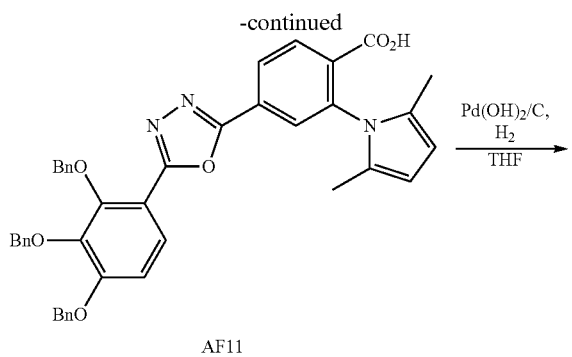

AF11

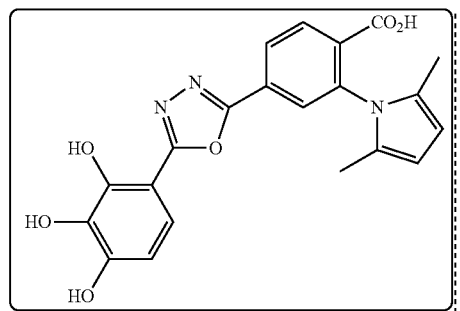

TL5X1

A mixture of Compound AF6 (2 g, 11.76 mmol) and BnBr (9.65 g, 56.43 mmol) in DMF (30 mL) was added $K_2CO_3$ (8.12 g, 58.78 mmol) at r.t., then the mixture was heated to 120° C. and stirred overnight. LCMS showed the reaction was completed. After the mixture was cooled to r.t., it was filtered and the filtrate was concentrated under vacuo to give the crude product. The crude product was purified by column to afford the Compound AF7 (6 g, purity: 90% on TLC). $^1$H NMR (400 MHz; CDCl$_3$) δ ppm 7.57 (d, J=8.8 Hz, 1 H), 7.32-7.19 (m, 20 H), 5.23 (s, 2 H), 5.05-4.94 (m, 6 H).

A mixture of Compound AF7 (1 g, 1.88 mmol) and NaOH (3.61 mL, 21.67 mmol) in MeOH (10 mL) was stirred at r.t. overnight. TLC showed the reaction was completed. The mixture was concentrated under vacuo. The residual was dissolved in H2O, and the solution was extracted with DCM three times, the organic layer was discarded. The aqueous phase was acidified with 1 N/L HCl solution to pH 3 and extracted with ethyl acetate. The organic layer was washed with water and brine, dried over Na$_2$SO$_4$, concentrated to afford the Compound AF8 (0.78 g, purity: 90% on TLC). $^1$H NMR (400 MHz; DMSO) δ ppm 12.61 (s, 1 H), 7.51-7.04 (m, 17 H), 5.20 (s, 2 H), 4.97 (d, J=13.2 Hz, 4 H).

A mixture of Compound AF8 (0.4 g, 0.91 mmol), HATU (0.38 g, 0.99 mmol) and DIPEA (0.29 g, 2.27 mmol) in DMF (8 mL) was stirred at r.t. for 10 min, then Compound AF3 (0.27 g, 0.95 mmol) was added. The reaction mixture was stirred at r.t. overnight. TLC showed the reaction was completed. The mixture was diluted with water, extracted with EA three times. The organic layers were washed with water and brine, dried over Na$_2$SO$_4$, concentrated to afford the Compound AF9 (0.5 g, purity: 90% on TLC). $^1$H NMR (400 MHz; CDCl$_3$) δ ppm 10.63 (d, J=3.6 Hz, 1 H), 9.55 (d, J=4.8 Hz, 1 H), 7.91-7.72 (m, 4 H), 7.35-7.21 (m, 15 H), 6.78 (d, J=9.2 Hz, 1 H), 5.81 (s, 2 H), 5.24 (s, 2 H), 5.09 (s, 2 H), 4.98 (s, 2 H), 3.63 (s, 3 H), 1.85 (s, 6 H).

A mixture of Compound AF9 (0.6 g, 0.84 mmol), PPh$_3$ (0.44 g, 1.69 mmol) and DIPEA (0.65 g, 5.07 mmol) in MeCN (10 mL) was stirred at r.t. for 10 min, then a solution of $C_2Cl_6$ (0.30 g, 1.27 mmol) in MeCN was added dropwise at r.t. After the addition, the mixture was stirred at r.t. for another 2 h. TLC showed the reaction was completed. The reaction mixture was concentrated and purified by column to afford the Compound AF10 (0.4 g, purity: 90% on TLC). $^1$H NMR (400 MHz; CDCl$_3$) δ ppm 8.04-8.00 (m, 2 H), 7.94 (s, 1 H), 7.80 (d, J=8.0 Hz, 1 H), 7.49-7.40 (m, 9 H), 7.33-7.32 (m, 3 H), 7.27-7.25 (m, 3 H), 6.95 (d, J=8.0 Hz, 1 H), 5.94 (s, 2 H), 5.25 (s, 2 H), 5.22 (s, 2 H), 5.15 (s, 2 H), 3.74 (s, 3 H), 1.97 (s, 6 H).

Compound AF10 (0.4 g, 0.58 mmol) was dissolved in the mixed solvent of THF (5 mL), MeOH (2 mL) and H$_2$O (1 mL), then LiOH.H$_2$O (0.12 g, 2.89 mmol) was added. The reaction mixture was stirred at r.t. for 2 h. TLC showed the reaction was completed. The solvent was removed and water was added, the solution was extracted with MTBE three times. The aqueous phase was acidified by 1N/L HCl solution to pH 3 and extracted with ethyl acetate three times, the organic layer was washed with water and brine, dried over Na$_2$SO$_4$, concentrated to afford the Compound AF11 (0.3 g, purity: 90% on TLC). $^1$H NMR: (400 MHz; DMSO) δ ppm 8.06-8.03 (m, 1 H), 7.96 (d, J=8.0 Hz, 1 H), 7.81 (d, J=8.0 Hz, 1 H), 7.72 (s, 1 H), 7.51 (d, J=8.0 Hz, 2 H), 7.45-7.33 (m, 7 H), 7.29-7.18 (m, 7 H), 5.78 (s, 2 H), 5.27 (s, 2 H), 5.12 (s, 2 H), 5.06 (s, 2 H), 1.87 (s, 6 H).

A mixture of Compound AF11 (0.1 g, 0.15 mmol) and Pd(OH)2/C (0.01 g, 0.06 mmol) in THF (5 mL) was stirred under a balloon H$_2$ at r.t. for 20 min. LCMS showed the reaction was completed. The reaction mixture was filtered and the filtrated was concentrated under vacuo at 30° C. to get the crude product. The crude product was purified by pre-HPLC to afford the TL5X1 (28 mg, purity: 93% on LCMS). $^1$H NMR (400 MHz; DMSO) δ ppm 13.23 (s, 1 H), 9.91 (s, 1 H), 9.64 (s, 1 H), 8.79 (s, 1 H), 8.26 (d, J=8.4 Hz, 1 H), 8.07 (d, J=8.0 Hz, 1 H), 7.91 (s, 1 H), 7.38 (d, J=8.8 Hz, 1 H), 6.52 (d, J=8.8 Hz, 1 H), 5.79 (s, 2 H), 1.91 (s, 6 H).

Additional characterization data for compounds described herein is shown in Table 1.

TABLE 1

Analytical data for exemplary compounds of the invention

| No. | Structure | m/z (M + H) |
|---|---|---|
| 60 | 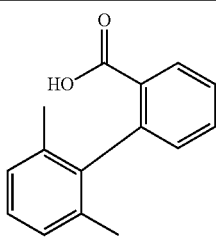 | 208.98 (M − OH) |

TABLE 1-continued

Analytical data for exemplary compounds of the invention

| No. | Structure | m/z (M + H) |
|---|---|---|
| 63 | 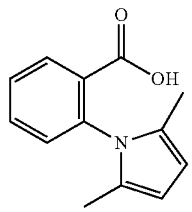 [SMILES: Cc1ccc(C)n1-c1ccccc1C(=O)O] | 216.073 |
| 64 | 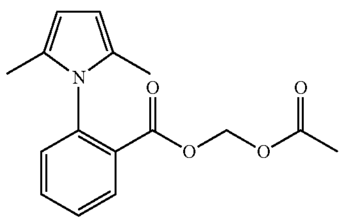 [SMILES: CC(=O)OCOC(=O)c1ccccc1-n1c(C)ccc1C] | 288.106 |
| 65 | 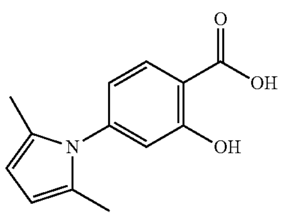 [SMILES: Cc1ccc(C)n1-c1ccc(C(=O)O)c(O)c1] | 232.047 |
| 66 | 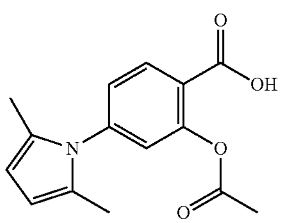 [SMILES: CC(=O)Oc1cc(-n2c(C)ccc2C)ccc1C(=O)O] | 274.017 |
| 67 | 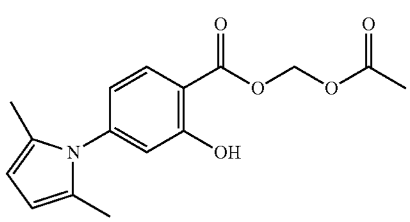 [SMILES: CC(=O)OCOC(=O)c1ccc(-n2c(C)ccc2C)cc1O] | 381.76 (2K+) |
| 68 | 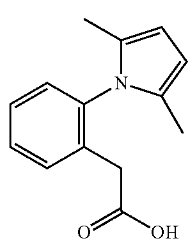 [SMILES: Cc1ccc(C)n1-c1ccccc1CC(=O)O] | 230.050 |

TABLE 1-continued

Analytical data for exemplary compounds of the invention

| No. | Structure | m/z (M + H) |
|---|---|---|
| 69 | 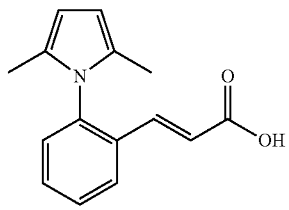 [SMILES: Cc1ccc(C)n1-c1ccccc1/C=C/C(=O)O] | 242.044 |
| 70 | 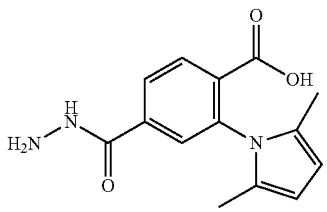 [SMILES: Cc1ccc(C)n1-c1cc(C(=O)NN)ccc1C(=O)O] | 274.136 |
| 71 | 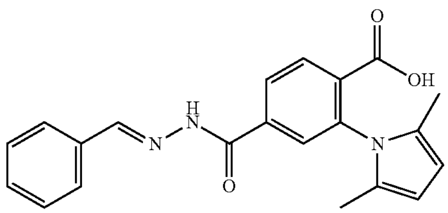 [SMILES: Cc1ccc(C)n1-c1cc(C(=O)N/N=C/c2ccccc2)ccc1C(=O)O] | 361.932 |
| 72 | 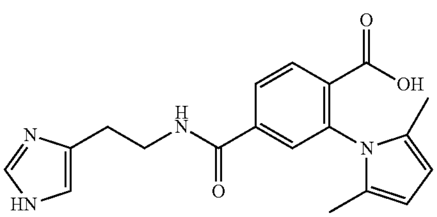 [SMILES: Cc1ccc(C)n1-c1cc(C(=O)NCCc2c[nH]cn2)ccc1C(=O)O] | 352.958 (M+) |
| 73 | 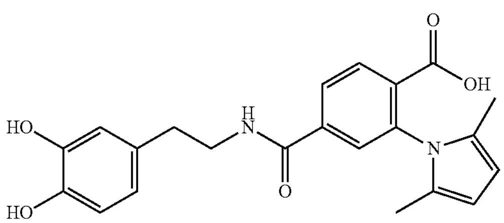 [SMILES: Cc1ccc(C)n1-c1cc(C(=O)NCCc2ccc(O)c(O)c2)ccc1C(=O)O] | 394.873 (M+) |
| 74 | 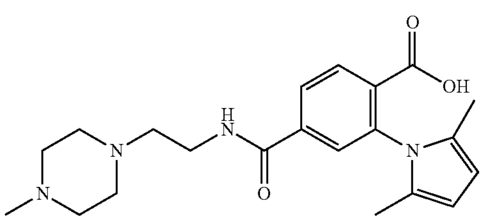 [SMILES: Cc1ccc(C)n1-c1cc(C(=O)NCCN2CCN(C)CC2)ccc1C(=O)O] | 384.96 (M+) |
| 75 | 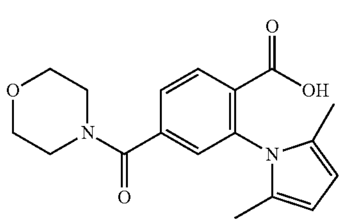 [SMILES: Cc1ccc(C)n1-c1cc(C(=O)N2CCOCC2)ccc1C(=O)O] | 328.971 (M+) |

TABLE 1-continued

Analytical data for exemplary compounds of the invention

| No. | Structure | m/z (M + H) |
|---|---|---|
| 76 | 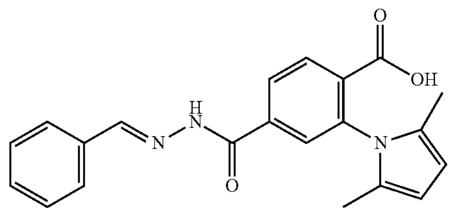 [SMILES: Cc1ccc(C)n1-c1cc(C(=O)N/N=C/c2ccccc2)ccc1C(=O)O] | 361.932 (M+) |
| 78 | 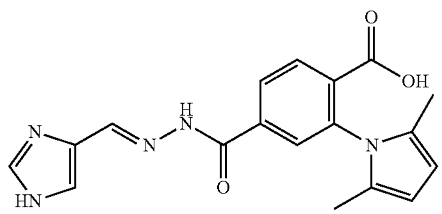 [SMILES: Cc1ccc(C)n1-c1cc(C(=O)N/N=C/c2c[nH]cn2)ccc1C(=O)O] | 351.91 (M+) |
| 79 | 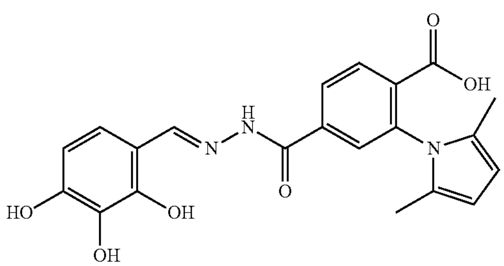 [SMILES: Cc1ccc(C)n1-c1cc(C(=O)N/N=C/c2ccc(O)c(O)c2O)ccc1C(=O)O] | 409.829 (M+) |
| 80 | 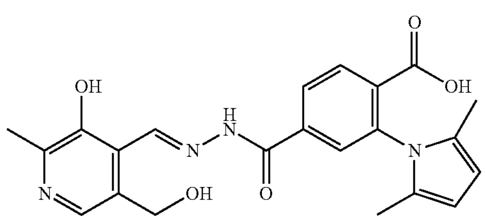 [SMILES: Cc1ncc(CO)c(/C=N/NC(=O)c2ccc(C(=O)O)c(-n3c(C)ccc3C)c2)c1O] | 422.788 (M+) |
| 81 | 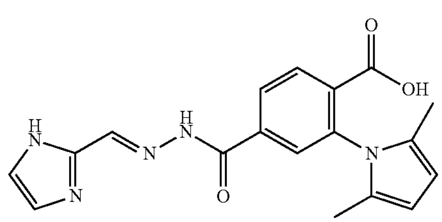 [SMILES: Cc1ccc(C)n1-c1cc(C(=O)N/N=C/c2ncc[nH]2)ccc1C(=O)O] | 351.915 (M+) |
| 82 | 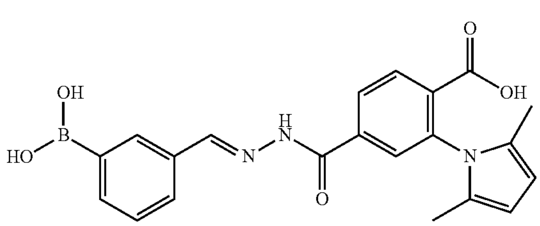 [SMILES: Cc1ccc(C)n1-c1cc(C(=O)N/N=C/c2cccc(B(O)O)c2)ccc1C(=O)O] | 405.838 (M+) |

TABLE 1-continued

Analytical data for exemplary compounds of the invention

| No. | Structure | m/z (M + H) |
|-----|-----------|-------------|
| 83 | 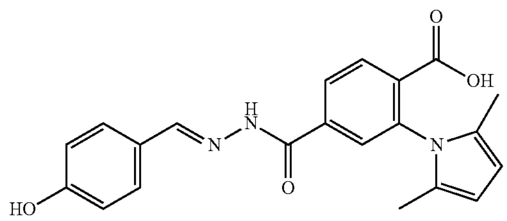 [SMILES: Cc1ccc(C)n1-c1cc(C(=O)N/N=C/c2ccc(O)cc2)ccc1C(=O)O] | 377.866 (M+) |
| 84 | 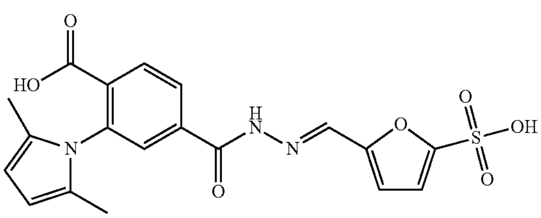 [SMILES: Cc1ccc(C)n1-c1cc(C(=O)N/N=C/c2ccc(S(=O)(=O)O)o2)ccc1C(=O)O] | 431.732 (M+) |
| 85 | 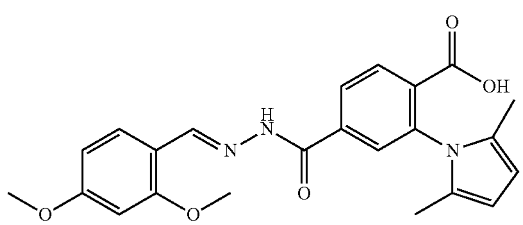 [SMILES: COc1ccc(/C=N/NC(=O)c2ccc(C(=O)O)c(-n3c(C)ccc3C)c2)c(OC)c1] | 421.846 (M+) |
| 86 | 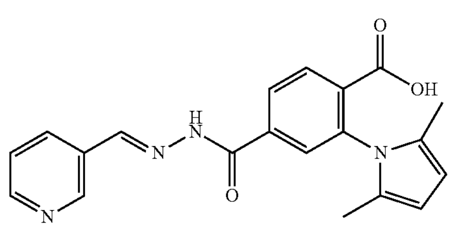 [SMILES: Cc1ccc(C)n1-c1cc(C(=O)N/N=C/c2cccnc2)ccc1C(=O)O] | 362.926 (M+) |
| 87 | 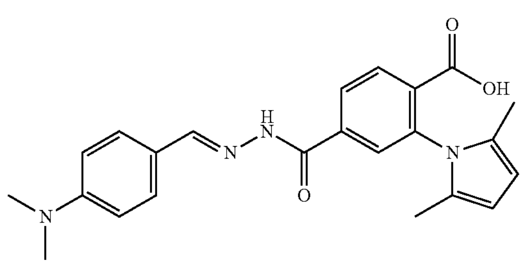 [SMILES: Cc1ccc(C)n1-c1cc(C(=O)N/N=C/c2ccc(N(C)C)cc2)ccc1C(=O)O] | 404.896 (M+) |
| 89 | 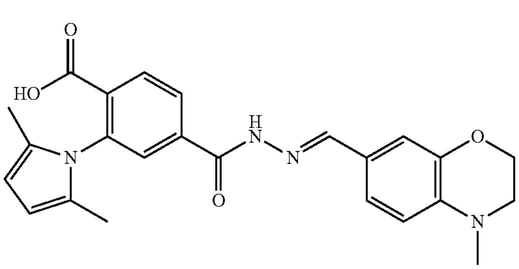 [SMILES: Cc1ccc(C)n1-c1cc(C(=O)N/N=C/c2ccc3c(c2)OCCN3C)ccc1C(=O)O] | 432.89 (M+) |

TABLE 1-continued

Analytical data for exemplary compounds of the invention

| No. | Structure | m/z (M + H) |
|---|---|---|
| 90 | 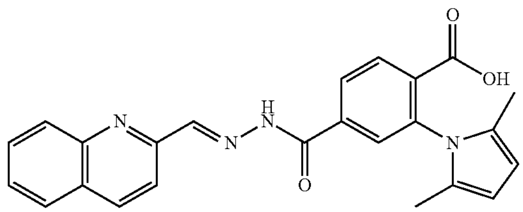 | 412.845 (M+) |
| 92 | 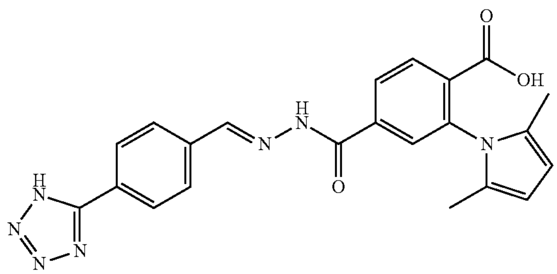 [SMILES: Cc1ccc(C)n1-c1cc(C(=O)N/N=C/c2ccc(-c3nnn[nH]3)cc2)ccc1C(=O)O] | 429.834 (M+) |
| 93 | 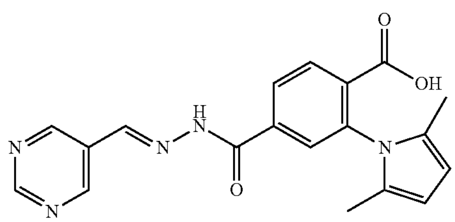 [SMILES: Cc1ccc(C)n1-c1cc(C(=O)N/N=C/c2cncnc2)ccc1C(=O)O] | 363.927 (M+) |
| 94 | 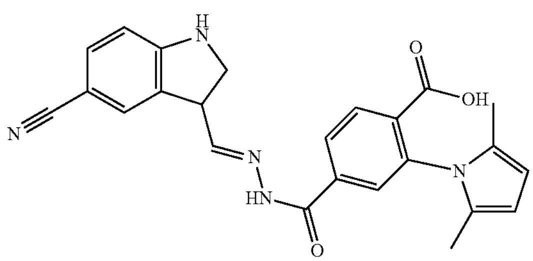 [SMILES: Cc1ccc(C)n1-c1cc(C(=O)N/N=C/C2CNc3ccc(C#N)cc32)ccc1C(=O)O] | 428.859 |
| 95 | 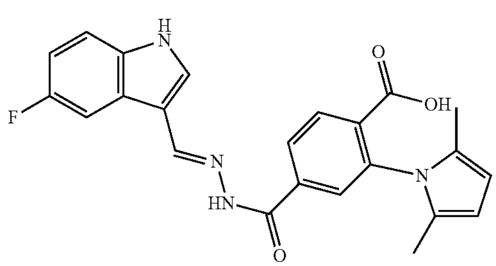 [SMILES: Cc1ccc(C)n1-c1cc(C(=O)N/N=C/c2c[nH]c3ccc(F)cc23)ccc1C(=O)O] | 418.818 (M+) |
| 96 | 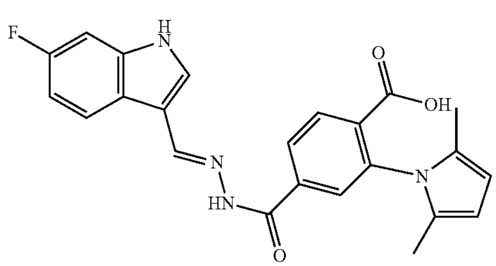 [SMILES: Cc1ccc(C)n1-c1cc(C(=O)N/N=C/c2c[nH]c3cc(F)ccc23)ccc1C(=O)O] | 418.856 (M+) |

TABLE 1-continued

Analytical data for exemplary compounds of the invention

| No. | Structure | m/z (M + H) |
|---|---|---|
| 97 | 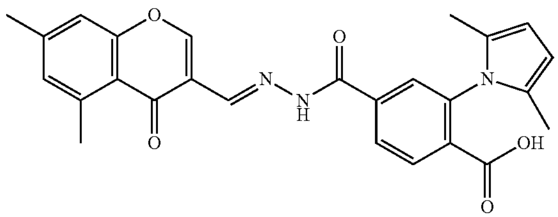 [SMILES: Cc1cc(C)c2c(=O)c(/C=N/NC(=O)c3ccc(C(=O)O)c(-n4c(C)ccc4C)c3)coc2c1] | 457.823 (M+) |
| 99 | 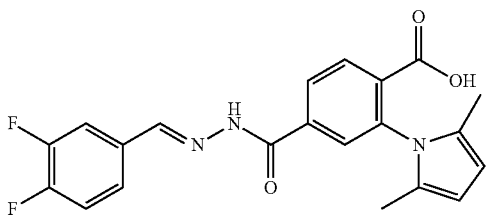 [SMILES: Cc1ccc(C)n1-c1cc(C(=O)N/N=C/c2ccc(F)c(F)c2)ccc1C(=O)O] | 397.856 (M+) |
| 100 | 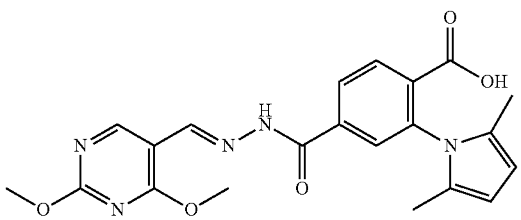 [SMILES: COc1ncc(/C=N/NC(=O)c2ccc(C(=O)O)c(-n3c(C)ccc3C)c2)c(OC)n1] | 423.85 (M+) |
| 101 | 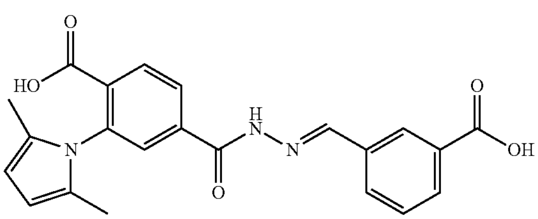 [SMILES: Cc1ccc(C)n1-c1cc(C(=O)N/N=C/c2cccc(C(=O)O)c2)ccc1C(=O)O] | 405.828 (M+) |
| 102 | 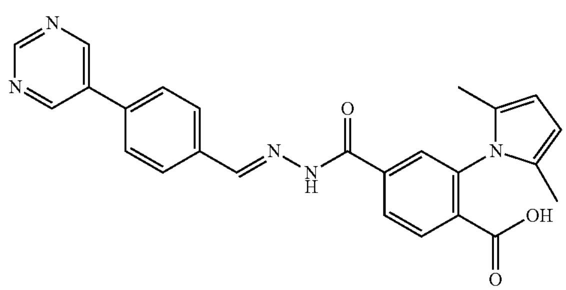 [SMILES: Cc1ccc(C)n1-c1cc(C(=O)N/N=C/c2ccc(-c3cncnc3)cc2)ccc1C(=O)O] | 439.845 (M+) |
| 103 | 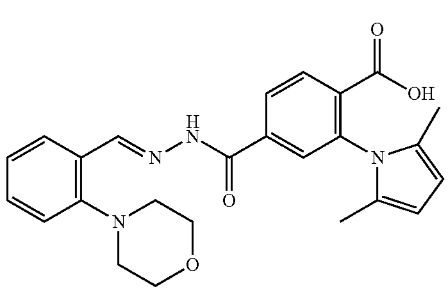 [SMILES: Cc1ccc(C)n1-c1cc(C(=O)N/N=C/c2ccccc2N2CCOCC2)ccc1C(=O)O] | 429.859 (M − OH) |

TABLE 1-continued

Analytical data for exemplary compounds of the invention

| No. | Structure | m/z (M + H) |
|---|---|---|
| 104 | 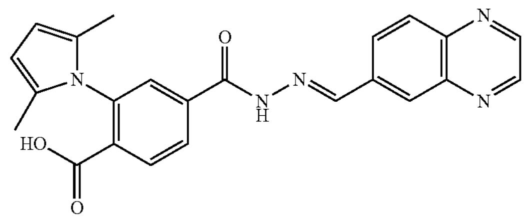 [SMILES: Cc1ccc(C)n1-c1cc(C(=O)N/N=C/c2ccc3nccnc3c2)ccc1C(=O)O] | 413.883 (M+) |
| 105 | 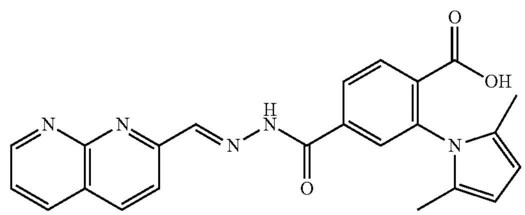 | 413.896 (M+) |
| 106 | 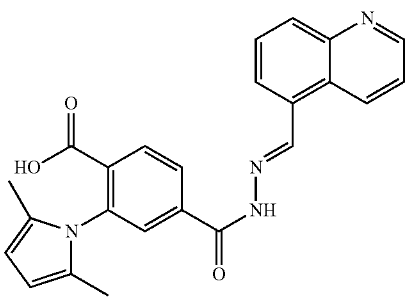 [SMILES: Cc1ccc(C)n1-c1cc(C(=O)N/N=C/c2cccc3ncccc23)ccc1C(=O)O] | 412.883 (M+) |
| 107 | 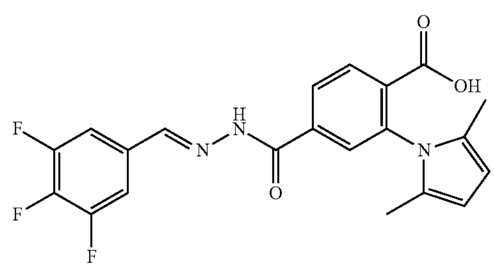 [SMILES: Cc1ccc(C)n1-c1cc(C(=O)N/N=C/c2cc(F)c(F)c(F)c2)ccc1C(=O)O] | 415.851 |
| 108 | 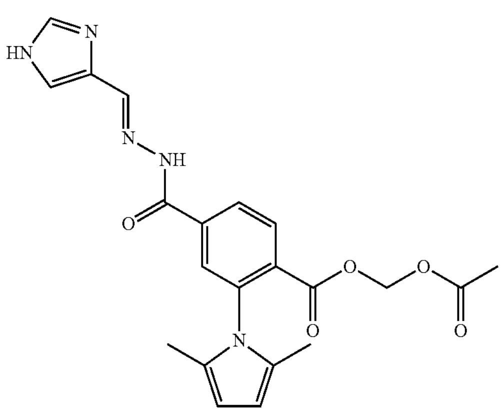 [SMILES: CC(=O)OCOC(=O)c1ccc(C(=O)N/N=C/c2c[nH]cn2)cc1-n1c(C)ccc1C] | 423.859 |

TABLE 1-continued
Analytical data for exemplary compounds of the invention
| No. | Structure | m/z (M + H) |
|---|---|---|
| 109 | 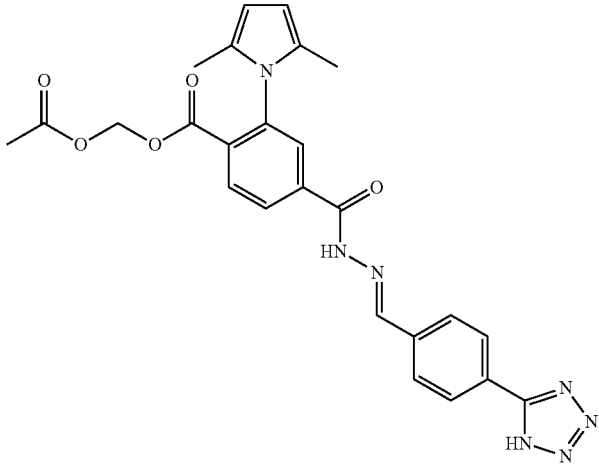 [SMILES: CC(=O)OCOC(=O)c1ccc(C(=O)N/N=C/c2ccc(-c3nnn[nH]3)cc2)cc1-n1c(C)ccc1C] | 501.756 (M+) |
| 110 | 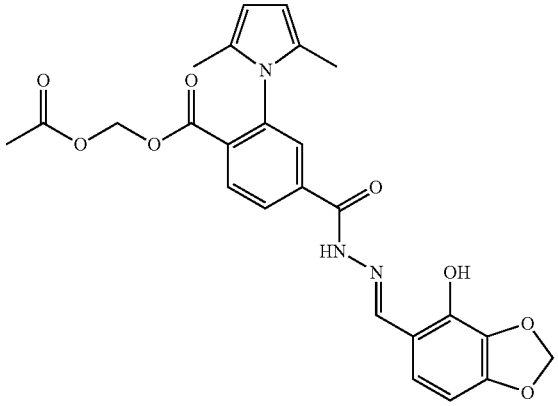 [SMILES: CC(=O)OCOC(=O)c1ccc(C(=O)N/N=C/c2ccc3c(c2O)OCO3)cc1-n1c(C)ccc1C] | 494.730 |
| 111 | 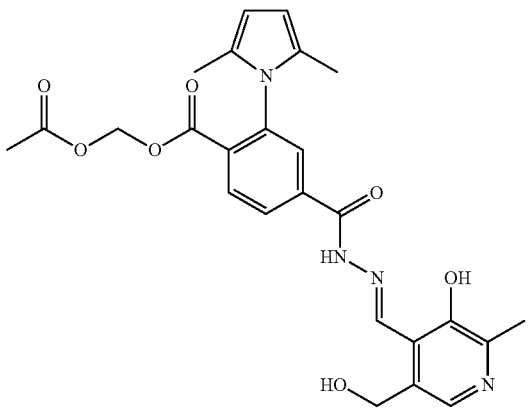 [SMILES: CC(=O)OCOC(=O)c1ccc(C(=O)N/N=C/c2c(CO)cnc(C)c2O)cc1-n1c(C)ccc1C] | 494.792 |

TABLE 1-continued

Analytical data for exemplary compounds of the invention

| No. | Structure | m/z (M + H) |
|-----|-----------|-------------|
| 112 | 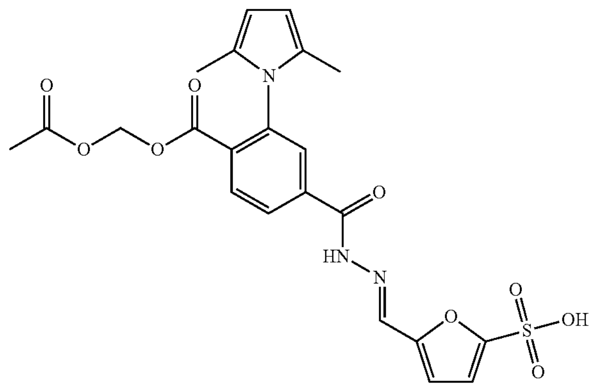 [SMILES: CC(=O)OCOC(=O)c1ccc(C(=O)N/N=C/c2ccc(S(=O)(=O)O)o2)cc1-n1c(C)ccc1C] | 503.759 (M+) |
| 113 | 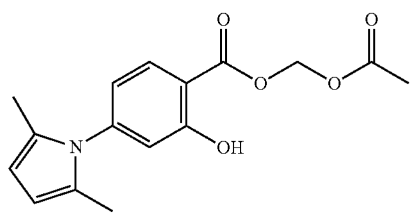 [SMILES: CC(=O)OCOC(=O)c1ccc(-n2c(C)ccc2C)cc1O] | 381.761 (2K+) |
| 114 | 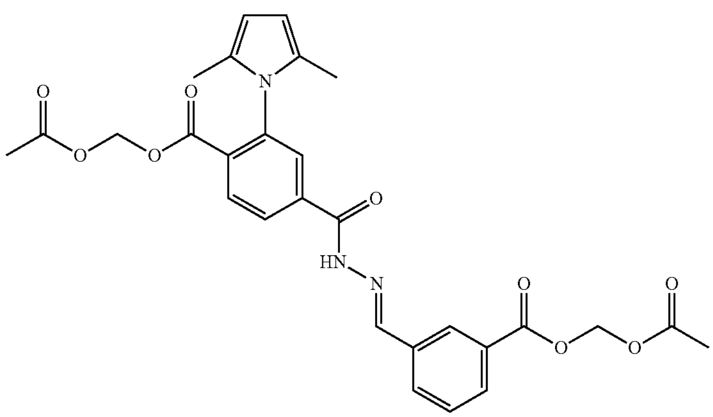 [SMILES: CC(=O)OCOC(=O)c1cccc(/C=N/NC(=O)c2ccc(C(=O)OCOC(C)=O)c(-n3c(C)ccc3C)c2)c1] | 549.9949 (M+) |
| 128 | 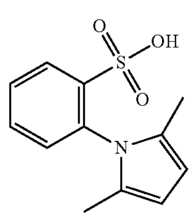 [SMILES: Cc1ccc(C)n1-c1ccccc1S(=O)(=O)O] | 251.921 (M+) |
| 129 | 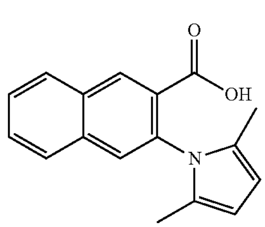 [SMILES: Cc1ccc(C)n1-c1cc2ccccc2cc1C(=O)O] | 265.943 (M+) |

TABLE 1-continued

Analytical data for exemplary compounds of the invention

| No. | Structure | m/z (M + H) |
|---|---|---|
| 130 | 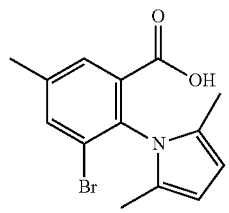 [SMILES: Cc1cc(Br)c(-n2c(C)ccc2C)c(C(=O)O)c1] | 309.774 |
| 131 | 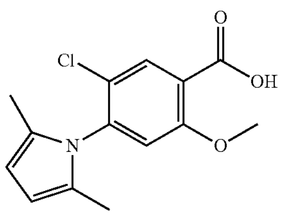 [SMILES: COc1cc(-n2c(C)ccc2C)c(Cl)cc1C(=O)O] | 279.874 (M+) |
| 132 | 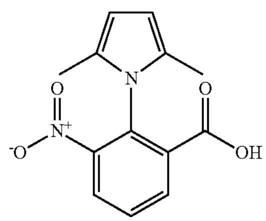 | 260.596 (M+) |
| 133 | 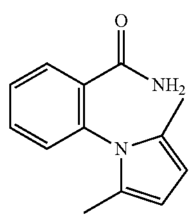 [SMILES: Cc1ccc(C)n1-c1ccccc1C(N)=O] | 214.984 (M+) |
| 134 | 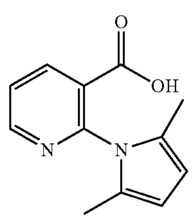 [SMILES: Cc1ccc(C)n1-c1ncccc1C(=O)O] | 216.954 (M+) |
| 135 | 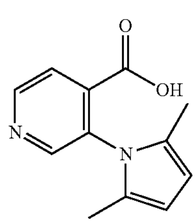 [SMILES: Cc1ccc(C)n1-c1cnccc1C(=O)O] | 216.950 (M+) |

TABLE 1-continued

Analytical data for exemplary compounds of the invention

| No. | Structure | m/z (M + H) |
|---|---|---|
| 136 | 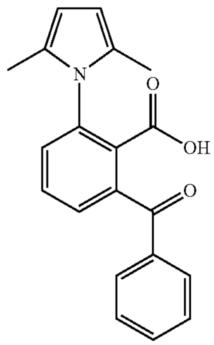 [SMILES: Cc1ccc(C)n1-c1cccc(C(=O)c2ccccc2)c1C(=O)O] | 319.866 (M+) |
| 137 | 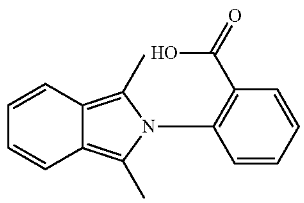 [SMILES: Cc1c2ccccc2c(C)n1-c1ccccc1C(=O)O] | 265.947 (M+) |
| 138 | 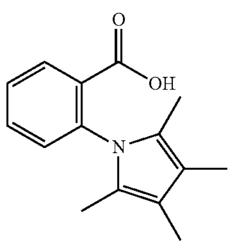 [SMILES: Cc1c(C)c(C)n(-c2ccccc2C(=O)O)c1C] | 243 (M+) |
| 139 | 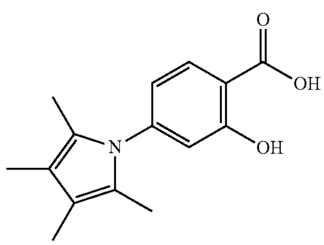 [SMILES: Cc1c(C)c(C)n(-c2ccc(C(=O)O)c(O)c2)c1C] | 259.974 (M+) |
| 140 | 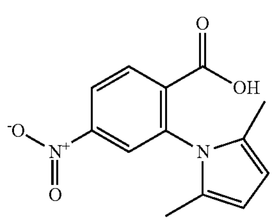 | 260.92 (M+) |
| 141 | 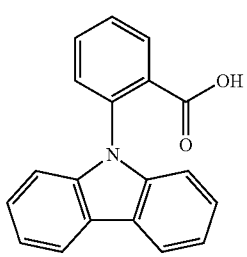 [SMILES: O=C(O)c1ccccc1-n1c2ccccc2c2ccccc21] | 287.915 (M+) |

TABLE 1-continued

Analytical data for exemplary compounds of the invention

| No. | Structure | m/z (M + H) |
|---|---|---|
| 142 | 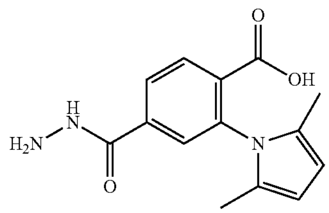 [SMILES: Cc1ccc(C)n1-c1cc(C(=O)NN)ccc1C(=O)O] | 273.941 (M+) |
| 146 | 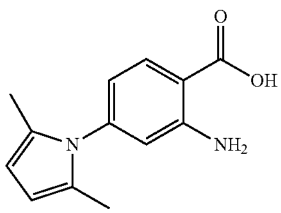 [SMILES: Cc1ccc(C)n1-c1ccc(C(=O)O)c(N)c1] | 230.982 (M+) |
| 148 | 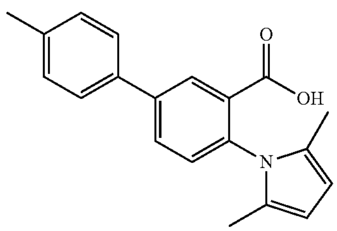 [SMILES: Cc1ccc(-c2ccc(-n3c(C)ccc3C)c(C(=O)O)c2)cc1] | 305.839 (M+) |
| 150 | 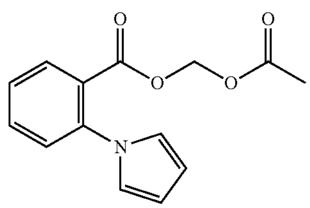 [SMILES: CC(=O)OCOC(=O)c1ccccc1-n1cccc1] | 259.942 (M+) |
| 151 | 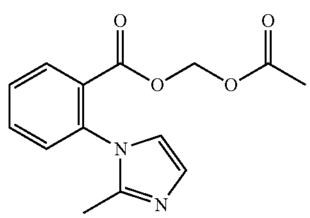 [SMILES: CC(=O)OCOC(=O)c1ccccc1-n1ccnc1C] | 274.914 (M+) |
| 152 | 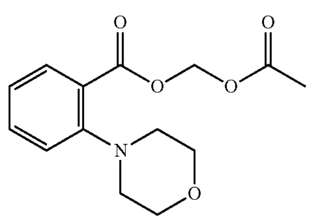 [SMILES: CC(=O)OCOC(=O)c1ccccc1N1CCOCC1] | 279.920 (M+) |
| 157 | 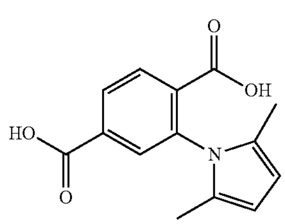 [SMILES: Cc1ccc(C)n1-c1cc(C(=O)O)ccc1C(=O)O] | 321.813 (M+) |

TABLE 1-continued

Analytical data for exemplary compounds of the invention

| No. | Structure | m/z (M + H) |
|---|---|---|
| 158 | 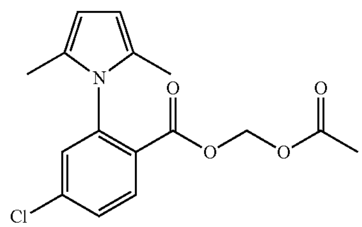 [SMILES: CC(=O)OCOC(=O)c1ccc(Cl)cc1-n1c(C)ccc1C] | 321.813 (M+) |
| 159 | 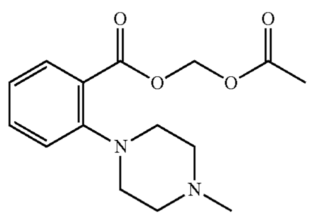 [SMILES: CC(=O)OCOC(=O)c1ccccc1N1CCN(C)CC1] | 292.964 (M+) |
| 160 | 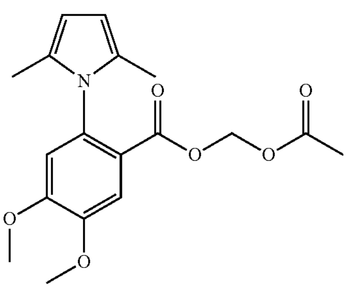 [SMILES: COc1cc(C(=O)OCOC(C)=O)c(-n2c(C)ccc2C)cc1OC] | 347.826 (M+) |
| 162 | 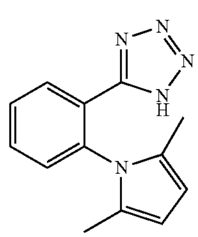 [SMILES: Cc1ccc(C)n1-c1ccccc1-c1nnn[nH]1] | 239.887 (M+) |
| 163 | 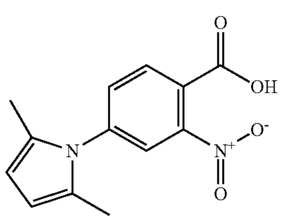 [SMILES: Cc1ccc(C)n1-c1ccc(C(=O)O)c([N+](=O)[O-])c1] | 260.863 (M+) |
| 164 | 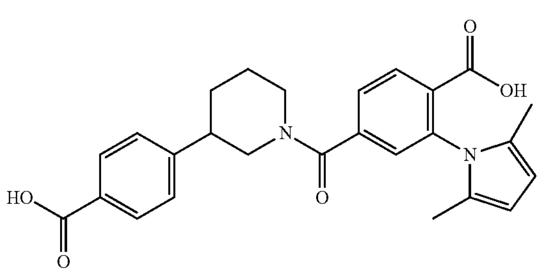 [SMILES: Cc1ccc(C)n1-c1cc(C(=O)N2CCCC(c3ccc(C(=O)O)cc3)C2)ccc1C(=O)O] | 447.036 |

TABLE 1-continued

Analytical data for exemplary compounds of the invention

| No. | Structure | m/z (M + H) |
|-----|-----------|-------------|
| 165 | 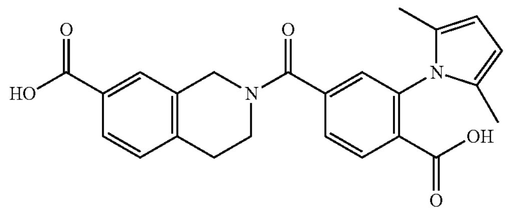 [SMILES: Cc1ccc(C)n1-c1cc(C(=O)N2CCc3ccc(C(=O)O)cc3C2)ccc1C(=O)O] | 419.046 |
| | | 360.952 (M+) |
| 77 | 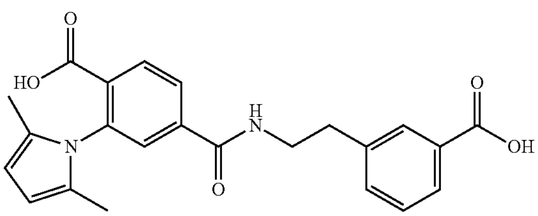 [SMILES: Cc1ccc(C)n1-c1cc(C(=O)NCCc2cccc(C(=O)O)c2)ccc1C(=O)O] | 407.824 |
| 166 | 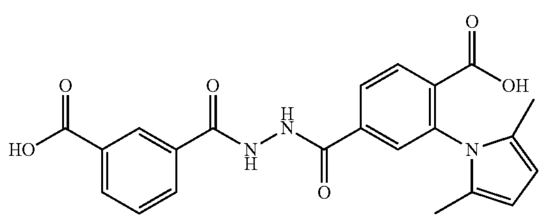 [SMILES: Cc1ccc(C)n1-c1cc(C(=O)NNC(=O)c2cccc(C(=O)O)c2)ccc1C(=O)O] | 421.947 (M+) |
| 167 | 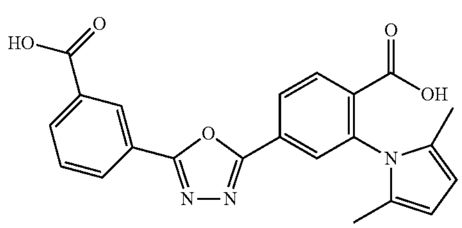 [SMILES: Cc1ccc(C)n1-c1cc(-c2nnc(-c3cccc(C(=O)O)c3)o2)ccc1C(=O)O] | 403.955 (M+) |
| 116 | 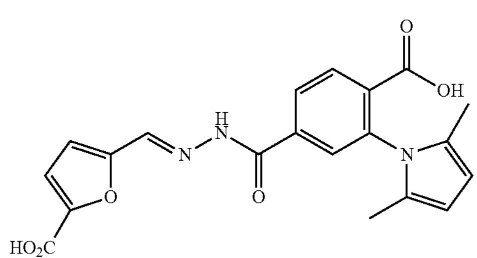 [SMILES: Cc1ccc(C)n1-c1cc(C(=O)N/N=C/c2ccc(C(=O)O)o2)ccc1C(=O)O] | 423.768 (M+) |

TABLE 1-continued

Analytical data for exemplary compounds of the invention

| No. | Structure | m/z (M + H) |
|---|---|---|
| 117 | 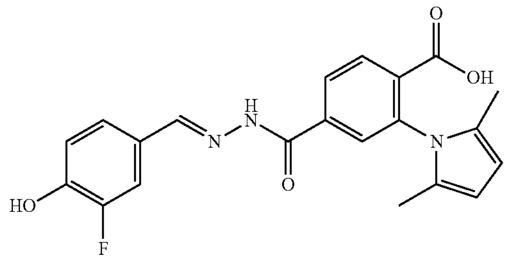 [SMILES: Cc1ccc(C)n1-c1cc(C(=O)N/N=C/c2ccc(O)c(F)c2)ccc1C(=O)O] | 395.9921 (M+) |
| 118 | 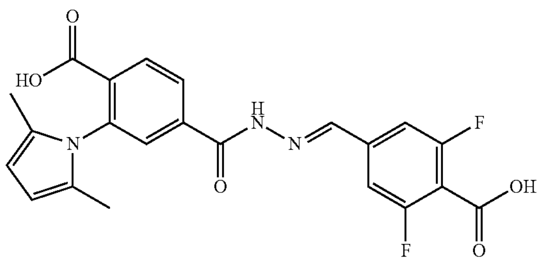 [SMILES: Cc1ccc(C)n1-c1cc(C(=O)N/N=C/c2cc(F)c(C(=O)O)c(F)c2)ccc1C(=O)O] | 441.957 (M+) |
| 119 | 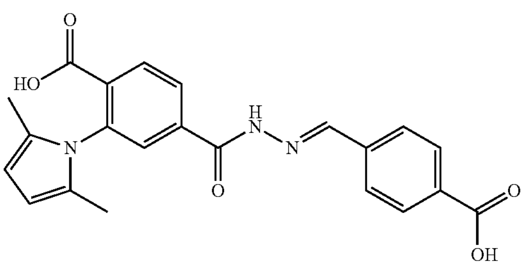 [SMILES: Cc1ccc(C)n1-c1cc(C(=O)N/N=C/c2ccc(C(=O)O)cc2)ccc1C(=O)O] | 406.033 |
| 121 | 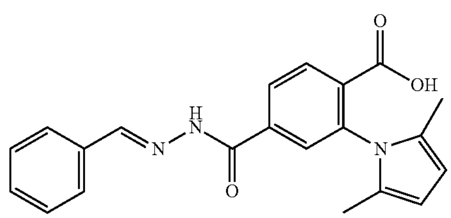 [SMILES: Cc1ccc(C)n1-c1cc(C(=O)N/N=C/c2ccccc2)ccc1C(=O)O] | 362.105 |
| 122 | 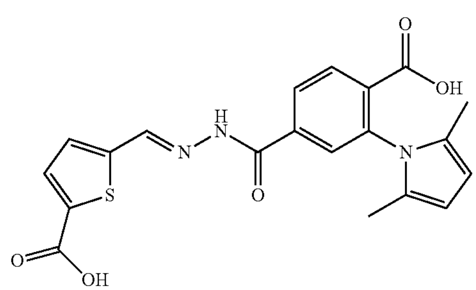 [SMILES: Cc1ccc(C)n1-c1cc(C(=O)N/N=C/c2ccc(C(=O)O)s2)ccc1C(=O)O] | 411.977 (M+) |
| 168 | 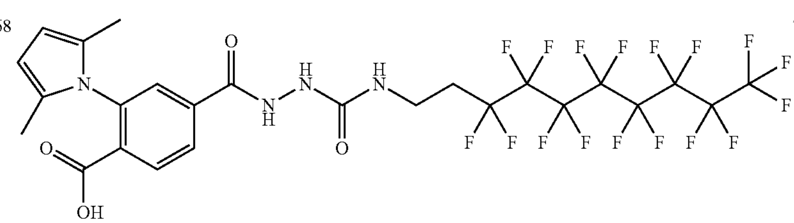 | 762.645 (M+) |

TABLE 1-continued

Analytical data for exemplary compounds of the invention

| No. | Structure | m/z (M + H) |
|---|---|---|
| 125 | [structure: 2-(2,5-dimethylpyrrol-1-yl)-4-(N'-((4-fluoro-3-carboxyphenyl)methylene)hydrazinecarbonyl)benzoic acid] | 423.768 (M+) |

Biochemical and cellular data for selected compounds are shown in Table 2.

TABLE 2

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 1 | [structure] | | 93.5 | 132 |
| 2 | [structure] | 74.5 | NT | NT |
| 3 | [structure] | 287 | NT | NT |
| 4 | [structure] | 34.1 | NT | NT |
| 5 | [structure] | 4.29 | NT | NT |

TABLE 2-continued

Biochemical and cellular data for exemplary compounds of the invention

| No. | Structure | Biochemical IC$_{50}$ (µM) | H2171 EC$_{50}$ (µM) | MM1S EC$_{50}$ (µM) |
|---|---|---|---|---|
| 6 | 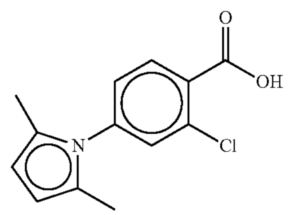 | 81.5 | 76.3 | 208 |
| 7 | 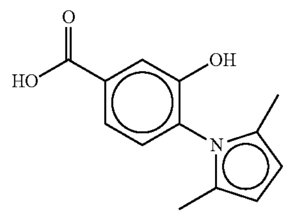 | 23.5 | 122 | NA |
| 8 | 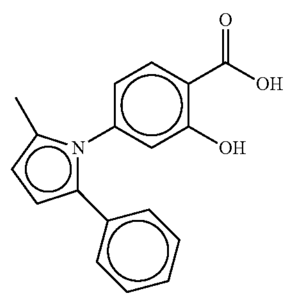 | NA | NA | NA |
| 9 | 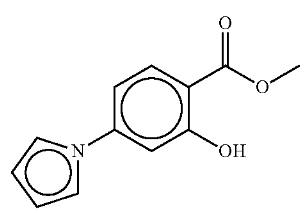 | NA | 229 | 127 |
| 10 | 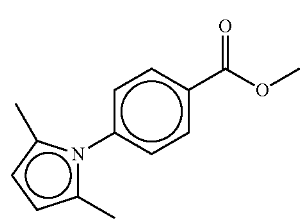 | NA | NA | NA |
| 11 | 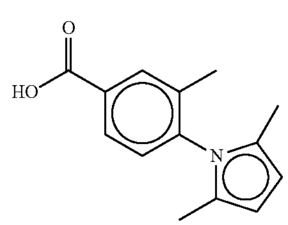 | 45.8 | 60.6 | NA |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 12 | 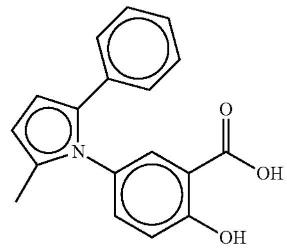 | 61.8 | 123 | 79.3 |
| 13 | 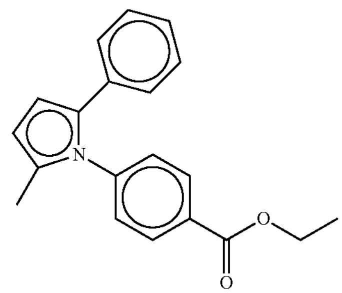 | 144 | 54.4 | 69.9 |
| 14 | 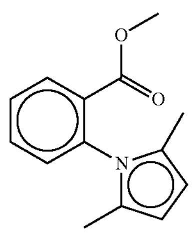 | 97.3 | 86.3 | 223 |
| 15 | 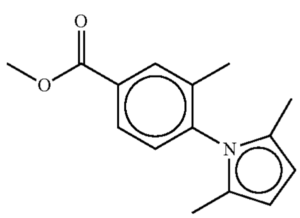 | NA | NA | NA |
| 16 | 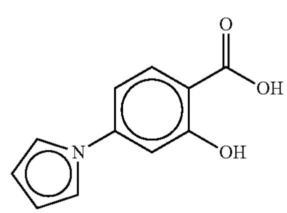 | 165 | 104 | 130 |
| 17 | 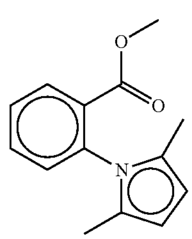 | NA | NA | NA |

TABLE 2-continued
Biochemical and cellular data for exemplary compounds of the invention
| No. | Structure | Biochemical IC$_{50}$ (μM) | H2171 EC$_{50}$ (μM) | MM1S EC$_{50}$ (μM) |
|---|---|---|---|---|
| 18 | 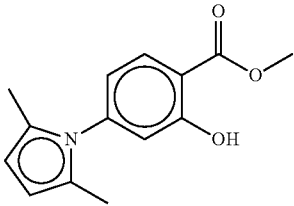 | 1.54 | NA | NA |
| 19 | 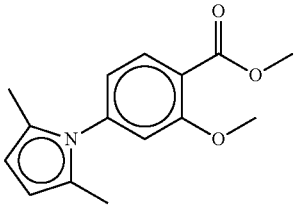 | NA | NA | NA |
| 20 | 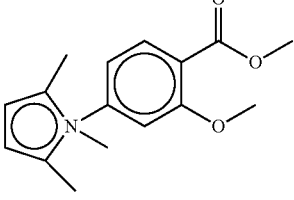 | NA | NA | NA |
| 21 | 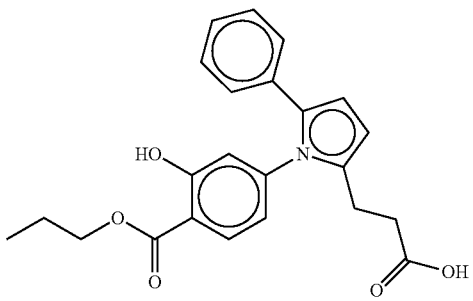 | 96.0 | 89.1 | 75.3 |
| 22 | 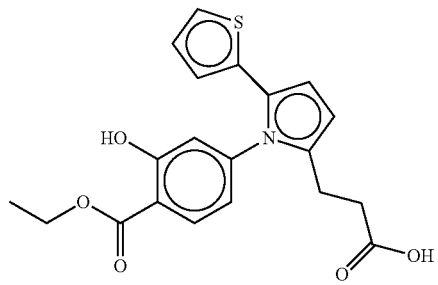 | 124 | 73.4 | 71.7 |

TABLE 2-continued

Biochemical and cellular data for exemplary compounds of the invention

| No. | Structure | Biochemical IC$_{50}$ (µM) | H2171 EC$_{50}$ (µM) | MM1S EC$_{50}$ (µM) |
|---|---|---|---|---|
| 23 | 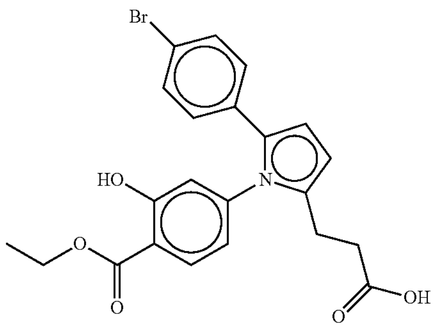 | 81.6 | 64.9 | 58.0 |
| 24 | 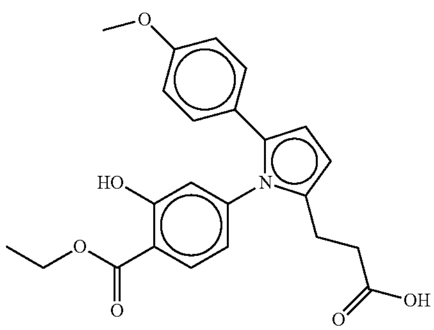 | 116 | 166 | 83.2 |
| 25 | 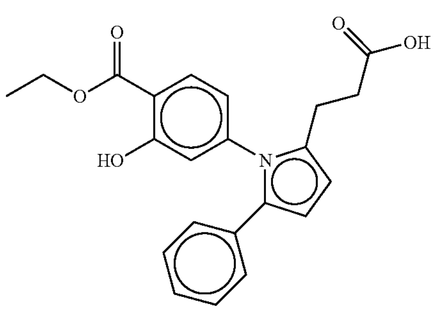 | 139 | 101 | 78.3 |
| 26 | 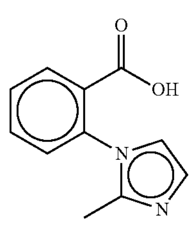 | 442 | 6.27 | 11.5 |
| 27 | 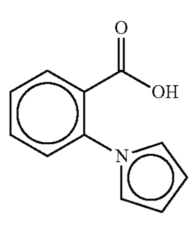 | NA | NA | NA |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 28 | 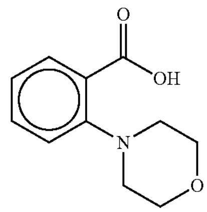 | NA | NA | NA |
| 29 | 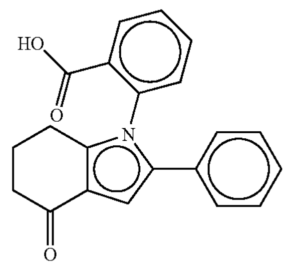 | 252 | NT | NT |
| 30 | 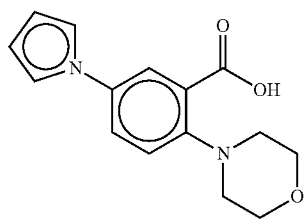 | 273 | NT | NT |
| 31 | 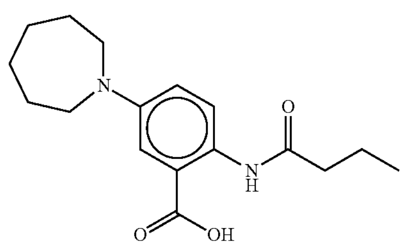 | 172 | NT | NT |
| 32 | 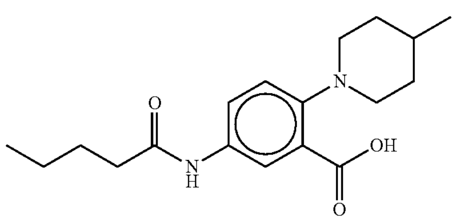 | 881 | NT | NT |
| 33 | 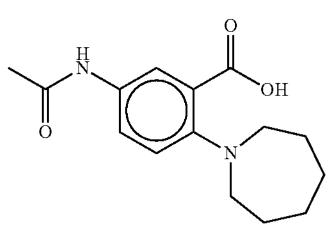 | 171 | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 34 | 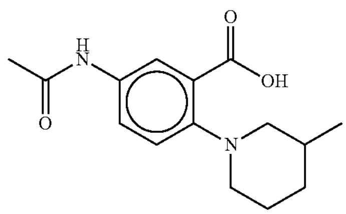 | 191 | NT | NT |
| 35 | 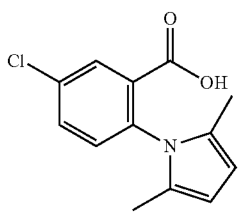 | 31.3 | NT | NT |
| 36 | 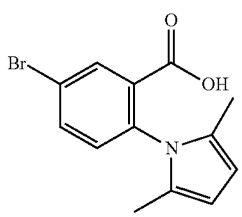 [SMILES: Cc1ccc(C)n1-c1ccc(Cl)cc1C(=O)O] | 64.7 | NT | NT |
| 37 | 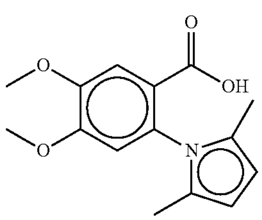 | 62.7 | NT | NT |
| 38 | 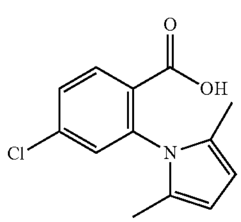 [SMILES: Cc1ccc(C)n1-c1cc(Cl)ccc1C(=O)O] | 63.7 | NT | NT |
| 39 | 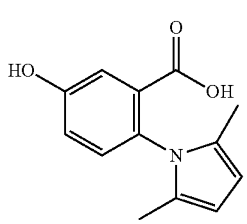 [SMILES: Cc1ccc(C)n1-c1ccc(O)cc1C(=O)O] | 27.9 | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 40 | 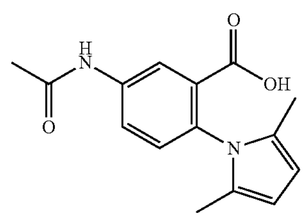 [SMILES: CC(=O)Nc1ccc(-n2c(C)ccc2C)c(C(=O)O)c1] | 34.4 | NT | NT |
| 41 | 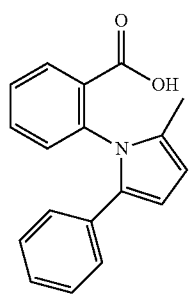 [SMILES: Cc1ccc(-c2ccccc2)n1-c1ccccc1C(=O)O] | 324 | NT | NT |
| 42 | 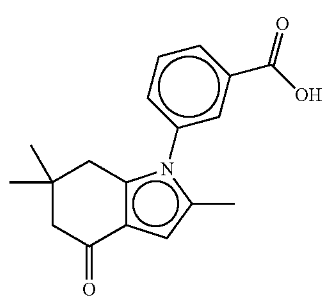 | 697 | NT | NT |
| 43 | 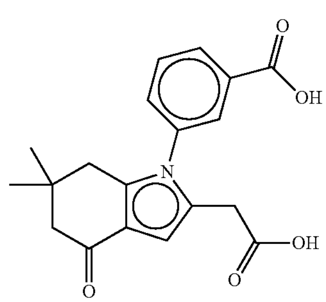 | 197 | NT | NT |
| 44 | 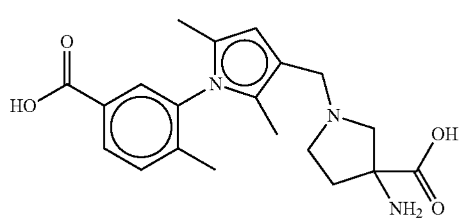 | 194 | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 45 | 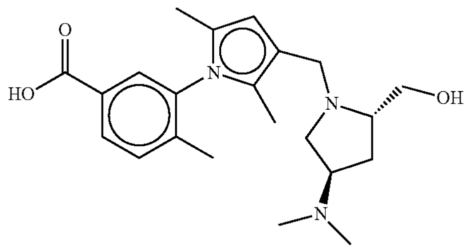 | 115 | NT | NT |
| 46 | 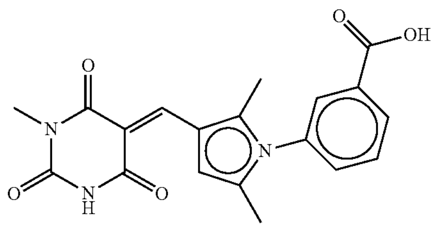 | 76.8 | NT | NT |
| 47 | 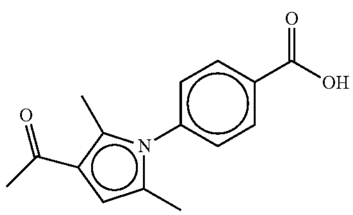 | 166 | NT | NT |
| 48 | 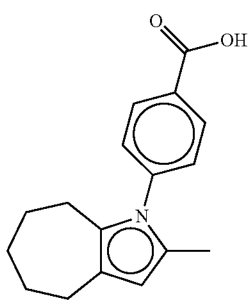 | 51.8 | NT | NT |
| 49 | 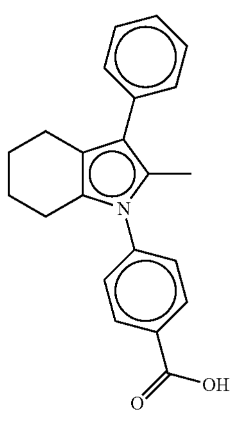 | 42.0 | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 50 | 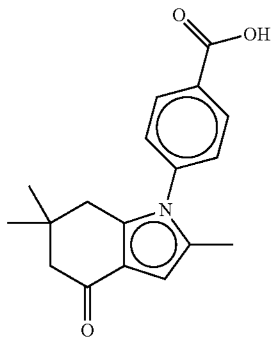 | 446 | NT | NT |
| 51 | 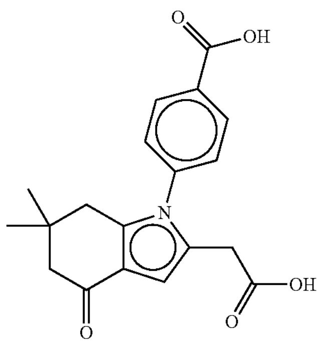 | 523 | NT | NT |
| 52 | 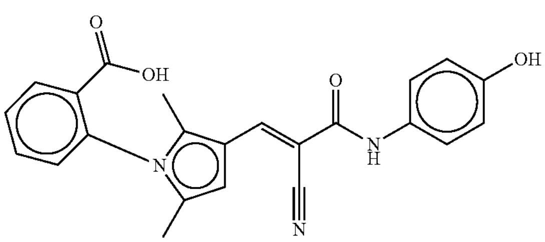 | 36.2 | NT | NT |
| 53 | 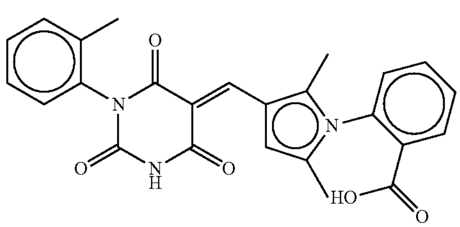 | 2510 | NT | NT |
| 54 | 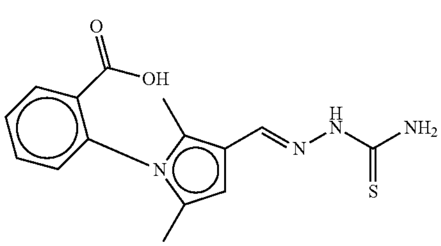 | 16.3 | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 55 | 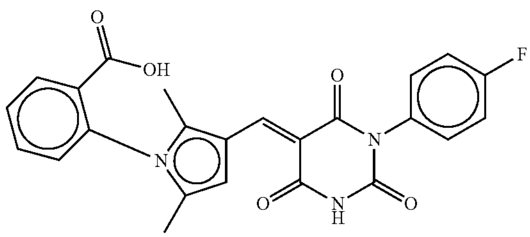 | 58.5 | NT | NT |
| 56 | 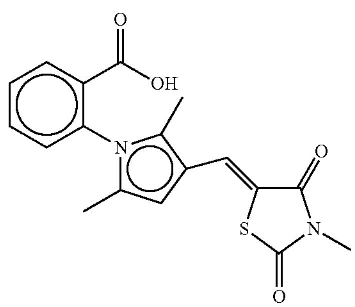 | 103 | NT | NT |
| 57 | 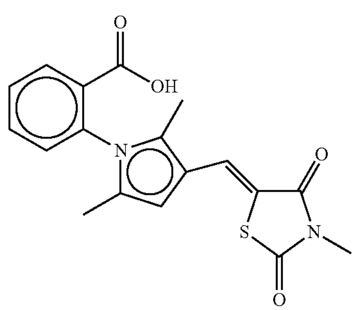 | 92.2 | NT | NT |
| 58 | 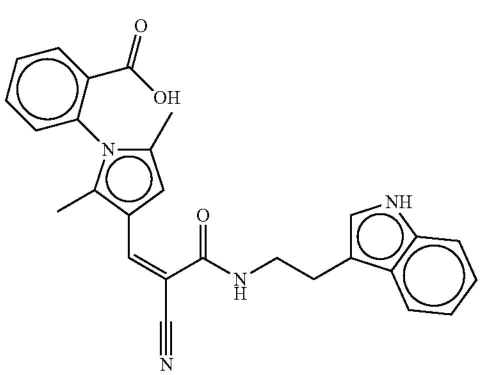 | 135 | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 59 | 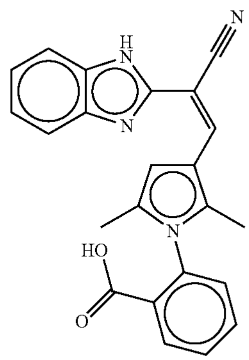 | 125 | NT | NT |
| 60 | 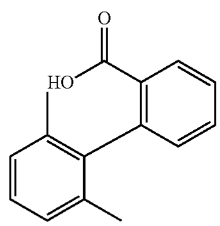 [SMILES: Cc1cccc(C)c1-c1ccccc1C(=O)O] | 89.1 | NT | NT |
| 61 | 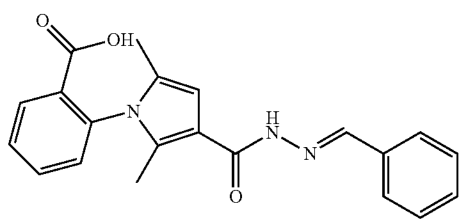 [SMILES: Cc1cc(C(=O)N/N=C/c2ccccc2)c(C)n1-c1ccccc1C(=O)O] | 49.2 | NA | NA |
| 62 | 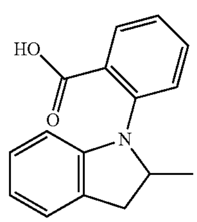 [SMILES: CC1Cc2ccccc2N1c1ccccc1C(=O)O] | NA | NA | NT |
| 63 | 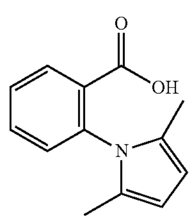 [SMILES: Cc1ccc(C)n1-c1ccccc1C(=O)O] | 24.2 | 96.9 | 322 |
| 64 | 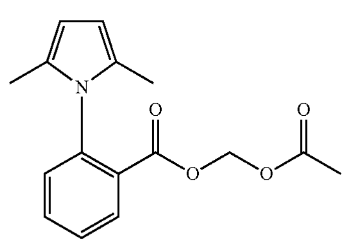 [SMILES: CC(=O)OCOC(=O)c1ccccc1-n1c(C)ccc1C] | 155 | 29.9 | 52.3 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 65 | 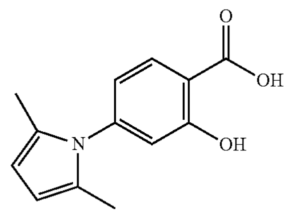 [SMILES: Cc1ccc(C)n1-c1ccc(C(=O)O)c(O)c1] | 61.9 | 189 | 1440 |
| 66 | 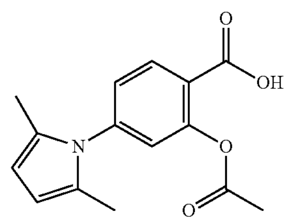 [SMILES: CC(=O)Oc1cc(-n2c(C)ccc2C)ccc1C(=O)O] | NA | 67.9 | 3570 |
| 67 | 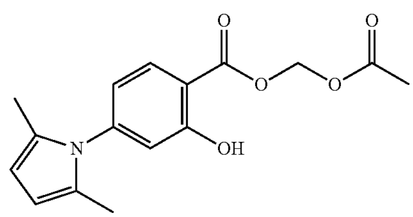 [SMILES: CC(=O)OCOC(=O)c1ccc(-n2c(C)ccc2C)cc1O] | 1910 | NT | NT |
| 68 | 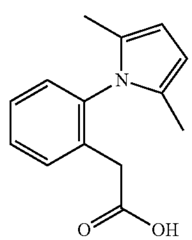 [SMILES: Cc1ccc(C)n1-c1ccccc1CC(=O)O] | 195 | 52.9 | 340 |
| 69 | 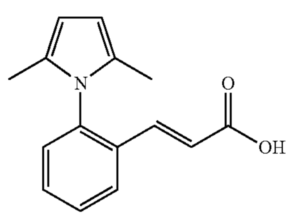 [SMILES: Cc1ccc(C)n1-c1ccccc1/C=C/C(=O)O] | 156 | 115 | 39.0 |
| 70 | 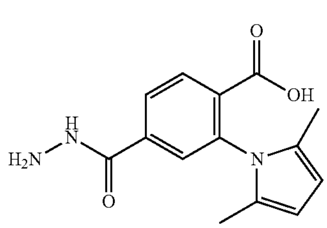 [SMILES: Cc1ccc(C)n1-c1cc(C(=O)NN)ccc1C(=O)O] | 6.98 | 43.7 | 1240 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 71 | 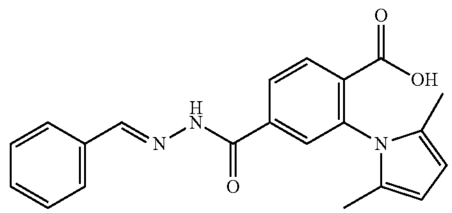 [SMILES: Cc1ccc(C)n1-c1cc(C(=O)N/N=C/c2ccccc2)ccc1C(=O)O] | 103 | 48.4 | 261 |
| 72 | 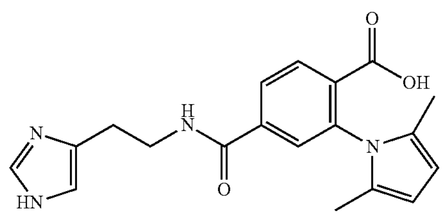 [SMILES: Cc1ccc(C)n1-c1cc(C(=O)NCCc2c[nH]cn2)ccc1C(=O)O] | 15.4 | 198 | 2760 |
| 73 | 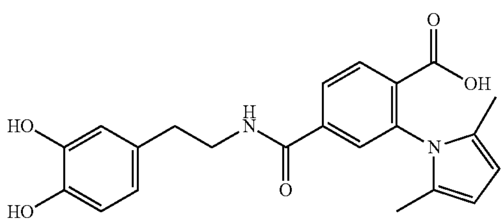 [SMILES: Cc1ccc(C)n1-c1cc(C(=O)NCCc2ccc(O)c(O)c2)ccc1C(=O)O] | 33.4 | 42.7 | 99.1 |
| 74 | 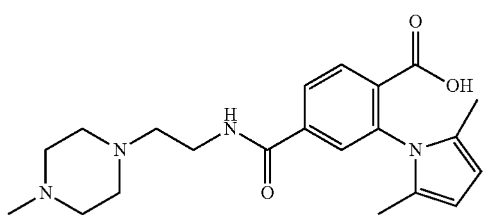 [SMILES: Cc1ccc(C)n1-c1cc(C(=O)NCCN2CCN(C)CC2)ccc1C(=O)O] | 104 | 120 | 27600 |
| 75 | 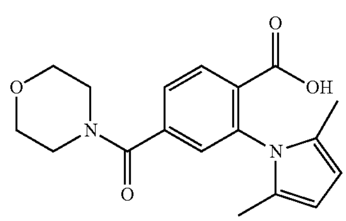 [SMILES: Cc1ccc(C)n1-c1cc(C(=O)N2CCOCC2)ccc1C(=O)O] | 8.58 | 114 | NA |
| 76 | 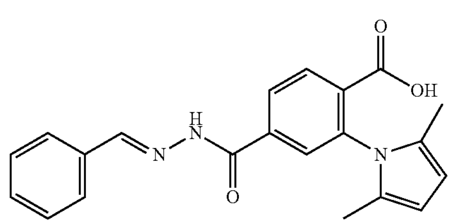 [SMILES: Cc1ccc(C)n1-c1cc(C(=O)N/N=C/c2ccccc2)ccc1C(=O)O] | NA | NA | NA |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 77 | 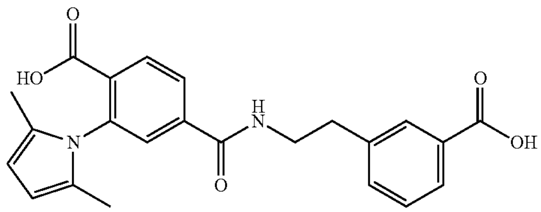 [SMILES: Cc1ccc(C)n1-c1cc(C(=O)NCCc2cccc(C(=O)O)c2)ccc1C(=O)O] | 7.27 | NT | NT |
| 78 | 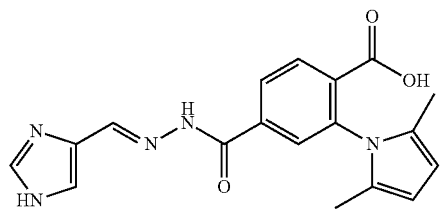 [SMILES: Cc1ccc(C)n1-c1cc(C(=O)N/N=C/c2c[nH]cn2)ccc1C(=O)O] | 1.75 | NA | NA |
| 79 | 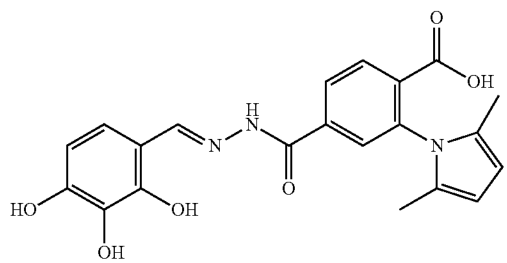 [SMILES: Cc1ccc(C)n1-c1cc(C(=O)N/N=C/c2ccc(O)c(O)c2O)ccc1C(=O)O] | 0.531 | 33.6 | 24.2 |
| 80 | 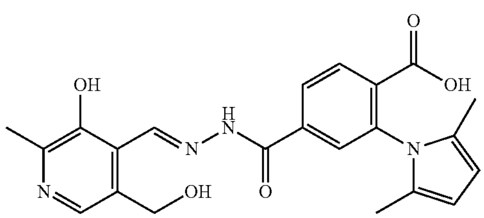 [SMILES: Cc1ncc(CO)c(/C=N/NC(=O)c2ccc(C(=O)O)c(-n3c(C)ccc3C)c2)c1O] | | 400 | NA |
| 81 | 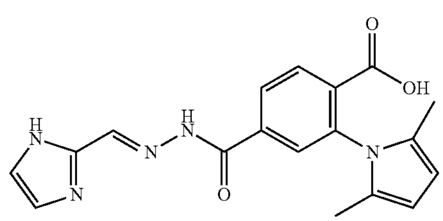 [SMILES: Cc1ccc(C)n1-c1cc(C(=O)N/N=C/c2ncc[nH]2)ccc1C(=O)O] | 2.72 | 106 | NA |
| 82 | 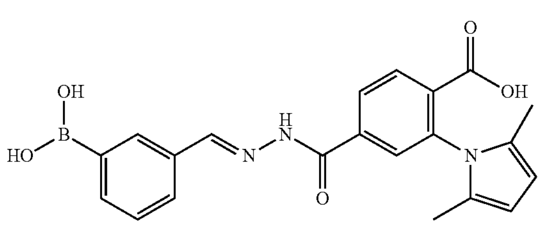 [SMILES: Cc1ccc(C)n1-c1cc(C(=O)N/N=C/c2cccc(B(O)O)c2)ccc1C(=O)O] | 2.95 | NA | NA |

TABLE 2-continued
Biochemical and cellular data for exemplary compounds of the invention
| No. | Structure | Biochemical IC$_{50}$ (μM) | H2171 EC$_{50}$ (μM) | MM1S EC$_{50}$ (μM) |
|---|---|---|---|---|
| 83 | 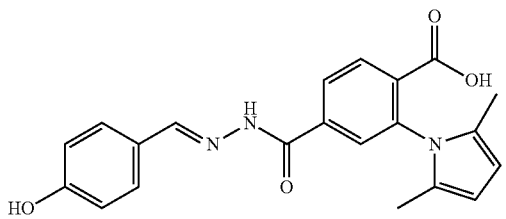 | 6.85 | NA | NA |
| 84 | 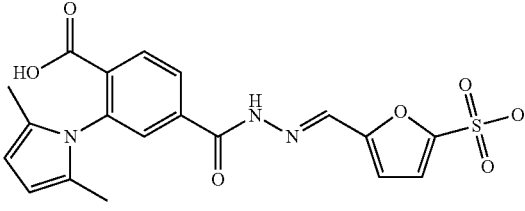 | 0.534 | 0.0026 | NA |
| 85 | 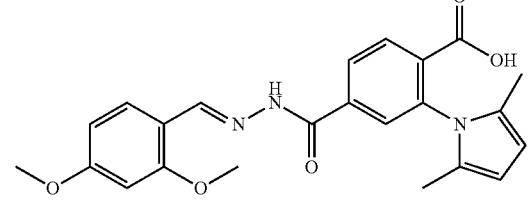 | 37.9 | 97.3 | NA |
| 86 | 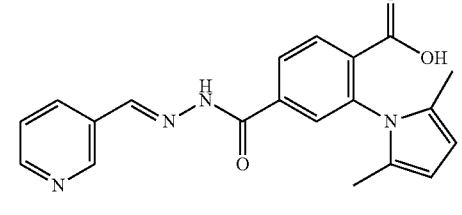 | 5.97 | NA | 3.95E+05 |
| 87 | 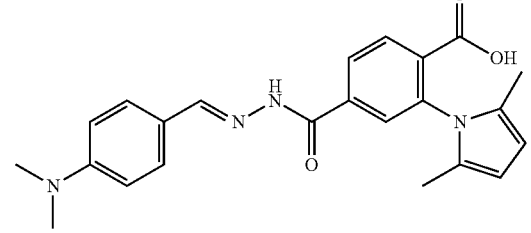 | 31.4 | NA | 86.5 |
| 88 | 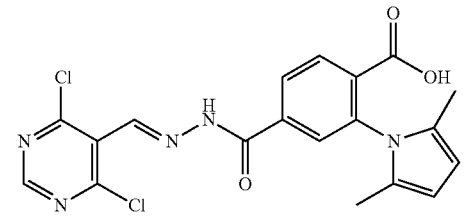 [SMILES: Cc1ccc(C)n1-c1cc(C(=O)N/N=C/c2c(Cl)ncnc2Cl)ccc1C(=O)O] | 4.88 | 2.51E+08 | 8080 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 89 | 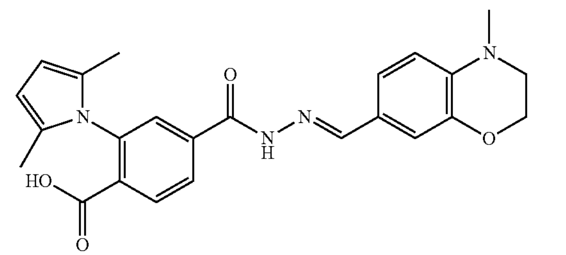 [SMILES: Cc1ccc(C)n1-c1cc(C(=O)N/N=C/c2ccc3c(c2)OCCN3C)ccc1C(=O)O] | 38.0 | 198 | 92.4 |
| 90 | 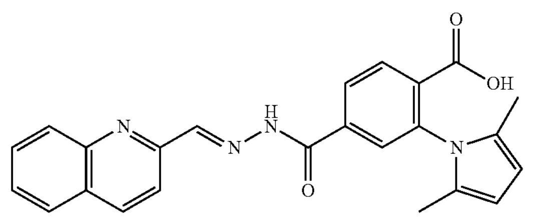 [SMILES: Cc1ccc(C)n1-c1cc(C(=O)N/N=C/c2ccc3ccccc3n2)ccc1C(=O)O] | 17.5 | NA | 52.5 |
| 91 | 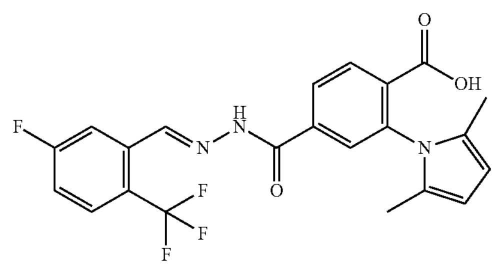 [SMILES: Cc1ccc(C)n1-c1cc(C(=O)N/N=C/c2cc(F)ccc2C(F)(F)F)ccc1C(=O)O] | 3.99 | 1.47E−7 | 4260 |
| 92 | 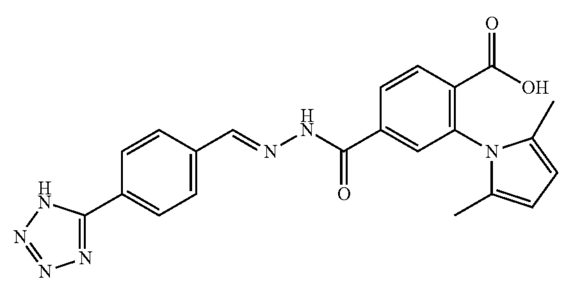 [SMILES: Cc1ccc(C)n1-c1cc(C(=O)N/N=C/c2ccc(-c3nnn[nH]3)cc2)ccc1C(=O)O] | 1.66 | 0.00259 | 731 |
| 93 | 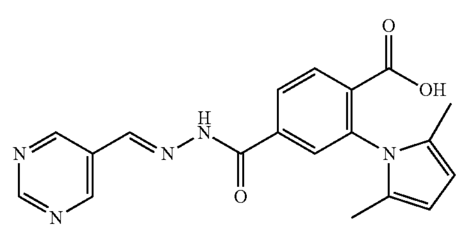 [SMILES: Cc1ccc(C)n1-c1cc(C(=O)N/N=C/c2cncnc2)ccc1C(=O)O] | 5.56 | 0.000553 | 263 |
| 94 | 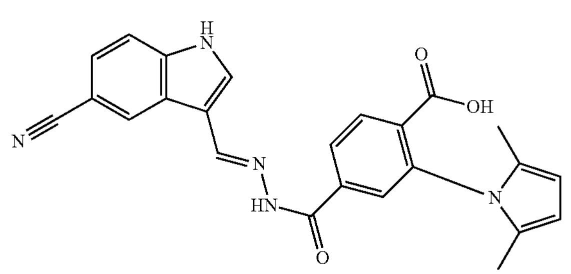 [SMILES: Cc1ccc(C)n1-c1cc(C(=O)N/N=C/c2c[nH]c3ccc(C#N)cc23)ccc1C(=O)O] | 17.1 | 3240 | 5.75 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 95 | 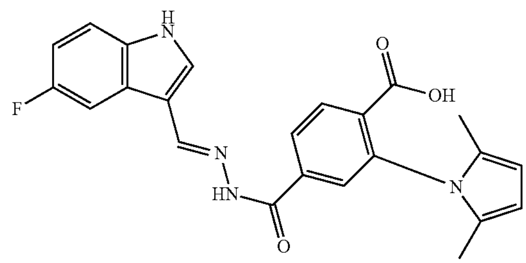 [SMILES: Cc1ccc(C)n1-c1cc(C(=O)N/N=C/c2c[nH]c3ccc(F)cc23)ccc1C(=O)O] | 23.3 | NA | NA |
| 96 | 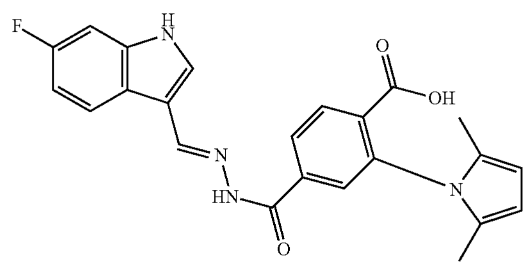 [SMILES: Cc1ccc(C)n1-c1cc(C(=O)N/N=C/c2c[nH]c3cc(F)ccc23)ccc1C(=O)O] | 34.4 | 38.1 | NA |
| 97 | 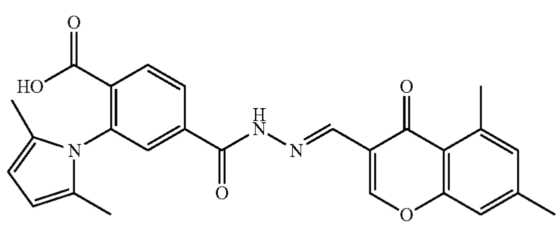 [SMILES: Cc1cc(C)c2c(=O)c(/C=N/NC(=O)c3ccc(C(=O)O)c(-n4c(C)ccc4C)c3)coc2c1] | 5.55 | NA | 1040 |
| 98 | 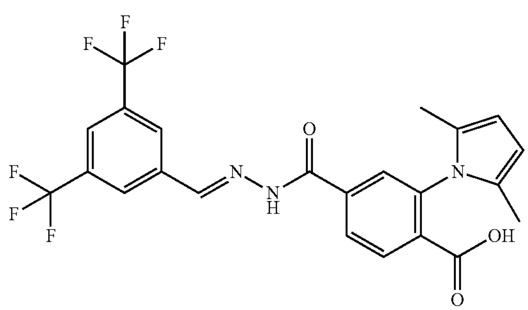 [SMILES: Cc1ccc(C)n1-c1cc(C(=O)N/N=C/c2cc(C(F)(F)F)cc(C(F)(F)F)c2)ccc1C(=O)O] | 3.84 | 24100 | 5170 |
| 99 | 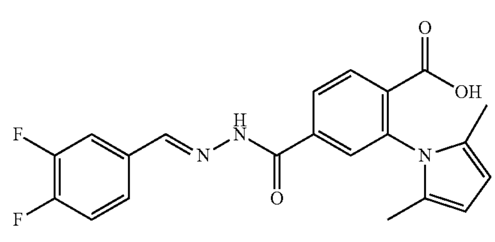 [SMILES: Cc1ccc(C)n1-c1cc(C(=O)N/N=C/c2ccc(F)c(F)c2)ccc1C(=O)O] | 4.82 | 106 | 492 |

TABLE 2-continued
Biochemical and cellular data for exemplary compounds of the invention
| No. | Structure | Biochemical IC$_{50}$ (µM) | H2171 EC$_{50}$ (µM) | MM1S EC$_{50}$ (µM) |
|---|---|---|---|---|
| 100 | 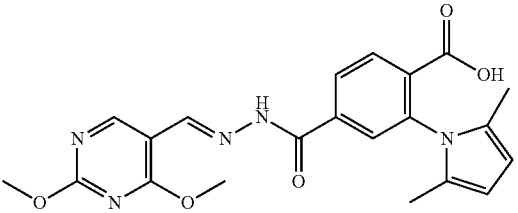 [SMILES: COc1ncc(/C=N/NC(=O)c2ccc(C(=O)O)c(-n3c(C)ccc3C)c2)c(OC)n1] | 7.67 | 266 | NA |
| 101 | 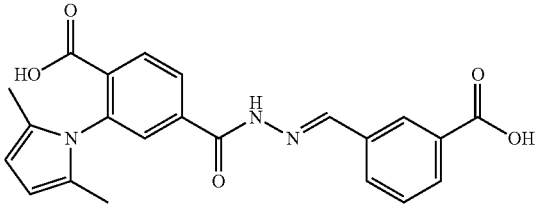 [SMILES: Cc1ccc(C)n1-c1cc(C(=O)N/N=C/c2cccc(C(=O)O)c2)ccc1C(=O)O] | | NA | NA |
| 102 | 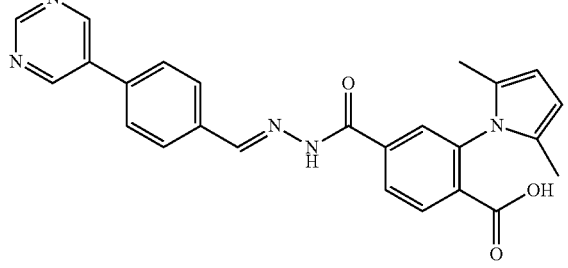 | 26.5 | NA | NA |
| 103 | 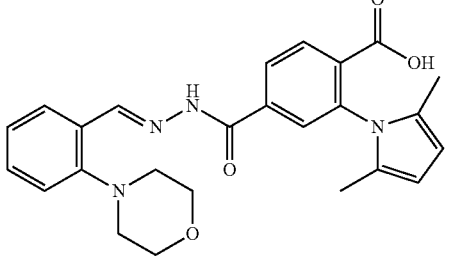 | 7.05 | NA | NA |
| 104 | 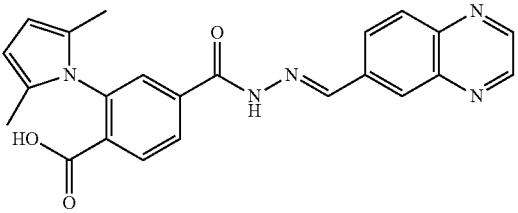 [SMILES: Cc1ccc(C)n1-c1cc(C(=O)N/N=C/c2ccc3nccnc3c2)ccc1C(=O)O] | 7.11 | NA | NA |
| 105 | 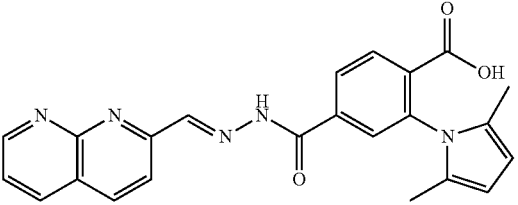 [SMILES: Cc1ccc(C)n1-c1cc(C(=O)N/N=C/c2ccc3cccnc3n2)ccc1C(=O)O] | 2.97 | NA | 118 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 106 | 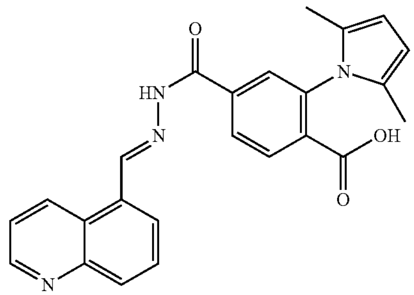 [SMILES: Cc1ccc(C)n1-c1cc(C(=O)N/N=C/c2cccc3ncccc23)ccc1C(=O)O] | 15.1 | 144 | NA |
| 107 | 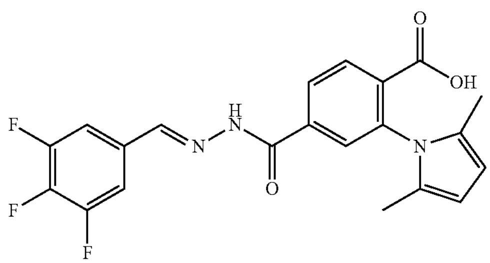 [SMILES: Cc1ccc(C)n1-c1cc(C(=O)N/N=C/c2cc(F)c(F)c(F)c2)ccc1C(=O)O] | 9.30 | 32.3 | NA |
| 108 | 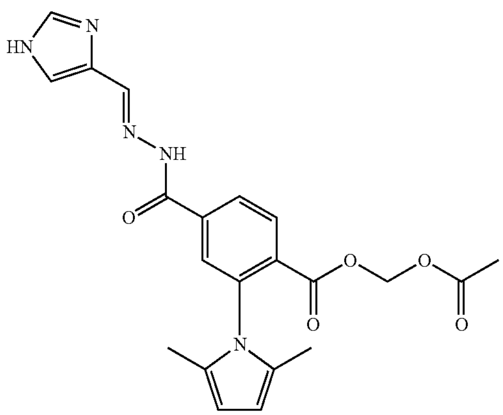 [SMILES: CC(=O)OCOC(=O)c1ccc(C(=O)N/N=C/c2c[nH]cn2)cc1-n1c(C)ccc1C] | NT | 0.556 | NA |
| 109 | 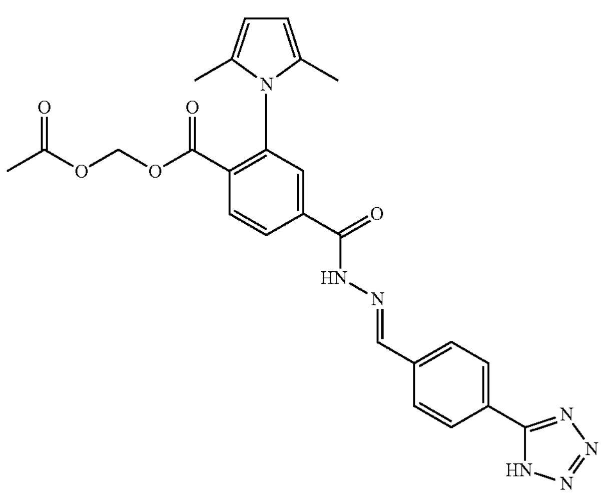 [SMILES: CC(=O)OCOC(=O)c1ccc(C(=O)N/N=C/c2ccc(-c3nnn[nH]3)cc2)cc1-n1c(C)ccc1C] | NT | 1.02 | 9.99 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 110 | 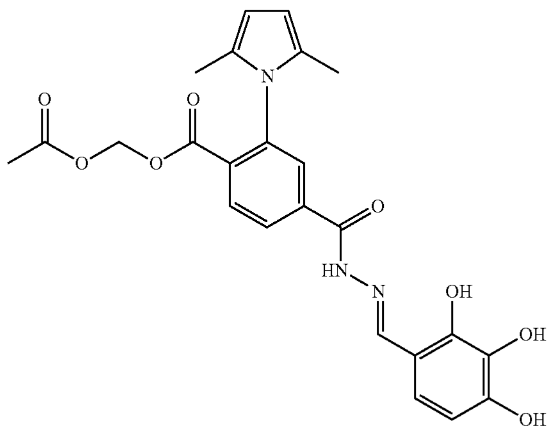 [SMILES: CC(=O)OCOC(=O)c1ccc(C(=O)N/N=C/c2ccc(O)c(O)c2O)cc1-n1c(C)ccc1C] | NT | 2.23 | 14.8 |
| 111 | 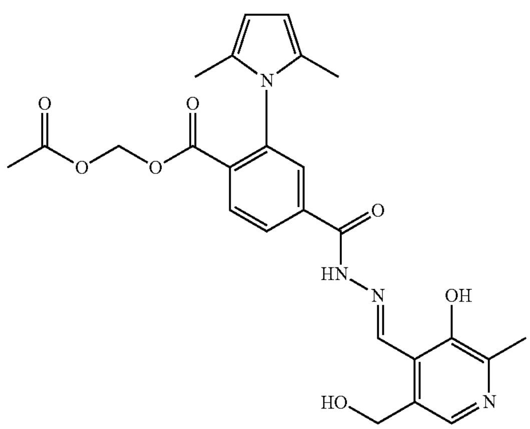 [SMILES: CC(=O)OCOC(=O)c1ccc(C(=O)N/N=C/c2c(CO)cnc(C)c2O)cc1-n1c(C)ccc1C] | NT | 2.40 | 21.8 |
| 112 | 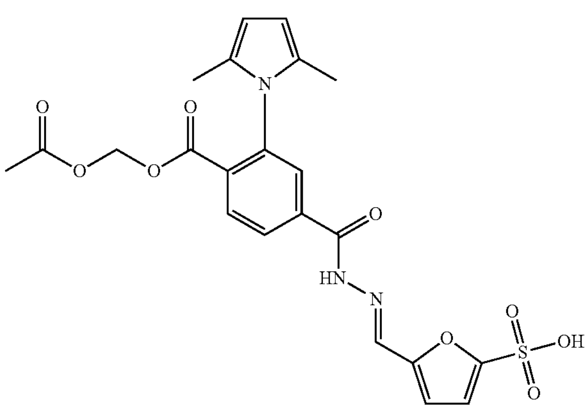 [SMILES: CC(=O)OCOC(=O)c1ccc(C(=O)N/N=C/c2ccc(S(=O)(=O)O)o2)cc1-n1c(C)ccc1C] | NT | 1.04 | 9.25 |
| 113 | 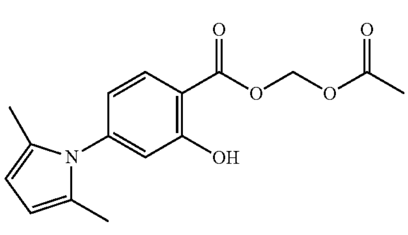 [SMILES: CC(=O)OCOC(=O)c1ccc(-n2c(C)ccc2C)cc1O] | NT | 2.80 | 11.0 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 114 | 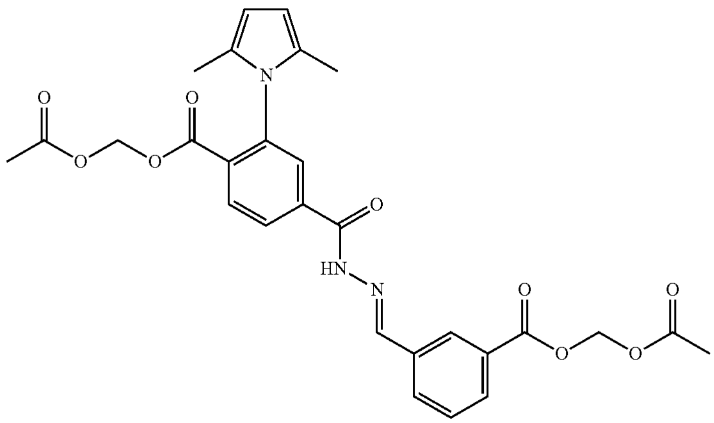 [SMILES: CC(=O)OCOC(=O)c1cccc(/C=N/NC(=O)c2ccc(C(=O)OCOC(C)=O)c(-n3c(C)ccc3C)c2)c1] | NT | 1.21 | 11.7 |
| 115 | 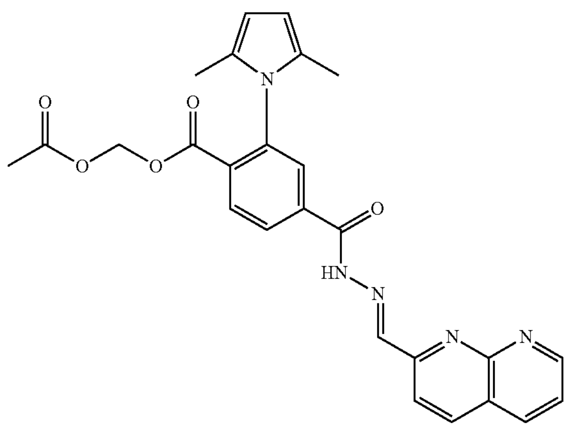 [SMILES: CC(=O)OCOC(=O)c1ccc(C(=O)N/N=C/c2ccc3cccnc3n2)cc1-n1c(C)ccc1C] | NT | 0.913 | 13.6 |
| 116 | 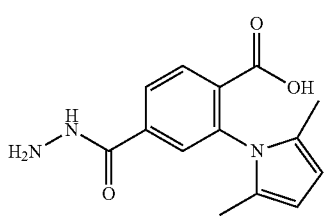 [SMILES: Cc1ccc(C)n1-c1cc(C(=O)NN)ccc1C(=O)O] | 0.420 | NA | NA |
| 117 | 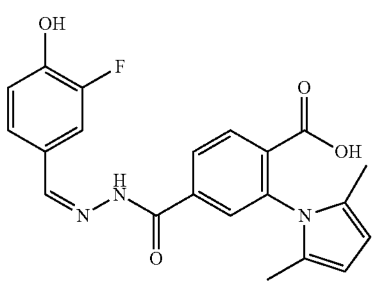 [SMILES: Cc1ccc(C)n1-c1cc(C(=O)N/N=C\c2ccc(O)c(F)c2)ccc1C(=O)O] | 6.52 | NA | NA |

TABLE 2-continued
Biochemical and cellular data for exemplary compounds of the invention
| No. | Structure | Biochemical IC$_{50}$ (μM) | H2171 EC$_{50}$ (μM) | MM1S EC$_{50}$ (μM) |
|---|---|---|---|---|
| 118 | 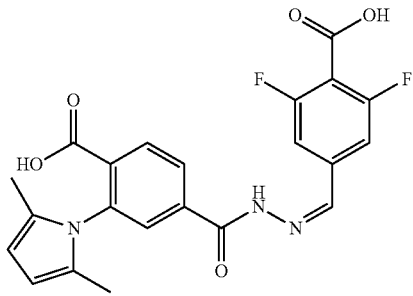 [SMILES: Cc1ccc(C)n1-c1cc(C(=O)N/N=C\c2cc(F)c(C(=O)O)c(F)c2)ccc1C(=O)O] | 0.480 | NA | NA |
| 119 | 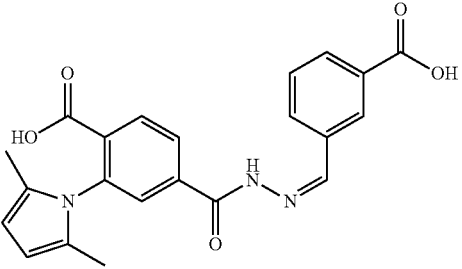 [SMILES: Cc1ccc(C)n1-c1cc(C(=O)N/N=C\c2cccc(C(=O)O)c2)ccc1C(=O)O] | 0.675 | NA | NA |
| 120 | 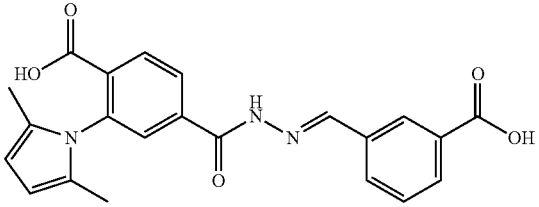 [SMILES: Cc1ccc(C)n1-c1cc(C(=O)N/N=C/c2cccc(C(=O)O)c2)ccc1C(=O)O] | 0.393 | NA | NA |
| 121 | 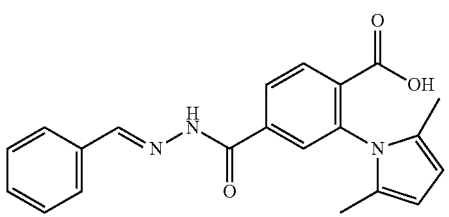 [SMILES: Cc1ccc(C)n1-c1cc(C(=O)N/N=C/c2ccccc2)ccc1C(=O)O] | 7.69 | NA | NA |
| 122 | 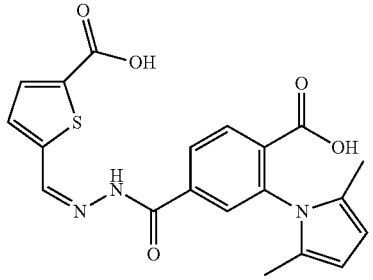 [SMILES: Cc1ccc(C)n1-c1cc(C(=O)N/N=C\c2ccc(C(=O)O)s2)ccc1C(=O)O] | 0.492 | 174 | NA |

TABLE 2-continued

Biochemical and cellular data for exemplary compounds of the invention

| No. | Structure | Biochemical IC$_{50}$ (µM) | H2171 EC$_{50}$ (µM) | MM1S EC$_{50}$ (µM) |
| --- | --- | --- | --- | --- |
| 123 | 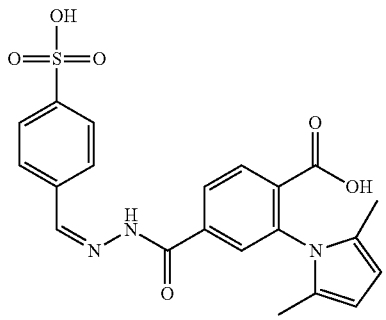 [SMILES: Cc1ccc(C)n1-c1cc(C(=O)N/N=C\c2ccc(S(=O)(=O)O)cc2)ccc1C(=O)O] | 0.291 | 96.4 | NA |
| 124 | 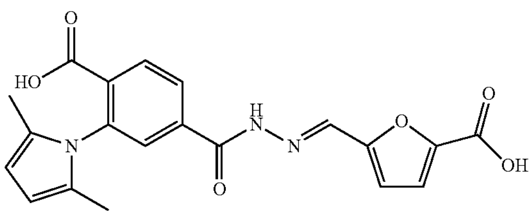 [SMILES: Cc1ccc(C)n1-c1cc(C(=O)N/N=C/c2ccc(C(=O)O)o2)ccc1C(=O)O] | 0.708 | NA | NA |
| 125 | 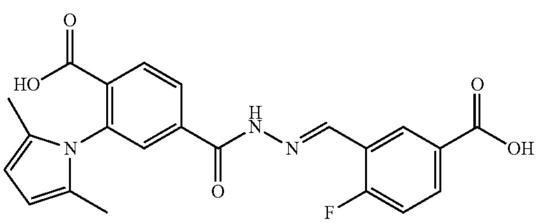 [SMILES: Cc1ccc(C)n1-c1cc(C(=O)N/N=C/c2cc(C(=O)O)ccc2F)ccc1C(=O)O] | 1.25 | NA | NT |
| 126 | 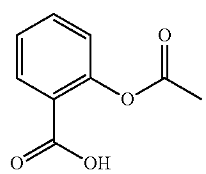 | NA | NA | NA |
| 127 | 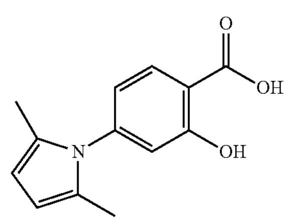 [SMILES: Cc1ccc(C)n1-c1ccc(C(=O)O)c(O)c1] | 53.3 | 517 | 517 |
| 128 | 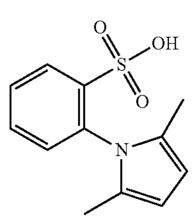 [SMILES: Cc1ccc(C)n1-c1ccccc1S(=O)(=O)O] | 252 | 303 | 243 |

TABLE 2-continued

Biochemical and cellular data for exemplary compounds of the invention

| No. | Structure | Biochemical IC$_{50}$ (µM) | H2171 EC$_{50}$ (µM) | MM1S EC$_{50}$ (µM) |
|---|---|---|---|---|
| 129 | 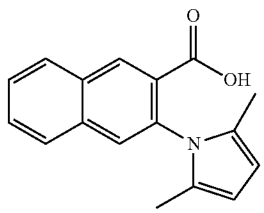 [SMILES: Cc1ccc(C)n1-c1cc2ccccc2cc1C(=O)O] | 31.0 | 151 | 264 |
| 130 | 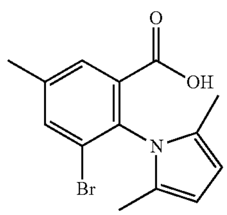 [SMILES: Cc1cc(Br)c(-n2c(C)ccc2C)c(C(=O)O)c1] | 51.5 | 224 | 300 |
| 131 | 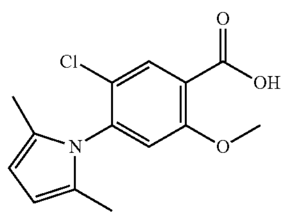 [SMILES: COc1cc(-n2c(C)ccc2C)c(Cl)cc1C(=O)O] | 493 | 3400 | 1.46E+05 |
| 132 | 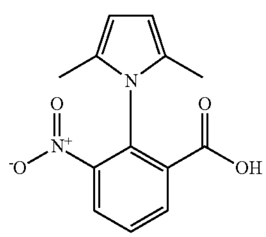 | NA | 310 | 647 |
| 133 | 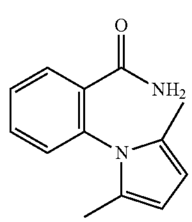 [SMILES: Cc1ccc(C)n1-c1ccccc1C(N)=O] | NA | 0.000502 | 450 |
| 134 | 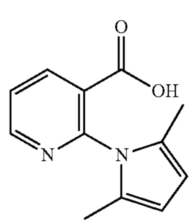 [SMILES: Cc1ccc(C)n1-c1ncccc1C(=O)O] | | 4.62E−8 | NA |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 135 | 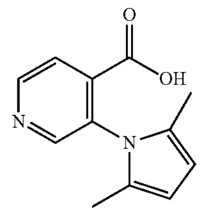 [SMILES: Cc1ccc(C)n1-c1cnccc1C(=O)O] | 6800 | NA | 305 |
| 136 | 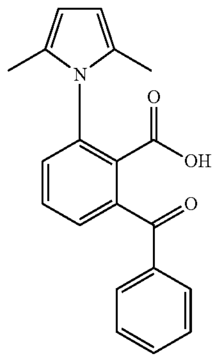 [SMILES: Cc1ccc(C)n1-c1cccc(C(=O)c2ccccc2)c1C(=O)O] | 94.7 | 215 | NA |
| 137 | 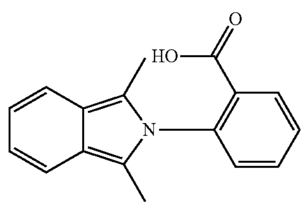 [SMILES: Cc1c2ccccc2c(C)n1-c1ccccc1C(=O)O] | 57.8 | NA | NA |
| 138 | 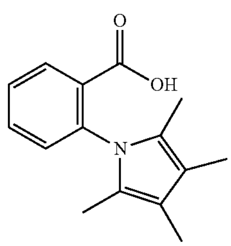 [SMILES: Cc1c(C)c(C)n(-c2ccccc2C(=O)O)c1C] | 83.4 | 270 | 194 |
| 139 | 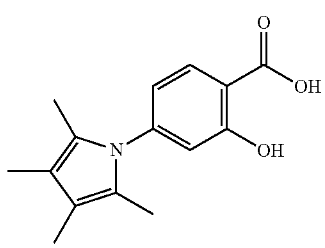 [SMILES: Cc1c(C)c(C)n(-c2ccc(C(=O)O)c(O)c2)c1C] | 96.4 | 564 | 329 |
| 140 | 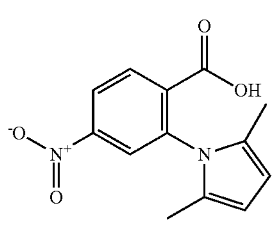 | NA | NA | NA |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
| --- | --- | --- | --- | --- |
| 141 | 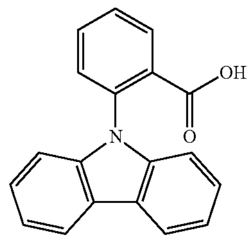 [SMILES: O=C(O)c1ccccc1-n1c2ccccc2c2ccccc21] | NA | 268 | 148 |
| 142 | 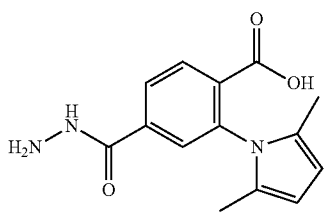 [SMILES: Cc1ccc(C)n1-c1cc(C(=O)NN)ccc1C(=O)O] | 7.58 | 0.00363 | 625 |
| 143 | 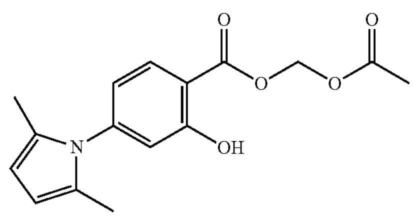 [SMILES: CC(=O)OCOC(=O)c1ccc(-n2c(C)ccc2C)cc1O] | 91.4 | 66.1 | 161 |
| 144 | 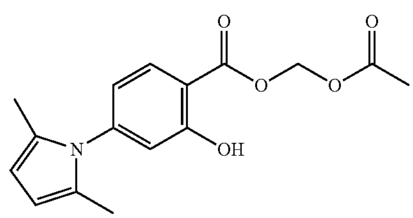 [SMILES: CC(=O)OCOC(=O)c1ccc(-n2c(C)ccc2C)cc1O] | NA | NA | 446 |
| 145 | 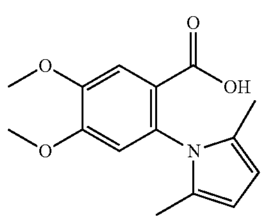 [SMILES: COc1cc(C(=O)O)c(-n2c(C)ccc2C)cc1OC] | 13.5 | 83.8 | 161 |
| 146 | 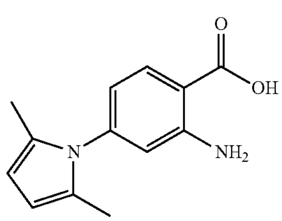 [SMILES: Cc1ccc(C)n1-c1ccc(C(=O)O)c(N)c1] | NA | NA | NA |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 147 | 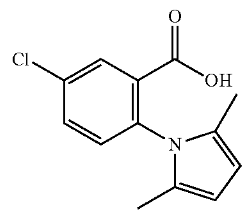 [SMILES: Cc1ccc(C)n1-c1ccc(Cl)cc1C(=O)O] | 11.5 | 170 | NA |
| 148 | 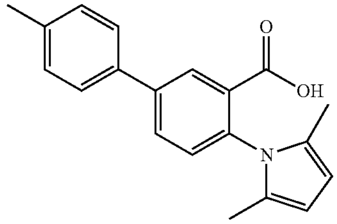 [SMILES: Cc1ccc(-c2ccc(-n3c(C)ccc3C)c(C(=O)O)c2)cc1] | 941 | 268 | 1690 |
| 149 | 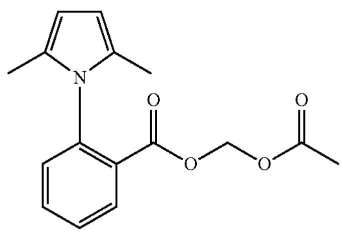 [SMILES: CC(=O)OCOC(=O)c1ccccc1-n1c(C)ccc1C] | 101 | 20.7 | 71.4 |
| 150 | 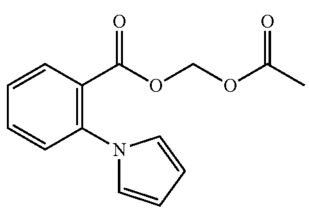 [SMILES: CC(=O)OCOC(=O)c1ccccc1-n1cccc1] | 150 | 28.0 | 99.1 |
| 151 | 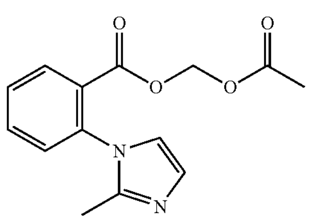 [SMILES: CC(=O)OCOC(=O)c1ccccc1-n1ccnc1C] | NA | 43.5 | 156 |
| 152 | 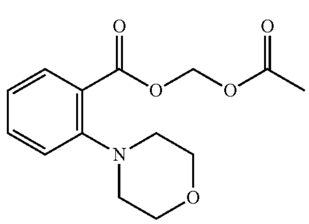 [SMILES: CC(=O)OCOC(=O)c1ccccc1N1CCOCC1] | 2480 | 22.8 | 71.9 |

TABLE 2-continued

Biochemical and cellular data for exemplary compounds of the invention

| No. | Structure | Biochemical IC$_{50}$ (µM) | H2171 EC$_{50}$ (µM) | MM1S EC$_{50}$ (µM) |
|---|---|---|---|---|
| 153 | 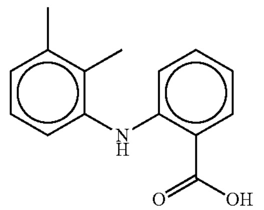 | 403 | 93.5 | 185 |
| 154 | 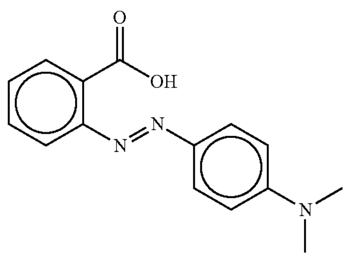 | 43.4 | 0.00531 | NA |
| 155 | 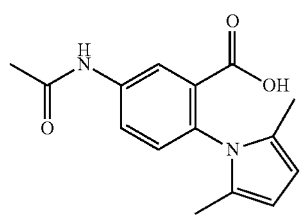 [SMILES: CC(=O)Nc1ccc(-n2c(C)ccc2C)c(C(=O)O)c1] | 1.80 | 247 | 222 |
| 156 | 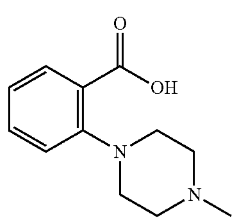 [SMILES: CN1CCN(c2ccccc2C(=O)O)CC1] | 346 | 9.61E−7 | NA |
| 157 | 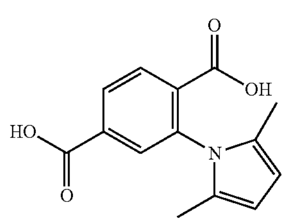 [SMILES: Cc1ccc(C)n1-c1cc(C(=O)O)ccc1C(=O)O] | 0.788 | NA | 11000 |
| 158 | 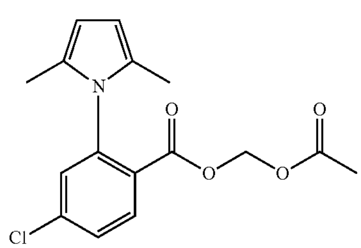 [SMILES: CC(=O)OCOC(=O)c1ccc(Cl)cc1-n1c(C)ccc1C] | 206 | 70.3 | 238 |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 159 | 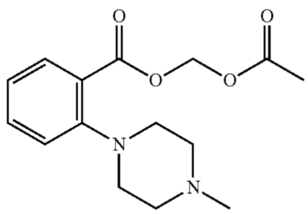 [SMILES: CC(=O)OCOC(=O)c1ccccc1N1CCN(C)CC1] | NA | 84.1 | 209 |
| 160 | 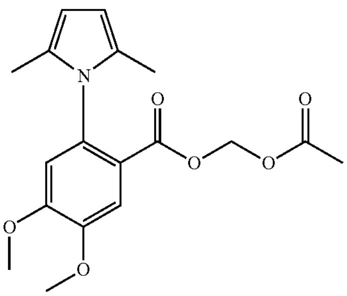 [SMILES: COc1cc(C(=O)OCOC(C)=O)c(-n2c(C)ccc2C)cc1OC] | 94.6 | 104 | 211 |
| 161 | 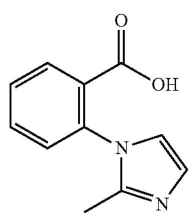 | NA | NA | NA |
| 162 | 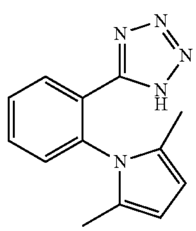 [SMILES: Cc1ccc(C)n1-c1ccccc1-c1nnn[nH]1] | 151 | 24.2 | 66.0 |
| 163 | 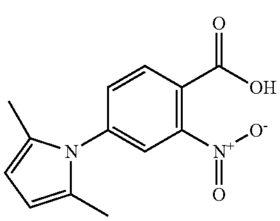 | 155 | NA | 98.5 |
| 164 | 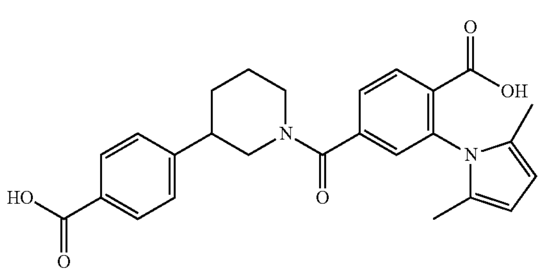 [SMILES: Cc1ccc(C)n1-c1cc(C(=O)N2CCCC(c3ccc(C(=O)O)cc3)C2)ccc1C(=O)O] | | NT | NT |

TABLE 2-continued

Biochemical and cellular data for exemplary compounds of the invention

| No. | Structure | Biochemical IC$_{50}$ (μM) | H2171 EC$_{50}$ (μM) | MM1S EC$_{50}$ (μM) |
|---|---|---|---|---|
| 165 | 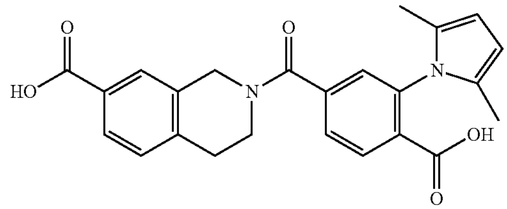 [SMILES: Cc1ccc(C)n1-c1cc(C(=O)N2CCc3ccc(C(=O)O)cc3C2)ccc1C(=O)O] | 0.343 | NT | NT |
| 166 | 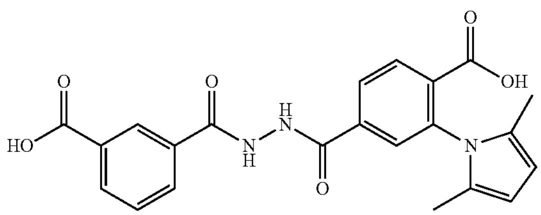 [SMILES: Cc1ccc(C)n1-c1cc(C(=O)NNC(=O)c2cccc(C(=O)O)c2)ccc1C(=O)O] | 1.89 | NA | NA |
| 167 | 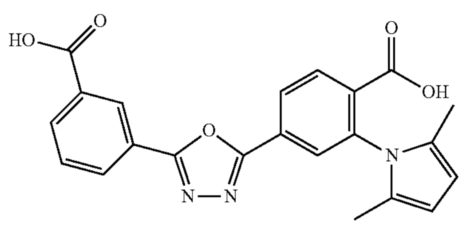 [SMILES: Cc1ccc(C)n1-c1cc(-c2nnc(-c3cccc(C(=O)O)c3)o2)ccc1C(=O)O] | | NA | NA |
| 168 | 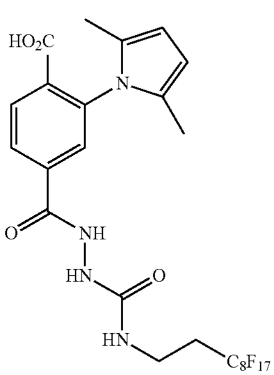 | NT | NT | NT |

NT: not tested; NA: inactive under assay conditions

Biochemical and cellular data for additional exemplary compounds are shown in Table 3. In Table 3, for Myc/Max IC$_{50}$ values, "A" represents a calculated IC$_{50}$ value of less than 1 μM; "B" represents a calculated IC$_{50}$ value of greater than or equal to 1 μM and less than 10 μM; "C" represents a calculated IC$_{50}$ value of greater than or equal to 10 μM and less than 100 μM; and "D" represents a calculated IC$_{50}$ value of 100 μM or greater. In Table 3, for Jurkat EC$_{50}$ values, "A" represents a calculated EC$_{50}$ value of less than 10 μM; "B" represents a calculated EC$_{50}$ value of greater than or equal to 10 μM and less than 100 μM; and "C" represents a calculated EC$_{50}$ value of 100 μM or greater.

TABLE 3
Biochemical and cellular data for exemplary compounds of the invention
| No. | Structure | Myc/Max IC$_{50}$ (μM) | Jurkat EC$_{50}$ (μM) |
|---|---|---|---|
| 1 | 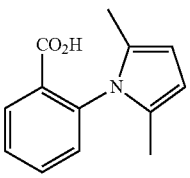 [SMILES: Cc1ccc(C)n1-c1ccccc1C(=O)O] | C | C |
| 64 | 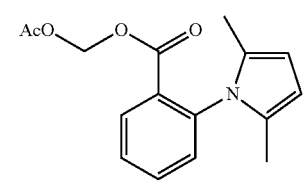 [SMILES: CC(=O)OCOC(=O)c1ccccc1-n1c(C)ccc1C] | D | B |
| 101 | 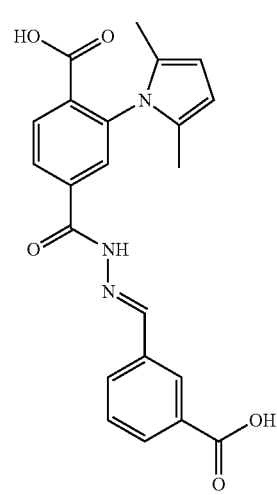 [SMILES: Cc1ccc(C)n1-c1cc(C(=O)N/N=C/c2cccc(C(=O)O)c2)ccc1C(=O)O] | B | B |
| 80 | 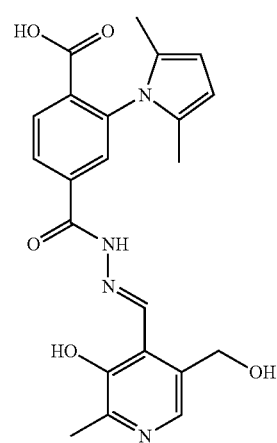 [SMILES: Cc1ncc(CO)c(/C=N/NC(=O)c2ccc(C(=O)O)c(-n3c(C)ccc3C)c2)c1O] | B | C |
| 162 | 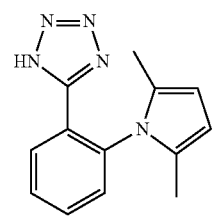 [SMILES: Cc1ccc(C)n1-c1ccccc1-c1nnn[nH]1] | D | C |

TABLE 3-continued

Biochemical and cellular data for exemplary compounds of the invention

| No. | Structure | Myc/Max IC$_{50}$ (μM) | Jurkat EC$_{50}$ (μM) |
|---|---|---|---|
| 134 | 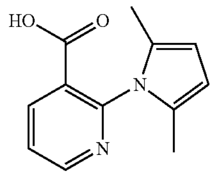 [SMILES: Cc1ccc(C)n1-c1ncccc1C(=O)O] | B | C |
| 179 | 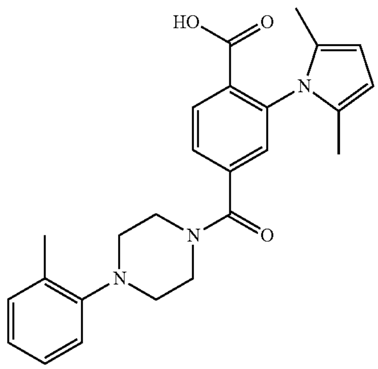 [SMILES: Cc1ccccc1N1CCN(C(=O)c2ccc(C(=O)O)c(-n3c(C)ccc3C)c2)CC1] | C | C |
| 180 | 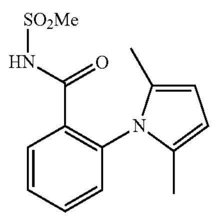 [SMILES: Cc1ccc(C)n1-c1ccccc1C(=O)NS(C)(=O)=O] | C | C |
| 181 | 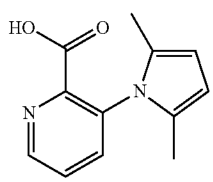 [SMILES: Cc1ccc(C)n1-c1cccnc1C(=O)O] | B | C |
| 164 | 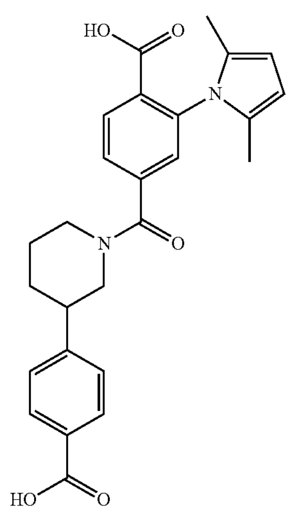 [SMILES: Cc1ccc(C)n1-c1cc(C(=O)N2CCCC(c3ccc(C(=O)O)cc3)C2)ccc1C(=O)O] | B | C |

TABLE 3-continued

Biochemical and cellular data for exemplary compounds of the invention

| No. | Structure | Myc/Max IC$_{50}$ (µM) | Jurkat EC$_{50}$ (µM) |
|---|---|---|---|
| 182 | 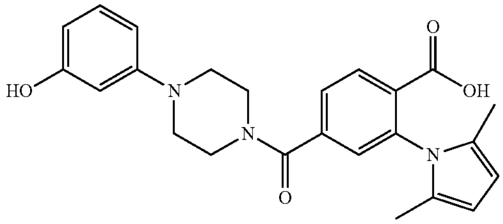 [SMILES: Cc1ccc(C)n1-c1cc(C(=O)N2CCN(c3cccc(O)c3)CC2)ccc1C(=O)O] | B | C |
| 183 | 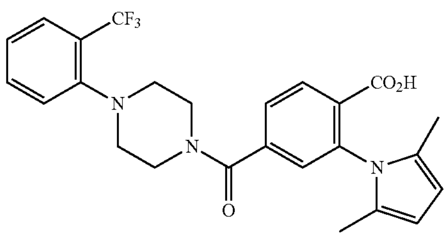 | NA | NA |
| 184 | 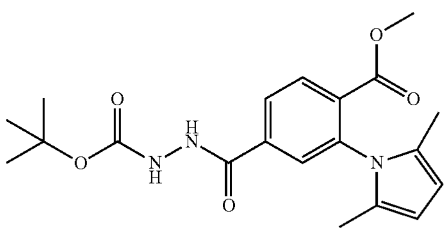 [SMILES: COC(=O)c1ccc(C(=O)NNC(=O)OC(C)(C)C)cc1-n1c(C)ccc1C] | D | C |
| 185 | 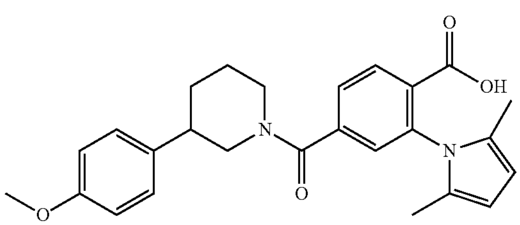 [SMILES: COc1ccc(C2CCCN(C(=O)c3ccc(C(=O)O)c(-n4c(C)ccc4C)c3)C2)cc1] | C | C |
| 186 | 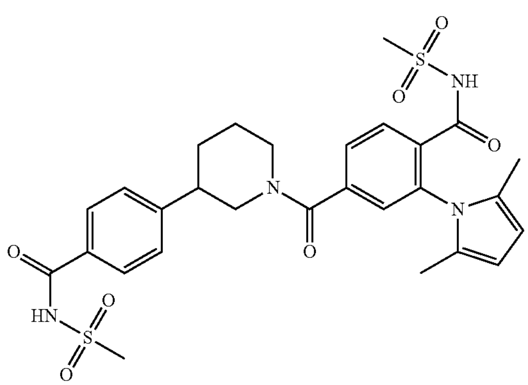 [SMILES: Cc1ccc(C)n1-c1cc(C(=O)N2CCCC(c3ccc(C(=O)NS(C)(=O)=O)cc3)C2)ccc1C(=O)NS(C)(=O)=O] | D | C |
| 187 | 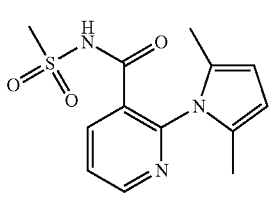 [SMILES: Cc1ccc(C)n1-c1ncccc1C(=O)NS(C)(=O)=O] | D | C |

TABLE 3-continued

Biochemical and cellular data for exemplary compounds of the invention

| No. | Structure | Myc/Max IC$_{50}$ (μM) | Jurkat EC$_{50}$ (μM) |
|---|---|---|---|
| 169 | 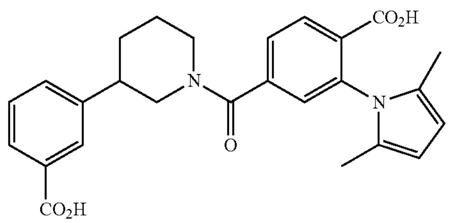 [SMILES: Cc1ccc(C)n1-c1cc(C(=O)N2CCCC(c3cccc(C(=O)O)c3)C2)ccc1C(=O)O] | B | C |
| 188 | 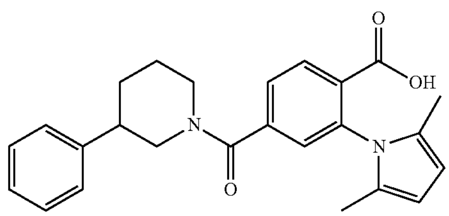 [SMILES: Cc1ccc(C)n1-c1cc(C(=O)N2CCCC(c3ccccc3)C2)ccc1C(=O)O] | C | C |
| 189 | 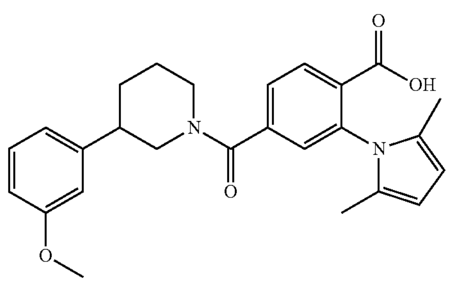 [SMILES: COc1cccc(C2CCCN(C(=O)c3ccc(C(=O)O)c(-n4c(C)ccc4C)c3)C2)c1] | B | B |
| 190 | 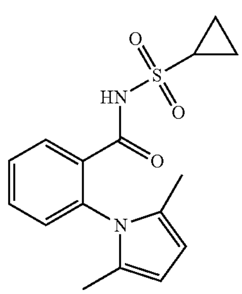 [SMILES: Cc1ccc(C)n1-c1ccccc1C(=O)NS(=O)(=O)C1CC1] | D | B |
| 191 | 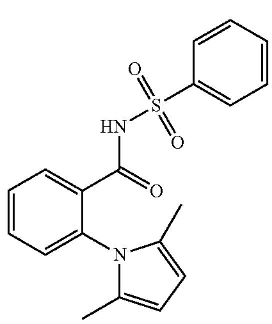 [SMILES: Cc1ccc(C)n1-c1ccccc1C(=O)NS(=O)(=O)c1ccccc1] | D | B |

TABLE 3-continued

Biochemical and cellular data for exemplary compounds of the invention

| No. | Structure | Myc/Max IC$_{50}$ (µM) | Jurkat EC$_{50}$ (µM) |
|---|---|---|---|
| 192 | 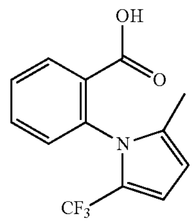 [SMILES: Cc1ccc(C(F)(F)F)n1-c1ccccc1C(=O)O] | D | B |
| 193 | 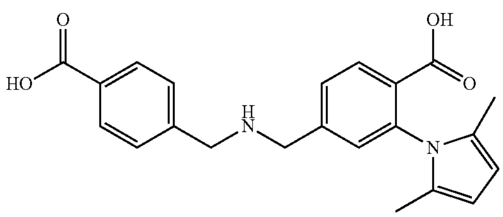 [SMILES: Cc1ccc(C)n1-c1cc(CNCc2ccc(C(=O)O)cc2)ccc1C(=O)O] | A | C |
| 194 | 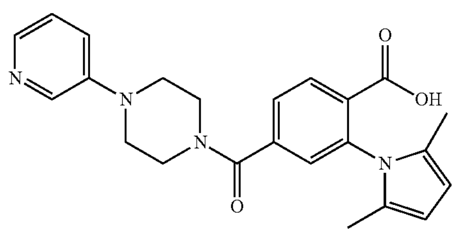 [SMILES: Cc1ccc(C)n1-c1cc(C(=O)N2CCN(c3cccnc3)CC2)ccc1C(=O)O] | D | B |
| 195 | 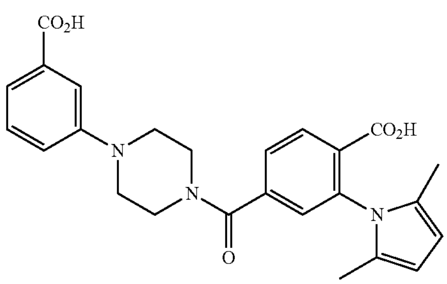 [SMILES: Cc1ccc(C)n1-c1cc(C(=O)N2CCN(c3cccc(C(=O)O)c3)CC2)ccc1C(=O)O] | A | C |
| 196 | 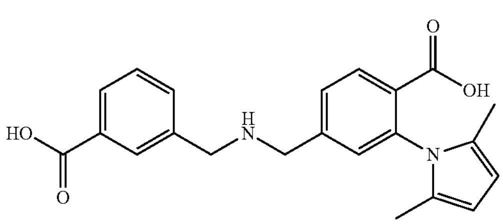 [SMILES: Cc1ccc(C)n1-c1cc(CNCc2cccc(C(=O)O)c2)ccc1C(=O)O] | B | C |
| 197 | 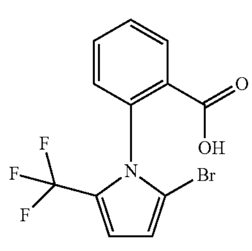 [SMILES: O=C(O)c1ccccc1-n1c(Br)ccc1C(F)(F)F] | C | C |

TABLE 3-continued

Biochemical and cellular data for exemplary compounds of the invention

| No. | Structure | Myc/Max IC$_{50}$ (µM) | Jurkat EC$_{50}$ (µM) |
|---|---|---|---|
| 198 | 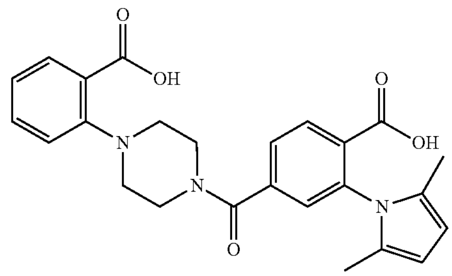 [SMILES: Cc1ccc(C)n1-c1cc(C(=O)N2CCN(c3ccccc3C(=O)O)CC2)ccc1C(=O)O] | B | C |
| 199 | 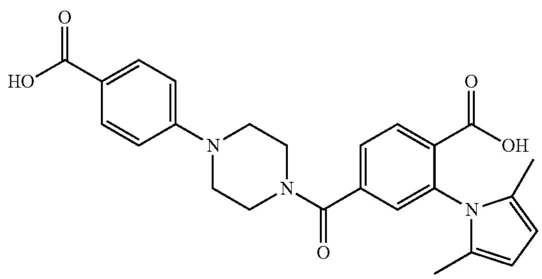 [SMILES: Cc1ccc(C)n1-c1cc(C(=O)N2CCN(c3ccc(C(=O)O)cc3)CC2)ccc1C(=O)O] | B | B |
| 200 | 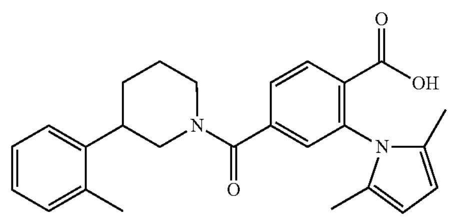 [SMILES: Cc1ccccc1C1CCCN(C(=O)c2ccc(C(=O)O)c(-n3c(C)ccc3C)c2)C1] | D | B |
| 201 | 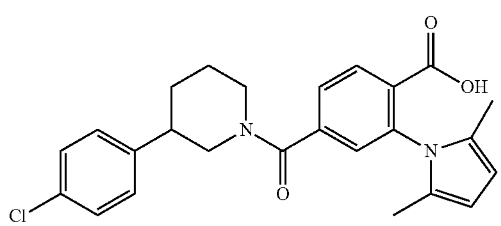 [SMILES: Cc1ccc(C)n1-c1cc(C(=O)N2CCCC(c3ccc(Cl)cc3)C2)ccc1C(=O)O] | C | B |
| 202 | 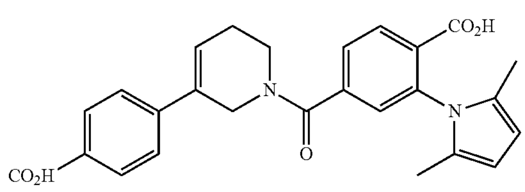 [SMILES: Cc1ccc(C)n1-c1cc(C(=O)N2CCC=C(c3ccc(C(=O)O)cc3)C2)ccc1C(=O)O] | C | B |
| 203 | 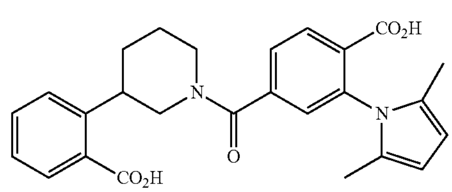 | A | C |

TABLE 3-continued
Biochemical and cellular data for exemplary compounds of the invention
| No. | Structure | Myc/Max IC$_{50}$ (µM) | Jurkat EC$_{50}$ (µM) |
|---|---|---|---|
| 204 | 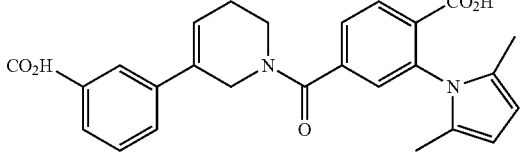 | C | B |
| 205 | 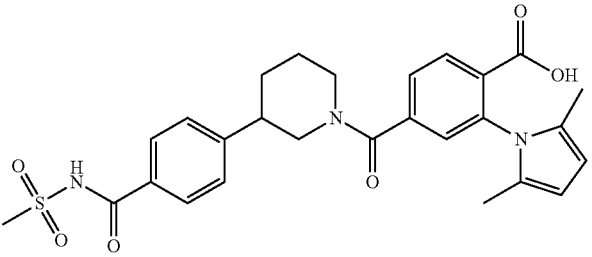 [SMILES: Cc1ccc(C)n1-c1cc(C(=O)N2CCCC(c3ccc(C(=O)NS(C)(=O)=O)cc3)C2)ccc1C(=O)O] | B | C |
| 206 | 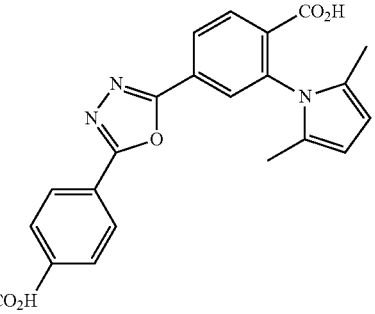 | C | B |
| 207 | 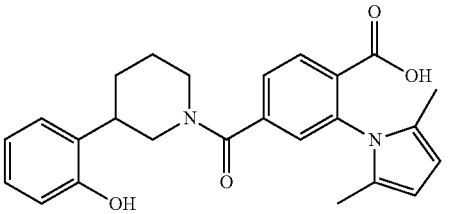 [SMILES: Cc1ccc(C)n1-c1cc(C(=O)N2CCCC(c3ccccc3O)C2)ccc1C(=O)O] | C | C |
| 208 | 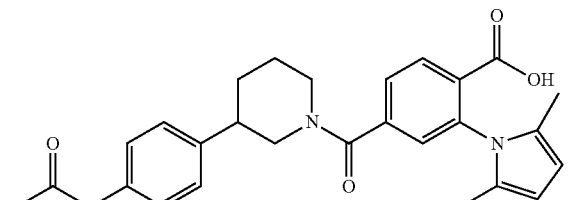 | B | B |
| 209 | 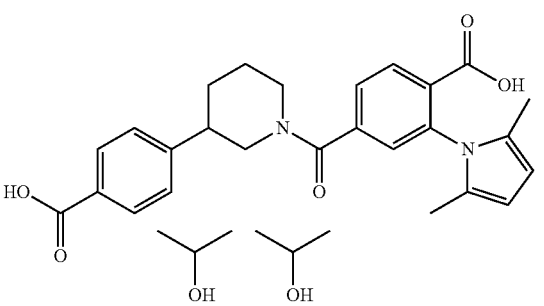 | C | C |

TABLE 3-continued

Biochemical and cellular data for exemplary compounds of the invention

| No. | Structure | Myc/Max IC$_{50}$ (μM) | Jurkat EC$_{50}$ (μM) |
|---|---|---|---|
| 210 | 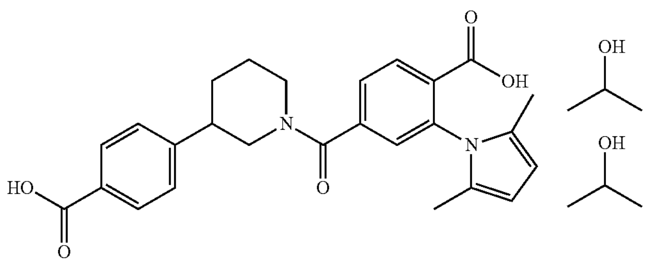 | C | C |
| 211 | 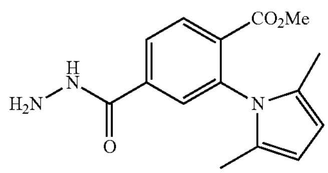 [SMILES: COC(=O)c1ccc(C(=O)NN)cc1-n1c(C)ccc1C] | D | C |
| 212 | 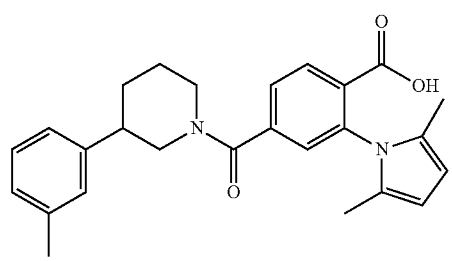 [SMILES: Cc1cccc(C2CCCN(C(=O)c3ccc(C(=O)O)c(-n4c(C)ccc4C)c3)C2)c1] | C | B |
| 213 | 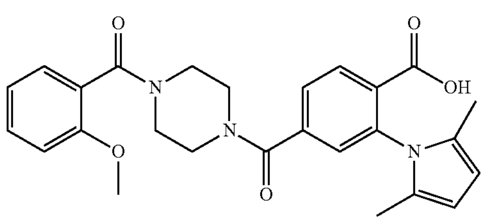 [SMILES: COc1ccccc1C(=O)N1CCN(C(=O)c2ccc(C(=O)O)c(-n3c(C)ccc3C)c2)CC1] | D | C |
| 214 | 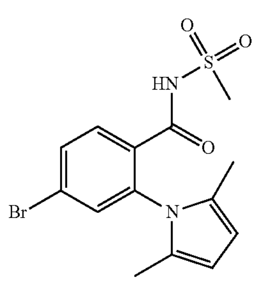 [SMILES: Cc1ccc(C)n1-c1cc(Br)ccc1C(=O)NS(C)(=O)=O] | D | B |
| 215 | 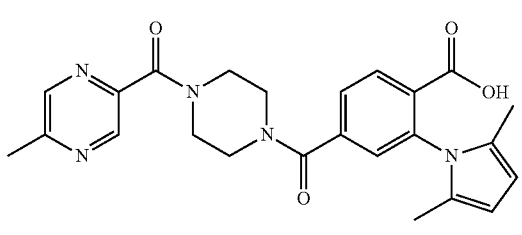 [SMILES: Cc1cnc(C(=O)N2CCN(C(=O)c3ccc(C(=O)O)c(-n4c(C)ccc4C)c3)CC2)cn1] | C | C |

TABLE 3-continued

Biochemical and cellular data for exemplary compounds of the invention

| No. | Structure | Myc/Max IC$_{50}$ (μM) | Jurkat EC$_{50}$ (μM) |
|---|---|---|---|
| 216 | 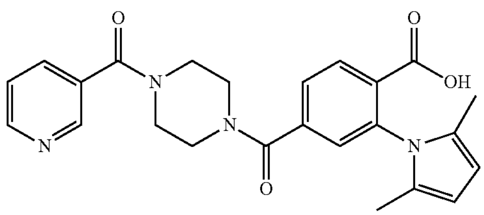 [SMILES: Cc1ccc(C)n1-c1cc(C(=O)N2CCN(C(=O)c3cccnc3)CC2)ccc1C(=O)O] | C | C |
| 217 | 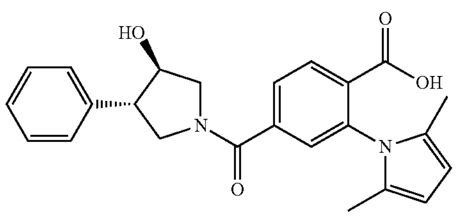 [SMILES: Cc1ccc(C)n1-c1cc(C(=O)N2C[C@H](c3ccccc3)[C@@H](O)C2)ccc1C(=O)O] | C | C |
| 218 | 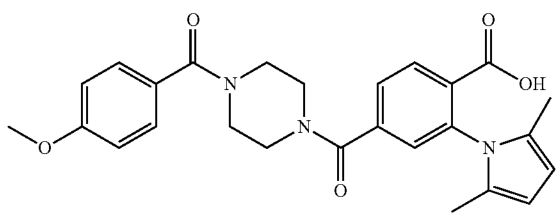 [SMILES: COc1ccc(C(=O)N2CCN(C(=O)c3ccc(C(=O)O)c(-n4c(C)ccc4C)c3)CC2)cc1] | C | B |
| 219 | 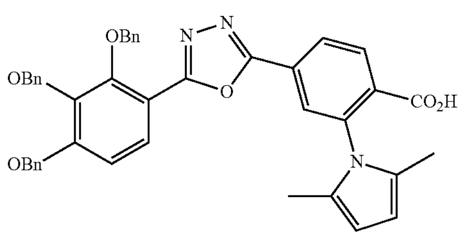 [SMILES: Cc1ccc(C)n1-c1cc(-c2nnc(-c3ccc(OCc4ccccc4)c(OCc4ccccc4)c3OCc3ccccc3)o2)ccc1C(=O)O] | B | A |
| 220 | 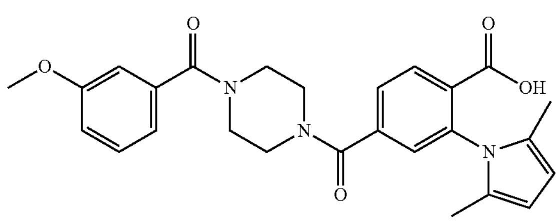 [SMILES: COc1cccc(C(=O)N2CCN(C(=O)c3ccc(C(=O)O)c(-n4c(C)ccc4C)c3)CC2)c1] | C | C |
| 167 | 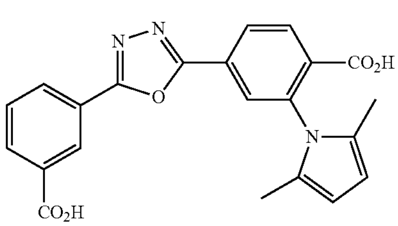 [SMILES: Cc1ccc(C)n1-c1cc(-c2nnc(-c3cccc(C(=O)O)c3)o2)ccc1C(=O)O] | C | B |

TABLE 3-continued

Biochemical and cellular data for exemplary compounds of the invention

| No. | Structure | Myc/Max IC$_{50}$ (µM) | Jurkat EC$_{50}$ (µM) |
|---|---|---|---|
| 221 | 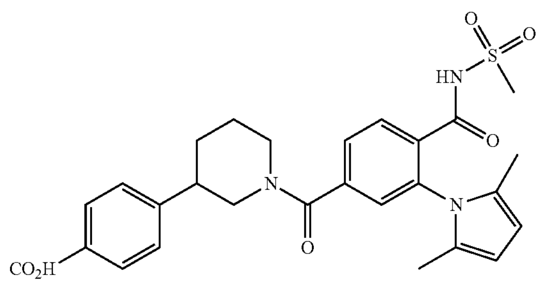 [SMILES: Cc1ccc(C)n1-c1cc(C(=O)N2CCCC(c3ccc(C(=O)O)cc3)C2)ccc1C(=O)NS(C)(=O)=O] | C | C |
| 222 | 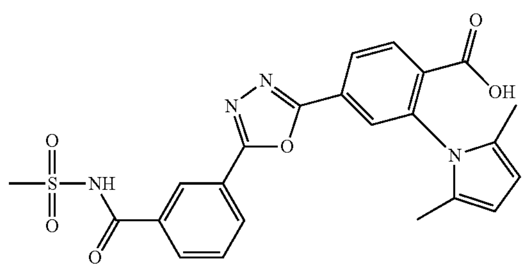 [SMILES: Cc1ccc(C)n1-c1cc(-c2nnc(-c3cccc(C(=O)NS(C)(=O)=O)c3)o2)ccc1C(=O)O] | C | B |
| 223 | 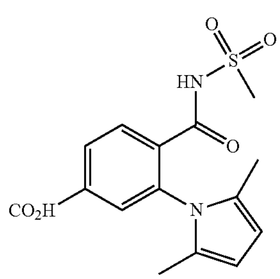 [SMILES: Cc1ccc(C)n1-c1cc(C(=O)O)ccc1C(=O)NS(C)(=O)=O] | C | C |
| 224 | 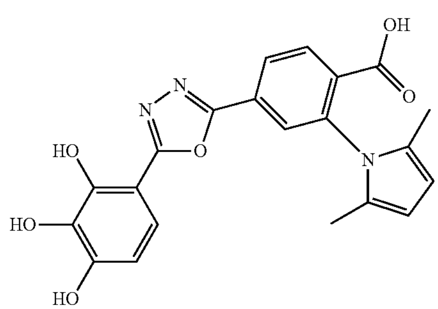 [SMILES: Cc1ccc(C)n1-c1cc(-c2nnc(-c3ccc(O)c(O)c3O)o2)ccc1C(=O)O] | A | A |
| 225 | 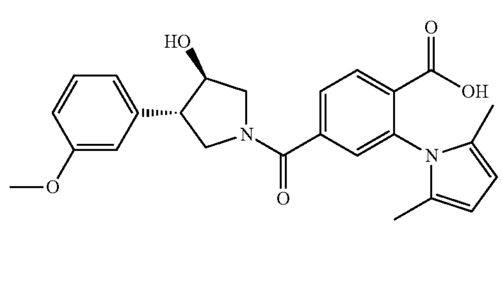 [SMILES: COc1cccc([C@H]2CN(C(=O)c3ccc(C(=O)O)c(-n4c(C)ccc4C)c3)C[C@@H]2O)c1] | D | B |

TABLE 3-continued
Biochemical and cellular data for exemplary compounds of the invention
| No. | Structure | Myc/Max IC$_{50}$ (µM) | Jurkat EC$_{50}$ (µM) |
|---|---|---|---|
| 226 | 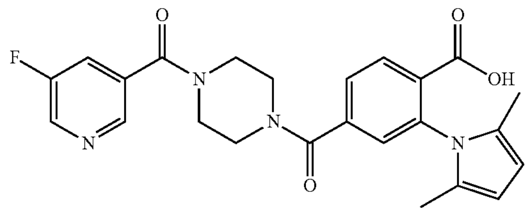 [SMILES: Cc1ccc(C)n1-c1cc(C(=O)N2CCN(C(=O)c3cncc(F)c3)CC2)ccc1C(=O)O] | C | C |
NA: not active under assay conditions.
Assay results for additional exemplary compounds (e.g., compounds 169 to 178) are shown in FIGS. 11 to 12.
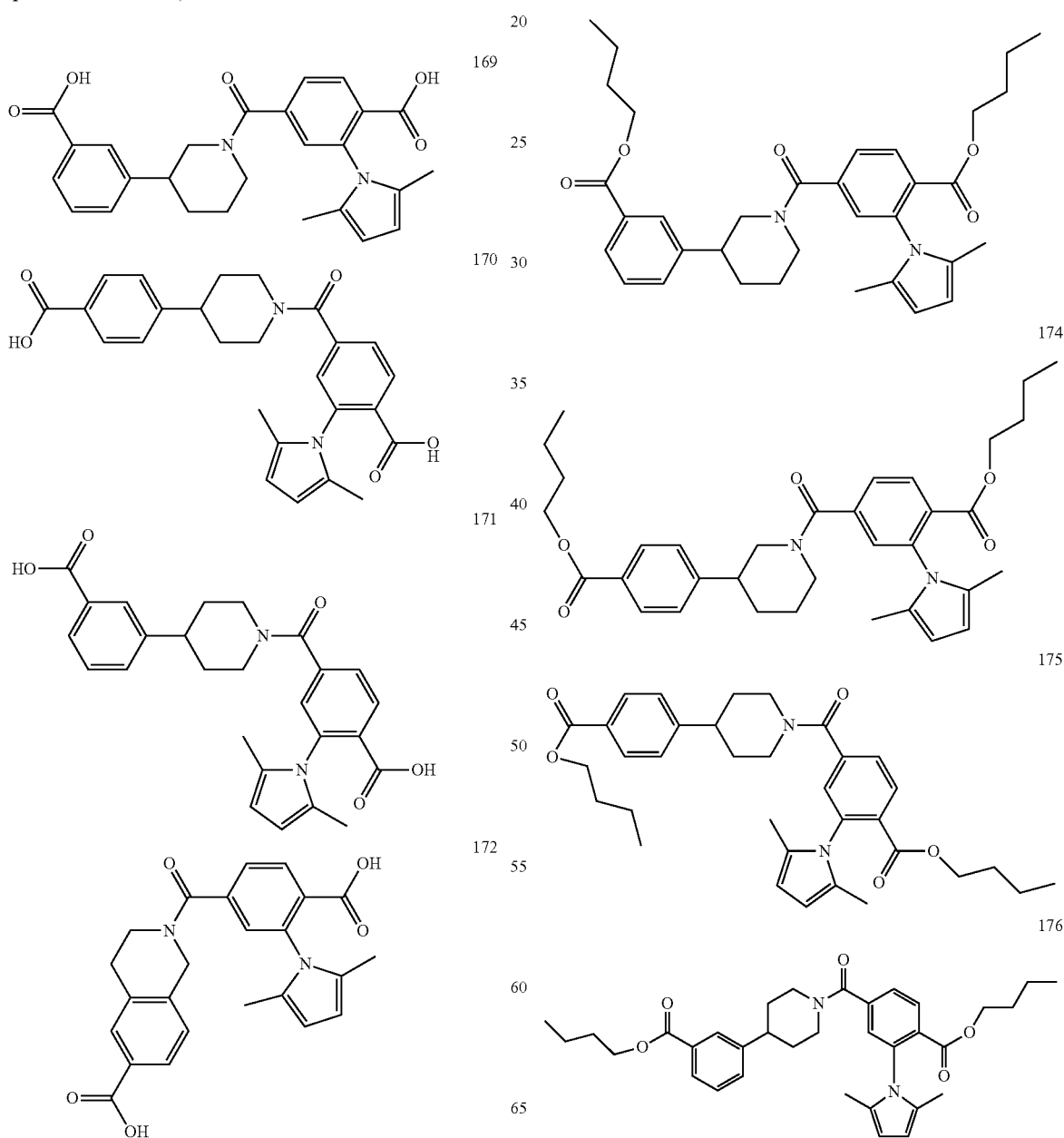

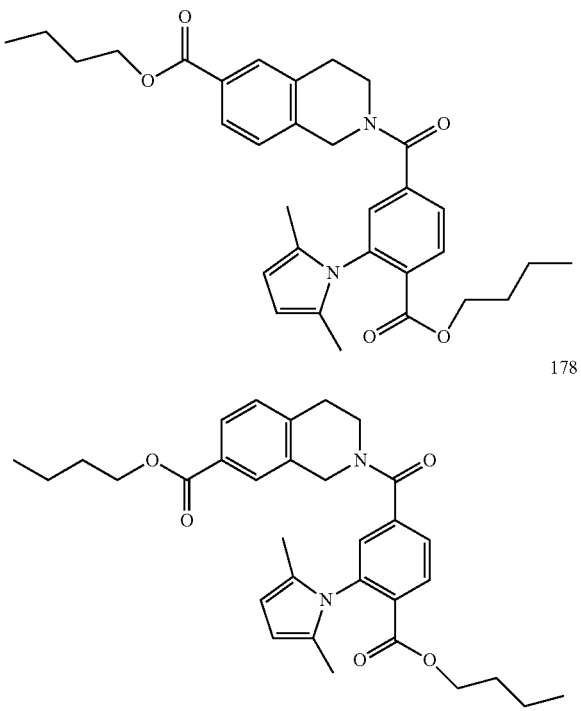

177

178

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in *haec verba* herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for identifying a test compound as a Myc inhibitor comprising:
   (a) combining a nucleic acid labeled with a fluorescence donor with Myc and a Max labeled with a fluorescence acceptor in presence of the test compound;
   (b) detecting the binding of Myc and the labeled Max to the labeled nucleic acid using proximity-based luminescence detection; and
   (c) identifying the test compound as a Myc inhibitor when the proximity-based luminescence detection signal is decreased in the presence of the test compound relative to the proximity-based luminescence detection signal in the absence of the test compound.

2. The method of claim 1, wherein the proximity-based luminescence detection is selected from the group consisting of fluorescence resonance energy transfer ("FRET"), luminescence resonance energy transfer ("LRET"), fluorescence cross-correlation spectroscopy ("FCCS"), scintillation proximity ("SPA"), chemiluminescence energy transfer ("CRET"), bioluminescence energy transfer ("BRET"), and excimer formation.

3. The method of claim 1, wherein the nucleic acid and/or Max are linked to a solid substrate.

4. The method of claim 3, wherein the nucleic acid and/or Max are linked to the solid substrate via a biotin/avidin interaction.

5. The method of claim 3, wherein the solid substrate is a microtiter plate, membrane, or bead.

6. The method of claim 1, wherein Max comprises c-Myc, l-Myc, n-Myc, s-Myc, b-myc, or a mutant, variant, homolog, fragment thereof.

7. The method of claim 1, wherein the nucleic acid comprises Enhancer box (E-box) sequences.

8. The method of claim 1, wherein the sequence of the E-box element is CANNTG, wherein N is independently G, A, T, or C.

9. The method of claim 3, wherein the nucleic acid and/or Max are linked to the solid substrate via a covalent or non-covalent interaction.

10. The method of claim 1, wherein the test compound is identified as a Myc inhibitor when the proximity-based luminescence detection signal is decreased by 5% or more in the presence of the test compound relative to the proximity-based luminescence detection signal in the absence of the test compound.

* * * * *